(12) United States Patent
Gruber

(10) Patent No.: US 11,518,801 B1
(45) Date of Patent: Dec. 6, 2022

(54) METHODS AND COMPOSITIONS FOR TREATING DIABETES AND DIABETIC COMPLICATIONS

(71) Applicant: Siwa Corporation, Chicago, IL (US)

(72) Inventor: Lewis S. Gruber, Chicago, IL (US)

(73) Assignee: Siwa Corporation, Chicago, IL (US)

( * ) Notice: Subject to any disclaimer, the term of this patent is extended or adjusted under 35 U.S.C. 154(b) by 268 days.

(21) Appl. No.: 16/228,293

(22) Filed: Dec. 20, 2018

Related U.S. Application Data

(60) Provisional application No. 62/610,034, filed on Dec. 22, 2017.

(51) Int. Cl.
| | | |
|---|---|---|
| *A61P 3/10* | (2006.01) | |
| *A61K 39/00* | (2006.01) | |
| *A61K 39/395* | (2006.01) | |
| *C07K 16/18* | (2006.01) | |
| *A61K 9/00* | (2006.01) | |

(52) U.S. Cl.
CPC ............ *C07K 16/18* (2013.01); *A61K 9/0019* (2013.01); *A61K 39/0003* (2013.01); *A61K 39/3955* (2013.01); *A61P 3/10* (2018.01)

(58) Field of Classification Search
None
See application file for complete search history.

(56) References Cited

U.S. PATENT DOCUMENTS

| | | | |
|---|---|---|---|
| 4,217,344 A | 8/1980 | Vanlerberghe et al. | |
| 4,900,747 A | 2/1990 | Vlassara et al. | |
| 4,911,928 A | 3/1990 | Wallach | |
| 4,917,951 A | 4/1990 | Wallach | |
| 4,965,288 A | 10/1990 | Palfreyman | |
| 5,494,791 A | 2/1996 | Cohen | |
| 5,518,720 A | 5/1996 | Cohen | |
| 5,601,526 A | 2/1997 | Chapelon et al. | |
| 5,620,409 A | 4/1997 | Venuto | |
| 5,620,479 A | 4/1997 | Diederich | |
| 5,664,570 A | 9/1997 | Bishop | |
| 5,693,762 A | 12/1997 | Queen et al. | |
| 5,702,704 A | 12/1997 | Bucala | |
| 5,766,590 A * | 6/1998 | Founds .................. | C07K 16/18 424/137.1 |
| 5,811,075 A | 9/1998 | Vlassara et al. | |
| 5,817,771 A | 10/1998 | Bayley et al. | |
| 5,984,882 A | 11/1999 | Rosenschein et al. | |
| 6,067,859 A | 5/2000 | Kas et al. | |
| 6,090,382 A | 7/2000 | Salfeld et al. | |
| 6,176,842 B1 | 1/2001 | Tachibana et al. | |
| 6,245,318 B1 | 6/2001 | Klibanov et al. | |
| 6,309,355 B1 | 10/2001 | Cain et al. | |
| 6,380,165 B1 | 4/2002 | Al-Abed et al. | |
| 6,387,373 B1 | 5/2002 | Wright et al. | |
| 6,410,598 B1 | 6/2002 | Vitek | |
| 6,670,136 B2 | 12/2003 | Schmidt et al. | |
| 6,676,963 B1 | 1/2004 | Lanza et al. | |
| 6,818,215 B2 | 11/2004 | Smith et al. | |
| 6,821,274 B2 | 11/2004 | McHale et al. | |
| 7,033,574 B1 | 4/2006 | Schneider et al. | |
| 7,101,838 B2 | 9/2006 | Stern et al. | |
| 7,256,273 B2 | 8/2007 | Basi et al. | |
| 7,347,855 B2 | 3/2008 | Eshel et al. | |
| 7,358,226 B2 | 4/2008 | Dayton et al. | |
| 7,367,988 B1 | 5/2008 | Litovitz | |
| 7,470,521 B2 | 12/2008 | O'Keefe | |
| 7,751,057 B2 | 7/2010 | Oldenburg et al. | |
| 7,815,570 B2 | 10/2010 | Eshel et al. | |
| 8,318,164 B2 | 11/2012 | Warne | |
| 8,323,651 B2 | 12/2012 | Gu et al. | |
| 8,343,420 B2 | 1/2013 | Cioanta et al. | |
| 8,398,977 B2 | 3/2013 | Bleck et al. | |
| 8,721,571 B2 | 5/2014 | Gruber | |
| 8,977,361 B2 | 3/2015 | Carpentier et al. | |
| 8,981,112 B2 | 3/2015 | Bukhtiyarov et al. | |
| 9,155,805 B2 | 10/2015 | Hamakubo | |
| 9,161,810 B2 | 10/2015 | Gruber | |
| 9,320,919 B2 | 4/2016 | Gruber | |
| 9,493,566 B2 | 11/2016 | Ryan | |
| 9,493,567 B2 | 11/2016 | Lieberburg | |
| 9,649,376 B2 | 5/2017 | Gruber | |

(Continued)

FOREIGN PATENT DOCUMENTS

| | | |
|---|---|---|
| AE | P6000510/2018 | 7/2022 |
| AU | 2009248945 | 11/2012 |

(Continued)

OTHER PUBLICATIONS

U.S. Appl. No. 15/720,912, filed Sep. 29, 2017.

(Continued)

*Primary Examiner* — Daniel C Gamett

(74) *Attorney, Agent, or Firm* — Evan Law Group LLC

(57) ABSTRACT

A method of treating or preventing the onset of diabetes or diabetic complications comprises administering to a subject a composition comprising an anti-AGE antibody. A composition for treating or preventing the onset of diabetes or diabetic complications comprises a first anti-AGE antibody, a second anti-AGE antibody and a pharmaceutically acceptable carrier. The first anti-AGE antibody is different from the second anti-AGE antibody. A method of treating or preventing the onset of diabetes or diabetic complications comprises immunizing a subject in need thereof against AGE-modified proteins or peptides of a cell.

20 Claims, 1 Drawing Sheet

Specification includes a Sequence Listing.

(56) References Cited

U.S. PATENT DOCUMENTS

| | | |
|---|---|---|
| 9,993,535 B2 | 6/2018 | Gruber |
| 10,226,531 B2 | 3/2019 | Gruber |
| 10,358,502 B2 | 7/2019 | Gruber |
| 10,584,180 B2 | 3/2020 | Gruber |
| 10,858,449 B1 | 12/2020 | Gruber |
| 10,889,634 B2 | 1/2021 | Gruber |
| 10,919,957 B2 | 2/2021 | Gruber |
| 10,925,937 B1 | 2/2021 | Gruber |
| 10,960,234 B2 | 3/2021 | Gruber |
| 10,961,321 B1 | 3/2021 | Gruber |
| 10,995,151 B1 | 5/2021 | Gruber |
| 11,213,585 B2 | 1/2022 | Gruber |
| 11,261,241 B2 | 3/2022 | Gruber |
| 2002/0122799 A1 | 9/2002 | Stern et al. |
| 2002/0193784 A1 | 12/2002 | McHale et al. |
| 2003/0073138 A1 | 4/2003 | Kientsch-Engel et al. |
| 2003/0115614 A1 | 6/2003 | Kanda |
| 2003/0170173 A1 | 9/2003 | Klaveness et al. |
| 2003/0229283 A1 | 12/2003 | Craig et al. |
| 2004/0039416 A1 | 2/2004 | Myhr |
| 2004/0141922 A1 | 7/2004 | Klaveness et al. |
| 2004/0142391 A1 | 7/2004 | Schmidt |
| 2004/0208826 A1 | 10/2004 | Schneider et al. |
| 2004/0210042 A1 | 10/2004 | Tsuchida |
| 2004/0229830 A1 | 11/2004 | Tachibana et al. |
| 2005/0084538 A1 | 4/2005 | Dayton et al. |
| 2005/0283098 A1 | 12/2005 | Conston et al. |
| 2006/0078501 A1 | 4/2006 | Goertz et al. |
| 2006/0122543 A1 | 6/2006 | Mayer et al. |
| 2006/0188883 A1 | 8/2006 | Murray et al. |
| 2006/0222646 A1 | 10/2006 | Treacy |
| 2006/0241524 A1 | 10/2006 | Lee |
| 2007/0059247 A1 | 3/2007 | Lindner et al. |
| 2007/0065415 A1 | 3/2007 | Kleinsek et al. |
| 2007/0065443 A1 | 3/2007 | Tobia |
| 2007/0071675 A1 | 3/2007 | Wu et al. |
| 2007/0078290 A1 | 4/2007 | Esenaliev |
| 2007/0083120 A1 | 4/2007 | Cain et al. |
| 2007/0128117 A1 | 6/2007 | Bettinger et al. |
| 2007/0129633 A1 | 6/2007 | Lee et al. |
| 2007/0225242 A1 | 9/2007 | Erler |
| 2008/0019986 A1 | 1/2008 | Stern et al. |
| 2008/0051680 A1 | 2/2008 | Luebcke |
| 2008/0063603 A1 | 3/2008 | Schneider et al. |
| 2008/0139942 A1 | 6/2008 | Gaud et al. |
| 2008/0160506 A1 | 7/2008 | Liu et al. |
| 2009/0022659 A1 | 1/2009 | Olson et al. |
| 2009/0076390 A1 | 3/2009 | Lee et al. |
| 2009/0306552 A1 | 12/2009 | Furuzono et al. |
| 2010/0028359 A1 | 2/2010 | Gu et al. |
| 2010/0226932 A1 | 9/2010 | Smith et al. |
| 2010/0249038 A1 | 9/2010 | Logsdon |
| 2011/0105961 A1 | 5/2011 | Gruber |
| 2011/0319499 A1 | 12/2011 | Semba et al. |
| 2012/0130287 A1 | 5/2012 | Gruber |
| 2012/0135918 A1 | 5/2012 | Bowers |
| 2012/0156134 A1 | 6/2012 | Squires |
| 2012/0183534 A1 | 7/2012 | Gruber |
| 2013/0058921 A1 | 3/2013 | Van Rhee |
| 2013/0131006 A1 | 5/2013 | Lee et al. |
| 2013/0243785 A1 | 9/2013 | Gruber |
| 2013/0288980 A1 | 10/2013 | De Keizer et al. |
| 2014/0234339 A1 | 8/2014 | Ohlsen |
| 2014/0234343 A1 | 8/2014 | Lee et al. |
| 2014/0303526 A1 | 10/2014 | Gruber |
| 2015/0376279 A1 | 12/2015 | Hansen |
| 2016/0083437 A1 | 3/2016 | Cho et al. |
| 2016/0091410 A1 | 3/2016 | Krug |
| 2016/0101299 A1 | 4/2016 | Gruber |
| 2016/0152697 A1 | 6/2016 | Gruber |
| 2016/0175413 A1 | 6/2016 | Gruber |
| 2016/0193358 A1 | 7/2016 | Algate |
| 2016/0215043 A1 | 7/2016 | Gruber |
| 2016/0279261 A1 | 9/2016 | Lee |
| 2016/0311907 A1 | 10/2016 | Brogdon et al. |
| 2016/0339019 A1 | 11/2016 | Laberge et al. |
| 2016/0340418 A1 | 11/2016 | Baron |
| 2017/0216286 A1 | 8/2017 | Kirkland |
| 2017/0216435 A1 | 8/2017 | Gruber |
| 2017/0240632 A1 | 8/2017 | Thomas |
| 2017/0247472 A1 | 8/2017 | Gruber |
| 2017/0259086 A1 | 9/2017 | Carpentier et al. |
| 2018/0036558 A1 | 2/2018 | Carpentier et al. |
| 2018/0044411 A1 | 2/2018 | Gruber |
| 2018/0111982 A2 | 4/2018 | Gruber |
| 2018/0298087 A1 | 10/2018 | Gruber |
| 2018/0312577 A1 | 11/2018 | Gruber |
| 2018/0326026 A1 | 11/2018 | Gruber |
| 2019/0031781 A1 | 1/2019 | Gruber |
| 2019/0119371 A1 | 4/2019 | Gruber |
| 2019/0328873 A1 | 10/2019 | Gruber |
| 2019/0328876 A1 | 10/2019 | Gruber |
| 2020/0054682 A1 | 2/2020 | Gojo et al. |
| 2020/0055957 A1 | 2/2020 | Gruber |
| 2020/0150131 A1 | 5/2020 | Gruber |
| 2020/0231706 A1 | 7/2020 | Gruber |
| 2021/0087297 A1 | 3/2021 | Gruber |
| 2021/0208533 A1 | 7/2021 | Gruber |
| 2021/0236860 A1 | 8/2021 | Gruber |
| 2021/0253737 A1 | 8/2021 | Gruber |
| 2021/0253739 A1 | 8/2021 | Gruber |
| 2022/0160869 A1 | 5/2022 | Gruber |
| 2022/0175916 A1 | 6/2022 | Gruber |

FOREIGN PATENT DOCUMENTS

| | | |
|---|---|---|
| AU | 2009248945 | 4/2013 |
| AU | 2009248945 | 2/2014 |
| AU | 2009/248945 | 5/2014 |
| AU | 2011332143 | 6/2015 |
| AU | 2014202548 | 6/2015 |
| AU | 2011332143 | 1/2016 |
| AU | 2014202548 | 1/2016 |
| AU | 2014202548 | 4/2016 |
| AU | 2014202548 | 6/2016 |
| AU | 2016204196 | 8/2016 |
| AU | 2015318036 | 6/2020 |
| AU | 2017219749 | 1/2021 |
| AU | 2017219749 | 2/2021 |
| AU | 2015318036 | 5/2021 |
| AU | 2018251183 | 3/2022 |
| CA | 2724886 | 6/2014 |
| CA | 2724886 | 2/2015 |
| CA | 2724886 | 9/2015 |
| CA | 2724886 | 4/2016 |
| CA | 2818647 | 10/2016 |
| CA | 2724886 | 2/2017 |
| CA | 2818647 | 4/2017 |
| CA | 2724886 | 5/2017 |
| CA | 2818647 | 10/2017 |
| CA | 2818647 | 11/2017 |
| CA | 2818647 | 6/2018 |
| CA | 2818647 | 7/2018 |
| CA | 2961603 | 5/2021 |
| CA | 3000815 | 5/2021 |
| CA | 3000815 | 10/2021 |
| CA | 3021150 | 3/2022 |
| CA | 3021150 | 9/2022 |
| CN | 200980118817.6 | 5/2012 |
| CN | 200980118817.6 | 2/2013 |
| CN | 200980118817.6 | 10/2013 |
| CN | 200980118817.6 | 5/2014 |
| CN | 200980118817.6 | 10/2014 |
| CN | 200980118817.6 | 3/2015 |
| CN | 201510303227.8 | 6/2016 |
| CN | 201510303227.8 | 12/2016 |
| CN | 201510303227.8 | 5/2017 |
| CN | 201580056616.3 | 4/2020 |
| CN | 2016800599975 | 1/2021 |
| CN | 2016800599975 | 2/2021 |
| CN | 201580056616.3 | 3/2021 |
| CN | 201780024206.X | 5/2021 |
| CN | 201580056616.3 | 9/2021 |
| CN | 201780037571.4 | 9/2021 |

(56) References Cited

FOREIGN PATENT DOCUMENTS

| | | |
|---|---|---|
| CN | 201780024206.X | 4/2022 |
| CN | 201780037571.4 | 4/2022 |
| CN | 2019139256 | 7/2022 |
| CN | 201780024206.X | 10/2022 |
| DE | 102008009461 | 8/2009 |
| EP | 0 259 893 | 3/1988 |
| EP | 1 219 639 | 7/2002 |
| EP | 1 415 997 | 5/2004 |
| EP | 1 867 659 | 12/2007 |
| EP | 09 751 639.7 | 11/2011 |
| EP | 09 751 639.7 | 6/2012 |
| EP | 09 751 639.7 | 1/2013 |
| EP | 09751639.7 | 7/2013 |
| EP | 09751639.7 | 1/2014 |
| EP | 16198527.0 | 2/2014 |
| EP | 2 294 178 | 7/2014 |
| EP | 14170802.4 | 9/2014 |
| EP | 14170802.4 | 7/2015 |
| EP | 14170802.4 | 12/2015 |
| EP | 14170802.4 | 4/2016 |
| EP | 14170802.4 | 11/2016 |
| EP | 11776932.3 | 3/2017 |
| EP | 11776932.3 | 8/2017 |
| EP | 11776932.3 | 9/2017 |
| EP | 11776932.3 | 1/2018 |
| EP | 11776932.3 | 2/2018 |
| EP | 11776932.3 | 3/2018 |
| EP | 15772116.8 | 9/2018 |
| EP | 15772116.8 | 1/2019 |
| EP | 17708098.3 | 1/2019 |
| EP | 18184822.7 | 1/2019 |
| EP | 11776932.3 | 2/2019 |
| EP | 15772116.8 | 2/2019 |
| EP | 17708098.3 | 2/2019 |
| EP | 18184822.7 | 6/2019 |
| EP | 17708098.3 | 7/2019 |
| EP | 17737078.0 | 8/2019 |
| EP | 17708098.3 | 12/2019 |
| EP | 18726656.4 | 12/2019 |
| EP | 15772116.8 | 3/2020 |
| EP | 19210193.9 | 5/2020 |
| EP | 17737078.0 | 6/2020 |
| EP | 15772116.8 | 7/2020 |
| EP | 19210193.9 | 7/2020 |
| EP | 18184822.7 | 3/2021 |
| EP | 18726656.4 | 3/2021 |
| EP | 19210193.9 | 5/2021 |
| EP | 15772116.8 | 12/2021 |
| EP | 19210193.9 | 3/2022 |
| EP | 16738275.3 | 5/2022 |
| EP | 22157145.8 | 9/2022 |
| IL | 209513 | 8/2012 |
| IL | 209513 | 5/2013 |
| IL | 209513 | 5/2014 |
| IL | 209513 | 12/2014 |
| IL | 240242 | 4/2016 |
| IL | 240242 | 1/2017 |
| IL | 248652 | 5/2017 |
| IL | 251210 | 6/2020 |
| IL | 258397 | 6/2020 |
| IL | 261006 | 3/2021 |
| IL | 283726 | 11/2021 |
| IL | 262222 | 1/2022 |
| IL | 251210 | 2/2022 |
| IN | 4875/KOLNP/2010 | 12/2016 |
| IN | 201737009367 | 6/2020 |
| IN | 201827014696 | 3/2022 |
| IN | 201837030621 | 5/2022 |
| JP | 09178740 | 7/1997 |
| JP | 11246599 | 9/1999 |
| JP | 2022-128911 | 10/2002 |
| JP | 2003/160599 | 6/2003 |
| JP | 2006-249015 | 9/2006 |
| JP | 2007-163407 | 6/2007 |
| JP | 2007277263 | 10/2007 |
| JP | 2011-511734 | 11/2013 |
| JP | 2011-511734 | 12/2014 |
| JP | 2015-076575 | 6/2015 |
| JP | 2015-076575 | 1/2016 |
| JP | 2016-098558 | 7/2016 |
| JP | 2016-098558 | 12/2016 |
| JP | 2017-086871 | 4/2018 |
| JP | 2017086871 | 3/2019 |
| JP | 2017-515740 | 7/2019 |
| JP | 2017-515740 | 1/2020 |
| JP | 2018-543120 | 3/2020 |
| JP | 2018-519727 | 5/2020 |
| JP | 2018-543120 | 5/2020 |
| JP | 2018-566505 | 6/2020 |
| JP | 2020-106264 | 8/2020 |
| JP | 2020-106264 | 11/2020 |
| JP | 2019-230026 | 12/2020 |
| JP | 2018-566505 | 5/2021 |
| JP | 2020-085180 | 6/2021 |
| JP | 2017-515740 | 7/2021 |
| JP | 2017-515740 | 10/2021 |
| JP | 2019-230026 | 12/2021 |
| JP | 2021-155024 | 12/2021 |
| JP | 2019-555873 | 2/2022 |
| JP | 2019-560086 | 3/2022 |
| JP | 2019-5560086 | 3/2022 |
| JP | 2021-155024 | 6/2022 |
| KR | 10-212-7026063 | 7/2012 |
| KR | 10-2010-7026063 | 2/2013 |
| KR | 10-2010-7026063 | 9/2013 |
| KR | 10-2010-7026063 | 12/2013 |
| KR | 10-2013-7028228 | 6/2014 |
| KR | 10-2010-7026063 | 7/2014 |
| KR | 10-2012-7026483 | 7/2014 |
| KR | 10-2012-77026483 | 2/2015 |
| KR | 10-2013-7028228 | 4/2015 |
| KR | 10-2015-7007520 | 4/2015 |
| KR | 10-2015-7007520 | 11/2015 |
| KR | 10-2017-7009539 | 9/2021 |
| KR | 10-2018-7031932 | 11/2021 |
| KR | 10-2017-7009539 | 5/2022 |
| KR | 10-2018-7026021 | 6/2022 |
| KR | 10-2018-7031932 | 7/2022 |
| KR | 10-2019-7035140 | 9/2022 |
| MX | 2010/012473 | 7/2013 |
| MX | 2010/012473 | 3/2014 |
| MX | 2010/012473 | 6/2014 |
| MX | MX/a/2013/013310 | 7/2015 |
| MX | MX/a/2013/013310 | 4/2016 |
| MX | MX/a/2013/013310 | 2/2017 |
| MX | MX/a/2017-003565 | 9/2021 |
| MX | MX/a/2017/003565 | 2/2022 |
| MX | MX/a/2018/009988 | 6/2022 |
| MX | MX/a/2018/009988 | 9/2022 |
| RU | 2 270 029 | 1/2006 |
| RU | 2010152693 | 12/2012 |
| RU | 2010152693 | 4/2013 |
| RU | 2010152693 | 5/2014 |
| RU | 2010152693 | 12/2014 |
| RU | 2015114990 | 7/2016 |
| RU | 2015114990 | 1/2017 |
| RU | 2617313 | 4/2017 |
| RU | 2017113349 | 5/2017 |
| RU | 2015114990 | 8/2017 |
| RU | 2015114990 | 10/2017 |
| RU | 2017113349 | 12/2018 |
| RU | 2017113349 | 4/2019 |
| RU | 2018110885 | 1/2020 |
| RU | 2017113349 | 3/2020 |
| RU | 2018132998 | 5/2020 |
| RU | 2019139256 | 8/2021 |
| RU | 2018110885 | 9/2021 |
| RU | 2018110885 | 12/2021 |
| RU | 20191392556 | 1/2022 |
| RU | 2019139256 | 7/2022 |
| WO | 1993/13421 | 7/1993 |
| WO | 1995/20979 | 8/1995 |
| WO | 1996/20958 | 7/1996 |
| WO | 1997/07803 | 3/1997 |

(56) References Cited

FOREIGN PATENT DOCUMENTS

| | | |
|---|---|---|
| WO | 1997/49429 | 12/1997 |
| WO | 1999/07893 | 2/1999 |
| WO | 1999/14587 | 3/1999 |
| WO | 1999/64463 | 12/1999 |
| WO | 2000/20458 | 4/2000 |
| WO | 2001/00245 | 1/2001 |
| WO | 2001/077342 | 10/2001 |
| WO | 2004/011460 | 2/2004 |
| WO | 2004/016229 | 2/2004 |
| WO | 2004/076677 | 9/2004 |
| WO | 2006/012415 | 2/2006 |
| WO | 2006/017647 | 2/2006 |
| WO | 2006/040597 | 4/2006 |
| WO | PCT/US2009/44951 | 7/2009 |
| WO | 2009/136382 | 11/2009 |
| WO | 2009/143411 | 11/2009 |
| WO | 2010/005531 | 1/2010 |
| WO | PCT/US2009/44951 | 12/2010 |
| WO | 2011/032633 | 3/2011 |
| WO | 2012/047629 | 4/2012 |
| WO | PCT/US2011/053399 | 4/2012 |
| WO | 2012/071269 | 5/2012 |
| WO | PCT/US12/31446 | 6/2012 |
| WO | PCT/US2011/0611387 | 6/2012 |
| WO | 2012/135616 | 10/2012 |
| WO | 2013/009785 | 1/2013 |
| WO | 2013/043161 | 3/2013 |
| WO | 11776932.3 | 4/2013 |
| WO | 2013/070468 | 5/2013 |
| WO | PCT/US2011/061387 | 5/2013 |
| WO | PCT/US2012/031446 | 10/2013 |
| WO | 2014/090991 | 6/2014 |
| WO | 2014/136114 | 9/2014 |
| WO | 2014/164693 | 10/2014 |
| WO | 2015/112835 | 7/2015 |
| WO | 2015/116740 | 8/2015 |
| WO | 2016/044252 | 3/2016 |
| WO | PCT/US2015/050154 | 3/2016 |
| WO | WO-2016044252 A2 * | 3/2016 ............ A61P 37/00 |
| WO | PCT/US2016/034880 | 8/2016 |
| WO | PCT/US2016/039076 | 12/2016 |
| WO | PCT/US2015/050154 | 3/2017 |
| WO | 2017/065837 | 4/2017 |
| WO | PCT/US2017/018185 | 5/2017 |
| WO | 2017/143073 | 8/2017 |
| WO | PCT/US2017/027773 | 9/2017 |
| WO | 2017/181116 | 10/2017 |
| WO | 2017/222535 | 12/2017 |
| WO | PCT/US2017/018185 | 8/2018 |
| WO | 2018/191718 | 10/2018 |
| WO | PCT/US2017/027773 | 10/2018 |
| WO | 2018/204679 | 11/2018 |
| WO | PCT/US2016/039076 | 12/2018 |
| WO | PCT/US2018/030931 | 11/2019 |
| WO | 2020/023532 | 1/2020 |
| WO | 2020/041625 | 2/2020 |
| WO | 2021/222758 | 11/2021 |
| WO | 2021/247397 | 12/2021 |
| WO | 2022/093195 | 5/2022 |

OTHER PUBLICATIONS

U.S. Appl. No. 16/265,875, filed Feb. 1, 2019.
U.S. Appl. No. 17/177,140, filed Feb. 16, 2021.
U.S. Appl. No. 16/440,747, filed Jun. 13, 2019.
U.S. Appl. No. 16/779,369, filed Jan. 31, 2020.
U.S. Appl. No. 15/977,587, filed May 11, 2018.
U.S. Appl. No. 16/092,743, filed Apr. 14, 2017.
U.S. Appl. No. 16/077,713, filed Feb. 16, 2017.
U.S. Appl. No. 17/544,636, filed Dec. 7, 2021.
U.S. Appl. No. 17/262,684, filed Jan. 22, 2021, Jul. 23, 2019.
U.S. Appl. No. 17/209,554, filed Mar. 23, 2021.
U.S. Appl. No. 17/089,999, filed Nov. 5, 2020.
U.S. Appl. No. 16/610,473, filed May 3, 2018.
U.S. Appl. No. 16/383,348, filed Apr. 12, 2019.
U.S. Appl. No. 17/268,413, filed Aug. 22, 2019.
Jun. 14, 2012, U.S. Appl. No. 12/994,421.
Jul. 2, 2012, U.S. Appl. No. 12/951,768.
Mar. 30, 2012, U.S. Appl. No. 12/951,768.
Jul. 20, 2012, U.S. Appl. No. 12/994,421.
Sep. 10, 2012, U.S. Appl. No. 12/994,421.
Nov. 5, 2012, U.S. Appl. No. 12/951,768.
Feb. 26, 2013, U.S. Appl. No. 12/994,421.
Mar. 21, 2013, U.S. Appl. No. 12/951,768.
Mar. 27, 2013, U.S. Appl. No. 12/951,768.
May 21, 2013, U.S. Appl. No. 12/994,421.
Jul. 18, 2013, U.S. Appl. No. 12/994,421.
Jul. 29, 2013, U.S. Appl. No. 12/951,768.
Nov. 15, 2013, U.S. Appl. No. 12/951,768.
Dec. 20, 2013, U.S. Appl. No. 12/951,768.
Sep. 3, 2014, U.S. Appl. No. 13/332,976.
Sep. 9, 2014, U.S. Appl. No. 14/247,081.
Nov. 18, 2014, U.S. Appl. No. 13/332,976.
Nov. 18, 2014, U.S. Appl. No. 12/994,421.
Jan. 13, 2015, U.S. Appl. No. 14/247,081.
Feb. 2, 2015, U.S. Appl. No. 14/247,081.
Mar. 13, 2015, U.S. Appl. No. 12/994,421.
Mar. 13, 2015, U.S. Appl. No. 13/332,976.
Mar. 27, 2015, U.S. Appl. No. 12/994,421.
Apr. 1, 2015, U.S. Appl. No. 13/332,976.
Apr. 23, 2015, U.S. Appl. No. 13/332,976.
May 1, 2015, U.S. Appl. No. 13/332,976.
May 6, 2015 U.S. Appl. No. 14/247,081.
Jun. 11, 2015, U.S. Appl. No. 13/332,976.
Jul. 10, 2015, U.S. Appl. No. 14/247,081.
Jul. 21, 2015, U.S. Appl. No. 14/278,081.
Sep. 10, 2015, U.S. Appl. No. 13/876,157.
Sep. 2, 2015, U.S. Appl. No. 12/994,421.
Jan. 19, 2016, U.S. Appl. No. 12/994,421.
Mar. 30, 2016, U.S. Appl. No. 13/876,157.
Oct. 17, 2016, U.S. Appl. No. 13/876,157.
Sep. 22, 2016, U.S. Appl. No. 14/974,095.
Jan. 5, 2017, U.S. Appl. No. 13/876,157.
Feb. 13, 2017, U.S. Appl. No. 14/974,095.
Jun. 13, 2017, U.S. Appl. No. 14/974,561.
Jun. 27, 2017, U.S. Appl. No. 14/974,095.
Sep. 22, 2017, U.S. Appl. No. 14/974,095.
Nov. 15, 2017, U.S. Appl. No. 14/974,561.
Nov. 30, 2017, U.S. Appl. No. 14/932,200.
Jan. 11, 2018, U.S. Appl. No. 14/974,095.
Jan. 30, 2018, U.S. Appl. No. 14/974,095.
Feb. 8, 2018, U.S. Appl. No. 14/974,561.
Feb. 21, 2018, U.S. Appl. No. 14/932,200.
May 11, 2018, U.S. Appl. No. 14/974,095.
May 14, 2018, U.S. Appl. No. 14/920,737.
May 21, 2018, U.S. Appl. No. 15/511,731.
May 21, 2018, U.S. Appl. No. 15/489,624.
May 29, 2018, U.S. Appl. No. 14/974,561.
Sep. 5, 2018, U.S. Appl. No. 14/932,200.
Sep. 12, 2018, U.S. Appl. No. 14/920,737.
Sep. 25, 2018, U.S. Appl. No. 14/974,561.
Oct. 23, 2018, U.S. Appl. No. 15/489,624.
Nov. 15, 2018, U.S. Appl. No. 15/511,731.
Nov. 28, 2018, U.S. Appl. No. 15/720,912.
Dec. 13, 2018, U.S. Appl. No. 14/932,200.
Jan. 23, 2019, U.S. Appl. No. 15/489,624.
Feb. 4, 2019, U.S. Appl. No. 15/863,811.
Feb. 6, 2019, U.S. Appl. No. 14/974,561.
Feb. 11, 2019, U.S. Appl. No. 15/863,784.
Feb. 14, 2019, U.S. Appl. No. 15/511,731.
Mar. 4, 2019, U.S. Appl. No. 14/920,737.
Mar. 12, 2019, U.S. Appl. No. 14/974,561.
Mar. 26, 2019, U.S. Appl. No. 15/720,912.
Apr. 10, 2019, U.S. Appl. No. 15/863,741.
Mar. 20, 2019, U.S. Appl. No. 15/863,828.
Jun. 7, 2019, U.S. Appl. No. 14/932,200.

(56) References Cited

OTHER PUBLICATIONS

Aug. 15, 2019, U.S. Appl. No. 14/920,737.
Jun. 27, 2019, U.S. Appl. No. 15/511,731.
Sep. 25, 2019, U.S. Appl. No. 15/863,811.
Sep. 30, 2019, U.S. Appl. No. 15/863,784.
Oct. 7, 2019, U.S. Appl. No. 15/863,828.
Oct. 11, 2019, U.S. Appl. No. 15/953,244.
Oct. 11, 2019, U.S. Appl. No. 15/768,425.
Oct. 15, 2019, U.S. Appl. No. 16/092,743.
Oct. 21, 2019, U.S. Appl. No. 15/511,731.
Oct. 30, 2019, U.S. Appl. No. 15/720,912.
Nov. 1, 2019, U.S. Appl. No. 15/863,811.
Nov. 20, 2019, U.S. Appl. No. 14/932,200.
Nov. 21, 2019, U.S. Appl. No. 15/863,784.
Dec. 5, 2019, U.S. Appl. No. 15/863,741.
Dec. 11, 2019, U.S. Appl. No. 15/977,587.
Dec. 20, 2019, U.S. Appl. No. 15/863,828.
Jan. 13, 2020, U.S. Appl. No. 14/920,737.
Jan. 27, 2020, U.S. Appl. No. 15/511,731.
Feb. 13, 2020, U.S. Appl. No. 15/863,741.
Feb. 7, 2020, U.S. Appl. No. 15/863,784.
Feb. 11, 2020, U.S. Appl. No. 15/863,181.
Mar. 17, 2020, U.S. Appl. No. 15/768,425.
Mar. 20, 2020, U.S. Appl. No. 15/953,244.
Mar. 31, 2020, U.S. Appl. No. 14/920,737.
Mar. 18, 2020, U.S. Appl. No. 16/092,743.
Apr. 16, 2020, U.S. Appl. No. 15/863,828.
Apr. 20, 2020, U.S. Appl. No. 15/863,741.
May 18, 2020, U.S. Appl. No. 15/720,912.
May 19, 2020, U.S. Appl. No. 14/932,200.
May 28, 2020, U.S. Appl. No. 15/977,587.
Jun. 2, 2020, U.S. Appl. No. 16/077,713.
Jun. 18, 2020, U.S. Appl. No. 15/863,784.
Jun. 23, 2020, U.S. Appl. No. 14/920,737.
Jul. 23, 2020, U.S. Appl. No. 15/720,912.
Jul. 24, 2020, U.S. Appl. No. 15/863,784.
Jul. 20, 2020, U.S. Appl. No. 15/863,811.
Aug. 4, 2020, U.S. Appl. No. 14/920,737.
Aug. 6, 2020, U.S. Appl. No. 15/953,244.
Aug. 12, 2020, U.S. Appl. No. 16/077,713.
Aug. 26, 2020, U.S. Appl. No. 15/768,425.
Sep. 9, 2020, U.S. Appl. No. 16/440,747.
Sep. 16, 2020, U.S. Appl. No. 15/863,784.
Sep. 16, 2020, U.S. Appl. No. 15/953,244.
Sep. 29, 2020, U.S. Appl. No. 15/768,425.
Sep. 29, 2020, U.S. Appl. No. 15/863,811.
Sep. 17, 2020, U.S. Appl. No. 15/863,828.
Oct. 13, 2020, U.S. Appl. No. 15/863,741.
Oct. 21, 2020, U.S. Appl. No. 16/311,149.
Oct. 22, 2020, U.S. Appl. No. 15/863,811.
Oct. 27, 2020, U.S. Appl. No. 15/863,828.
Oct. 27, 2020, U.S. Appl. No. 15/863,741.
Nov. 5, 2020, U.S. Appl. No. 15/863,741.
Nov. 6, 2020, U.S. Appl. No. 16/092,743.
Nov. 12, 2020, U.S. Appl. No. 15/953,244.
Nov. 9, 2020, U.S. Appl. No. 14/920,737.
Nov. 19, 2020, U.S. Appl. No. 16/228,293.
Nov. 24, 2020, U.S. Appl. No. 15/768,425.
Dec. 3, 2020, U.S. Appl. No. 15/863,784.
Dec. 9, 2020, U.S. Appl. No. 15/768,425.
Dec. 17, 2020, U.S. Appl. No. 15/863,741.
Dec. 17, 2020, U.S. Appl. No. 15/863,784.
Dec. 17, 2020, U.S. Appl. No. 15/863,828.
Jan. 13, 2021, U.S. Appl. No. 15/863,741.
Jan. 6, 2021, U.S. Appl. No. 15/720,912.
Jan. 29, 2021, U.S. Appl. No. 16/092,743.
Jan. 28, 2021, U.S. Appl. No. 14/920,737.
Feb. 3, 2021, U.S. Appl. No. 15/977,587.
Feb. 10, 2021, U.S. Appl. No. 14/920,737.
Feb. 23, 2021, U.S. Appl. No. 16/077,713.
Mar. 12, 2021, U.S. Appl. No. 15/863,784.
Mar. 15, 2021, U.S. Appl. No. 16/311,149.
Mar. 25, 2021, U.S. Appl. No. 15/863,784.
Apr. 1, 2021, U.S. Appl. No. 16/228,293.
Jun. 17, 2021, U.S. Appl. No. 16/311,149.
Jun. 29, 2021, U.S. Appl. No. 151720,912.
Jul. 7, 2021, U.S. Appl. No. 15/720,912.
Aug. 6, 2021, U.S. Appl. No. 16/077,713.
Aug. 12, 2021, U.S. Appl. No. 15/977,587.
Aug. 30, 2021, U.S. Appl. No. 16/077,713.
Sep. 24, 2021, U.S. Appl. No. 16/311,149.
Oct. 7, 2021, U.S. Appl. No. 16/228,293.
Oct. 20, 2021, U.S. Appl. No. 15/977,587.
Oct. 28, 2021, U.S. Appl. No. 16/077,713.
Oct. 26, 2021, U.S. Appl. No. 15/720,912.
Oct. 28, 2021, U.S. Appl. No. 16/440,747.
Nov. 15, 2021, U.S. Appl. No. 17/089,999.
Nov. 18, 2021, U.S. Appl. No. 16/311,149.
Dec. 8, 2021, U.S. Appl. No. 16/092,743.
Dec. 16, 2021, U.S. Appl. No. 16/383,348.
Dec. 17, 2021, U.S. Appl. No. 15/720,912.
Jan. 12, 2022, U.S. Appl. No. 16/228,293.
Jan. 18, 2022, U.S. Appl. No. 17/089,999.
Feb. 1, 2022, U.S. Appl. No. 15/720,912.
Feb. 28, 2022, U.S. Appl. No. 16/228,293.
International Search Report dated Jul. 21, 2009 for PCT application No. PCT/US2009/44951.
Lindsey, J.B. et al., "Receptor for advanced glycation end-products (RAGE) and soluble RAGE (sRAGE): Cardiovascular implications", Diabetes Vascular Disease Research, vol. 6, No. 1, pp. 7-14, (2009).
Ando, K. et al., "Membrane proteins of human erythrocytes are modified by advanced glycation end products during aging in the circulation", Biochemical and Biophysical Research Communications, vol. 258, pp. 123-127, (1999).
Jandeleit-Dahm, K. et al., "The AGE/RAGE axis in diabetes-accelerated atherosclerosis", Clinical and Experimental Pharmacology and Physiology, vol. 35, pp. 329-334, (2008).
Sakata, N. et al., "Immunohistochemical localization of different epitopes of advanced glycation end products in human atherosclerotic lesions", Atherosclerosis, vol. 141, pp. 61-75, (1998).
Karachalias, N. et al., "Accumulation of fructosyl-lysine and advanced glycation end products in the kidney, retina and peripheral nerve of streptozotocin-induced diabetic rats", Biochemical Society Transactions, vol. 31, pp. 1423-1425, (2003).
Aroian, R. et al., "Pore-forming toxins and cellular non-immune defenses (CNIDs)", Current Opinion in Microbiology, vol. 10, pp. 57-61, (2007).
Dobson, J., "A twist on tumour targeting", Nature Materials, vol. 9, pp. 95-96, (2010).
Gutensohn, K. et al., "Extracorporeal plateletpheresis induces the interaction of activated platelets with white blood cells", Vox Sanguinis, vol. 78, No. 2, pp. 101-105, (2000).
Horiuchi, S. et al., "Immunochemical approach to characterize advanced glycation end products of the maillard reaction", The Journal of Biological Chemistry, vol. 266, No. 12, pp. 7329-7332, (1991).
Soetanto, K. et al., "Fundamental examination of cattle red blood cells damage with ultrasound exposure microscopic system (UEMS)", Japanese Journal of Applied Physics, vol. 37, part 1, No. 5B, pp. 3070-3073, (1998).
Harja, E. et al., "Vascular and inflammatory stresses mediate atherosclerosis via RAGE and its ligands in apoE-/- mice", The Journal of Clinical Investigation, vol. 118, No. 1, pp. 183-194, (2008).
Carstensen, E.L. et al., "Lysis of erythrocytes by exposure to cw ultrasound", Ultrasound in Medicine and Biology, vol. 19, No. 2, pp. 147-165, (1993).
Miller, M.W. et al., "Comparative sensitivity of human erythrocytes and lymphocytes to sonolysis by 1-MHz ultrasound", Ultrasound in Medicine and Biology, vol. 23, No. 4, pp. 635-638, (1997).

(56) References Cited

OTHER PUBLICATIONS

Iwata, H. et al., "Effect of carbonyl compounds on red blood cells deformability", Biochemical and Biophysical Research Communications vol. 321, pp. 700-706, (2004).
Schmitt, A. et al., "The binding of advanced glycation end products to cell surfaces can be measured using bead-reconstituted cellular membrane proteins", Biochimica et Biophysica Acta, vol. 1768, pp. 1389-1399, (2007).
Self-Medlin, Y. et al., "Glucose promotes membrane cholesterol crystalline domain formation by lipid peroxidation", Biochimica et Biophysica Acta, vol. 1788, pp. 1398-1403, (2009).
Singh, N. et al., "The PPAR-γ activator, rosiglitazone, inhibits actin polymerisation in monocytes: involvement of Aktand intracellular calcium", Biochemical and Biophysical Research Communications, vol. 333, pp. 455-462, (2005).
Li, Y-M. et al., "Effects of high glucose on mesenchymal stem cell proliferation and differentiation", Biochemical and Biophysical Research Communications, vol. 363, pp. 209-215, (2007).
Takata, K. et al., "Endocytic uptake of nonenzymatically glycosylated proteins is mediated by a scavenger receptor for aldehyde-modified proteins", The Journal of Biological Chemistry, vol. 263, No. 29, pp. 14819-14825, (1988).
Mi, Y. et al., "Apoptosis in leukemia cells is accompanied by alterations in the levels and localization of nucleolin", Journal of Biological Chemistry, vol. 278, pp. 8572-8579, (2003).
Christian, S. et al., "Nucleolin expressed at the cell surface is a marker of endothelial cells in angiogenic blood vessels", Journal of Cell Biology, vol. 163, No. 4, pp. 871-878, (2003).
Loo, T.W. et al., "Identification of residues in the drug translocation pathway of the human multidrug resistance P-glycoprotein by arginine mutagenesis", Journal of Biological Chemistry, vol. 284, No. 36, pp. 24074-24087, (2009).
Brundin, P. et al., "Prion-like transmission of protein aggregates in neurodegenerative diseases", Nature Reviews Molecular Cell Biology, vol. 11, No. 4, pp. 301-307, (2010).
Perez, C. et al., "Translational control of the abundance of cytoplasmic poly(A) binding protein in human cytomegalovirus-infected cells", Journal of Virology, vol. 85, No. 1, pp. 156-164, (2011).
Persson, J. et al., "Interleukin-1beta and tumour necrosis factor-alpha impede neutral lipid turnover in macrophage-derived foam cells", BMC Immunology, vol. 9, No. 70, pp. 1-11, (2008).
Vergne, I. et al., "Cell biology of mycobacterium tuberculosis phagosome", Annu. Rev. Cell Dev. Biology, vol. 20, pp. 367-394, (2004).
Moskowitz, S.M. et al., "The role of *pseudomonas* lipopolysaccharide in cystic fibrosis airway Infection", Subcell Biochemistry, vol. 53, pp. 241-253, (2010).
Hall-Stoodley, L. et al., "Direct detection of bacterial biofilms on the middle-ear mucosa of children with chronic otitis media", JAMA, vol. 296, No. 2, pp. 202-211, (2006).
Franke-Fayard, B. et al., "Sequestration and tissue accumulation of human malaria parasites: Can we learn anything from rodent models of malaria?", PLoS Pathogens, vol. 6, issue 9, pp. 1-10, e1001032, (2010).
Zhang, S. et al., "Delineation of diverse macrophage activation programs in response to intracellular parasites and cytokines", PLoS Neglected Tropical Diseases, vol. 4, No. 3, e648 (2010).
Ma, Y. et al., "NS3 helicase domains involved in infectious intracellular hepatitis C virus particle assembly", Journal of Virology, vol. 82, No. 15, pp. 7624-7639, (2008).
Korant, B.D. et al., "Inhibition by zinc of rhinovirus protein cleavage: interaction of zinc with capsid polypeptides", Journal of Virology, vol. 18, No. 1, pp. 298-306, (1976).
Ameli, S. et al., "Effect of immunization with homologous LDL and oxidized LDL on early atherosclerosis in hypercholesterolemia rabbits", Arteriosclerosis, Thrombosis, and Vascular Biology, vol. 16, pp. 1074-1079, (1996).
Nilsson, J. et al., "Inflammation and immunity in diabetic vascular complications", Current Opinion in Lipidology, vol. 19, issue 5, pp. 519-524, (2008).
Schiopu, A. et al., "Recombinant antibodies to an oxidized low-density lipoprotein epitope induce rapid regression of atherosclerosis in apobec-1$^{-/-}$/low-density lipoprotein receptor$^{-/-}$-mice", Journal of the American College of Cardiology, vol. 50, No. 24, pp. 2313-2318, (2007).
Schiopu, A. et al., "Recombinant human antibodies against aldehyde-modified apolipoprotein B-100 peptide sequences inhibit atherosclerosis", Circulation, vol. 110, pp. 2047-2052, (2004).
Bassirat, M. et al., "Short- and long-term modulation of microvascular responses in streptozotocin-induced diabetic rats by glycosylated products", Journal of Diabetes and its Complications, vol. 24, pp. 64-72, (2010).
Ge, J. et al., "Advanced glycosylation end products might promote atherosclerosis through inducing the immune maturation of dendritic cells", Arteriosclerosis, Thrombosis, and Vascular Biology, vol. 25, pp. 2157-2163, (2005).
Gugliucci, A. et al., "Circulating advanced glycation peptides in streptozotocin-induced diabetic rats: evidence for preferential modification of IgG light chains", Life Sciences, vol. 62, No. 23, pp. 2141-2150, (1998).
Pullerits, R. et al., "Synovial fluid expression of autoantibodies specific for RAGE relates to less erosive course of rheumatoid arthritis", Rheumatology, vol. 46, pp. 1367-1371, (2007).
Bro, S. et al., "A neutralizing antibody against receptor for advanced glycation end products (RAGE) reduces atherosclerosis in uremic mice", Atherosclerosis, vol. 201, pp. 274-280, (2008).
Turk, Z. et al., "Detection of autoantibodies against advanced glycation endproducts and AGE-immune complexes in serum of patients with diabetes mellitus", Clinica Chimica Acta, vol. 303, pp. 105-115, (2001).
Li, M. et al., "Glycan changes: cancer metastasis and anti-cancer vaccines", Journal of Biosciences, vol. 35, No. 4, pp. 665-673, (2010).
Kyte, J.A. et al., "Third international conference on cancer vaccines/adjuvants/delivery for the next decade (CVADD 2009)", Expert Reviews Vaccines, vol. 9, No. 2, pp. 119-123, (2010).
Akbulut, H. et al., "Chemotherapy targeted to cancer tissue potentiates antigen-specific immune response induced by vaccine for in vivo antigen loading and activation of dendritic cells", Molecular Therapy, vol. 16, No. 10, pp. 1753-1760, (2008).
Li, Y.M. et al., "Glycation products in aged thioglycollate medium enhance the elicitation of peritoneal macrophages", Jounal of Immunological Methods, vol. 201, issue 2, pp. 183-188, (1997).
Poggioli, S. et al., "Age-related increase of protein glycation in peripheral blood lymphocytes is restricted to preferential target proteins", Experimental Gerontology, vol. 37, issue 10-11, pp. 1207-1215, (2002).
Poggioli, S. et al., "Evidence of preferential protein targets for age-related modifications in peripheral blood lymphocytes", Annals of the New York Academy of Sciences, vol. 1019, issue 1, pp. 211-214, (2004).
Dominaitiene, R. et al., "Effects of differently oxidized LDL on the expression of pro-inflammatory molecules in human monocytes in vitro", In Vitro and Molecular Toxicology, vol. 14, No. 2, pp. 83-97, (2001).
Jiang, Z-H. et al., "Synthetic vaccines: the role of adjuvants in immune targeting", Current Medicinal Chemistry, vol. 10, No. 15, pp. 1423-1439, (2003).
Buskas, T. et al., "Immunotherapy for cancer: Synthetic carbohydrate-based vaccines", Chemical Communications, Issue 36, pp. 5335-5349, (2009).
Cohen, M.P. et al., "Amelioration of diabetic nephropathy by treatment with monoclonal antibodies against glycated albumin", Kidney International, vol. 45, pp. 1673-1679, (1994).
Davis, P.J. et al., "How can thermal processing modify the antigenicity of proteins?", Allergy, vol. 56, supplemental 67, pp. 56-60, (2001).
Koga, M. et al. "Clinical impact of glycated albumin as another glycemic control marker", Endocrine Journal, vol. 57, No. 9, pp. 751-762, (2010).

(56) References Cited

OTHER PUBLICATIONS

Shcheglova, T. et al., "Reactive immunization suppresses advanced glycation and mitigates diabetic nephropathy", Journal of the American Society of Nephrology, vol. 20, No. 5, pp. 1012-1019, (2009).
Virella, G. et al., "Autoimmune response to advanced glycosylation end-products of human LDL", Journal of Lipid Research, vol. 44, pp. 487-493, (2003).
Ihssen, J. et al., "Production of glycoprotein vaccines in *Escherichia coli*", Microbial Cell Factories, vol. 9, No. 61, pp. 1-13, (2010).
Habets, K.L.L. et al., "Vaccination using oxidized low-density lipoprotein-pulsed dendritic cells reduces atherosclerosis in LDL receptor-deficient mice", Cardiovascular Research, vol. 85, pp. 622-630, (2010).
Mironova, R. et al., "Glycation and post-translational processing of human interferon-γ expressed in *Escherichia coli*", The Journal of Biological Chemistry, vol. 278, No. 51, pp. 51068-51074, (2003).
Vogel, F.R. et al., "A compendium of vaccine adjuvants and excipients", Pharmaceutical Biotechnology, vol. 6, pp. 141-228, (1995).
Monograph series, World Health Organization, "Methods of Vaccine Production", part 4, chapters 18-29, pp. 189-267, (1973).
Cohen, M.P. et al., "Prevention of diabetic nephropathy in db/db mice with glycated albumin antagonists: A novel treatment strategy", The Journal of Clinical Investigation, vol. 95, pp. 2338-2345, (1995).
Naka, Y. et al., "RAGE Axis, Animal models and novel insights into the vascular complications of diabetes", Arteriosclerosis, Thrombosis, and Vascular Biology, vol. 24, pp. 1342-1349, (2004).
European Search Report dated Nov. 8, 2011 for PCT application No. PCT/US2009/044951.
Bierhaus, A. et al., "AGEs and their interaction with AGE-receptors in vascular disease and diabetes mellitus. I. the AGE concept", Cardiovascular Research, vol. 37, No. 3, pp. 586-600, (1998).
Murphy, J.F. "Trends in cancer immunotherapy", Clinical Medicine Insights: Oncology, vol. 4, pp. 67-80, (2010).
Beier, K.C., "Master switches of T-cell activation and differentiation", European Respiratory Journal, vol. 29, pp. 804-812, (2007).
Schmidlin, H., "New insights in the regulation of human B cell differentiation", Trends in Immunology, vol. 30, No. 6, pp. 277-285, (2009).
Coler, R.N. et al., "Development and characterization of synthetic glucopyranosyl lipid adjuvant system as a vaccine adjuvant", PLoS One, vol. 6, No. 1, e16333, pp. 1-12, (2011).
Cheadle, E.J., "Bugs as drugs for cancer", Immunology, vol. 107, pp. 10-19, (2002).
The Pink Book, Epidemiology and Prevention of vaccine preventable diseases, 11$^{th}$ Ed., pp. B7-B13, (2009), Found at www.cdc.gov/vaccines/pubs/pinkbook/downloads/appendices/b/excipient-table-1.pdf.
The Pink Book, Epidemiology and Prevention of vaccine preventable diseases, 11$^{th}$ Ed., 4 pages, (2009), Found at www.cdc.gov/vaccines/pubs/pinkbook/downloads/appendices/b/excipient-table-2.pdf.
Book Reviews, International Microbiology, vol. 7, pp. 291-295, (2004).
"Glycation: How eating sugar causes wrinkles", www.brighthub.com/health/diet-nutrition/articles/18410.aspx, 1 page, published Oct. 8, 2009.
Ellis, G., "The myth of the glycemic index and its child: good carbs-bad carbs", Targeted Body Systems, www.targetedbodysystems.com/tag/low-carb-diet-plans/, pp. 1-5, published Feb. 16, 2009.
"Diabetic glycation and inflammation—what diabetes does to your coronary arteries", www.rebelheartsurgeon-antioxidants.net/diabetic-glycation.html, pp. 1-9, downloaded Aug. 17, 2010.
Dziarski, R., "Cell-bound albumin is the 70-kDa peptidoglycan-, lipopolysaccharide-, and lipoteichoic acid-binding protein on lymphocytes and macrophages", The Journal of Biological Chemistry, vol. 269, No. 32, pp. 20431-20436, (1994).

Peters Jr. T.,"5-Metabolism: Albumin in the body", All About Albumin Biochemistry, Genetics, and Medical Applications, Chapter 5, pp. 188-250, (1995).
Vlassara, H. et al., "High-affinity-receptor-mediated uptake and degradation of glucose-modified proteins: A potential mechanism for the removal of senescent macromolecules", Proceeding of the National Academy of Science, USA, Biochemistry, vol. 82, pp. 5588-5592, (1985).
Wade, N., "Purging cells in mice is found to combat aging ills", New York Times, found at NYTimes.com, pp. 1-3, (2011).
Roll, P. et al., "Anti-CD20 therapy in patients with rheumatoid arthritis", Arthritis & Rheumatism, vol. 58, No. 6, pp. 1566-1575, (2008).
Kajstura J. et al., "Myocyte turnover in the aging human heart", Circulation Research, vol. 107, pp. 1374-1386, (2010).
Baker, D.J. et al., "Clearance of p16Ink4a-positive senescent cells delays ageing-associated disorders", Nature, vol. 479, pp. 232-236, (2011).
Breyer, V. et al., "Intracellular glycation of nuclear DNA, mitochondrial DNA, and cytosolic proteins during senescence-like growth arrest", DNA Cell Biology, vol. 30, No. 9, pp. 681-689, (2011).
Ravelojaona, V. et al., "Expression of senescence-associated beta-galactosidase (SA-beta-Gal) by human skin fibroblasts, effect of advanced glycation end-products and fucose or rhamnose-rich polysaccharides", Archives of Gerontology and Geriatrics, vol. 48, issue 2, pp. 151-154, (2009).
International Search Report dated Apr. 26, 2012 for PCT application No. PCT/US2011/053399.
International Search Report dated Jun. 13, 2012 for PCT application No. PCT/US2011/061387.
Wautier, J.-L. et al., "Advanced glycation end products (AGEs) on the surface of diabetic erythrocytes bind to the vessel wall via a specific receptor inducing oxidant stress in the vasculature: A link between surface-associated AGEs and diabetic complications", Proc. Natl. Acad. Sci. USA, vol. 91, No. 16, pp. 7742-7746, (1994).
Siegel, R. J. et al., "Ultrasonic plaque ablation: A new method for recanalization of partially or totally occluded arteries", Circulation, vol. 78, No. 6, pp. 1443-1448, (1988).
International Search Report dated Jun. 27, 2012 for PCT application No. PCT/US2012/031446.
Immuno, Catalog No. 637061, 637062, "Mouse, anti-age (advanced glycation end products), monoclonal antibody", http://www.mpbio.com/detailed_info.php?family_key=0863706, 2 pages, accessed Jul. 26, 2012.
Ahmed, E. K. et al., "Protein modification and replicative senescence of WI-38 human embryonic fibroblasts", Aging Cell, vol. 9, pp. 252-272, (2010).
Vlassara, H. et al., "Advanced glycosylation endproducts on erythrocyte cell surface induce receptor-mediated phagocytosis by macrophages", J. Exp. Med., The Rockefeller University Press, vol. 166, pp. 539-549, (1987).
Yang, Z. et al., "Two novel rat liver membrane proteins that bind advanced glycosylation endproducts: Relationship to macrophage receptor for glucose-modified proteins", J. Exp. Med., The Rockefeller University Press, vol. 174, pp. 515-524, (1991).
Vlassara, H. et al., "Advanced glycation endproducts promote adhesion molecule (VCAM-1, ICAM-1) expression and atheroma formation in normal rabbits", Molecular Medicine, vol. 1, No. 4, pp. 447-456,(1995).
Vaysse, J. et al., "Adhesion and erythrophagocytosis of human senescent erythrocytes by autologous monocytes and their inhibition by β-galactosyl derivatives", Proc. Natl. Acad. Sci. USA, Cell Biology, vol. 83, pp. 1339-1343, (1986).
Li, Y. M et al.. "Prevention of cardiovascular and renal pathology of aging by the advanced glycation inhibitor aminoguanidine", Proc. Natl. Acad. Sci. USA, Medical Sciences, vol. 93, pp. 3902-3907, (1996).
Manesso, E. et al., "Dynamics of β-cell turnover: evidence for β-cell turnover and regeneration from sources of β-cells other than β-cell replication in the HIP rat", American Journal of Physiology—Endocrinology and Metabolism, vol. 297, pp. E323-E330, (2009).
Stepanov, A.V. et al., "Design of targeted B cell killing agents", PLoS ONE, vol. 6, issue 6, e20991, pp. 1-10, (2011).

(56) References Cited

OTHER PUBLICATIONS

Fact Sheet, "Targeted Cancer Therapies", www.cancer.gov/cancertopics/factsheet/Therapy/Fs7_49.pdf, pp. 1-8, (2012).
Kay, M.M. "Generation of senescent cell antigen on old cells initiates IgG binding to a neoantigen", Cellular and Molecular Biology (Noisy-le-Grand, France), vol. 39, No. 2, pp. 131-153, (1993), Abstract Only.
Cirocchi, R. et al., "Meta-analysis of thyroidectomy with ultrasonic dissector versus conventional clamp and tie", World Journal of Surgical Oncology, vol. 8, No. 112, pp. 1-7, (2010).
Lingeman, J.E. et al., "Current perspective on adverse effects in shock wave lithotripsy", White Paper, American Urological Association Education and Research, found at www.auanet.org/content/guidelines-and-quality-care/clinical-guidelines/main-reports/whitepaper.pdf, 17 pages, (2009).
De Groot, K. et al., "Vascular endothelial damage and repair in antineutrophil cytoplasmic antibody—associated vasculitis", Arthritis & Rheumatism, vol. 56, No. 11, pp. 3847-3853, (2007).
Imani, F. et al., "Advanced glycosylation endproduct-specific receptors on human and rat t-lymphocytes mediate synthesis of interferon γ: role in tissue remodeling", J. Exp. Med., vol. 178, pp. 2165-2172, (1993).
Kirstein, M. et al., "Receptor-specific induction of insulin-like growth factor I in human monocytes by advanced glycosylation end product-modified proteins", J. Clin. Invest., vol. 90, pp. 439-446, (1992).
Le Grand, F. et al., "Skeletal muscle satellite cells and adult myogenesis", Curr. Opin. Cell Biology, vol. 19, No. 6, pp. 628-633, (2007).
Sasaki, M. et al., "Mesenchymal stem cells are recruited into wounded skin and contribute to wound repair by transdifferentiation into multiple skin cell type". The Journal of Immunology, vol. 180, pp. 2581-2587, (2008).
Misur, I. et al., "Advanced glycation endproducts in peripheral nerve in type 2 diabetes with neuropathy", Acta Diabetol, vol. 41, pp. 158-166, (2004).
Saltykov, B.B., "Mechanisms of development of diabetic macroangiopathy", Arkh Patol., vol. 63, No. 2, pp. 21-26, (2001), Abstract Only.
Grossin, N. et al., "Red blood cell adhesion in diabetes mellitus is mediated by advanced glycation end product receptor and is modulated by nitric oxide", Biorheology, vol. 46, No. 1, pp. 63-72, (2009).
Liang, Y. et al., "Rituximab for children with immune thrombocytopenia: A systematic review", PLoS ONE, vol. 7, issue 1, pp. 1-11, (2012).
Fehrenbach, H. et al., "Up-regulated expression of the receptor for advanced glycation end products in cultured rat hepatic stellate cells during transdifferentiation to myofibroblasts", Hepatology, vol. 34, No. 5, pp. 943-952, (2001).
Agostini, A. et al., "Targeted cargo delivery in senescent cells using capped mesoporous silica nanoparticles", Angewandte Chemie International Edition, vol. 51, pp. 10556-10560, (2012).
Larson, R.A. et al., "Tumor lysis syndrome: Definition, pathogenesis, clinical manifestations, etiology and risk factors", found at www.uptodate.com/contents/tumor-lysis-syndrome-definition-pathogenesis-clinical-manifestations-etiology-and-risk-factors?detectedLanguage=en&source=search_result&search=tumor+lysis+syndrome&selectedTitle=2~69&provider=noProvider, pp. 1-4, printed on Jun. 11, 2013.
Hansel, T.T. et al., "The safety and side effects of monoclonal antibodies", Nature Reviews, vol. 9, pp. 325-337, (2010).
Nass, N. et al., "Advanced glycation end products, diabetes and ageing", Zeitschrift fur Gerontologie und Geriatrie, vol. 40, issue 5, pp. 349-356, (2007).
Wautier, J-L. et al., Protein Glycation: "A firm link to endothelial cell dysfunction", Circulation Research, Journal of the American Heart Association, vol. 95, pp. 233-238, (2004).
Meuter, A. et al., "Markers of cellular senescence are elevated in murine blastocysts cultured in vitro: molecular consequences of culture in atmospheric oxygen", Journal of Assisted Reproduction and Genetics, vol. 31, issue 10, pp. 1259-1267, (2014).
Freund, A. et al., "Inflammatory networks during cellular senescence: causes and consequences", Trends in Molecular Medicine, vol. 16, No. 5, pp. 238-246, (2010).
Hadrabová, J. et al., "Chicken immunoglobulins for prophylaxis: Effect of inhaled antibodies on inflammatory parameters in rat airways", Journal of Applied Biomedicine, 4 pages, Available online May 5, 2014.
Ferraccioli, G. et al., "Interleukin-1β and Interleukin-6 in arthritis animal models: Roles in the early phase of transition from acute to chronic inflammation and relevance for human rheumatoid arthritis", Molecular Medicine, vol. 16, issue 11-12, pp. 552-557, (2010).
Zhao, Y. et al., "The bovine antibody repertoire", Developmental & Comparative Immunology, vol. 30, issues 1-2, pp. 175-186, (2006).
Wagner, B. et al., "The complete map of the Ig heavy chain constant gene region reveals evidence for seven IgG isotypes and for IgD in the horse", Journal of Immunology, vol. 173, No. 5, pp. 3230-3242, (2004).
Strietzel, C.J. et al., "In vitro functional characterization of feline IgGs", Veterinary Immunology and Immunopathology, vol. 158, issues 3-4, pp. 214-223, (2014).
Patel, M. et al., "Sequence of the dog immunoglobulin alpha and epsilon constant region genes", Immunogenetics, vol. 41, issue 5, pp. 282-286, (1995).
Maass, D.R. et al., "Alpaca (*Lama pacos*) as a convenient source of recombinant camelid heavy chain antibodies (VHHs)", Journal of Immunology Methods, vol. 324, issues 1-2, pp. 13-25, (2007).
European Search Report dated Sep. 12, 2014 for EP application No. EP14170802.4-1408.
Fessler, J. et al., "Senescent T cells promote bone loss in rheumatoid arthritis", Abstracts of the American College of Rheumatology/Association of Rheumatology Health Professionals, Annual Scientific Meeting, Washington, DC, Nov. 9-14, 2012, Arthritis & Rheumatism, vol. 64, supplement 10, p. 2312, (2012) found at http://blackwellpublishing.com/acrmeeting/abstract.asp?MeetingID=789&id=103040.
Weyand, C.M. et al., Abstract of "T-cell aging in rheumatoid arthritis", Current Opinion in Rheumatology, vol. 26, No. 1, pp. 93-100, (2014) found at http://www.ncbi.nlm.nih.gov/rn/pubmed/24296720/.
Dvergsten, J. et al., "Prevalence of functionally active, senescent T cells in juvenile idiopathic arthritis", Abstracts of the American College of Rheumatology/Association of Rheumatology Health Professionals, Annual Scientific Meeting, Philadelphia, Oct. 16-21, 2009, Arthritis & Rheumatism, vol. 60, supplement 10, p. 1313, (2009), found at http://blackwellpublishing.com/acrmeeting/abstract.asp?MeetingID=761&id=80937.
Definition of "Dissociation constant" printed from Wikipedia, the free encyclopedia on Sep. 17, 2014 found at http://en.wikipedia.org/wiki/Dissociation_constant.
Sigma-Aldrich product specification of "Nα,Nα-Bis(carboxymethyl)-L-lysine trifluoroacetate salt ≥95% (TLC)", found at http://sigmaaldrich.com/catalog/product/sigma/c3205?lang=en&region=US, printed on Sep. 17, 2014.
"Pulmatrix demonstrates iSPERSE capabilities for inhaled dry powder delivery of antibiotics and antibodies", data presented at Respiratory Drug Delivery 2012, 3 pages, printed on Sep. 4, 2014, found at http://businesswire.com/news/home/20120515005279/en/Pulmatrix-Demonstrates-iSPERSE-Capabilities-Inhaled-Dry-Powder#.VEgU4hauNbs.
Chan, A.C. et al., "Therapeutic antibodies for autoimmunity and inflammation", Nature Reviews Immunology, vol. 10, pp. 301-316, (2010).
Pradat, P.F. et al., "Abnormalities of satellite cells function in amyotrophic lateral sclerosis", Amyotrophic Lateral Sclerosis, vol. 12, No. 4, pp. 264-271, (2011).
Tchkonia, T. et al., "Cellular senescence and the senescent secretory phenotype: therapeutic opportunities", The Journal of Clinical Investigation, vol. 123, No. 3, pp. 966-972, (2013).
Kitada, K. et al., "Aldosterone induces p21-regulated apoptosis via increased synthesis and secretion of tumour necrosis factor-α in

(56) References Cited

OTHER PUBLICATIONS human proximal tubular cells", Clinical and Experimental Pharmacology and Physiology, vol. 39, No. 10, pp. 858-863, (2012).
Definition of "TNF inhibitor", printed from Wikipedia, the free encyclopedia on Oct. 4, 2014, 4 pages, found at http://en.wikipedia.org/wiki/TNF_inhibitor?oldid=628250399.
Definition of "Etanercept", printed from Wikipedia, the free encyclopedia on Aug. 24, 2014, 6 pages, found at http://en.wikipedia.org/wiki/Etanercept?oldid=622648157.
AbbVie, Inc., "Humira adalimumab: Learn about Humira", found at https://www.humira.com/rheumatoid-arthritis, 7 pages, printed on Aug. 11, 2014.
AbbVie, Inc., "Medication Guide for Humira", found at https://www.humira.com/rheumatoid-arthritis, 9 pages, printed on Aug. 11, 2014.
AbbVie, Inc., "Humira: A biologic that targets and helps block TNF-alpha", found at https://www.humira.com/rheumatoid-arthritis/how-humira-works-for-ra, 8 pages, printed on Aug. 11, 2014.
AbbVie, Inc., "How Humira (adalimumab) works video transcript", found at https://www.humira.com/rheumatoid-arthritis/how-humira-works-video-transcript, 5 pages, printed on Aug. 11, 2014.
AbbVie, Inc., "Humira and methotrexate—a combination that has demonstrated results", found at https://www.humira.com/rheumatoid-arthritis/humira-and-methotrexate, 7 pages, printed on Aug. 11, 2014.
Madhur, M.S. et al., "Senescent T cells and hypertension: New ideas about old cells", Hypertension, vol. 62, pp. 13-15, (2013).
James, P.E. et al., "Vasorelaxation by red blood cells and impairment in diabetes: Reduced nitric oxide and oxygen delivery by glycated hemoglobin", Circulation Research, vol. 94, pp. 976-983, (2004).
Shibayama, R. et al., "Autoantibody against N(epsilon)-(carboxymethyl)lysine: an advanced glycation end product of the Maillard reaction", Diabetes, vol. 48, No. 9, pp. 1842-1849, (1999).
Bumol, T.F. et al., "Monoclonal antibody and an antibody-toxin conjugate to a cell surface proteoglycan of melanoma cells suppress in vivo tumor growth", Proceeding of the National Academy of Science, vol. 80, pp. 529-533, (1983).
"AGEs (all species) antibody—Product Details", Antibodies Online, 4 pages, found at www.web.archive.org/web/20081229071154/http://www.antibodies-online.com/antibody/289931/AGEs+All+Species/, printed on Dec. 10, 2014.
"Antibody Engineering", Fusion Antibodies, 2 pages, found at www.web.archive.org/web/20080628225818/http://www.fusionantibodies.com/index.cfm/area/information/page/engineering?, printed on Dec. 16, 2014.
Hargreaves, R.E.G. et al., "Selective depletion of activated T cells: the CD40L-specific antibody experience", Trends in Molecular Medicine, vol. 10, No. 3, pp. 130-135, (2004).
Leinenga, G. et al., "Scanning ultrasound removes amyloid-β and restores memory in an Alzheimer's disease mouse model", Science Translational Medicine, vol. 7, issue 278, pp. 1-11, (2015).
Peppa, M. et al., "Glucose, advanced glycation end products, and diabetes complications: What is new and what works", Clinical Diabetes, vol. 21, No. 4, pp. 186-187, (2003).
Lv, Y. et al., "Low-intensity ultrasound combined with 5-aminolevulinic acid administration in the treatment of human tongue squamous carcinoma", Cellular Physiology and Biochemistry, vol. 30, pp. 321-333, (2012).
Campisi, J. et al., "Cellular senescence: when bad things happen to good cells", Nature Reviews: Molecular Cell Biology, vol. 8, pp. 729-749, (2007).
"ALSUntangled No. 23: The Rife Machine and retroviruses", Amyotrophic Lateral Sclerosis and Frontotemporal Degeneration, vol. 15, pp. 157-159, (2014).
Roylance, D., "Mechanical properties of materials", pp. 1-128, (2008), available at www.web.mit.edu/course/3/3.225/book.pdf.
Vidarsson, G. et al., "IgG subclasses and allotypes: from structure to effector functions", Frontiers in Immunology, vol. 5, article 520, pp. 1-17, (2014).

Lin, H-T. et al., "Stem cell therapy: an exercise in patience and prudence", Philosophical Transactions of the Royal Society B: Biological Sciences 368, (2013).
Waldmann, T.A., "Immunotherapy:past, present and future", Nature Medicine, vol. 9, No. 3, pp. 269-277, (2003).
Okamoto, T. et al., "Advanced glycation end products induce angiogenesis in vivo", Microvascular Research, vol. 63, pp. 186-195, (2002).
Nagal, R. et al., "Application of monoclonal antibody libraries for the measurement of glycation adducts", Biochemical Society Transactions, vol. 31, part 6, pp. 1438-1440, (2003).
De Genst, E. et al., "Antibody repertoire development in camelids". Developmental and Comparative Immunology, vol. 30, pp. 187-198, (2006).
Griffin, L.M. et al., "Analysis of hevy and light chain sequences of conventional camelid antibodies from Camelus dromedarius and Camelus bactrianus species", Journal of Immunological Methods, vol. 405, pp. 35-46, (2014).
Hamers-Casterman, C. et al., "Naturally occurring antibodies devoid of light chains", Nature, vol. 363, pp. 446-448, (1993).
Muyldermans, S. et al., "Sequence and structure of $V_H$ domain from naturally occurring camel heavy chain immunoglobulins lacking light chains", Protein Engineering, vol. 7, No. 9, pp. 1129-1135, (1994).
Nguyen, V. K. et al., "Camel heavy-chain antibodies: diverse germline VHH and specific mechanisms enlarge the antigen-binding repertoire", The EMBO Journal, vol. 19, No. 5, pp. 921-930, (2000).
Kirstein, et al., "Advanced protein glycosylation induces transendothelial human monocyte chemotaxis and secretion of platelet-derived growth factor: roll in vascular disease of diabetes and aging", PNAS, vol. 87, No. 22, pp. 9010-9014, (1990).
Invitation to Pay Additional Fees and Partial International Search Report dated Jan. 13, 2016 for PCT application No. PCT/US2015/050154.
Feldmann, M. et al., "Anti-TNFalpha therapy of rheumatoid arthritis: What have we learned?", Annual Review of Immunology, vol. 19, pp. 163-196, (2001).
Drinda, S. et al., "Identification of the advanced glycation end products N-carboxymethyllysine in the synovial tissue of patients with rheumatoid arthritis", Annals of the Rheumatic Diseases, vol. 61, No. 6. pp. 488-492, (2002).
Ahmad, S. et al., "Preferential recognition of epitopes on AGE-IgG by the autoantibodies in rheumatoid arthritis patients", Human Immunology, vol. 74, No. 1, pp. 23-27, (2013).
Johns, L.D., "Nonthermal effects of therapeutic ultrasound: The frequency resonance hypothesis", Journal of Athletic Training, vol. 37, No. 3, pp. 293-299, (2002).
Wang, B-L. et al., "Identification of monoclonal antibody of advanced glycation end products", Chinese Journal of Arteriosclerosis, vol. 14, No. 5, pp. 409-412, (2006).
Wang, J.C. et al., "Aging and Atherosclerosis mechanisms, functional consequences, and potential therapeutics for cellular senescence", Circulation Research, vol. 111, pp. 245-259, (2012).
Minamino, T. et al., "Vascular cell senescence contribution to Atherosclerosis", Circulation Research, vol. 100, pp. 15-26, (2007).
Isoda, K. et al., "Glycated LDL increases monocyte CC chemokine receptor 2 expression and monocyte chemoattractant protein-1-mediated chemotaxis", Atherosclerosis, vol. 198, No. 2, pp. 307-312, (2008).
Roos, C.M. et al., "Chronic senolytic treatment alleviates established vasomotor dysfunction in aged or atherosclerotic mice", Aging Cell, 8 pages, (2016).
Hall, B.M. et al., "Aging of mice is associated with p16(Ink4a)- and β-galactosidase-positive macrophage accumulation that can be induced in young mice by senescent cells", Aging, vol. 8, No. 7, pp. 1-18, (2016).
Mera, K. et al., "An autoantibody against $N^\varepsilon$-(carboxyethyl)lysine (CEL): Possible involvement in the removal of CEL-modified proteins by macrophages", Biochemical and Biophysical Research Communications, vol. 407, pp. 420-425, (2011).

(56) References Cited

OTHER PUBLICATIONS

Reddy, S. et al., "N$^\varepsilon$-(Carboxymethyl)lysine is a dominant advanced glycation end product (AGE) antigen in tissue proteins", Biochemistry, vol. 34, pp. 10872-10878, (1995).
Katcher, H.L., "Studies that shed new light on aging", Biochemistry (Moscow), vol. 78, No. 9, pp. 1061-1070, (2013).
Naylor, R.M. et al., "Senescent Cells: A novel therapeutic target for aging and age-related diseases", Clinical Pharmacology & Therapeutics, vol. 93, No. 1, pp. 105-116, (2013).
Beaulieu, L-P. et al., "Inhibitory effect of the cree traditional medicine wiishichimanaanh (vaccinium vitis-idaea) on advanced glycation endproduct formation: identification of active principles", Phytotherapy Research, vol. 24, pp. 741-747, (2010).
Ulrich, P. et al., "Protein glycation, diabetes, and aging". Recent Progress in Hormone Research, vol. 56, pp. 1-21, (2000).
Van Heijst, J.W.J. et al., "Advanced glycation end products in human cancer tissues: detection of N$^\varepsilon$-(carboxymethyl)lysine and argpyrimidine", Annals of the New York Academy of Sciences, vol. 1043, pp. 725-733, (2005).
Fielding, R.A. et al., "Sarcopenia: An undiagnosed condition in older adults. Current consensus definition: Prevalence, etiology, and consequences", Journal of the American Medical Directors Association, vol. 12, No. 4, pp. 249-256, (2011).
Definition of "Sarcopenia", printed from Wikipedia, the free encyclopedia on Jul. 25, 2016, 5 pages, found at http://en.wikipedia.org/wiki/Sarcopenia.
"What is Sarcopenia?", International Osteoporosis Foundation, 2 pages, found at www.iofbonehealth.org/what-sarcopenia, (2014).
"Sarcopenia with aging", Webmd, 2 pages, found at www.webmd.com/healthy-aging/sarcopenia-with-aging, (2014).
Definition of "Keyhole limpet hemocyanin", printed from Wikipedia, the free encyclopedia on Jul. 25, 2016, 4 pages, found at https://en.wikipedia.org/wiki/Keyhole_limpet_hemocyanin.
Cell Biolabs, Inc., "CML-BSA Product Data Sheet", 3 pages, found at http://www.cellbiolabs.com/sites/default/files/STA-314-cml-bsa.pdf, (2010).
Cell Biolabs, Inc., "CML (N-epsilon-(Caboxymethyl)Lysine) Assays and Reagents", 1 page, found at http://www.cellbiolabs.com/cml-assays, (2014).
Cruz-Jentoft, A.J. et al., "Sarcopenia: European consensus on definition and diagnosis", Age and Ageing, vol. 39, pp. 412-423, (2010).
Rolland, Y. et al., "Sarcopenia: Its assessment, etiology, pathogenesis, consequences and future perspectives", The Journal of Nutrition, Health & Aging, vol. 12, No. 7, pp. 433-450, (2008).
Centers for Disease Control and Prevention, "Vaccine excipient and media summary", 4 pages, found at www.cdc.gov/vaccines/pubs/pinkbook/downloads/appendices/B/excipient-table-2.pdf?utm_content=buffer4538f&utm_medium=social&utm_source=linkedin.com&utm_campaign=buffer, (2015).
Definition of "N(6)-Carboxymethyllysine", printed from Wikipedia, the free encyclopedia on Dec. 8, 2013, 1 page, found at http://en.wikipedia.org/wiki/N(6)-Carboxymethyllysine.
Definition of "Lysine", printed from Wikipedia, the free encyclopedia on Dec. 8, 2013, 1 page, found at http://en.wikipedia.org/wiki/Lysine.
Jarvis, L.M., "Rethinking antibody-drug conjugates", Chemical & Engineering News, vol. 90, issue 25, pp. 12-18, (2012).
Mullin, R., "Cell-free approach to antibody-drug conjugates", Chemical & Engineering News, vol. 91, issue 44, 2 pages, (2013).
Thayer, A.M., "Building antibody-drug conjugates", Chemical & Engineering News, vol. 92, issue 3, pp. 13-21, (2014).
Feige, M.J. et al., "The structural analysis of shark IgNAR antibodies reveals evolutionary principles of immunoglobulins", Proceedings of the National Academy of Sciences, vol. 111, No. 22, pp. 8155-8160, (2014).
Philipot, D. et al., "p16$^{INK4a}$ and its regulator miR-24 link senescence and chondrocyte terminal differentiation-associated matrix remodeling in osteoarthritis", Arthritis Research & Therapy, vol. 16, No. 1, pp. 1-12, (2014).
International Search Report and Written Opinion dated Mar. 31, 2016 for PCT application No. PCT/US2015/050154.
Zhu, Y. et al., "The achilles' heel of senescent cells: from transcriptome to senolytic drugs", Aging Cell, vol. 14, pp. 644-658, (2015).
Zhu, L. et al., "Immunization with advanced glycation end products modified low density lipoprotein inhibits atherosclerosis progression in diabetic apoE and LDLR null mice", Cardiovascular Diabetology, vol. 13, No. 151, pp. 1-12, (2014).
DeNardo, S.J. et al., "Development of tumor targeting bioprobes ($^{111}$in-chimeric L6 monoclonal antibody nanoparticles) for alternating magnetic field cancer therapy", Clinical Cancer Research, vol. 11, 19 supplemental, pp. 7087s-7092s, (2005).
Chen, L. et al., "Cytolysis of human erythrocytes by a covalent antibody-selenium immunoconjugate", Free Radical Biology & Medicine, vol. 19, No. 6, pp. 713-724, (1995).
Yuan, Y. et al., "Advanced glycation end products (AGEs) increase human mesangial foam cell formation by increasing Golgi SCAP glycosylation in vitro", American Journal of Physiology—Renal Physiology, vol. 301.1, pp. F236-F243, (2011).
Hashimoto, M. et al., "Elimination of p19$^{ARF}$-expressing cells enhances pulmonary function in mice", JCI Insight, vol. 1, No. 12, pp. 1-15, (2016).
Yan, S.F. et al., "Soluble RAGE: Therapy & biomarker in unraveling the RAGE axis in chronic disease and aging", Biochemical Pharmacology, vol. 79, No. 10, pp. 1379-1386, (2010).
Xue, J. et al., "Advanced glycation end product (AGE) recognition by the receptor for AGEs (RAGE)", Structure, vol. 19, No. 5, pp. 722-732, (2011).
Chang, J. et al., "Clearance of senescent cells by ABT263 rejuvenates aged hematopoietic stem cells in mice", Nature Medicine, vol. 22, No. 1, pp. 78-83, (2016).
Geiger, H., "Depleting senescent cells to combat aging", Nature Medicine, vol. 22, No. 1, pp. 23-24, (2016).
Ni, J. et al., "Plasma protein pentosidine and carboxymethyllysine, biomarkers for age-related macular degeneration", Molecular & Cellular Proteomics, vol. 8, No. 8, pp. 1921-1933, (2009).
R&D Systems, a biotechne brand, product specification of "Carboxymethyl Lysine Antibody", found at https://www.rndsystems.com/products/carboxymethyl-lysine-antibody-318003_mab3247, 1 page, (2015).
Schalkwijk, C.G. et al., "Increased accumulation of the glycoxidation product N$^\varepsilon$-(carboxymethyl)lysine in hearts of diabetic patients: generation and characterization of a monoclonal anti-CML antibody", Biochimica et Biophysica Acta (BBA)—Molecular and Cell Biology of Lipids, vol. 1636, No. 2, pp. 82-89, (2004).
LaPak, K.M. et al., "The molecular balancing act of p16$^{INK4a}$ in cancer and aging", Molecular Cancer Research, vol. 12, No. 2, pp. 167-183, (2013).
Larsen, S.A. et al., "Glucose metabolite glyoxal induces senescence in telomerase-immortalized human mesenchymal stem cells", Chemistry Central Journal, vol. 6, No. 18, pp. 1-13, (2012).
Ahmed, M.U. et al., "N$^\varepsilon$-(carboxymethyl)lysine, a product of the chemical modification of proteins by methylglyoxal, increases with age in human lens proteins", Biochemical Journal, vol. 324, pp. 565-570, (1997).
Dunn, J.A. et al., "Age-dependent accumulation of N$^\varepsilon$-(Carboxymethyl)lysine and N$^\varepsilon$-(Carboxymethyl)hydroxylysine in human skin collagen", Biochemistry, vol. 30, pp. 1205-1210, (1991).
Finco, A.B. et al., "Generation and characterization of monoclonal antibody against advanced glycation end products in chronic kidney disease", Biochemistry and Biophysics Reports, vol. 6, pp. 142-148, (2016).
International Search Report and Written Opinion dated Aug. 10, 2016 for PCT application No. PCT/US2016/034880.
Liu, H. et al., "Abstract 154: Vaccination using advanced glycation end product of low-density lipoprotein pulsed dendritic cells reduces atherosclerosis in diabetic apoe$^{-/-}$ mice", Arteriosclerosis, Thrombosis, and Vascular Biology, pp. 1-4, (2012).
Mashitah, M.W. et al., "Immunization of AGE-modified albumin inhibits diabetic nephropathy progression in diabetic mice", Diabetes, Metabolic Syndrome and Obesity: Targets and Therapy, vol. 8, pp. 347-355, (2015).

(56) References Cited

OTHER PUBLICATIONS

Sayej, W.N. et al., "Advanced glycation end products induce obesity and hepatosteatosis in CD-1 wild-type mice", BioMed Research International, vol. 6, No. 39, pp. 1-12, (2016).

Srikanth, V. et al., "Advanced glycation endproducts and their receptor RAGE in alzheimer's disease", Neurobiology of Aging, vol. 32. No. 5, pp. 763-777, (2011).

International Search Report and Written Opinion dated Dec. 2, 2016 for PCT application No. PCT/US2016/039076.

Fu, M-X. et al., "The advanced glycation end product, N-(Carboxymethyl)lysine, is a product of both lipid peroxidation and glycoxidation reactions", The Journal of Biological Chemistry, vol. 271, No. 17, pp. 9982-9986, (1996).

Jorgensen, L. et al., "The relationship between atherosclerosis of the thoracic aorta and renal scarring in an autopsy material", Acta Pathol Microbiol Immunol Scand A., vol. 93, No. 5, pp. 251-255, (1985) Abstract Only.

"Senescent cells drive plaque formation in animal models of atherosclerosis, research shows", Mayo Clinic, pp. 1-2, (2016), found at www.news-medical.net/news/20161027/Senescent-cells-drive-plaque-formation-in-animal-models-of-atherosclerosis-research-shows.aspx.

Baker, D.J. et al., "Naturally occurring p16$^{ink4a}$-positive cells shorten healthy lifespan", Nature, vol. 530, issue 7589, pp. 184-189, (2016).

Raquib, R., "The key to youth via senescent cell removal", Young Investigators Review, pp. 1-4, (2017), found at sbyireview.com/2017/01/23/the-key-to-youth-via-senescent-cell-removal.

Tiner, S., "Mayo clinic research links senescent cells and atherosclerosis progression", Mayo Clinic News Network, pp. 1-3, (2016), found at newsnetwork.mayoclinic.org/discussion/mayo-clinic-research-links-senescent-cells-and-atherosclerosis-progression.

Wiley, C., "Aging Fundamentals: Cellular senescence", Science of Aging Blog at the Buck Institute, pp. 1-4, (2015), found at sage.buckinstitute.org/aging-fundamentals-cellular-senescence.

Arichika, S. et al., "Correlation of retinal arterial wall thickness with atherosclerosis predictors in type 2 diabetes without clinical retinopathy", British Journal of Ophthalmology, vol. 101, pp. 69-74, (2017).

Lin, Z. et al., "Vaccination against AGE-LDL significant attenuates atherosclerosis in diabetic apoe mice", Heart, vol. 97, No. 21, supplement 3, p. A18, (2011) Abstract Only.

Thompson, L.V., "Age-related muscle dysfunction", Experimental Gerontology, vol. 44, pp. 106-111,(2009).

Sun, K. et al., "Elevated serum carboxymethyl-Lysine, an advanced glycation end product, predicts severe walking disability in older women: The women's health and aging study I", Journal of Aging Research, vol. 2012, pp. 1-8, (2012).

Kislinger, T. et al., "N$^\varepsilon$-(Carboxymethyl)Lysine adducts of proteins are ligands for receptor for advanced glycation end products that activate cell signaling pathways and modulate gene expression", The Journal of Biological Chemistry, vol. 274, No. 44, pp. 31740-31749, (1999).

Nakayama, H. et al., "Production and characterization of antibodies to advanced glycation products on proteins", Biochemical and Biophysical Research Communications, vol. 162, No. 2, pp. 740-745, (1989).

Gupta, R.K., "Aluminum compounds as vaccine adjuvants", Advanced Drug Delivery Review, vol. 32, No. 3, pp. 155-172, (1998), Abstract Only.

Tracy, J.M. et al., "Preservatives for poliomyelitis (Salk) vaccine II: Formaldehyde and esters of p-hydroxybenzoic acid", Journal of Pharmaceutical Sciences, vol. 53, Issue 6, pp. 659-663, (1964), Abstract Only.

Koito, W. et al., "Conventional antibody against N$^\varepsilon$-(Carboxymethyl)Lysine (CML) shows cross-reaction to N$^\varepsilon$-(Carboxyethyl)Lysine (CEL): Immunochemical quantification of CML with a specific antibody", The Journal of Biochemistry, vol. 135, No. 6, pp. 831-837, (2004).

Product Description of "Anti-Advanced Glycation End Products (AGE), Carboxy-Methyl Lysine (CML) [6C7] Antibody", Kerafast, www.kerafast.com/product/1779/anti-advanced-glycation-end-products-age-carboxy-methyl-lysine-cml-6c7-antibody, printed on Feb. 2, 2017.

Ikeda, K. et al., "N$^\varepsilon$-(Carboxymethyl)lysine protein adduct is a major immunological epitope in proteins modified with advanced glycation end products of the maillard reaction", Biochemistry, vol. 35, No. 24, pp. 8075-8083, (1996).

Dunn, J.A. et al., "Oxidation of glycated proteins: Age-dependent accumulation of N$^\varepsilon$-(Carboxymethyl)lysine in lensproteins". Biochemistry, vol. 28, No. 24, pp. 9464-9468, (1989).

Peppa, M. et al., "The role of advanced glycation end products in the development of atherosclerosis", Current Diabetes Reports, vol. 4, pp. 31-36, (2004).

Glenn, J.V. et al., "The role of advanced glycation end products in retinal ageing and disease", Biochimica Et Biophysica Acta, vol. 1790, No. 10. pp. 1109-1116, (2009).

European Search Report dated Feb. 21, 2017 for EP application No. 16198527.0.

Xu, M. et al., "Transplanted senescent cells induce an osteoarthritis-like condition in mice", The Journals of Gerontology Series A: Biological Sciences and Medical Sciences, pp. 1-6, (2016).

Ratliff, M. et al., "In senescence, age-associated B cells secrete TNFα and inhibit survival of B-cell precursors", Aging Cell, vol. 12, pp. 303-311, (2013).

Manestar-Blazic, T. et al., "The dynamic of senescent cells accumulation can explain the age-specific incidence of autoimmune diseases", Medical Hypotheses, vol. 73, pp. 667-669, (2009).

Tchkonia, T. et al., "Fat tissue, aging, and cellular senescence", Aging Cell, vol. 9, pp. 667-684, (2010).

Robbins, P. et al., "Scripps research, Mayo Clinic scientists find new class of drugs that dramatically increases healthy lifespan", The Scripps Research Institute, pp. 1-3, found at www.scripps.edu/news/press/2015/20150309agingcell.html, printed on Mar. 14, 2015.

Dorr, J.R. et al., "Synthetic lethal metabolic targeting of cellular senescence in cancer therapy", Nature, vol. 501, No. 7467, pp. 421-425, (2013).

Xu, M. et al., "Targeting senescent cells enhances adipogenesis and metabolic function in old age", eLife, vol. 4, pp. 1-20, (2015).

Minamino, T. et al., "Endothelial cell senescence in human atherosclerosis: Role of telomere in endothelial dysfunction", Circulation, vol. 105, issue 13, pp. 1541-1544, (2002).

Takino, J-I. et al., "Cancer malignancy is enhanced by glyceraldehyde-derived advanced glycation end-products", Journal of Oncology, vol. 2010, pp. 1-8, (2010).

Laberge, R-M. et al., "Epithelial-mesenchymal transition induced by senescent fibroblasts", Cancer Microenvironment, vol. 5, pp. 39-44, (2012).

Abe, R. et al. "Regulation of human melanoma growth and metastasis by AGE-AGE receptor interactions", Journal of Investigative Dermatology, vol. 122, No. 2, pp. 461-467, (2004).

Porporato, P.E. et al., "A mitochondrial switch promotes tumor metastasis", Cell Reports, vol. 8, pp. 754-766, (2014).

Boquio, A. et al., "Reversible cell cycle inhibition and premature aging features imposed by conditional expression of p16$^{ink4a}$", Aging Cell, vol. 14, pp. 139-147, (2015).

Nelson, G. et al., "A senescent cell bystander effect: senescence-induced senescence", Aging Cell, vol. 11, pp. 345-349, (2012).

Rayess, H. et al., "Cellular senescence and tumor suppressor gene p16", International Journal of Cancer, vol. 130, No. 8, pp. 1715-1725, (2012).

Greenfieldboyce, N., "Boosting life span by clearing out cellular clutter", npr.org, 4 pages, found at www.npr.org/sections/health-shots/2016/02/03/465354874/boosting-lifespan-by-clearing-out-cellular-clutter, printed on Feb. 4, 2016.

Matus, D.Q. et al., "Invasive cell fate requires G1 cell-cycle arrest and histone deacetylase-mediated changes in gene expression", Developmental Cell, vol. 35, pp. 162-174, (2015).

Stony Brook University, "Targeting invasive cells not dividing cells to halt cancer, study suggests", ScienceDaily, pp. 1-2, found at www.sciencedaily.com/releases/2015/10/151026181610.htm, (2015).

Liu, D. et al., "Senescent human fibroblasts increase the early growth of xenograft tumors via matrix metalloproteinase secretion", Cancer Research, vol. 67, No. 7, pp. 3117-3126, (2007).

(56) References Cited

OTHER PUBLICATIONS

Hoke, Z. "Belgian researchers discover way to block cancer metastasis", VOZ News, pp. 1-3, found at www.voanews.com/a/belgian-researchers-discover-way-to-block-cancer-metastasis/2453790.html, (2014).
Di, G-H. et al., "IL-6 secreted from senescent mesenchymal stem cells promotes proliferation and migration of breast cancer cells", PloS one, vol. 9, No. 11, pp. 1-15, (2014).
Huang, L-W. et al., "P16$^{ink4a}$ overexpression predicts lymph node metastasis in cervical carcinomas". Journal of Clinical Pathology, vol. 65, pp. 117-121, (2012).
Romagosa, C. et al., "P16$^{ink4a}$ overexpression in cancer: a tumor suppressor gene associated with senescence and high-grade tumors", Oncogene, vol. 30, pp. 2087-2097, (2011).
Terman, A. et al., "Mitochondrial turnover and aging of long-lived postmitotic cells: The mitochondrial-lysosomal axis theory of aging", Antioxidants & Redox Signaling, vol. 12, No. 4, pp. 503-535, (2010).
Ralph, A. et al., "P16 and HPV discordance in metastatic carcinoma of cervical lymph nodes of unknown primary", Clinical Case Reports, vol. 3, No. 10, pp. 817-818, (2015).
Hipkiss, A.R. "Aging, proteotoxicity, mitochondria, glycation, NAD+ and carnosine: possible inter-relationships and resolution of the oxygen paradox", Frontiers in Aging Neuroscience, vol. 2, article 10, pp. 1-6, (2010).
Bakala, H. et al., "Changes in rat liver mitochondria with aging Ion protease-like activity and N$^\varepsilon$-carboxymethyllysine accumulation in the matrix", European Journal of Biochemistry, vol. 270, No. 10, pp. 2295-2302, (2003).
Leslie, M. "Suicide of aging cells prolongs life span in mice", Sciencemag.org, pp. 1-4, found at www.sciencemag.orq/news/2016/02/suicide-aging-cells-prolongs-life-span-mice, (2016).
Eto, H. et al., "Selective imaging of malignant ascites in a mouse model of peritoneal metastasis using in vivo dynamic nuclear polarization-magnetic resonance imaging", Analytical Chemistry, vol. 88, pp. 2021-2027, (2016).
May Jr. K.F. et al., "Anti-human CTLA-4 monoclonal antibody promotes T-cell expansion and immunity in a hu-PBL-SCID model: a new method for preclinical screening of costimulatory monoclonal antibodies", Blood, vol. 105, pp. 1114-1120, (2005).
Schmitt, C.A. "Cellular senescence and cancer treatment", Biochimica et Biophysics Acta—Reviews on Cancer, vol. 1775, No. 1, pp. 5-20, (2007).
Gordon, R.R. et al., "Cellular senescence and cancer chemotherapy resistance", Drug Resistance Updates, vol. 15, No. 1-2, pp. 123-131, (2012).
Eyman, D. et al., "CCL5 secreted by senescent aged fibroblasts induces proliferation of prostate epithelial cells and expression of genes that modulate angiogenesis", Journal of Cellular Physiology, vol. 220, No. 2, pp. 376-381, (2009).
Nguyen, D.X. et al., "Metastasis: from dissemination to organ-specific colonization", Nature Reviews Cancer, vol. 9, No. 4, pp. 274-284, (2009).
Smit, M.A. et al., "Deregulating EMT and senescence: Double impact by a single twist", Cancer Cell, pp. 5-7, (2008).
Degenhardt, T.P. et al., "Chemical modification of proteins by methylglyoxal", Cellular and Molecular Biology (Noisy-le-Grand, France), vol. 44, No. 7, pp. 1139-1145, (1998) Abstract Only.
Gao, S.H. et al., "Monoclonal antibody humanness score and its applications", BMC Biotechnology, vol. 13, No. 1, pp. 1-12, (2013).
ClinicalTrials.gov, "A study evaluating the safety of ABT-263 in combination with etoposide/cisplatin in subjects with cancer", ClinicalTrials.gov, 4 pages, found at https://clinicaltrials.gov/ct2/show/NCT00878449?term=A+study+evaluating+the+safety+of+ABT-263+in+combination+with+etoposide%2Fcisplatin+in+subjects+with+cancer&rank=1, printed on Aug. 4, 2016.
Keating, D.J. "Mitochondrial dysfunction, oxidative stress, regulation of exocytosis and their relevance to neurodegenerative diseases", vol. 104, No. 2, pp. 298-305, (2008). Abstract Only.
Sas, K. et al., "Mitochondria, metabolic disturbances, oxidative stress and the kynurenine system, with focus on neurodegenerative disorders", Journal of the neurological sciences, vol. 257, No. 1, pp. 221-239, (2007). Abstract Only.
Ott, M. et al., "Mitochondria, oxidative stress and cell death", Apoptosis, vol. 12, No. 5, pp. 913-922, (2007). Abstract Only.
Trushina, E. et al., "Oxidative stress and mitochondrial dysfunction in neurodegenerative diseases", Neuroscience, vol. 145, No. 4, pp. 1233-1248, (2007). Abstract Only.
Moreira, P.I. et al., "Lipoic acid and N-acetyl cysteine decrease mitochondrial-related oxidative stress in Alzheimer disease patient fibroblasts", Journal of Alzheimer's Disease, vol. 12, No. 2, pp. 195-206, (2007). Abstract Only.
Yel, L. et al., "Thimerosal induces neuronal cell apoptosis by causing cytochrome c and apoptosis-inducing factor release from mitochondria", International Journal of Molecular Medicine, vol. 16, No. 6, pp. 971-977, (2005). Abstract Only.
Humphrey, M.L. et al., "Mitochondrial mediated thimerosal-induced apoptosis in a human neuroblastoma cell line (SK-N-SH)", Neurotoxicology, vol. 26, No. 3, pp. 407-416, (2005). Abstract Only.
Makani, S. et al., "Biochemical and molecular basis of thimerosal-induced apoptosis in T cells: a major role of mitochondrial pathway", Genes and Immunity, vol. 3, No. 5, pp. 270-278, (2002). Abstract Only.
Freitag, H. et al., "Inhibition of malate transport and activation of phosphate transport in mitochondria by ethylmercurithiosalicylate", FEBS Letters, vol. 117, No. 1, pp. 149-151, (1980). Citation Only.
Freitag, H. et al., "Ethylmercurithiosalicylate—a new reagent for the study of phosphate transport in mitochondria", FEBS Letters, vol. 114, No. 2, pp. 295-298, (1980). Citation Only.
Windham, G.C. et al., "Autism spectrum disorders in relation to distribution of hazardous air pollutants in the San Francisco bay area", Environmental Health Perspectives, pp. 1438-1444, (2006). Citation Only.
Ooe, H. et al., "Induction of reactive oxygen species by bisphenol A and abrogation of bisphenol A-induced cell injury by DJ-1", Toxicological Sciences, vol. 88, No. 1, pp. 114-126, (2005). Abstract Only.
Hanzel, C.E. et al., "Thallium induces hydrogen peroxide generation by impairing mitochondrial function", Toxicology and Applied Pharmacology, vol. 216, No. 3, pp. 485-492, (2006). Abstract Only.
Murugavel, P. et al., "Cadmium induced mitochondrial injury and apoptosis in vero cells: protective effect of diallyl tetrasufide from garlic", The International Journal of Biochemistry & Cell Biology, vol. 39, No. 1, pp. 161-170, (2007). Abstract Only.
Lasfer, M. et al., "Cadmium induces mitochondria-dependent apoptosis of normal human hepatocytes", Cell Biology and Toxicology, vol. 24, No. 1, pp. 55-62, (2008). Abstract Only.
Gash, D.M. et al., "Trichloroethylene: Parkinsonism and complex 1 mitochondrial neurotoxicity", Annals of neurology, vol. 63, No. 2, pp. 184-192, (2008). Abstract Only.
Banerjee, N. et al., "Arsenic-induced mitochondrial instability leading to programmed cell death in the exposed individuals", Toxicology, vol. 246, No. 2, pp. 101-111, (2008). Abstract Only.
Partridge, M.A. et al., "Arsenic induced mitochondrial DNA damage and altered mitochondrial oxidative function: Implication for genotoxic mechanisms in mammalian cells", Cancer Research, vol. 67, No. 11, pp. 5239-5247, (2007). Abstract Only.
Santra, A. et al., "Arsenic induces apoptosis in mouse liver is mitochondria dependent and is abrogated by N-acetylcysteine", Toxicology and Applied Pharmacology, vol. 220, No. 2, pp. 146-155, (2007). Abstract Only.
Bouchard, H. et al., "Antibody-drug conjugates—A new wave of cancer drugs", Bioorganic & Medicinal Chemistry Letters, vol. 24, pp. 5357-5363, (2014).
Yang, H.M. et al., "Doxorubicin conjugated with a monoclonal antibody directed to a human melanoma-associated proteoglycan suppresses the growth of established tumor xenografts in nude mice", Proceeding of the National Academy of Science, vol. 85, pp. 1189-1193, (1988).

(56) References Cited

OTHER PUBLICATIONS

Childs, B.G. et al., "Senescent intimal foam cells are deleterious at all stages of atherosclerosis", Science, vol. 354, No. 6311, pp. 472-477, (2016).
Loaiza, N. et al., "Cellular senescence and tumor promotion: Is aging the key?", Biochimica et Biophysica Acta, vol. 1865, pp. 155-167, (2016).
Rodier, F. et al., "Four faces of cellular senescence", The Journal of Cell Biology, vol. 192, No. 4, pp. 547-556, (2011).
Shay, J.W. et al., "Hallmarks of senescence in carcinogenesis and cancer therapy". Oncogene, vol. 23, pp. 2919-2933, (2004).
Davalos, A.R. et al., "Senescent cells as a source of inflammatory factors for tumor progression", Cancer Metastasis Reviews, vol. 29, pp. 273-283, (2010).
Roninson, I.B., "Tumor cell senescence in cancer treatment", Cancer Research, vol. 63, pp. 2705-2715, (2003).
International Search Report and Written Opinion dated May 17, 2017 for PCT application No. PCT/US2017/018185.
Kobayashi, S. et al., "Overproduction of N(epsilon)-(carboxymethyl) lysine-induced neovascularization in cultured choroidal explant of aged rat", Biological & Pharmaceutical Bulletin, vol. 30, No. 1, pp. 133-138, (2007).
Foster, D. et al., "AGE metabolites: A biomarker linked to cancer disparity?" Cancer Epidemiology, Biomarkers and Prevention, vol. 23, No. 10, pp. 2186-2191, (2014).
Mir, A.R. et al., "Structural changed in histone H2A by methylglyoxal generate highly immunogenic amorphous aggregates with implications in auto-immune response in cancer", Glycobiology, vol. 26, No. 2, pp. 129-141, (2016).
Ko, S-Y. et al., "Cell migration is regulated by AGE-RAGE interaction in human oral cancer cells in vitro", PLOS One, vol. 9, No. 10, pp. 1-9, e0110542, (2014).
Chen, H. et al., "Advanced glycation end products increase carbohydrate responsive element binding protein expression and promote cancer cell proliferation", Molecular and Cellular Endocrinology, vol. 395, No. 1-2, pp. 69-78, (2014).
Mercado-Pimentel, M.E. et al., "The S100P/RAGE signaling pathway regulates expression of microRNA-21 in colon cancer cells", FEBS Letters, vol. 589, No. 18, pp. 2388-2393, (2015).
Product description, "Carboxymethyl Lysine Antibody", R&D Systems, a biotechne brand, catalog No. MAB3247,1 page, found at https://resources.rndsystems.com/pdfs/datasheets/mab3247.pdf, (2015).
Bhat, R. et al., "Astrocyte senescence as a component of Alzheimer's Disease", PLOS One, vol. 7, No. 9, pp. 1-10, (2012).
Flanary, B.E. et al., "Evidence that aging and amyloid promote microglial cell senescence", Rejuvenation Research, vol. 10, No. 1, pp. 61-74, (2007).
Takeda, A. et al., "Advanced glycation end products co-localize with astrocytes and microglial cells in Alzheimer's disease brain", Acta Neuropathologica, vol. 95, pp. 555-558, (1998).
Chinta, S.J. et al., "Environmental stress, ageing and glial cell senescence: a novel mechanistic link to Parkinson's disease?", Journal of Internal Medicine, vol. 273, pp. 429-436, (2013).
Mori, M., "The Parkinsonian Brain: Cellular senescence and neurodegeneration", SAGE, found at sage.buckinstitute.org/the-parkinsonian-brain-cellular-senescence-and-neurodegeneration, (2015).
Das, M.M. et al., "Astrocytes show reduced support of motor neurons with aging that is accelerated in a rodent model of ALS", Neurobiology of Aging, vol. 36, pp. 1130-1139, (2015).
Luessi, F. et al., "Neurodegeneration in multiple sclerosis: novel treatment strategies", Expert Review of Neurotherapeutics, vol. 12, No. 9, pp. 1061-1077, (2012).
Wright, W.E., "Myoblast senescence in Muscular Dystrophy", Experimental Cell Research, vol. 157, pp. 343-354, (1985).
King, O.D., et al., "The tip of the iceberg: RNA-binding proteins with prion-like domains in neurodegenerative disease", Brain Research, vol. 1462, pp. 61-80, (2012).
Dobson, D.M., "The structural basis of protein folding and its links with human disease", Philosophical Transactions of the Royal Society of London B: Biological Sciences, vol. 356, No. 1406, pp. 133-145, (2001).
Kato, S. et al., "Advanced glycation end product-modified superoxide dismutase-1 (SOD1)-positive inclusions are common to familial amyotrophic lateral sclerosis patients with SOD1 gene mutations and transgenic mice expressing human SOD1 with a G85R mutation", Acta Neuropathologica, vol. 100, pp. 490-505, (2000).
International Search Report and Written Opinion dated Sep. 29, 2017 for PCT application No. PCT/US2017/027773.
Capparelli, C. et al., "Autophagy and senescence in cancer-associated fibroblasts metabolically supports tumor growth and metastasis via glycolysis and ketone production", Cell Cycle, vol. 11, No. 12, pp. 2285-2302, (2012).
""Shelf life" of blood? Shorter than we think", Johns Hopkins Medicine, pp. 1-2 found at www.hopkinsmedicine.org/news/media/releases/shelf_life_of_blood_shorter_than_we_think, (2013).
Garay-Sevilla, M.E. et al., "Advanced glycosylation end products in skin, serum, saliva and urine and its association with complications of patients with Type 2 diabetes mellitus", Journal of Endocrinological Investigation, vol. 28, No. 5, pp. 223-230, (2005).
Joyal, S.V., "Aging and Glycation", Life Extension Magazine, issue 4, pp. 1-7, found at www.lifeextension.com/Magazine/2008/4/Aging-And-Glycation/Page-01, (2008).
Egberts, J-H. et al., "Anti-tumor necrosis factor therapy inhibits pancreatic tumor growth and metastasis", Cancer Research, vol. 68, pp. 1443-1450, (2008).
Lowe, R. et al., "Buccals are likely to be a more informative surrogate tissue than blood for epigenome-wide association studies", Epigenetics, vol. 8, No. 4, pp. 445-454, (2013).
Bian, C. et al., "Clinical outcome and expression of mutant P53, P16, and Smad4 in lung adenocarcinoma: a prospective study", World Journal of Surgical Oncology, vol. 13, No. 128, pp. 1-8, (2015).
Tape, C.J. et al., "Oncogenic KRAS regulates tumor cell signaling via stromal reciprocation", Cell, vol. 165, pp. 910-920, (2016).
Product description for "CD8+CD57+ T Cell Isolation Kit, human", Miltenyi Biotec, pp. 1-4, found at www.miltenyibiotec.com/en/products-and-services/macs-cell-separation/cell-separation-reagents/t-cells/cd8-cd57-t-cell-isolation-kit-human.aspx, printed on Aug. 16, 2017.
Warrington, K.J. et al. "CD28 loss in senescent $CD4^+T$ cells: reversal by interleukin-12 stimulation", Blood, vol. 101, No. 9, pp. 3543-3549, (2003).
Kared, H. et al., "CD57 in human natural killer cells and T-lymphocytes", Cancer Immunology, Immunotherapy, vol. 65, issue 4, pp. 441-452, (2016).
Li, Z. et al., "Cdkn2a suppresses metastasis in squamous cell carcinomas induced by the gain-of-function mutant $p53^{R172H}$", The Journal of Pathology, vol. 240, issue 2, pp. 224-234, (2016). (Abstract Only).
Demaria, M. et al., "Cellular senescence promotes adverse effects of chemotherapy and cancer relapse", Cancer Discovery, vol. 7, pp. 165-176, (2017).
Niu, L. et al., "Free and protein-bound $N^\varepsilon$-carboxymethyllysine and $N^\varepsilon$-carboxyethyllysine in fish muscle: Biological variation and effects of heat treatment", Journal of Food Composition and Analysis, vol. 57, pp. 56-63, (2017).
Yoon, M-S. et al., "Characterisation of advanced glycation endproducts in saliva from patients with diabetes mellitus", Biochemical and Biophysical Research Communications, vol. 323, issue 2, pp. 377-381, (2004).
Product description for "Carboxymethyl Lysine (CML) ELISA", Kamiya Biomedical Company, pp. 1-7, found at www.k-assay.com/pdf/KT-32428.pdf, printed on Aug. 16, 2017.
Baar, M.P. et al., "Targeted apoptosis of senescent cells restores tissue homeostasis in response to chemotoxicity and aging", Cell, vol. 169, pp. 132-147, (2017).
Kim, Y.H. et al., "Senescent tumor cells lead the collective invasion in thyroid cancer", Nature Communications, pp. 1-14, (2017).
Ciccone, T.G. et al., "Reversing OA-new treatment on the horizon", Practical Pain Management, pp. 1-5, found at www.practicalpainmanage-

(56) References Cited

OTHER PUBLICATIONS ment.com/resources/news-and-research/reversing-oa-new-treatment-horizon, printed on Aug. 17, 2017.
Cook, L.S., "Learning about blood component therapy", Nursing, vol. 39, No. 4, pp. 30-33, (2009).
Landesberg, R. et al., "The expression of the receptor for glycation endproducts (RAGE) in oral squamous cell carcinomas", Oral Surgery Oral Medicine Oral Pathology Oral Radiology, vol. 105, issue 5, pp. 617-624, (2008).
Zhou, H.W., "Recovery of function in osteoarthritic chondrocytes induced by $p16^{NK4a}$-specific siRNA in vitro", Rheumatology, vol. 43, pp. 555-568, (2004).
Fuijkschot, W.W. et al., "Prevention of age-induced N($\varepsilon$)-(carboxymethyl)lysine accumulation in the microvasculature", European Journal of Clinical Investigation, vol. 46, issue 4, pp. 334-341, (2016). (Abstract Only).
Rasheed, Z.A. et al., "Pathology of pancreatic stroma in PDAC", Pancreatic Cancer and Tumor Microenvironment, pp. 1-10, (2012).
Morton, J.P. et al., "Mutant p53 drives metastasis and overcomes growth arrest/senescence in pancreatic cancer", PNAS, vol. 107, No. 1, pp. 246-251, (2010).
Verzijl, N. et al., "AGEing and osteoarthritis: a different perspective", Current Opinion in Rheumatology, vol. 15, issue 5, pp. 616-622, (2003).
Frescas, D. et al., "Senescent cells expose and secrete an oxidized form of membrane-bound vimentin as revealed by a natural polyreactive antibody", PNAS, vol. 114, No. 9, pp. E1668-E1677, (2017).
Oren, M. et al., "Mutant p53 gain-of-function in cancer", Cold Spring Harbor Perspectives in Biology, vol. 2, pp. 1-15, (2010).
"Senescence promotes chemotherapy side effects and cancer relapse", Medical Xpress, pp. 1-4, found at https://m.medicalxpress.com/news/2017-01-senescence-chemotherapy-side-effects-cancer.html, (2017).
Oh, J. et al., "Local clearance of senescent cells attenuates the development of post-traumatic osteoarthritis and creates a pro-regenerative environment", Nature Medicine, vol. 23, No. 6, pp. 1-9, (2017).
Protocols for "Isolation of untouched human T cells from peripheral blood mononuclear cells (PBMC)", Thermo Fisher Scientific, pp. 1-4, found at www.thermofisher.com/us/en/home/references/protocols/proteins-expression-isolation-and-analysis/cell-separation-methods/human-cell-separation-protocols/isolation-of-untouched-human-t-cells-.html, printed on Aug. 17, 2017.
Henrich, C.J. et al., "Isolation and characterization of a glycopeptide from human senescent erythrocytes", Carbohydrate Research, vol. 120, pp. 55-66, (1983).
Tsai, K.K.C. et al., "Low-dose radiation-induced senescent stromal fibroblasts render nearby breast cancer cells radioresistant". Radiation Research, vol. 172, pp. 306-313, (2009).
Nie, H et al., "Impaired glial glutamate uptake induces extrasynaptic glutamate spillover in the spinal sensory synapses of neuropathic rats", Journal of Neurophysiology, vol. 103, pp. 2570-2580, (2010).
Garcia-Matas, S. et al., "Dysfunction of astrocytes in senescence-accelerated mice SAMP8 reduces their neuroprotective capacity", Aging Cell, vol. 7, pp. 630-640, (2008).
Danysz, W. et al., "Alzheimer's disease, β-amyloid, glutamate, NMDA receptors and memantine-searching for the connections", British Journal of Pharmacology, vol. 167, pp. 324-352, (2012).
Blasko, I. et al., "Glial cells: Astrocytes and oligodendrocytes during normal brain aging", Encyclopedia of Neuroscience, pp. 743-747, (2009).
Leonard, B.W. et al., "Subventricular zone neural progenitors from rapid brain autopsies of elderly subjects with and without neurodegenerative disease", The Journal of Comparative Neurology, vol. 515, pp. 269-294, (2009).
Louveau, A. et al., "Structural and functional features of central nervous system lymphatic vessels", Nature, vol. 523, issue 7560, pp. 337-341, (2015).

Torgan, C., "Lymphatic vessels discovered in central nervous system", NIH Research Matters, pp. 1-4, found at www.nih.gov/news-events/nih-research-matters/lymphatic-vessels-discovered-central-nervous-system, Jun. 15, 2015.
Boskovitz, A. et al., "Monoclonal antibodies for brain tumour treatment", Expert Opinion on Biological Therapy, vol. 4, No. 9, pp. 1453-1471, (2004).
Takami, A. et al., "Treatment of primary central nervous system lymphoma with induction of complement-dependent cytotoxicity by intraventricular administration of autologous-serum-supplemented rituximab", Cancer Science, vol. 97, No. 1, pp. 80-83, (2006).
Biran, A. et al., "Senescent cells communicate via intercellular protein transfer", Genes & Development, vol. 29, pp. 791-802, (2015).
Golde, T.E. et al., "Proteinopathy-induced neuronal senescence: a hypothesis for brain failure in Alzheimer's and other neurodegenerative diseases", Alzheimer's Research & Therapy, vol. 1, No. 2, pp. 1-12, (2009).
Ouroboros, "Sweet madness: Sporadic prion disease and age-related changes in protein glycosylation", Research in the Biology of Aging, pp. 1-4, found at https://ouroboros.wordpress.com/2006/12/14/sweet-madness-sporadic-prion-disease-and-age-related-changes-in-protein-glycosylation/, (2006).
Xellbiogene, "Amyotrophic lateral sclerosis, immunotherapy is offering some hope", Xellbiogene.com, pp. 1-3, (2014).
Definition of "Complement system" printed from Wikipedia, the free encyclopedia on Aug. 4, 2015 found at http://en.wikipedia.org/wiki/Complement_system.
Definition of "Ventricular system" printed from Wikipedia, the free encyclopedia on Oct. 30, 2017 found at http://en.wikipedia.org/wiki/Ventricular_system.
Urushitani, M., "Future perspectives of immunotherapy against ALS", Rinsho Shinkeigaku, vol. 49, No. 11, pp. 818-820, (2009). (Abstract Only).
Cabezas, I.L. et al., "The role of glial cells in Alzheimer disease: potential therapeutic implications", Neurologia, vol. 29, No. 5, pp. 305-309, (2014).
Definition of "Prion" printed from Wikipedia, the free encyclopedia on Nov. 17, 2015 found at http://en.wikipedia.org/wiki/Prion.
"Prion Diseases", National Institute of Allergy and Infectious Diseases, pp. 1-2, found at www.niaid.nih.gov/diseases-conditions/prion-diseases, printed on Oct. 30, 2017.
"Alzheimer basics: Plaques and tangles", ALZ.org, pp. 1-2, found at www.alz.org/norcal/in_my_community_20545.asp, printed on Nov. 17, 2015.
Definition of "Lewy body" printed from Wikipedia, the free encyclopedia on Nov. 17, 2015 found at http://en.wikipedia.org/wiki/Lewy_body.
Definition of "Myocyte" printed from Wikipedia, the free encyclopedia on Nov. 17, 2015 found at http://en.wikipedia.org/wiki/Myocyte.
Definition of "Myosatellite cell" printed from Wikipedia, the free encyclopedia on Nov. 17, 2015 found at http://en.wikipedia.org/wiki/Myosatellite_cell.
Definition of "Microglia" printed from Wikipedia, the free encyclopedia on Oct. 30, 2017 found at http://en.wikipedia.org/wiki/Microglia.
Definition of "Astrocyte" printed from Wikipedia, the free encyclopedia on Oct. 30, 2017 found at http://en.wikipedia.org/wiki/Astrocyte.
Ouroboros, "A role for microglial senescence in Alzheimer's?", Research in the Biology of Aging, pp. 1-3, found at https://ouroboros.wordpress.com/?s=a+role+for+microglial, (2007).
Chen, K.S et al., "Monoclonal antibody therapy for malignant glioma", Glioma: Immunotherapeutic Approaches, chapter 10, pp. 121-141, (2012).
Reardon, S., "Alzheimer's drug sneaks through blood-brain barrier", Nature News, pp. 1-4, (2014).
"Astrocytes as a novel target in Alzheimer's disease", Expertsvar, pp. 1-2, (2012).
Myslinski, N., "Alzheimer's disease and the blood-brain barrier", Today's Geriatric Medicine, vol. 7, No. 1, pp. 1-10, (2014).

(56) References Cited

OTHER PUBLICATIONS

Hutter-Saunders, J.A.L. et al., "Pathways towards an effective immunotherapy for Parkinson's disease", Expert Reviews in Neurotherapeutics, vol. 11, No. 12, pp. 1703-1715, (2011).
Definition of "Intrathecal administration" printed from Wikipedia, the free encyclopedia on Oct. 30, 2017 found at http://en.wikipedia.org/wiki/Intrathecal_administration.
"What is ALS?", ALSA.org, found atwww.alsa.org/2015-non-responsive-pages/about-als/what-is-als.html, printed on Mar. 31, 2016.
Rouger, K. et al., "Systemic delivery of allogenic muscle stem cells induces long-term muscle repair and clinical efficacy in Duchenne muscular dystrophy dogs", The American Journal of Pathology, vol. 179, No. 5, pp. 2501-2518, (2011).
Anderson, J.L. et al., "Brain function in Duchenne muscular dystrophy", Brain, vol. 125, pp. 4-13, (2002).
Jarius, S. et al., "AQP4 antibodies in neuromyelitis optica: diagnostic and pathogenetic relevance", Nature Reviews, vol. 6, pp. 383-392, (2010).
Wesolowski, J. et al., "Single domain antibodies: promising experimental and therapeutic tools in infection and immunity", Medical Microbiology and Immunology, vol. 198, pp. 157-174, (2009).
Definition of "Antibody" printed from Wikipedia, the free encyclopedia on Sep. 21, 2015 found at http://en.wikipedia.org/wiki/Antibody.
Definition of "Antibody-dependent cell-mediated cytotoxicity" printed from Wikipedia, the free encyclopedia on Dec. 28, 2015 found at http://en.wikipedia.org/wiki/Antibody-dependent_cell-mediated_cytotoxicity.
Definition of "Blocking antibody" printed from Wikipedia, the free encyclopedia on Dec. 28, 2015 found at http://en.wikipedia.org/wiki/Blocking_antibody.
Definition of "Fc receptor" printed from Wikipedia, the free encyclopedia on Dec. 28, 2015 found at http://en.wikipedia.org/wiki/Fc_receptor.
Definition of "Fragment crystallizable region" printed from Wikipedia, the free encyclopedia on Dec. 28, 2015 found at http://en.wikipedia.org/wiki/Fragment_crystallizable_region.
Definition of "Neutralizing antibody" printed from Wikipedia, the free encyclopedia on Dec. 28, 2015 found at http://en.wikipedia.org/wiki/Neutralizing_antibody.
Company Information on "NantKwest", pp. 1-4, found at www.nantkwest.com, printed on Apr. 1, 2016.
Forbes, J.M. et al., "Below the radar: Advanced glycation end products that detour "around the side"", Clinical Biochemist Reviews, vol. 26, pp. 123-134, (2005).
Paul, W.E., "Fundamental immunology, third edition", Raven Press New York, chapter 9, pp. 292-295, (1993).
Rudikoff, S. et al., "Single amino acid substitution altering antigen-binding specificity", Proceedings of the National Academy of Science USA, vol. 79, pp. 1979-1983, (1982).
Wu, H. et al., "Humanization of a murine monoclonal antibody by simultaneous optimization of framework and CDR residues", Journal of Molecular Biology, vol. 294, pp. 151-162, (1999).
Golay, J. et al., "Mechanism of action of therapeutic monoclonal antibodies: Promises and pitfalls of in vitro and in vivo assays", Archives of Biochemistry and Biophysics, vol. 526, pp. 146-153, (2012).
Tang, S-S. et al., "Reaction of aortic lysyl oxidase with β-Aminopropionitrile", The Journal of Biological Chemistry, vol. 258, No. 7, pp. 4331-4338, (1983).
Saito, H. et al., "Regulation of a novel gene encoding a lysyl oxidase-related protein in cellular adhesion and senescence", The Journal of Biological Chemistry, vol. 272, No. 13, pp. 8157-8160, (1997).
Choi, Y-G. et al., "$N^\varepsilon$-carboxymethyl modification of lysine residues in pathogenic prion isoforms", Molecular Neurobiology, vol. 53, pp. 3102-3112, (2016).
Wendel, U et al., "A novel monoclonal antibody targeting carboxymethyllysine, an advanced glycation end product in atherosclerosis and pancreatic cancer", PLoS One, vol. 13, No. 2, pp. 1-22, (2018).
Hsia, T-C. et al., "Carboxymethyllysine, an advanced glycation end-product, promotes the invasion and migration of lung cancer A549 cells", Clinical Medicine Research, vol. 6, No. 5, pp. 149-156, (2017).
Nowotny, K. et al., "Advanced glycation end products and oxidative stress in type 2 diabetes mellitus", Biomolecules, vol. 5, pp. 194-222, (2015).
Yun, M.H. et al., "Recurrent turnover of senescent cells during regeneration of a complex structure". eLIFE, elifesciences.org, pp. 1-16, (2015).
Barja, G., "Aging in vertebrates, and the effect of caloric restriction: a mitochondrial free radical production-DNA damage mechanism?", Biological Reviews, vol. 79, No. 2, pp. 235-251, (2004). Abstract Only.
Pamplona, R. et al., "Aging increases nepsilon-(carboxymethyl)lysine and caloric restriction decreases nepsilon-(carboxyethyl)lysine and nepsilon-(malondialdehyde)lysine in rat heart mitochondrial proteins", Free Radical Research, vol. 36, No. 1, pp. 47-54, (2002). Abstract Only.
Yun, M.H., "Cellular senescence in regeneration", The Node, pp. 1-8, found at httD://thenode.biologists.com/cellular-senescence-in-regeneration/research/, Jun. 28, 2015.
Kasper, M. et al., "Age-related changes in cells and tissues due to advanced glycation end products (AGEs)", Archives of Gerontology and Geriatrics, vol. 32, issue 3, pp. 233-243, (2001).
Wang, Z. et al., "Advanced glycation end-product $N_\varepsilon$-carboxymethyl-Lysine accelerates progression of atherosclerotic calcification in diabetes", Atherosclerosis, vol. 221, issue 2, pp. 387-396, (2012). Abstract Only.
Draber, P. et al., "Stability of monoclonal IgM antibodies freeze-dried in the presence of trehalose", Journal of Immunological Methods, vol. 181, issue 1, pp. 37-43, (1995).
Kesari, S. et al., "Pritumumab binding to glioma cells induces ADCC and inhibits tumor growth", Journal of Clinical Oncology, vol. 35, No. 15 Supplemental, e14004-e14004, (2017). Abstract Only.
Babic, I. et al., "Pritumumab, the first therapeutic antibody for glioma patients", Human Antibodies, vol. 26, No. 2, pp. 95-101, (2017). Abstract Only.
Riva, P. et al., "Treatment of intracranial human glioblastoma by direct intratumoral administration of $^{131}$I-labelled anti-tenascin monoclonal antibody BC-2", International Journal of Cancer, vol. 51, No. 1, pp. 7-13, (1992). Abstract Only.
Ruster, M. et al., "Detection of elevated $N^\varepsilon$-carboxymethyllysine levels in muscular tissue and in serum of patients with fibromyalgia", Scandinavian Journal of Rheumatology, vol. 34, issue 6, pp. 460-463, (2005). Abstract Only.
Niwa, H. et al., "Accelerated formation of $N^\varepsilon$-(carboxymethyl) lysine, an advanced glycation end product, by glyoxal and 3-deoxyglucosone in cultured rat sensory neurons", Biochemical and Biophysical Research Communications, vol. 248, issue 1, pp. 93-97, (1998). Abstract Only.
Daly, C. et al., "Monocyte chemoattractant protein-1 (CCL2) in inflammatory disease and adaptive immunity: Therapeutic opportunities and controversies", Microcirculation, vol. 10, pp. 247-257, (2003).
Lee, S.T. et al., "Decreased number and function of endothelial progenitor cells in patients with migraine", Neurology, vol. 70, No. 17, pp. 1510-1517, (2008). Abstract Only.
Brown, J.N. et al., "Class effect of erythropoietin therapy on hemoglobin $A_{1c}$ in a patient with diabetes mellitus and chronic kidney disease not undergoing hemodialysis", Pharmacotherapy, The Journal of Human Pharmacology and Drug Therapy, vol. 29, No. 4, pp. 468-472, (2009). Abstract Only.
Liu, J. et al., "Accelerated senescence of renal tubular epithelial cells is associated with disease progression of patients with immunoglobulin A (IgA) nephropathy", Translational Research, vol. 159, issue 6, pp. 454-463, (2012). Abstract Only.

(56) References Cited

OTHER PUBLICATIONS

Khaw, K-T. et al., "Association of hemoglobin $A_{1c}$ with cardiovascular disease and mortality in adults: The European prospective investigation into cancer in Norfolk", Annals of Internal Medicine, vol. 141, pp. 413-420, (2004).
Kohnert, K.D. et al., "Destruction of pancreatic beta cells in rats by complete Freund's adjuvant combined with non-diabetogenic doses of streptozotocin". Diabetes Research, vol. 5, No. 1, pp. 1-11, (1987). Abstract Only.
Staud, R., "Fibromyalgia pain: do we know the source?", Current Opinion in Rheumatology, vol. 16, issue 2, pp. 157-163, (2004). Abstract Only.
Fleurence, J. et al., "Targeting and killing glioblastoma with monoclonal antibody to O-acetyl GD2 ganglioside", Oncotarget, vol. 7, No. 27, pp. 41172-41185, (2016).
Velarde, M.C. et al., "Senescent cells and their secretory phenotype as targets for cancer therapy", Interdisciplinary Topics in Gerontology, vol. 38, pp. 17-27, (2013).
Wang, Z. et al., "CML/RAGE signal induces calcification cascade in diabetes", Diabetology & Metabolic Syndrome, vol. 8, No. 83, pp. 1-12, (2016).
Freise, A.C. et al., "In vivo imaging with antibodies and engineered fragments", Molecular Immunology, vol. 67, issue 2, pp. 142-152, (2015).
Pavlides, S. et al., "The reverse Warburg effect: Aerobic glycolysis in cancer associated fibroblasts and the tumor stroma", Cell Cycle, vol. 8, No. 23, pp. 3984-4001, (2009).
Dunn, G.P. et al., "Principles of immunology and its nuances in the central nervous system", Neuro-Oncology, vol. 17, pp. vii3-vii8, (2015).
Rettig, M.P. et al., "Evaluation of biochemical changes during in vivo erythrocyte senescence in the dog", Blood, vol. 93, No. 1, pp. 376-384, (1999).
Baraibar, M.A. et al., "Proteomic quantification and identification of carbonylated proteins upon oxidative stress and during cellular aging", Journal of Proteomics, vol. 92, pp. 63-70, (2013). Abstract Only.
Chaudhuri, J. et al., "A Caenorhabditis elegans model elucidates a conserved role for TRPA1-Nrf signaling in reactive α-dicarbonyl detoxification", Current Biology, vol. 26, pp. 3014-3025, (2016).
Saleh, T. et al., "Reversibility of chemotherapy-induced senescence is independent of autophagy and a potential model for tumor dormancy and cancer recurrence", bioRxiv, pp. 1-29, 5 figures, (2017).
Hubert, P. et al., "Antibody-dependent cell cytotoxicity in monoclonal antibody-mediated tumor immunotherapy", OncoImmunology, vol. 1, issue 1, pp. 103-105, (2012).
Ouchi, R. et al., "Senescence from glioma stem cell differentiation promotes tumor growth", Biochemical and Biophysical Research Communications, vol. 470, No. 2, pp. 275-281, (2016).
Evans, A. et al., "Differentiating benign from malignant solid breast masses: value of shear wave elastography according to lesion stiffness combined with greyscale ultrasound according to BI-RADS classification", British Journal of Cancer, vol. 107, pp. 224-229, (2012).
Walen, K.H., "Normal human cell conversion to 3-D cancer-like growth: Genome damage, endopolyploidy, senescence escape, and cell polarity change/loss", Journal of Cancer Therapy, vol. 2, pp. 181-189, (2011).
Virella, G. et al., "Development of capture assays for different modifications of human low-density lipoprotein", Clinical and Diagnostic Laboratory Immunology, vol. 12, No. 1, pp. 68-75, (2005).
Moghaddam, A.E. et al., "Reactive carbonyls are a major Th2-inducing damage-associated molecular pattern generated by oxidative stress", The Journal of Immunology, vol. 187, pp. 1626-1633, (2011).
Kuilman, T. et al., "The essence of senescence", Genes & Development, vol. 24, pp. 2463-2479, (2010).
James, E.L. et al., "Senescent human fibroblasts show increased glycolysis and redox homeostasis with extracellular metabolomes that overlap with those of irreparable DNA damage, aging, and disease", Journal of Proteome Research, vol. 14, pp. 1854-1871, (2015).
Hein, G. et al., "Are advanced glycation end-product-modified proteins of pathogenetic importance in fibromyalgia?" Rheumatology, vol. 41, pp. 1163-1167, (2002).
Beausejour, C.M. et al., "Reversal of human cellular senescence: roles of the p53 and p16 pathways", The EMBO Journal, vol. 22, No. 16, pp. 4212-4222, (2003).
Simpson, R.J., "Aging, persistent viral infections, and immunosenescence: Can exercise "make space"?", Exercise and Sport Sciences Reviews, vol. 39, No. 1, pp. 23-33, (2011).
Gudkov, A., "Andrei Gudkov taped an expanded presentation of the slides he presented at 2017 Biology of Aging conference at Scripps, Florida, Jan. 22-27", Everon Biosciences, found at everonbio.com/Andrei-gudkov-taped-an-expanded-presentation-of-the-slides-he-presented-at-2017-biology-of-aging-conference-at-scripps-florida-22-27-january, 2 pages, Mar. 21, 2017. Abstract Only.
Radoi, V. et al., "Advanced glycation end products in diabetes mellitus: Mechanism of action and focused treatment". Proceedings of the Romanian Academy, Series B, vol. 1, pp. 9-19, (2012).
Sieben, C.J. et al., "Two-step senescence-focused cancer therapies", Trends in Cell Biology, pp. 1-15, (2018).
Gaens, K.H.J. et al., "$N^\varepsilon$-(carboxymethyl)lysine-receptor for advanced glycation end product axis is a key modulator of obesity-induced dysregulation of adipokine expression and insulin resistance", Arteriosclerosis, Thrombosis, and Vascular Biology, vol. 34, issue 6, pp. 1199-1208, pp. s1-s9, (2014).
Semba, R.D. et al., "Relationship of an advanced glycation end product, plasma carboxymethyl-lysine, with slow walking speed in older adults: the inCHIANTI study", European Journal of Applied Physiology, vol. 108, No. 1, pp. 191-195, (2010).
Wu, J. et al., "Sonoporation, anti-cancer drug and antibody delivery using ultrasound", Ultrasonics, vol. 44, supplement, pp. e21-e25, (2006). Abstract Only.
Meerwaldt, R. et al., "Skin autofluorescence is a strong predictor of cardiac mortality in diabetes", Diabetes Care, vol. 30, No. 1, pp. 107-112, (2007).
Nagai, R. et al., "Antibody-based detection of advanced glycation end-products: promises vs. limitations", Glycoconjugate Journal, vol. 33, No. 4, pp. 545-552, (2016).
Schmidt, A.M. et al., "The biology of the receptor for advanced glycation end products and its ligands", Biochimica et Biophysica Acta, vol. 1498, pp. 99-111, (2000).
Berens, M.E. et al., ""... those left behind." Biology and oncology of invasive glioma cells", Neoplasia, vol. 1, No. 3, pp. 208-219, (1999).
Hansen, K. et al., "Microneedle enabled intradermal delivery of biologics", 3M Drug Delivery Systems, 1 page, printed on Jul. 25, 2018.
Ikeda, K. et al., "Immunochemical approaches to AGE-structures: characterization of anti-AGE antibodies", Journal of Immunological Methods, vol. 215, No. 1-2, pp. 95-104, (1998).
De Vriese, A.S. et al., "Inhibition of the interaction of AGE-RAGE prevents hyperglycemia-induced fibrosis of the peritoneal membrane", Journal of the American Society of Nephrology, vol. 14, pp. 2109-2118, (2003).
Ott, C. et al., "Role of advanced glycation end products in cellular signaling", Redox Biology, vol. 2, pp. 411-429, (2014).
International Search Report and Written Opinion dated Aug. 7, 2018 for PCT application No. PCT/US2018/027653.
International Search Report and Written Opinion dated Sep. 10, 2018 for PCT application No. PCT/US2018/030931.
Edwards, B.M. et al., "The remarkable flexibility of the human antibody repertoire; Isolation of over one thousand different antibodies to a single protein, BLyS", The Journal of Molecular Biology, vol. 334, pp. 103-118, (2003).
Lloyd, C. et al., "Modelling the human immune response: performance of a $10^{11}$ human antibody repertoire against a broad panel of therapeutically relevant antigens", Protein Engineering, Design & Selection, vol. 22, No. 3, pp. 159-168, (2009).

(56) References Cited

OTHER PUBLICATIONS

Ansari, N.A. et al., "Glycated lysine residues: A marker for non-enzymatic protein glycation in age-related diseases", Disease Markers, vol. 30, pp. 317-324, (2011).
Blagosklonny, M.V. et al., "Cancer and aging", Cell Cycle, vol. 7, No. 17, pp. 2615-2618, (2008).
Chow, H-M. et al., "Senescent neurons in the alzheimer's brain kill nearby healthy neurons by blocking their WNT lifeline: The continuing saga of the zombie apocalypse", Alzheimer's & Dementia, vol. 12. No. 7(S), p. P658. (2016).
Dvorakova, E. et al., "Development of monoclonal antibodies specific for glycated prion protein", Journal of Toxicology and Environmental Health, Part A, vol. 74, pp. 1469-1475, (2011).
Search Results for "Carboxy Methyl Lysine Anitbody", 7 pages, antibodies-online.com, (2018).
Awwad, S. et al., "Overview of antibody drug delivery", Pharmaceutics, vol. 10, No. 83, pp. 1-24, (2018).
Farr, J.N. et al., "Targeting cellular senescence prevents age-related bone loss in mice", Nature Medicine, vol. 23, No. 9, pp. 1072-1079, (2017).
Hoenicke, L. et al., "Immune surveillance of senescent cells—biological significance in cancer- and non-cancer pathologies", Carcinogenesis, vol. 33, No. 6, pp. 1123-1126, (2012).
Kemmler, W. et al., "Prevalence of sarcopenia in Germany and the corresponding effect of osteoarthritis in females 70 years and older living in the community: results of the FORMoSA study", Clinical Interventions in Aging, vol. 10, pp. 1565-1573, (2015).
Myrianthopoulos, V. et al., "Senescence and senotherapeutics: a new field in cancer therapy", Pharmacology & Therapeutics, vol. 193, pp. 31-49, (2019).
Salahuddin, P. et al., "The role of advanced glycation end products in various types of neurodegenerative disease: A therapeutic approach", Cellular & Molecular Biology Letters, vol. 19, pp. 407-437, (2014).
Schosserer, M. et al., "The dual role of cellular senescence in developing tumors and their response to cancer therapy", Frontiers in Oncology, vol. 7, article 278, pp. 1-13, (2017).
Bussian, T.J. et al., "Clearance of senescent glial cells prevents tau-dependent pathology and cognitive decline", Nature Letters, vol. 562, pp. 578-582, (2018).
Penney, J. et al., "Senescence mediates neurodegeneration", Nature, vol. 562, pp. 503-504, (2018).
Trivedi, P.M. et al., "Repurposed JAK1/JAK2 inhibitor reverses established autoimmune insulitis in NOD mice", Diabetes, vol. 66, p. 1650-1660, (2017).
Wang, C. et al., "DNA damage response and cellular senescence in tissues of aging mice", Aging Cell, vol. 8, pp. 311-323, (2009).
Iizuka, K. et al., "Dasatinib improves insulin sensitivity and affects lipid metabolism in a patient with chronic myeloid leukaemia", BMJ Case Rep, pp. 1-3, (2016).
Jeon, O.H. et al., "Local clearance of senescent cells attenuates the development of post-traumatic osteoarthritis and creates a pro-regenerative environment", Nature Medicine, vol. 23, pp. 775-781, (2017). Abstract Only.
Duke Health News & Media, "Duke team finds missing immune cells that could fight lethal brain tumors", Duke University School of Medicine, pp. 1-5, (2018).
Apple, S., "An old idea, revived: Starve cancer to death", NYTimes.com, pp. 1-15, (2016).
Dock, J.N. et al., "Role of CD8 T cell replicative senescence in human aging and in HIV-mediated immunosenescence", Aging and Disease, vol. 2, No. 5, pp. 382-397, (2011).
Rayavarapu, S. et al., "Idiopathic inflammatory myopathies: pathogenic mechanisms of muscle weakness", Skeletal Muscle, vol. 3, No. 13, pp. 1-13, (2013).
Kudryashova, E. et al., "Satellite cell senescence underlies myopathy in a mouse model of limb-girdle muscular dystrophy 2H", The Journal of Clinical Investigation, vol. 122, No. 5, pp. 1764-1776, (2012).

Ratelade, J. et al., "Neuromyelitis optica IgG and natural killer cells produce NMO lesions in mice without myelin loss", Acta Neuropathologica, vol. 123, issue 6, pp. 861-872, (2012).
Vincent, T. et al., "Functional consequences of neuromyelitis optica-IgG astrocyte interactions on blood-brain barrier permeability and granulocyte recruitment", The Journal of Immunology, vol. 181, pp. 5730-5737, (2008).
Baarine, M. et al., "ABCD1 deletion-induced mitochondrial dysfunction is corrected by SAHA: implication for adrenoleukodystrophy", Journal of Neurochemistry, vol. 133, pp. 380-396, (2015).
Durieu, I. et al., "Subepithelial fibrosis and degradation of the bronchial extracellular matrix in cystic fibrosis", American Journal of Respiratory and Critical Care Medicine, vol. 158, No. 2, pp. 580-588, (1998).
Shapiro, B.L. et al., "Premature senescence in cultured skin fibroblasts from subjects with cystic fibrosis", Science, vol. 203, issue 4386, pp. 1251-1253, (1979). Abstract Only.
Fischer, B.M. et al., "Increased expression of senescence markers in cystic fibrosis airways", American Journal of Physiology Lung Cellular and Molecular Physiology, vol. 304, No. 6, pp. L394-L400, (2013).
Thom, M. et al., "An investigation of the expression of $G_1$-phase cell cycle proteins in focal cortical dysplasia type IIB", Journal of Neuropathology and Experimental Neurology, vol. 66, No. 11, pp. 1045-1055, (2007).
Valdivieso, A.G. et al., "CFTR activity and mitochondrial function", Redox Biology, vol. 1, pp. 190-202, (2013).
Chilosi, M. et al., "Premature lung aging and cellular senescence in the pathogenesis of idiopathic pulmonary fibrosis and COPD/emphysema", Translational Research, vol. 162, issue 3, pp. 156-173, (2013). Abstract Only.
Ribeiro, C.M.P., "The role of intracellular calcium signals in inflammatory responses of polarized cystic fibrosis human airway epithelia", Drugs in R&D, vol. 7, issue 1, pp. 17-31, (2006), Abstract Only.
Velisek L. et al., "Aging: effects of aging on seizures and epilepsy", Encyclopedia of Basic Epilepsy Research, pp. 37-40, (2009). Abstract Only.
Muller, S. et al., "Analysis of senescence markers in rodent pancreatic stellate cells", The Pancreapedia, pp. 1-8, (2013).
Lim, M., "Acute immunology, temporal lobe epilepsy and other disorders", YoungEpilepsy.Org, pp. 1-70, found at http://youngepilepsy.org.uk/dmdocuments/MIND-THE-GAP2015_Ming%20Lim.pdf, (2015).
Definition of "Cachexia" printed from Wikipedia, the free encyclopedia on Dec. 28, 2015 found at http://en.wikipedia.org/wiki/Cachexia.
Lok, C., "The last illness, researchers are gaining insight into the causes of Cachexia—a devastating form of muscle wasting that is often the final stage of cancer and other diseases", Nature, vol. 528, pp. 182-183, (2015).
Da Rocha, O.M. et al., "Sarcopenia in rheumatoid cachexia: definition, mechanisms, clinical consequences and potential therapies", Revista Brasileira de Reumatologia, vol. 49, No. 3, pp. 294-301, (2009).
Tisdale, M.J., "Biology of Cachexia", Journal of the National Cancer Institute, vol. 89, No. 23, pp. 1763-1773, (1997).
Romanick, M. et al., "Murine models of atrophy, cachexia, and sarcopenia in skeletal muscle", Biochimica et Biophysics Acta—Molecular Basis of Disease, vol. 1832, issue 9, pp. 1410-1420, (2013).
Ali, S. et al., "Sarcopenia, cachexia and aging: Diagnosis, mechanisms and therapeutic options", Gerontology, vol. 60, No. 4, pp. 294-305, (2014).
Angelini, P.D. et al., "Constitutive HER2 signaling promotes breast cancer metastasis through cellular senescence", Cancer Research, vol. 73, No. 1, pp. 450-458, (2013).
Arai, Y. et al., "Inflammation, but not telomere length, predicts successful ageing at extreme old age: A longitudinal study of semi-supercentenarians", EBioMedicine, vol. 2, pp. 1549-1558, (2015).

(56) References Cited

OTHER PUBLICATIONS

Bedard, N. et al., "Inactivation of the ubiquitin-specific protease 19 deubiquitinating enzyme protects against muscle wasting". The FASEB Journal, vol. 29, No. 9, pp. 3889-3898, (2016).
Figueroa-Clarevega, A. et al., "Malignant *Drosophila* tumors interrupt insulin signaling to induce cachexia-like wasting", Developmental Cell, vol. 33, pp. 47-55, (2015).
Giacconi, R. et al., "Cellular senescence and inflammatory burden as determinants of mortality in elderly people until the extreme old age", EBioMedicine, vol. 2, pp. 1316-1317, (2015).
Jin, H. et al., "Protein modifications as potential biomarkers in breast cancer", Biomarker Insights, vol. 4, pp. 191-200, (2009).
Lee, S-J. et al., "Treating cancer cachexia to treat cancer", Skeletal Muscle, vol. 1, No. 2, pp. 1-5, (2011).
Mohamed, M.M. et al., "Human monocytes augment invasiveness and proteolytic activity of inflammatory breast cancer", Biological Chemistry, vol. 389, No. 8, pp. 1117-1121, (2008).
Pare, R. et al., "The significance of the senescence pathway in breast cancer progression", Journal of Clinical Pathology, vol. 66, pp. 491-495, (2013). Abstract Only.
Pinto, N.I. et al., "Cancer as a proinflammatory environment: Metastasis and cachexia", Mediators of Inflammation, vol. 2015, pp. 1-13, (2015).
Tesarova, P. et al., "Carbonyl and oxidative stress in patients with breast cancer—is there a relation to the stage of the disease?", Neoplasma, vol. 54, No. 3, pp. 219-224, (2007).
Tseng, Y-C., et al., "Preclinical investigation of the novel histone deacetylase inhibitor AR-42 in the treatment of cancer-induced cachexia", Journal of the National Cancer Institute, vol. 107, No. 12, pp. 1-14, (2015).
Wang, S. et al., "Characterization of IGFBP-3, PAI-1 and SPARC mRNA expression in senescent fibroblasts", Mechanisms of Ageing and Development, vol. 92, issues 2-3, pp. 121-132, (1996). Abstract Only.
Yang, S. et al., "Impact of oxidative stress biomarkers and carboxymethyllysine (an advanced glycation end product) on prostate cancer: A prospective study", Clinical Genitourinary Cancer, vol. 13, issue 5, pp. e347-e351, (2015).
"Global Arthritis Research Network: $4^{th}$ World Congress on Arthritis in Montreal", Arthritis Research & Therapy, vol. 6, supplement 3, meeting abstracts, pp. S1-S41, Sep. 20-22, 2004.
Miller, R.E. et al., "Osteoarthritis joint pain: The cytokine connection", Cytokine, vol. 70, No. 2, pp. 185-193, (2014).
LifeExtension, "Chronic Pain", Lifeextension.com, pp. 1-18, found at www.lifeextension.com/protocols/health-concerns/chronic-pain/page-03, (2016).
Rush University Medical Center, "Scientists home in on cause of osteoarthritis pain". Science Daily, found at www.sciencedaily.com/releases/2012/12/121227173053.htm, pp. 1-4, (2012).
Kidd, B.L. et al., "Mechanisms of inflammatory pain", British Journal of Anesthesia, vol. 87, No. 1, pp. 3-11, (2001).
Price, J.S. et al., "The role of chondrocyte senescence in osteoarthritis", Aging Cell, vol. 1, pp. 57-65, (2002).
Morales, T.I., "Chondrocyte moves: clever strategies?", OsteoArthritis and Cartilage, vol. 15, pp. 861-871, (2007).
Martin, J.A. et al., "Effects of oxidative damage and telomerase activity on human articular cartilage chondrocyte senescence", Journal of Gerontology: Biological Sciences, vol. 59A, No. 4, pp. 324-337, (2004).
Ang, D.C. et al., "MCP-1 and IL-8 as pain biomarkers in fibromyalgia: A pilot study", Pain Medicine, vol. 12, pp. 1154-1161, (2011).
Burton, D.G.A. et al., "Microarray analysis of senescent vascular smooth muscle cells: A link to atherosclerosis and vascular calcification", Experimental Gerontology, vol. 44, issue 10, pp. 659-665, (2009).
Konttinen, Y.T. et al., "Chondrocyte-mediated collagenolysis correlates with cartilage destruction grades in osteoarthritis", Clinical and Experimental Rheumatology, vol. 23, pp. 19-26, (2005).
"Low back pain", U.S. Department of Health and Human Services, Public Health Service National Institutes of Health, 1-28, (2014).

Bicer, F. "CCL2 (MCP-1) mediates chronic pelvic pain through mast cells in experimental autoimmune cystitis", ETD Archive, pp. 1-120, (2012).
Loeser, R.F. "Aging and osteoarthritis: The role of chondrocyte senescence and aging changes in the cartilage matrix", Osteoarthritis and Cartilage, vol. 17, No. 8, pp. 971-979, (2009).
Zhou, H-W. et al., "Expressions of p16INK4a in healthy and osteoarthritic human articular cartilage and difference analysis", Research Gate, pp. 2148-2149, found at www.researchgate.net/publication/290275008_Expressions_of_p16INK4a_in_healthy_and_osteoarthritic_human_articular_cartilage_and_difference_analysis, (2004). Abstract Only.
Martin, J.A. et al., "Post-traumatic osteoarthritis: the role of accelerated chondrocyte senescence", Biorheology, vol. 41, pp. 479-491, (2004).
Martin, J.A. et al., "Human chondrocyte senescence and osteoarthritis", Biorheology, vol. 39, No. 1,2, pp. 145-152, (2002). Abstract Only.
Forliti, M., "Mayo clinic researchers link senescent cells to most common form of arthritis", Mayo Clinic, pp. 1-2, found at www.eurekalert.org/pub_releases/2016-08/mc-mcr081016.php, (2016).
Roubenoff, R., "Sarcopenic obesity: Does muscle loss cause fat gain? Lessons from Rheumatoid arthritis and osteoarthritis", Annals of the New York Academy of Sciences, vol. 904, pp. 553-557, (2000). Abstract Only.
De Cauninck, F. et al., "Bearing arms against osteoarthritis and sarcopenia: When cartilage and skeletal muscle find common interest in talking together", Drug Discovery Today, vol. 19, issue 3, pp. 305-311, (2014). Abstract Only.
Chatterjea, D. "Mast cells and pain", Mastcell Basophil, pp. 1-5, found at www.mastcell-basophil.net/wiki/wiki-start/mast-cells-and-pain/, (2013).
Bach, B. "New drug promises relief for inflammatory pain, scientists say", News Center, Stanford Medicine PASiN, found at med.stanford.edu/news/all-news/2014/08/new-drug-promises-relief-for-inflammatory-pain--scientists-say.html, 3 pages, (2014).
Daly, C. et al., "Monocyte chemoattractant protein-1 (CCL2) in inflammatory disease and adaptive immunity: Therapeutic opportunities and controversies", Microcirculation, vol. 10, issue 3-4, pp. 247-257, (2003).
"MMP13 gene", NIH U.S. National Library of Medicine, found at ghr.nlm.nih.gov/gene/MMP13, 4 pages, (2016).
Hayami, T. et al., "MMP-1 (Collagenase-1) and MMP-13 (Collagenase-3) differentially regulate blastic differentiation in osteogenic cells", Matrix Biology, vol. 27, issue 8, pp. 682-692, (2008).
Attur, M.G. et al., "Autocrine production of IL-1 beta by human osteoarthritis-affected cartilage and differential regulation of endogenous nitric oxide, IL-6, prostaglandin E2, and IL-8", Proceeding of the Association of American Physicians, vol. 110, No. 1, pp. 65-72, (1998). Abstract Only.
Xu, Y-K. et al., "The role of MCP-1-CCR2 ligand-receptor axis in chondrocyte degradation and disease progress in knee osteoarthritis", Biological Research, vol. 48, No. 64, pp. 1-8, (2015).
Goldring, M.B., "The role of the chondrocyte in osteoarthritis", Arthritis & Rheumatism, vol. 43, No. 9, pp. 1916-1926, (2000).
Mobasheri, A. et al., "Chondrocyte and mesenchymal stem cell-based therapies for cartilage repair in osteoarthritis and related orthopaedic conditions", Maturitas, vol. 78, pp. 188-198, (2014).
"What are chondrocytes?", wiseGeek, found at www.wisegeek.org/what-are-chondrocytes.htm, 1 page, printed on Nov. 29, 2016.
Woolf, A.D. et al., "Burden of major musculoskeletal conditions", Bulletin of the World Health Organization, vol. 81, No. 9, pp. 646-656, (2003).
Pereira, D. et al., "The effect of osteoarthritis definition on prevalence and incidence estimates: a systematic review", Osteoarthritis and Cartilage, vol. 19, pp. 1270-1285, (2011).
Martin, J.A. et al., "Aging, articular cartilage chondrocyte senescence and osteoarthritis", Biogerontology, vol. 3, pp. 257-264, (2002).
"What is osteoarthritis?", NIH National Institute of Arthritis and Musculoskeletal and Skin Diseases, pp. 1-4, (2014).
Definition of "Osteoarthritis" printed from Wikipedia, the free encyclopedia, found at en.wikipedia.org/wiki/Osteoarthritis, Dec. 13, 2016.

(56) References Cited

OTHER PUBLICATIONS

"At a glance 2016, Arthritis, Improving the quality of life for people with arthritis", National Center for Chronic Disease Prevention and Health Promotion, pp. 1-4, (2016).
"IASP Taxonomy", International Association for the Study of Pain, found at www.iasp-pain.org/Taxonomy, pp. 1-9, (2014).
"Pain: Hope through research", National Institute of Neurological Disorders and Stroke, National Institutes of Health, pp. 1-46, (2014).
Definition of "Allodynia" printed from Wikipedia, the free encyclopedia, found at en.wikipedia.org/wiki/Allodynia, Dec. 13, 2016.
Quadras, A.U. et al., "Dynamic weight bearing is an efficient and predictable method for evaluation of arthritic nociception and its pathophysiological mechanisms in mice", Nature, Scientific Reports, pp. 1-11, (2015).
Leung, L. et al., "TNF-α and neuropathic pain—a review", Journal of Neuroinflammation, vol. 7, No. 27, pp. 1-11, (2010).
Schafers, M. et al., "Tumor necrosis factor-α induces mechanical allodynia after spinal nerve ligation by activation of p38 MAPK in primary sensory neurons", The Journal of Neuroscience, vol. 23, No. 7, pp. 2517-2521, (2003).
Sun, J.L et al., "CX3CL1/CX3CR1 regulates nerve injury-induced pain hypersensitivity through the ERK5 signaling pathway", Journal of Neuroscience Research, vol. 91, No. 4, pp. 545-553, (2013). Abstract Only.
Watkins, L.R et al., "Mechanisms of tumor necrosis factor-α (TNF-α) hyperalgesia", Brain Research, vol. 692, issues 1-2, pp. 244-250, (1995). Abstract Only.
American Diabetes Association, "Diagnosis and classification of diabetes mellitus". Diabetes Care, vol. 31, supp. 1, pp. S55-S60, (2008).
"Global report on diabetes", World Health Organization, pp. 1-88, (2016).
"National diabetes statistics report, 2017: Estimates of diabetes and its burden in the United States", U.S. Department of Health and Human Services, Centers for Disease Control and Prevention, pp. 1-20, (2017).
O'Brien, P.D. et al., "Mouse models of diabetic neuropathy", Institute for Laboratory Animal Research Journal, vol. 54, No. 3, pp. 259-272, (2014).
O'Brien, P.D. et al., "BTBR ob/ob mice as a novel diabetic neuropathy model: Neurological characterization and gene expression analyses", Neurobiology of Disease, vol. 73, pp. 348-355, (2015).
Alpers, C.E. et al., "Mouse models of diabetic nephropathy", Current Opinion in Nephrology and Hypertension, vol. 20, No. 3, pp. 278-284, (2011).
Hudkins, K.L. et al., "BTBR ob/ob mutant mice model progressive diabetic nephropathy", Journal of the American Society of Nephrology, vol. 21, pp. 1533-1542, (2010).
O'Brien, K.D. et al., "Divergent effects of vasodilators on cardiac hypertrophy and inflammation in a murine model of diabetic cardiomyopathy", Journal of the American College of Cardiology, vol. 57, issue 17, p. e193, (2011). Abstract Only.
Lee, J-T. et al., "Macrophage metalloelastase (MMP12) regulates adipose tissue expansion, insulin sensitivity, and expression of inducible nitric oxide synthase", Endocrinology, vol. 155, No. 9, pp. 3409-3420, (2014).
Xu, X. et al., "A glimpse of matrix metalloproteinases in diabetic nephropathy", Current Medicinal Chemistry, vol. 21, No. 28, pp. 3244-3260, (2014).
Tsioufis, C. et al., "The role of matrix metalloproteinases in diabetes mellitus", Current Topics in Medicinal Chemistry, vol. 12, No. 10, pp. 1159-1165, (2012). Abstract Only.
Pechhold, K. et al., "Blood glucose levels regulate pancreatic β-cell proliferation during experimentally-induced and spontaneous autoimmune diabetes in mice", PLoS One, vol. 4, No. 3, pp. e4827, (2009).
Oh, K-J. et al., "Metabolic adaptation in obesity and type II diabetes: myokines, adipokines and hepatokines", International Journal of Molecular Sciences, vol. 18, No. 1, article 8, pp. 1-31, (2017).
Micov, A. et al., "Levetiracetam synergises with common analgesics in producing antinociception in a mouse model of painful diabetic neuropathy", Pharmacological Research, vol. 97, pp. 131-142, (2015). Abstract Only.
Feldman, E., "Tail flick assay", Animal Models of Diabetic Complications Consortium, pp. 1-3, (2004).
Bratwur, W., "ABT 263 was formulated in 10 ethano", found at www.selleckchem.com/blog/ABT-263-was-formulated-in-10-ethano.html, (2013). Abstract Only.
"Beta cell dysfunction", Diabetes and the Environment, found at www.diabetesandenvironment.org/home/mech/betacells, pp. 1-7, printed on Feb. 27, 2019.
Edelman, D., "Understanding beta cell exhaustion in Type 2 diabetics", Diabetes Daily, found at www.diabetesdaily.com/blog/2008/06/podcast-understanding-beta-cell-exhaustion-in-type-2-diabetics, pp. 1-6, (2008).
Cao, Y. et al., "Mechanisms of endothelial to mesenchymal transition in the retina in diabetes", Investigative Ophthalmology & Visual Science, vol. 55, pp. 7321-7331, (2014).
Palmer, A.K. et al., "Cellular senescence in Type 2 diabetes: a therapeutic opportunity", Diabetes, vol. 64, pp. 2289-2298, (2015).
Cummings, B.P. et al., "Maternal ileal interposition surgery confers metabolic improvements to offspring independent of effects on maternal body weight in UCD-T2DM rats", Obesity Surgery, vol. 23, No. 12, pp. 2042-2049, (2013).
Cummings, B.P. et al., "Development and characterization of a novel rat model of type 2 diabetes mellitus: the UC Davis type 2 diabetes mellitus UCD-T2DM rat", American Journal of Physiology Regulatory, Integrative and Comparative Physiology, vol. 295, pp. R1782-R1793, (2008).
Cummings, B.P. et al., "Bile-acid-mediated decrease in endoplasmic reticulum stress: a potential contributor to the metabolic benefits of ileal interposition surgery in UCD-T2DM rats", Disease Models & Mechanisms, vol. 6, No. 2, pp. 443-456, (2013).
Cummings, B.P. et al., "Vertical sleeve gastrectomy improves glucose and lipid metabolism and delays diabetes onset in the UCD-T2DM rats", Endocrinology, vol. 153, No. 8, pp. 3620-3632, (2012).
Cummings, B.P. et al., "Ileal interposition surgery improves glucose and lipid metabolism and delays diabetes onset in the UCD-T2DM rat", Gastroenterology, vol. 138, pp. 2437-2446, (2010).
American Diabetes Association, "Standards of medical care in diabetes—2016 abridged for primary care providers", Diabetes, vol. 34, No. 1, pp. 3-21, (2016).
Definition of "Methylglyoxal" printed from Wikipedia, the free encyclopedia, found at en.wikipedia.org/wiki/Methylglyoxal, Jun. 5, 2017.
Boesten, D.M.P.H.J. et al., "Effect of Nε-carboxymethyllysine on oxidative stress and the glutathione system in beta cells", Toxicology Reports, vol. 1, pp. 973-980, (2014).
Molla, B. et al., "Two different pathogenic mechanisms, dying-back axonal neuropathy and pancreatic senescence, are present in the YG8R mouse model of Friedreich ataxia", Disease Models & Mechanisms, vol. 9, pp. 647-657, (2016).
Kender, Z. et al., "Effect of metformin on methylglyoxal metabolism in patients with type 2 diabetes", Experimental and Clinical Endocrinology & Diabetes, vol. 122, No. 5, pp. 316-319, (2014). Abstract Only.
Ehrenmann, F. et al., "IMGT/3Dstructure-DB and IMGT/DomainGapAlign: a database and a tool for immunoglobulins or antibodies, T cell receptors, MHC, IgSF and MhcSF", Nucleic Acids Research, vol. 38, pp. D301-D307, (2010).
Glover, A., "Of mice and men", European Biophamaceutical Review, pp. 30-34, (2016).
"The basic guide to magnetic bead cell separation", Sepmag.eu, pp. 1-15, found at www.sepmag.eu/free-basic-guide-magnetic-bead-cell-separation, (2017).

(56) References Cited

OTHER PUBLICATIONS

Su, W-S. et al., "Controllable permeability of blood-brain barrier and reduced brain injury through low-intensity pulsed ultrasound stimulation", Oncotarget, vol. 6, No. 39, pp. 42290-42299, (2015).
Haslbeck, K.M. et al., "The RAGE pathway in inflammatory myopathies and limb girdle muscular dystrophy", Acta Neuropathologica, vol. 110, issue 3, pp. 247-254, (2005).
Sternberg, Z. et al., "AGE-RAGE in multiple sclerosis brain", Immunological Investigations, vol. 40, issue 2, pp. 197-205, (2011). Abstract Only.
Miyata, T. et al., "Increased pentosidine, an advanced glycation end product, in plasma and synovial fluid from patients with rheumatoid arthritis and its relation with inflammatory markers", Biochemical and Biophysical Research Communications, vol. 244, pp. 45-49, (1998).
Mulrennan, S. et al., "The role of receptor for advanced glycation end products in airway inflammation in CF and CF related diabetes", Scientific Reports, vol. 5, No. 8931, pp. 1-9, (2015).
Weber, K. et al., "Distribution of advanced glycation end products in the cerebellar neurons of dogs", Brain Research, vol. 791, pp. 11-17, (1998).
Berg, T.J. et al., "The advanced glycation end product $N^\varepsilon$-(carboxymethyl)lysine is increased in serum from children and adolescents with type 1 diabetes", Diabetes Care, vol. 21, No. 11, pp. 1997-2002, (1998).
Degenhardt, T.P. et al., "The serum concentration of the advanced glycation end-product $N^\varepsilon$-(carboxymethyl)lysine is increased in uremia", Kidney International, vol. 52, pp. 1064-1067, (1997).
Hayase, F. et al., "Aging of proteins: Immunological detection of a glucose-derived pyrrole formed during maillard reaction in vivo", The Journal of Biological Chemistry, vol. 263, No. 7, pp. 3758-3764, (1989).
Ikeda, K. et al., "Immunochemical approaches to AGE-structures: characterization of anti-AGE antibodies", The Maillard Reaction in Foods and Medicine, pp. 310-315, (1998).
Kume, S. et al., "Immunohistochemical and ultrastructural detection of advanced glycation end products in atherosclerotic lesions of human aorta with a novel specific monoclonal antibody", American Journal of Pathology, vol. 147, No. 3, pp. 654-667, (1995).
Makita, A. et al., "Immunochemical detection of advanced glycosylation end products in vivo", The Journal of Biological Chemistry, vol. 267, No. 8, pp. 5133-5138, (1992).
Niwa, T. et al., "Immunohistochemical detection of advanced glycation end products in dialysis-related amyloidosis", Kidney International, vol. 48, pp. 771-778, (1995).
Papanastasiou, P. et al., "Immunological quantification of advanced glycosylation end-products in the serum of patients on hemodialysis of CAPD", Kidney International, vol. 46, pp. 216-222, (1994).
Schleicher, E.D. et al., "Increased accumulation of the glycoxidation product N(epsilon)-(carboxymethyl)lysine in human tissues in diabetes and aging", The Journal of Clinical Investigation, vol. 99, No. 3, pp. 457-468, (1997).
Takeuchi, M. et al., "Immunological detection of a novel advanced glycation end-product", Molecular Medicine, vol. 7, No. 11, pp. 783-791, (2001).
Kobayashi, S. et al., "$N^\varepsilon$-(Carboxymethyl)lysine-induced choroidal angiogenic potential facilitates retinal neovascularization in advanced-diabetic rat in vitro", The Open Pharmacology Journal vol. 2, pp. 79-85, (2008).
Tamemoto, H. et al., "AGE inhibitor-recent development". Diabetes Frontier, vol. 16, No. 5, pp. 541-546, (2005).
Nagai, R. et al., "Prevention of diabetic complication by AGE inhibitors", Progress of Medicine, vol. 207, No. 9, pp. 663-667, (2003).
Vistoli, G. et al., "Advanced glycoxidation and lipoxidation end products (AGEs and ALEs): an overview of their mechanisms of formation", Free Radical Research, vol. 47, supple. 1, pp. 3-27, (2013).
Bachmeier, B.E. et al., "Maillard products as biomarkers in cancer", Annals of the New York Academy of Sciences, vol. 1126, No. 1, pp. 283-287, (2008). Abstract Only.
Chen, Z. et al., "Senescent cells re-engineered to express soluble programmed death receptor-1 for inhibiting programmed death receptor-1/programmed death ligand-1 as a vaccination approach against breast cancer", Cancer Science, vol. 109, pp. 1753-1763, (2018).
Leontieva, O.V. et al., "Yeast-like chronological senescence in mammalian cells: phenomenon, mechanism and pharmacological suppression", Aging, vol. 3, No. 11, pp. 1-14, (2011).
Moser, A.C. et al., "Immunoaffinity chromatography: an introduction to applications and recent developments", Bioanalysis, vol. 2, No. 4, pp. 769-790, (2010).
Prosser, C.G. et al., "$N^\varepsilon$-carboxymethyllysine in nutritional milk formulas for infants", Food Chemistry, vol. 274, pp. 886-890, (2019).
Takeuchi, M. et al., "Detection of noncarboxymethyllysine and carboxymethyllysine advanced glycation end products (AGE) in serum of diabetic patients", Molecular Medicine, vol. 5, pp. 393-405, (1999).
Teodorowicz, M. et al., Immunomodulation by processed animal feed: The role of maillard reaction products and advanced glycation end-products (AGEs), Frontiers in Immunology, vol. 9, article 2088, pp. 1-15, (2018).
Kwak, T. et al., "Targeting of RAGE-ligand signaling impairs breast cancer cell invasion and metastasis", Oncogene, vol. 11, pp. 1559-1572, (2017). Abstract Only.
Inui, H. et al., "A scFv antibody-based immunoaffinity chromatography column for clean-up of bisphenol a-contaminated water samples", Journal of Agricultural and Food Chemistry, vol. 57, No. 2, pp. 353-358, (2009). Abstract Only.
Casset, F. et al., "A peptide mimetic of an anti-CD4 monoclonal antibody by rational design", Biochemical and Biophysical Research Communications, vol. 307, pp. 198-205, (2003).
Chikazawa, M. et al., "Multispecificity of immunoglobulin M antibodies raised against advanced glycation end products", The Journal of Biological Chemistry, vol. 288, No. 19, pp. 13204-13214, (2013).
De Pascalis, R. et al., "Grafting of "abbreviated" complementarity-determining regions containing specificity-determining residues essential for ligand contact to engineer a less immunogenic humanized monoclonal antibody", The Journal of Immunology, vol. 169, pp. 3076-3084, (2002).
Hirose, J. et al., "Immunohistochemical distribution of advanced glycation end products (AFEs) in human osteoarthritic cartilage", Acta Histochemica, vol. 113, No. 6, pp. 613-618, (2011).
Kumar, S. et al., "Molecular cloning and expression of the fabs of human autoantibodies in *Escherichia coli*", The Journal of Biological Chemistry, vol. 275, No. 45, pp. 35129-35136, (2000).
Lamminmaki, U. et al., "Crystal structure of a recombinant anti-estradiol fab fragment in complex with 17β-estradiol", The Journal of Biological Chemistry, vol. 276, No. 39, pp. 36687-36694, (2001).
Padlan, E.A et al., "Structure of an antibody-antigen complex: Crystal structure of the hyhel-10 fab-lysozyme complex", Proceedings of the National Academy of Science, fol. 86, pp. 5938-5942, (1989).
Schwab, W. et al., "Immunohistochemical demonstration of $N^\varepsilon$-(carboxymethyl)lysine protein adducts in normal and osteoarthritic cartilage", Histochemistry and Cell Biology, vol. 117, issue 6, pp. 541-546, (2002).
Smith-Gill, S.J. et al., "Contributions of immunoglobulin heavy and light chains to antibody specificity for lysozyme and two haptens" The Journal of Immunology, vol. 139, No. 12, pp. 4135-4144, (1987).
Song, M-K, et al., "Light chain of natural antibody plays a dominant role in protein antigen binding", Biochemical and Biophysical Research Communications, vol. 268, pp. 390-394, (2000).
Ward, E.S. et al., "Binding activities of a repertoire of single immunoglobulin variable domains secreted from *Escherichia coli*", Nature, vol. 341, pp. 544-546, (1989.

(56) References Cited

OTHER PUBLICATIONS

Jeon O.H. et al., "Senescent cells and osteoarthritis: a painful connection", The Journal of Clinical Investigation, vol. 128, No. 4, pp. 1229-1237, (2018).
Guan, Z. et al., "Contemporary views on inflammatory pain mechanisms: TRPing over innate and microglial pathways", F1000Research, vol. 5, pp. 1-11, (2016).
Musi, N. et al., "Tau protein aggregation is associated with cellular senescence in the brain", Aging Cell, vol. 17, pp. 1-13, (2018).
International Search Report and Written Opinion dated Nov. 25, 2019 for PCT application No. PCT/US2019/047762.
Dillon, P., "Focused ultrasound and pembrolizumab in metastatic breast cancer (breast-48)", ClinicalTrials.gov, pp. 1-7. (2017).
Masui, T. et al., "Low-intensity ultrasound enhances the anticancer activity of cetuximab in human head and neck cancer cells", Experimental and Therapeutic Medicine, vol. 5, pp. 11-16, (2013).
Khaibullina, A. et al., "Pulsed high-intensity focused ultrasound enhances uptake of radiolabeled monoclonal antibody to human epidermoid tumor in nude mice", The Journal of Nuclear Medicine, vol. 49, pp. 295-302, (2008).
Liao, A-H. et al., "Enhanced therapeutic epidermal growth factor receptor (EGFR) antibody delivery via pulsed ultrasound with targeting microbubbles for glioma treatment", Journal of Medical and Biological Engineering, vol. 35, pp. 156-164, (2015).
Liu, H-L. et al., "Focused ultrasound enhances central nervous system delivery of bevacizumab for malignant glioma treatment", Radiology, vol. 281, No. 1, pp. 99-108, (2016).
Kobus, T. et al., "Growth inhibition in a brain metastasis model by antibody delivery using focused ultrasound-mediated blood-brain barrier disruption", Journal of Controlled Release, vol. 238, pp. 281-288, (2016).
Linetsky, M. et al., "UVA light-excited kynurenines oxidize ascorbate and modify lens proteins through the formation of advanced glycation end products, Implications for Human Lens Aging and Cataract Formation", Journal of Biological Chemistry, vol. 289, No. 24, pp. 17111-17123, (2014).
Chaudhary, M.K. et al., "Redox imbalance in a model of rat mimicking Hutchinson-Gilford progeria syndrome", Biochemical and Biophysical Research Communications, vol. 491, No. 2, pp. 361-367, (2017). Abstract Only.
Hause F. et al., "Accumulation of glycated proteins suggesting premature ageing in lamin B receptor deficient mice", Biogerontology, vol. 19, No. 1, pp. 95-100, (2017). Abstract Only.
International Search Report and Written Opinion dated Nov. 27, 2019 for PCT application No. PCT/US2019/043071.
Zhang, J-M. et al., "Cytokines, Inflammation and Pain", International Anesthesiology Clinics, vol. 45, No. 2, pp. 27-37, (2007).
Bhatt A.N. et al., "Transient elevation of glycolysis confers radio-resistance by facilitating DNA repair in cells", BMC Cancer, vol. 15, Article 335, pp. 1-12, (2015).
Callier, V., "Cancer cells can't proliferate and invade at the same time", Scientific American, pp. 1-5, (2016), found at www.scientificamerican.com/article/cancer-cells-can-t-proliferate-and-invade-at-the-same-time.
Drews, G. et al., "Oxidative stress and beta-cell dysfunction", European Journal of Physiology, vol. 460, pp. 703-718, (2010).
Huang, C-C. et al., "Glycolytic inhibitor 2-deoxyglucose simultaneously targets cancer and endothelial cells to suppress neuroblastoma growth in mice", Disease Models and Mechanisms, vol. 8, pp. 1247-1254, (2015).
Kehm, R. et al., "age-related oxidative changes in pancreatic islets are predominantly located in the vascular system", Redox Biology, vol. 15, pp. 387-393, (2018).
Kohrman, A.Q. et al., "Divide or conquer: Cell cycle regulation of invasive behavior", Trends in Cell Biology, vol. 27, issue 1, pp. 12-25, (2017).
Menini, S. et al., "The advanced glycation end-product $N^\epsilon$-carboxymethyllysine promotes progression of pancreatic cancer: implications for diabetes-associated risk and its prevention", Journal of Pathology, vol. 245, pp. 197-208, (2018).
Wang, J. et al., "Oxidative stress in pancreatic beta cell regeneration", Oxidative Medicine and Cellular Longevity, vol. 2017, Article id 1930261, pp. 1-9, (2017).
Nerlich, A.G. et al., "$N^\epsilon$-(carboxymethyl)lysine in atherosclerotic vascular lesions as a marker for local oxidative stress", Atherosclerosis, vol. 144, issue 1, pp. 41-47, (1999). Abstract Only.
Soreide, K. et al., "Epidemiological-molecular evidence of metabolic reprogramming on proliferation, autophagy and cell signaling in pancreas cancer", Cancer Letters, vol. 356, issue 2, part A, pp. 281-288, (2015) Abstract Only.
Krautwald, M. et al., "Advanced glycation end products as biomarkers and gerontotoxins—a basis to explore methylglyoxal-lowering agents for Alzheimer's disease?", Experimental Gerontology, vol. 45, issue 10, pp. 744-751, (2010). Abstract Only.
Leclerc, E., "Development of monoclonal antibodies to inhibit RAGE activation in pancreatic tumors", North Dakota State University, Center for diagnostic and therapeutic strategies in pancreatic cancer, 1 page, (2019), found at www.ndsu.edu/centers/pancreaticcancer/former_investigators/leclerc_project/.
Yamagishi, S-I., et al., "DNA-aptamers raised against AGEs as a blocker of various aging-related disorders", Glycoconjugate Journal, vol. 33, pp. 683-690, (2016).
Kawaguchi, M. et al., "Glyoxal inactivates glutamate transporter-1 in cultured rat astrocytes", Neuropathology, vol. 25, pp. 27-36, (2005).
Scicchitano, B.M. et al., "Counteracting muscle wasting in aging and neuromuscular diseases: the critical role of IGF-1", Aging, vol. 1, No. 5, pp. 451-457, (2009).
Southern, L. et al., "Immunohistochemical study of N-epsilon-carboxymethyl lysine (CML) in human brain: relation to vascular dementia", BMC Neuology, vol. 7, article No. 35, pp. 1-8, (2007).
Hanssen, N.M.J. et al., "Higher levels of advanced glycation endproducts in human carotid atherosclerotic plaques are associated with a rupture-prone phenotype", European Heart Journal, vol. 35, pp. 1137-1146, (2014).
Ramunas, J. et al., "Transient delivery of modified mRNA encoding TERT rapidly extends telomeres in human cells", The FASEB Journal, vol. 29, No. 5, pp. 1930-1939, (2015).
Gutierrez-Reyes, G. et al., "Cellular senescence in livers from children with end stage liver disease", Plos One, vol. 5, issue 4, pp. 1-5, (2010).
Extended European Search Report dated May 29, 2020 for European application No. 19210193.9-1111, 8 pages.
Taguchi, A. et al., "Blockade of RAGE-amphoterin signalling suppresses tumour growth and metastases", Nature, vol. 405, pp. 354-360, (2000).
Janeway, C.A. Jr. et al., "Appendix I. Immunologists' toolbox", Immunobiology: The immune system in health and disease, $5^{th}$ edition, Garland Science, (2001), found at www.ncbi.nim.nih.gov/books/NBK10755/, (2001).
Haus, J.M. et al., "Collagen, cross-linking, and advanced glycation end products in aging human skeletal muscle", Journal of Applied Physiology, vol. 103, pp. 2068-2076, (2007).
Yi, H-S. et al., "T-cell senescence contributes to abnormal glucose homeostasis in humans and mice", Cell Death and Disease, vol. 10, No. 249, pp. 1-15, (2019).
Al-Motawa, M. et al., "Vulnerabilities of the SARS-CoV-2 virus to proteotoxicity—opportunity for repurposed chemotherapy of COVID-19 infection", Cell—Reports, 43 pages, found at www.ssrn.com/abstract=3582068, (2020).
D'Adda di Fagagna, F., "Living on a break: cellular senescence as a DNA-damage response", Nature Reviews Cancer, vol. 8, pp. 512-522, (2008).
"New biomarker for the prevention of arteriosclerosis", Atherosclerosis Prevention, vol. 14, No. 1, pp. 22-27, (2015).
Baxevanis, C.N. "Antibody-based cancer therapy", Expert Opinion Drug Discovery, vol. 3, No. 4, pp. 441-452, (2008).
Malatesta, M. "skeletal muscle features in myotonic dystrophy and sarcopenia: do similar nuclear mechanisms lead to skeletal wasting?", European Journal of Histochemistry, vol. 56, pp. 228-230, (2012).
Wingerchuk, D.M. et al., "Multiple sclerosis: Current and emerging disease-modifying therapies and treatment strategies", Mayo Clinic Proceedings, vol. 89, No. 2, pp. 225-240, (2014).

(56) References Cited

OTHER PUBLICATIONS

Matias-Guiu J.A. et al., "Amyloid proteins and their role in multiple sclerosis. Considerations in the use of amyloid-PET imaging", Frontiers in Neurology, vol. 7, article 53, pp. 1-7, (2016).
Sternberg, Z. et al., "Diagnostic potential of plasma carbxymethyllysine and carboxyethyllysine in multiple sclerosis", Journal of Neuroinflammation, vol. 7, No. 72, pp. 1-8, (2010).
Gunawan, M. et al., "A novel human systemic lupus erythematosus model in humanised mice", Nature Scientific Reports, vol. 7, pp. 1-11, (2017).
"Grants for Health Science of the Ministry of Health and Welfare, Comprehensive Research Project on Longevity Science", Long-Term Longitudinal Epidemiology, vol. 5, pp. 223-227, (1998).
Office Action dated Dec. 21, 2020 for Japanese application No. 2019-230026.
Shi, M. et al., "Low intensity-pulsed ultrasound induced apoptosis of human hepatocellular carcinoma cells in vitro", Ultrasonics, vol. 64, pp. 43-53, (2016). abstract only.
Myers, R. et al., "Ultrasound-mediated cavitation does not decrease the activity of small molecule, antibody or viral-based medicines", International Journal of Nanomedicine, vol. 13, pp. 337-349, (2018).
Danno, D. et al., "Effects of ultrasound on apoptosis induced by anti-CD20 antibody in CD20-positive B lymphoma cells", Ultrasonics Sonochemistry, vol. 15, pp. 463-471, (2008). abstract only.
Nande, R. et al., "Ultrasound-mediated oncolytic virus delivery and uptake for increased therapeutic efficacy: state of art", Oncolytic Virotherapy, vol. 4, pp. 193-205, (2015).
Abe, H. et al., "Targeted sonodynamic therapy of cancer using a photosensitizer conjugated with antibody against carcinoembryonic antigen", Anticancer Research, vol. 22, No. 3, pp. 1575-1580, (2002).
Jordao, J.F. et al., "Antibodies targeted to the brain with image-guided focused ultrasound reduces amyloid-β plaque load in the TgCRND8 mouse model of alzheimer's disease", Plos One, vol. 5, issue 5, pp. 1-8, (2010).
Idbaih, A. et al., "Phase I/II study of an implantable device delivering low intensity pulsed ultrasound (LIPU) to disrupt the blood-brain barrier (BBB) followed by intravenous carboplatin chemotherapy in patients with recurrent glioblastoma (GBM)", Journal of Clinical Oncology, vol. 35, issue 15, supplemental 2034, pp. 1-6, (2017). abstract only.
Etame, A.B. et al., "Focused ultrasound disruption of the blood brain barrier: a new frontier for therapeutic delivery in molecular neuro-oncology", Neurosurg Focus, vol. 32, No. 1, pp. 1-17, (2012).
Wang, S. et al., "Pulsed high intensity focused ultrasound increases penetration and therapeutic efficacy of monoclonal antibodies in murine xenograft tumors", Journal of Controlled Release, vol. 162, No. 1, pp. 218-224, (2012).
Miller, D. et al., "Overview of therapeutic ultrasound applications and safety considerations", Journal of Ultrasound in Medicine, vol. 31, No. 4, pp. 623-634, (2012).
Udroiu, I., "Ultrasonic drug delivery in oncology", Journal of the Balkan Union of Oncology, vol. 20, No. 2, pp. 381-390, (2015).
Yu, T. et al., "Ultrasound: A chemotherapy sensitizer", Technology in Cancer Research and Treatment, vol. 5, No. 1, pp. 51-60, (2006).
Zhang, Z. et al., "Low intensity ultrasound promotes the sensitivity of rat brain glioma to doxorubicin by down-regulating the expressions of P-Glucoprotein and multidrug resistance protein 1 in vitro and in vivo", PLOS One, vol. 8, issue 8, pp. 1-13, (2013).
Sawai, Y. et al., "Effects of low-intensity pulsed ultrasound on osteosarcoma and cancer cells", Oncology Reports, vol. 28, pp. 481-486, (2012).
Takeuchi, R. et al., "Low-intensity pulsed ultrasound activates the phosphatidylinositol 3 kinase/Akt pathway and stimulates the growth of chondrocytes in three-dimensional cultures: a basic science study", Arthritis Research & Therapy, vol. 10, pp. 1-11, (2008).
Cui, J.H. et al., "Effects of low-intensity ultrasound on chondrogenic differentiation of mesenchymal stem cells embedded in polyglycolic acid: an in vivo study", Tissue Engineering, vol. 12, No. 1, pp. 75-82, (2006).

Muhlfeld, J. et al., "Influence of ultrasonic waves and enzymes on antigenic properties of human erythrocytes. I. Ultrasonic waves", Blut., vol. 30, No. 5, pp. 349-352, (1975). Abstract Only.
Rosenfeld, E. et al., "Positive and negative effects of diagnostic intensities of ultrasound on erythrocyte blood group markers", Ultrasonics, vol. 28, issue 3, pp. 155-158, (1990). Abstract Only.
Aviles Jr., F., "Contact low-frequency ultrasound used to accelerate granulation tissue proliferation and rapid removal of nonviable tissue in colonized wounds: A case study", Wound Management and Prevention, pp. 1-6, (2011).
Chen, R. et al., "Ultrasound-accelerated immunoassay, as exemplified by enzyme immunoassay of choriogonadotropin", Clinical Chemistry, vol. 30, No. 9, pp. 1446-1451, (1984).
Lin, C-H. et al., "Advanced glycosylation end products induce nitric oxide synthase expression in C6 glioma cells involvement of a p38 MAP kinase-dependent mechanism", Life Sciences, vol. 69, pp. 2503-2515, (2001).
Stoczynska-Fidelus, E. et al., "Spontaneous in vitro senescence of glioma cells confirmed by an antibody against $IDH1^{R132H}$" Anticancer Research, vol. 34, pp. 2859-2868, (2014).
Kinoshita, M. et al., "Noninvasive localized delivery of Herceptin to the mouse brain by MRI-guided focused ultrasound-induced blood-brain barrier disruption", Proceedings of the National Academy of Science, vol. 103, No. 31, pp. 11719-11723, (2006).
Nisbet, R.M. et al., "Combined effects of scanning ultrasound and a tau-specific single chain antibody in a tau transgenic mouse model", Brain, A Journal of Neurology, vol. 140, pp. 1220-1230, (2017).
Sun, T. et al., "Closed-loop control of targeted ultrasound drug delivery across the blood-brain/tumor barriers in a rat glioma model", Proceedings of the National Academy of Science, pp. e10281-e10290, (2017).
Liu, H-L. et al., "Blood-brain barrier disruption with focused ultrasound enhances delivery of chemotherapeutic drugs for glioblastoma treatment", Radiology, vol. 255, No. 2, pp. 415-425, (2010).
Zhao, B. et al., "Blood-brain barrier disruption induced by diagnostic ultrasound combined with microbubbles in mice", Oncotarget, vol. 9, No. 4, pp. 4897-4914, (2018).
Neergaard, L., "Ultrasound opens brain barrier, a step to better care", AZCentral.com, pp. 1, (2018).
Houston-Edwards, K., "Wave of the Future?", PBS.org, pp. 1-6, found at www.pbs.org/wgbh/nova/article/hifu/, (2016).
Allen, K.D. et al., "Evaluating intra-articular drug delivery for the treatment of osteoarthritis in a rat model", Tissue Engineering: Part B, vol. 16, No. 1, pp. 81-92, (2010).
Eguchi, K. et al., "Whole-brain low-intensity pulsed ultrasound therapy markedly improves cognitive dysfunctions in mouse models of dementia—crucial roles of endothelial nitric oxide synthase", Brain Stimulation, vol. 11, pp. 959-973, (2018).
Ninomiya, K. et al., "Targeted sonodynamic therapy using protein-modified $TiO_2$ nanoparticles", Ultrasonics Sonochemistry, vol. 19, pp. 607-614, (2012).
Watson, K.D. et al., "Ultrasound increases nanoparticle delivery by reducing intratumoral pressure and increasing transport in epithelial and epithelial-mesenchymal transition tumors", Cancer Research, vol. 72, No. 6, pp. 1485-1493, (2012).
Endo, S. et al., "Porphyrin derivatives-mediated sonodynamic therapy for malignant gliomas in vitro", Ultrasound in Medicine and Biology, vol. 41, issue 9, pp. 2458-2465, (2015).
Zhang, Z. et al., "Low frequency and intensity ultrasound induces apoptosis of brain glioma in rats mediated by caspase-3, Bcl-2, and survivin". Brain Research, vol. 1473, pp. 25-34, (2012). Abstract Only.
Wang, P. et al., "Membrane damage effect of continuous wave ultrasound on K562 human leukemia cells", Journal of Ultrasound in Medicine, vol. 31, pp. 1977-1986, (2012).
Wood, A.K.W. et al., "A review of low-intensity ultrasound for cancer therapy", Ultrasound in Medicine and Biology, vol. 41, No. 4, pp. 905-928, (2015).
Lejbkowicz, F. et al., "Distinct sensitivity of normal and malignant cells to ultrasound in vitro", Environmental Health Perspectives, vol. 105, supplement 6, pp. 1575-1578, (1997).

(56) References Cited

OTHER PUBLICATIONS

Purkayastha, S. et al., "Transcranial doppler ultrasound: Technique and application", Seminars in Neurology, vol. 32, No. 4, pp. 411-420, (2012).
Liman, J. et al., "Transcranial ultrasound in adults and children with movement disorders", Perspectives in Medicine, vol. 1, pp. 349-352, (2012).
Product Description of "US 1000 3$^{rd}$ Edition Portable Ultrasound Unit 1-mHz", TENSpros, found at www.tenspros.com/US-1000-3rd-edition-portable-ultrasound-du1025.html, printed on Oct. 24, 2018.
El-Taieb, M.A. et al., "Oxidative stress and acrosomal morphology: A cause of infertility in patients with normal semen parameters", Middle East Fertility Society Journal, vol. 20, pp. 79-85, (2015).
Liu, D.Y. et al., "Defective sperm-zona pellucida interaction: a major cause of failure of fertilization in clinical in-vitro fertilization", Human Reproduction, vol. 15, No. 3, pp. 702-708, (2000).
Uhler, M.L., "Sperm morphology", Fertility Centers of Illinois, pp. 1-2, printed on Apr. 12, 2018.
Mallidis, C. et al., "Advanced glycation end products accumulate in the reproductive tract of men with diabetes", International Journal of Andrology, vol. 32, pp. 295-305, (2008).
Henkel, R.R. et al., "Sperm preparation for ART", Reproductive Biology and Endocrinology, vol. 1, pp. 1-22, (2003).
Ng, K.K. et al., "Sperm output of older men", Human Reproduction, vol. 19, No. 8, pp. 1811-1815, (2004).
Harris, I.D. et al., "Fertility and the aging male", Reviews in Urology, vol. 13, No. 4, pp. e184-e190, (2011).
Almeida, S. et al., "Fertility and sperm quality in the aging male", Current Pharmaceutical Design, vol. 23, issue 30, pp. 4429-4437, (2017). Abstract Only.
Kidd, S.A. et al., "Effects of male age on semen quality and fertility: a review of the literature", Fertility and Sterility, vol. 75, No. 2, pp. 237-248, (2001).
Sugimoto, K. et al., "The application of life style diseases—animal models to the research for sarcopenia", Clinical Calcium, vol. 24, No. 10, pp. 51-58, (2014).
International Search Report and written opinion dated Jul. 16, 2021 for PCT application No. PCT/US2020/057539.
Lilienthal, G-M, et al., "Potential of murine IgG1 and human IgG4 to inhibit the classical complement and Fcγ receptor activation pathways", Frontiers in Immunology, vol. 9, article 958, pp. 1-9, (2018).
Kiyoshi M. et al., "Affinity improvement of a therapeutic antibody by structure-based computational design: generation of electrostatic interactions in the transition state stabilizes the antibody-antigen complex", PLOS ONE, vol. 9, issue 1, pp. 1-9, (2014).
Yamashita, K. et al., "Kotai antibody builder: automated high-resolution structural modeling of antibodies", Bioinofrmatics, vol. 30, No. 22, pp. 3279-3280, (2014).
Ye, J. et al., "IgBLAST: an immunoglobulin variable domain sequence analysis tool", Nucleic Acids Research, vol. 41, pp. W34-W40, (2013).
Esquivel, R.O. et al., "Decoding the building blocks of life from the perspective of quantum information", Advances in Quantum Mechanics, chapter 27, pp. 641-669, (2013).
Chilelli, N.C. et al., "AGEs, rather than hyperglycemia, are responsible for microvascular complications in diabetes: a "glycoxidation-centric" point of view", Nutrition, Metabolism & Cardiovascular Diseases, vol. 23, issue 10, pp. 913-919, (2013).
Palmer, A.K. et al., "Targeting senescent cells alleviates obesity-induced metabolic dysfunction", Aging Cell, vol. 18, pp. 1-15, (2019).
Thompson, P.J. et al., "Targeted elimination of senescent beta cells prevents type 1 diabetes", Cell Metabolism, vol. 29, pp. 1045-1060, (2019).
Bardeesy, N. et al., "Both p16$^{Ink4a}$ and the p19$^{Arf}$-p53 pathway constrain progression of pancreatic adenocarcinoma in the mouse", PNAS, vol. 103, No. 15, pp. 5947-5952, (2006).
Sharpless, N.E. et al., "The differential impact of P16$^{Ink4a}$ or p19$^{ARF}$ deficiency on cell growth and tumorigenesis", Oncogene, vol. 23, pp. 379-385, (2004).
Pan, Q., et al., "Blocking neuropilin-1 function has an additive effect with anti-VEGF to inhibit tumor growth", Cancer Cell, vol. 11, pp. 53-67, (2007).
Hung, L-F. et al., "Advanced glycation end products induce T cell apoptosis: Involvement of oxidative stress, capsase and the mitochondrial pathway", Mechanisms of Ageing and Development, vol. 131, pp. 682-691, (2010).
Son, S. et al., "Advanced glycation end products impair NLRP3 inflammasome-mediated innate immune responses in macrophages", Journal of Biological Chemistry, vol. 292, No. 50, pp. 20437-20448, (2017).
Farboud, B. et al., "Development of a polyclonal antibody with broad epitope specificity for advanced glycation endproducts and localization of these epitopes in bruch's membrane of the aging eye", Molecular Vision, vol. 5, No. 11, 6 pages, (1999).
Invitation to Pay Additional Fee and Partial International Search Report dated Aug. 13, 2021 PCT application No. PCT/US2021/030184.
Tamura, M. et al., "Structural correlates of an anticarcinoma antibody: Identification of specificity-determining residues (SDRs) and development of a minimally immunogenic antibody variant by retention of SDRs only", The Journal of Immunology, vol. 164, No. 3, pp. 1432-1441, (2000).
International Search Report and written opinion dated Oct. 18, 2021 for PCT application No. PCT/US2021/030184.
Yamamoto, Y. et al., "Advanced glycation endproducts-receptor interactions stimulate the growth of human pancreatic cancer cells through the induction of platelet-derived growth factor-B", Biochemical and Biophysical Research Communications, vol. 222, pp. 700-705, (1996).
Sellegounder, D. et al., "Advanced glycation end products (AGEs) and its receptor, RAGE, modulate age-dependent COVID-19 morbidity and mortality. A review and hypothesis", International Immunopharmacology, vol. 98, pp. 107806-1-107806-8, (2021).
International Search Report and written opinion dated Nov. 24, 2021 for PCT application No. PCT/US2021/034777.
Graham, F.L et al., "Characteristics of a human cell line transformed by DNA from human adenovirus type 5", Journal of General Virology, vol. 36, issue 1, pp. 59-74, (1977).
Munch, G. et al., "Advanced glycation endproducts and their pathogenic roles in neurological disorders", Amino Acids, vol. 42, No. 4, pp. 1221-1236, (2010).
Lin, J-A., et al., "Glycative stress from advanced glycation end products (AGEs) and dicarbonyls: An emerging biological factor in cancer onset and progression", Molecular Nutrition & Food Research, vol. 60, No. 8, pp. 1850-1864, (2016).
Muyldermans, S. et al., "Distinct antibody species: Structural differences creating therapeutic opportunities", Current Opinion in Immunology, vol. 40, pp. 7-13, (2016).
Rosenberg, C. et al., "Age is an important determinant in humoral and T cell responses to immunization with hepatitis B surface antigen", Human Vaccines & Immunotherapeutics, vol. 9, No. 7, pp. 1466-1476, (2013).
Choi, Y-G. et al., "Characterization of anti-advanced glycation end product antibodies to nonenzymatically lysine-derived and arginine-derived glycated products", Journal of Immunoassay and Immunochemistry, vol. 30, No. 4, pp. 386-399, (2009).
Kirkland, J.L. et al., "Senolytic drugs: from discovery to translation", Journal of Internal Medicine, vol. 288, No. 5, pp. 518-536, (2020).
Dunbar, J. et al., "SAbPred: a structure-based antibody prediction server", Nucleic Acids Research, vol. 44, Web Server Issue, pp. W474-W478, (2016).
Pedotti, M. et al., "Computational docking of antibody-antigen complexes, opportunities and pitfalls illustrated by influenza hemagglutinin", International Journal of Molecular Sciences, vol. 12, pp. 226-251, (2011).
Drevin, V.E. et al., "Biological age and methods for its determination", Volgograd State Agrarian University, Monograph, Volgograd, pp. 1-143, (2015).

(56) References Cited

OTHER PUBLICATIONS

Yabuuchi, J. et al., "Association of advanced glycation end products with sarcopenia and frailty in chronic kidney disease", Scientific Reports, pp. 1-12, (2020).
Zhang, C. et al., "FOXO1 mediates advanced glycation end products induced mouse osteocyte-like MLO-Y4 cell apoptosis and dysfunctions", Journal of Diabetes Research, vol. 2019, pp. 1-11, (2019).
Dubey, N.K et al., "Adipose-derived stem cells attenuates diabetic osteoarthritis via inhibition of glycation-mediated inflammatory cascade", Aging and Disease, vol. 10, No. 3, pp. 483-496, (2019).
Tanaka, K. et al., "$N_\varepsilon$-(carboxymethyl) lysine represses hair follicle formation by inhibiting sonic hedgehog expression in a NF-$_\kappa$B-independent manner", International Journal of Dermatology and Clinical Research, vol. 5, No. 1, pp. 006-011, (2019).
Bao, Z. et al., "$N_\varepsilon$-carboxymethyl-lysine negatively regulates foam cell migration via the vav1/rac1 pathway", Journal of Immunology Research, vol. 2020, pp. 1-10, (2020).
Upton, J.H. et al., "Oxidative stress-associated senescence in dermal papilla cells of men with androgenetic alopecia", Journal of Investigative Dermatology, vol. 135, pp. 1244-1252, (2015).
Waaijer, M.E.C. et al., "P16INK4a positive cells in human skin are indicative of local elastic fiber morphology, facial wrinkling, and perceived age", Journals of Gerontology: Biological Sciences, vol. 71, No. 8, pp. 1022-1028, (2016).
Scott, A.M. et al., "Antibody therapy of cancer", Nature Reviews, vol. 12, pp. 278-287, (2012).
Apr. 8, 2022, U.S. Appl. No. 16/077,713.
Mar. 18, 2022, U.S. Appl. No. 17/089,999.
Mar. 21, 2022, U.S. Appl. No. 16/610,473.
Mar. 21, 2022, U.S. Appl. No. 16/228,293.
Apr. 1, 2022, U.S. Appl. No. 16/077,713.
Apr. 11, 2022, U.S. Appl. No. 16/228,293.
Jun. 13, 2022, U.S. Appl. No. 17/089,999.
Jun. 22, 2022, U.S. Appl. No. 16/228,293.
Jun. 23, 2022, U.S. Appl. No. 15/977,587.
Jun. 27, 2022, U.S. Appl. No. 16/383,348.
Jun. 30, 2022, U.S. Appl. No. 16/265,875.
Jul. 6, 2022, U.S. Appl. No. 16/440,747.
Allen, T.M. et al., "Humanized immune system mouse models: progress, challenges and opportunities", Nature Immunology, vol. 20, No. 7, pp. 770-774, (2019).
Krtolica, A. et al., "Senescent fibroblasts promote epithelial cell growth and tumorigenesis: A link between cancer and aging", Proceedings of the National Academy of Science, vol. 98, No. 21, pp. 12072-12077, (2001).
Shaw, T.J. et al., "Wound-associated skin fibrosis: mechanisms and treatments based on modulating the inflammatory response", Endocrine, Metabolic & Immune Disorders—Drug Targets, vol. 10, No. 4, pp. 320-330, (2010). Abstract Only.
Bitterman, P.B. et al., "Fibroproliferative disorders", Chest, vol. 99, No. 3, pp. 81S-84S, (1991).
Pan, J. et al., "Inhibition of Bcl-2/xl with ABT-263 selectively kills senescent type II pneumocytes and reverses persistent pulmonary fibrosis induced by ionizing radiation in mice", International Journal of Radiation Oncology, vol. 99, No. 2, pp. 353-361, (2017).
Yilmaz, O. et al., "Dasatinib attenuated bleomycin-induced pulmonary fibrosis in mice", Growth Factors, pp. 1-10, (2015).
Kato, M. et al., "Dasatinib suppresses TGβ-induced epithelial mesenchymal transition and inhibits pulmonary fibrosis", European Respiratory Journal, vol. 44, pp. 1-4, (2014).
Yagmur, E. et al., "Elevation of Nε-(carboxymethyl)lysine-modified advanced glycation end products in chronic liver disease is an indicator of liver cirrhosis", Clinical Biochemistry, vol. 39, pp. 39-45, (2006).
Duffield, J.S., "Cellular and molecular mechanisms in kidney fibrosis", The Journal of Clinical Investigation, vol. 124, No. 6, pp. 2299-2306, (2014).
Weiler-Normann, C. et al., "Mouse models of liver fibrosis", Z Gastroenterol, vol. 45, pp. 43-50, (2007).

Midgley, A.C. et al., "Transforming growth factor-β1 (TGF-⊕1)-stimulated fibroblast to myofibroblast differentiation is mediated by hyaluronan (HA)-facilitated epidermal growth factor receptor (EGFR) and CD44 co-localization in lipid rafts", The Journal of Biological Chemistry, vol. 288, No. 21, pp. 14824-14838, (2013).
Schafer, M.J. et al., "Cellularsenescence mediated fibrotic pulmonary disease", Nature Communications, vol. 8, pp. 1-11, (2017).
Harris, W.T. et al., "Myofibroblast differentiation and enhanced Tgf-B signaling in cystic fibrosis lung disease", PLOS ONE, vol. 8, issue 8, pp. 1-8, (2013).
Bataller, R. et al., "Liver fibrosis", The Journal of Clinical Investigation, vol. 115, No. 2, pp. 209-218, (2005).
Wynn, T.A., "Fibrotic disease and the $T_H1/T_H2$ paradigm", Nature Reviews Immunology, vol. 4, No. 8, pp. 583-594, (2004).
Calhoun, C. et al., "Senescent cells contribute to the physiological remodeling of aged lungs", Journals of Gerontology: Biological Sciences, vol. 71, No. 2, pp. 153-160, (2016).
"About PF", The Pulmonary Fibrosis Foundation, pp. 1-9, printed on Jul. 18, 2017.
Definition of "Idiopathic pulmonary fibrosis" printed from Wikipedia, the free encyclopedia on Aug. 4, 2014 found at http://en.wikipedia.org/wiki/Idiopathic_pulmonary_fibrosis.
Definition of "Epithelial-mesenchymal transition" printed from Wikipedia, the free encyclopedia on Apr. 4, 2010 found at http://en.wikipedia.org/wiki/Epithelial-mesenchymal_transition.
Definition of "Pulmonary fibrosis" printed from Wikipedia, the free encyclopedia on Mar. 27, 2022 found at http://en.wikipedia.org/wiki/Pulmonary_fibrosis.
Mayo Clinic Staff, "Myelofibrosis", Mayo Clinic, pp. 1-2, (2017).
Bristol-Myers Squibb, "Safety evaluation of Dasatinib in subjects with scleroderma pulmonary fibrosis", Clinical Trials, 12 pages, (2012).
University of Michigan, "Beneficial effects of quercetin in chronic obstructive pulmonary disease (COPP) (Quercetin)", Clinical Trials, 14 pages, (2012).
Wake Forest University Health Sciences, "Targeting proinflammatory cells in idiopathic pulmonary fibrosis: a human trial (IPF)", Clinical Trials, 7 pages, (2017).
Scleroderma Research Foundation, "For patients, current treatments available for scleroderma patients", Scleroderma Research Foundation, pp. 1-2, printed on Feb. 26, 2018.
"Scleroderma, What is it?", National Institute of Arthritis and Musculoskeletal and Skin Diseases, pp. 1-8, printed on Feb. 26, 2018.
Definition of "Progeroid syndromes" printed from Wikipedia, the free encyclopedia on May 25, 2022 found at http://en.wikipedia.org/wiki/Progeroid_syndromes.
Haddadi, G.H. et al., "Hesperidin as radioprotector against radiation-induced lung damage in rat: A histopathological study", Journal of Medical Physics, vol. 42, No. 1, pp. 25-32, (2017).
Wilgus, T.A. et al., "Regulation of scar formation by vascular endothelial growth factor", Laboratory Investigation, vol. 88, pp. 579-590, (2008).
Leeman, K.T. et al., "Lung stem and progenitor cells in tissue homeostasis and disease", Current Topics in Developmental Biology, vol. 107, pp. 207-233, (2014).
Shaw, J.N. et al., "$N^\varepsilon$-(carbosymethyl)lysine (CML) as a biomarker of oxidative stress in long-lived tissue proteins", Methods in Molecular Biology, vol. 186, pp. 129-137, (2002).
Palmer, J.L. et al., "Combined radiation and burn injury results in exaggerated early pulmonary inflammation", Radiation Research, vol. 180, No. 3, pp. 276-283, (2013).
Meng, A. et al., "Ionizing radiation and busulfan induce premature senescence in murine bone marrow hematopoietic cells", Cancer Research, vol. 63, pp. 5414-5419, (2003).
Formenti, S.C. et al., "Combining radiotherapy and cancer immunotherapy: A paradigm shift", Journal of the National Cancer Institute, vol. 105, issue 4, pp. 256-265, (2013).
Flament, F. et al., "Effect of the sun on visible clinical signs of aging in Caucasian skin", Clinical, Cosmetic and Investigational Dermatology, vol. 6, pp. 221-232, (2013).
Richardson, R.B. et al., "Ionizing radiation and aging: rejuvenating an old idea", Aging, vol. 1, No. 11, pp. 887-902, (2009).

(56) References Cited

OTHER PUBLICATIONS

Rohani, A. et al., "A case control study of cardiovascular health in chemical war disabled Iranian victims", Indian Journal of Critical Care Medicine, vol. 14, No. 3, pp. 109-112, (2010).
Cupit-Link, M.C. et al., "Biology of premature ageing in survivors of cancer", ESMO Open Cancer Horizons, vol. 2, pp. 1-8, (2017).
Smith, R.L. et al., "Premature and accelerated aging: HIV or HAART?", Frontiers in Genetics, vol. 3, article 328, pp. 1-10, (2013).
Zota, A.R. et al., "Associations of cadmium and lead exposure with leukocyte telomere length: Finding from National Health and Nutrition Examination Survey, 1999-2002", American Journal of Epidemiology, vol. 181, No. 2, pp. 127-136, (2015).
White S.S. et al., "An overview of the effects of dioxins and dioxin-like compounds on vertebrates, as documented in human and ecological epidemiology", Journal of Environmental Science and Health, Part C, Environmental Carcinogenesis and Ecotoxicology Reviews, vol. 27, No. 4, pp. 197-211, (2009).
Ribas, J. et al., "Biomechanical strain exacerbates inflammation on a progeria-on-a-chip model", Small, vol. 13, issue 15, pp. 1-3, (2017). Abstract Only.
D'Orazio, J. et al., "UV radiation and the skin", International Journal of Molecular Sciences, vol. 14, pp. 12222-12248, (2013).
Eisenreich, W. et al., "How viral and intracellular bacterial pathogens reprogram the metabolism of host cells to allow their intracellular replication", Frontiers in Cellular and Infection Microbiology, vol. 9, article 42, pp. 1-24, (2019).
Mayer, K.A. et al., "Hijacking the supplies: Metabolism as a novel facet of virus-host interaction", Frontiers in Immunology, vol. 10, article 1533, pp. 1-9, (2019).
"Covid-19: novel coronavirus, tackling coronavirus with WP1122", Moleculin, pp. 1-10, found at www.moleculin.com/covid-19/, (2020).
Wei, C. et al., "uPAR isoform 2 forms a dimer and induces severe kidney disease in mice", The Journal of Clinical Investigation, vol. 129, No. 5, pp. 1946-1959, (2019).
Wei, C. et al., "Circulating CD40 autoantibody and suPAR synergy drives glomerular injury". Annals of Translational Medicine, vol. 3, No. 19, pp. 1-5, (2015).
Reiser, J., "A humanized mouse model of FSGS", Rush University Medical Center, pp. 1-3, printed on Apr. 10, 2020.
Tanji, N. et al., "Expression of advanced glycation end product and their cellular receptor RAGE in diabetic nephropathy and nondiabetic renal disease", Journal of the American Society of Nephrology, vol. 11, No. 9, pp. 1656-1666, (2000).
Oldfield, M.D. et al., "Advanced glycation end products cause epithelial-myofibroblast transdifferentiation via the receptor for advanced glycation end products (RAGE)", The Journal of Clinical Investigation, vol. 108, No. 12, pp. 1853-1863, (2001).
Suzuki, D. et al., "Immunohistochemical evidence for an increased oxidative stress and carbonyl modification of proteins in diabetic glomerular lesions", Journal of the American Society of Nephrology, vol. 10, pp. 822-832, (1999).
Horie, K. et al., "Immunohistochemical colocalization of glycoxidation products and lipid peroxidation products in diabetic renal glomerular lesions. Implication for glycoxidative stress in the pathogenesis of diabetic nephropathy", The Journal of Clinical Investigation, vol. 100, No. 12, pp. 2995-3004, (1997).
Kushiro, M. et al., "Accumulation of Nsigma-(carboxymethyl)lysine and changes in glomerular extracellular matrix components in Otsuka long-evans tokushima fatty rat: A model of spontaneous NIDDM", Nephron, vol. 79, No. 4, pp. 458-468, (1998). Abstract Only.
Valentijn, F.A. et al., "Cellular senescence in the aging and diseased kidney", Journal of Cell Communication and Signaling, vol. 12, No. 1, pp. 69-82, (2018).
Wang, W-J. et al., "Cellular senescence, senescence-associated secretory phenotype, and chronic kidney disease", Oncotarget, vol. 8, No. 38, pp. 64520-64533, (2017).
DiCarlo, A.L. et al., "Aging in the context of immunological architecture, function and disease outcomes", Trends in Immunology, vol. 30, No. 7, pp. 293-294, (2009).
Stortz, J.A. et al., "Old mice demonstrate organ dysfunction as well as prolonged inflammation, Immunosuppression, and weight loss in a modified surgical sepsis model", Critical Care Medicine, vol. 47, No. 11, pp. e919-e929, (2019).
Cannizzo, E.S. et al., "Oxidative stress, inflamm-aging and immunosenescence", Journal of Proteomics, vol. 74, issue 11, pp. 2313-2323, (2011).
Bourke, C.D. et al., "Immune dysfunction as a cause and consequence of malnutrition", Trends in Immunology, vol. 3 7, No. 6, pp. 386-398, (2016).
Aranow, C., "Vitamin D and the immune system", Journal of Investigative Medicine, vol. 59, No. 6, pp. 881-886, (2011).
Taneja, V., "Sex hormones determine immune response", Frontiers in Immunology, vol. 9, article 1931, pp. 1-5, (2018).
Bryant, P.A. et al., "Sick and tired: does sleep have a vital role in the immune system?", Nature Reviews Immunology, vol. 4, pp. 457-467, (2004).
Aw, D. et al., "Immunosenescence: emerging challenges for an ageing population", Immunology, vol. 120, pp. 435-446, (2007).
Traore, K. et al., "Do advanced glycation end-products play a role in malaria susceptibility?", Parasite, vol. 23, No. 15, pp. 1-10, (2016).
Duggal, N.A. et al., "Major features of immunesenescence, including reduced thymic output, are ameliorated by high levels of physical activity in adulthood", Aging Cell, vol. 17, No. 2, pp. 1-13, (2018).
Montecino-Rodriguez, E. et al., "Causes, consequences, and reversal of immune system aging", The Journal of Clinical Investigation, vol. 123, No. 3, pp. 958-965, (2013).
Desai, S. et al., "Early immune senescence in HIV disease", Current HIV/AIDS Reports, vol. 7, No. 1, pp. 4-10, (2010).
Vivier, E., et al., "Innate or adaptive immunity? The example of natural killer cells", Science, vol. 331, No. 6013, pp. 44-49, (2011).
Kvell, K., "Thymic senescence", In tech open, pp. 1-11, found at http://dx.doi.org/10.5772/intechopen.87063, (2019).
Palmer, S. et al., "Thymic involution and rising disease incidence with age", Proceedings of the National Academy of Science, vol. 115, No. 8, pp. 1883-1888, (2018).
Wertheimer, T. et al., "Production of BMP4 by endothelial cells is crucial for endogenous thymic regeneration", Science Immunology, vol. 3, No. 19, pp. 1-11, (2018).
"Oxidative stress and cellular senescence in age-related thymic involution", Fight Aging!, pp. 1-4, found at www.fightaging.org/archives/2020/03/oxidative-stress-and-cellular-senescence-in-age-related-thymic-involution/,(2020).
Barbouti, A. et al., "Implications of oxidative stress and cellular senescence in age-related thymus involution", Oxidative Medicine and Cellular Longevity, vol. 2020, article ID 7986071, pp. 1-14, (2020).
El-Torky, M. et al., "Collagens in scar carcinoma of the lung", The American Journal of Pathology, vol. 121 No. 2, pp. 322-326, (1985).
Jul. 29, 2022, U.S. Appl. No. 17/089,999.
Aug. 2, 2022, U.S. Appl. No. 16/228,293.
Aug. 18, 2022, U.S. Appl. No. 16/092,743.
Sep. 21, 2022, U.S. Appl. No. 16/610,473.
Extended European Search Report dated Sep. 2, 2022 for European application No. 22157145.8-1111, 22 pages.
Johmura, Y. et al., "Senolysis by glutaminolysis inhibition ameliorates various age-associated disorders", Science, vol. 371, pp. 265-270, (2021).
Toullec, A. et al., "Oxidative stress promotes myofibroblast differentiation and tumour spreading", EMBO Molecular Medicine, vol. 2, pp. 211-230, (2010).
Oya, T. et al., "Methylglyoxal modification of protein", The Journal of Biological Chemistry, vol. 274, No. 26, pp. 18492-18502, (1999).
Oct. 12, 2022, U.S. Appl. No. 16/228,293.
Oct. 12, 2022, U.S. Appl. No. 17/089,999.
Oct. 14, 2022, U.S. Appl. No. 15/977,587.

\* cited by examiner

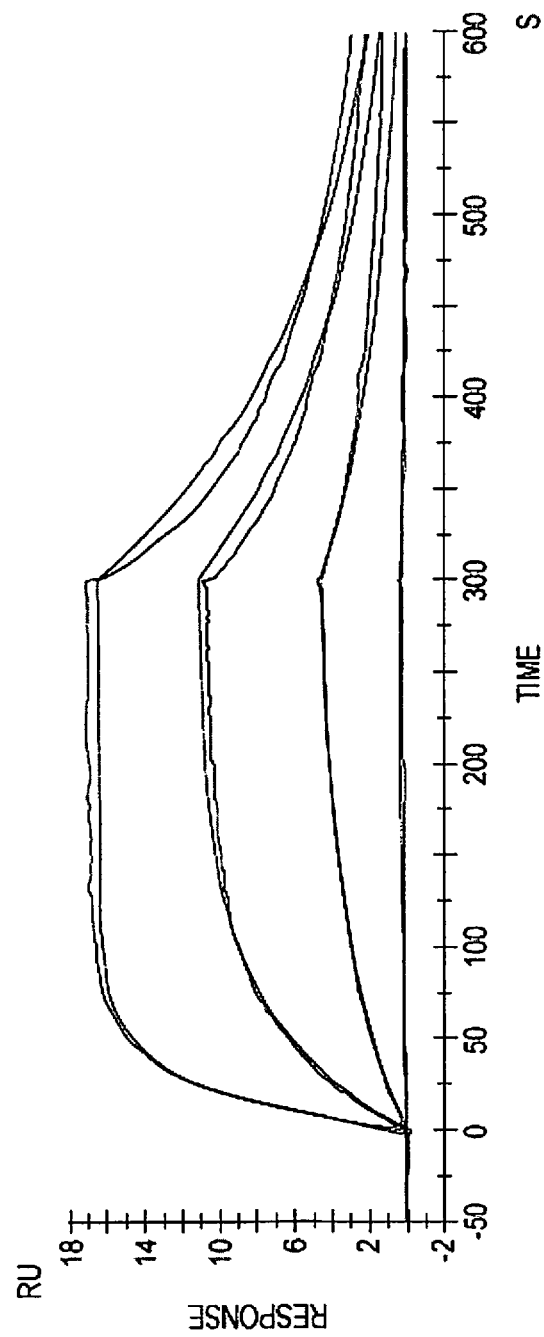

SEQUENCE LISTING

```
<160> NUMBER OF SEQ ID NOS: 66

<210> SEQ ID NO 1
<211> LENGTH: 463
<212> TYPE: PRT
<213> ORGANISM: Artificial sequence
<220> FEATURE:
<223> OTHER INFORMATION: Modified Homo sapiens immunoglobulin G1 heavy
      chain

<400> SEQUENCE: 1

Met Asn Leu Leu Leu Ile Leu Thr Phe Val Ala Ala Val Ala Gln
1               5                   10                  15

Val Gln Leu Leu Gln Pro Gly Ala Glu Leu Val Lys Pro Gly Ala Ser
                20                  25                  30

Val Lys Leu Ala Cys Lys Ala Ser Gly Tyr Leu Phe Thr Thr Tyr Trp
            35                  40                  45

Met His Trp Leu Lys Gln Arg Pro Gly Gln Gly Leu Glu Trp Ile Gly
    50                  55                  60

Glu Ile Ser Pro Thr Asn Gly Arg Ala Tyr Tyr Asn Ala Arg Phe Lys
65                  70                  75                  80

Ser Glu Ala Thr Leu Thr Val Asp Lys Ser Ser Asn Thr Ala Tyr Met
                85                  90                  95
```

```
Gln Leu Ser Ser Leu Thr Ser Glu Ala Ser Ala Val Tyr Tyr Cys Ala
                100                 105                 110

Arg Ala Tyr Gly Asn Tyr Glu Phe Ala Tyr Trp Gly Gln Gly Thr Leu
            115                 120                 125

Val Thr Val Ser Val Ala Ser Thr Lys Gly Pro Ser Val Phe Pro Leu
        130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
450                 455                 460

<210> SEQ ID NO 2
<211> LENGTH: 118
<212> TYPE: PRT
<213> ORGANISM: Mus musculus

<400> SEQUENCE: 2

Gln Val Gln Leu Leu Gln Pro Gly Ala Glu Leu Val Lys Pro Gly Ala
1               5                   10                  15
```

```
Ser Val Lys Leu Ala Cys Lys Ala Ser Gly Tyr Leu Phe Thr Thr Tyr
         20                  25                  30

Trp Met His Trp Leu Lys Gln Arg Pro Gly Gln Gly Leu Glu Trp Ile
         35                  40                  45

Gly Glu Ile Ser Pro Thr Asn Gly Arg Ala Tyr Tyr Asn Ala Arg Phe
50                   55                  60

Lys Ser Glu Ala Thr Leu Thr Val Asp Lys Ser Ser Asn Thr Ala Tyr
65                   70                  75                  80

Met Gln Leu Ser Ser Leu Thr Ser Glu Ala Ser Ala Val Tyr Tyr Cys
                 85                  90                  95

Ala Arg Ala Tyr Gly Asn Tyr Glu Phe Ala Tyr Trp Gly Gln Gly Thr
             100                 105                 110

Leu Val Thr Val Ser Val
         115

<210> SEQ ID NO 3
<211> LENGTH: 234
<212> TYPE: PRT
<213> ORGANISM: Artificial sequence
<220> FEATURE:
<223> OTHER INFORMATION: Modified Homo sapiens immunoglobulin G1 kappa
      light chain

<400> SEQUENCE: 3

Met Asn Leu Leu Leu Ile Leu Thr Phe Val Ala Ala Ala Val Ala Asp
1               5                   10                  15

Val Val Met Thr Gln Thr Pro Leu Ser Leu Pro Val Ser Leu Gly Asp
             20                  25                  30

Gln Ala Ser Ile Ser Cys Arg Ser Gln Ser Leu Val Asn Ser Asn
         35                  40                  45

Gly Asn Thr Phe Leu Gln Trp Tyr Leu Gln Lys Pro Gly Gln Ser Pro
50                  55                  60

Lys Leu Leu Ile Tyr Lys Val Ser Leu Arg Phe Ser Gly Val Pro Asp
65                  70                  75                  80

Arg Phe Ser Gly Ser Gly Ser Gly Thr Asp Phe Thr Leu Lys Ile Ser
                85                  90                  95

Arg Val Glu Ala Glu Asp Leu Gly Leu Tyr Phe Cys Ser Gln Ser Thr
            100                 105                 110

His Val Pro Pro Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230
```

```
<210> SEQ ID NO 4
<211> LENGTH: 113
<212> TYPE: PRT
<213> ORGANISM: Mus musculus

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val Asn Ser
            20                  25                  30

Asn Gly Asn Thr Phe Leu Gln Trp Tyr Leu Gln Lys Pro Gly Gln Ser
        35                  40                  45

Pro Lys Leu Leu Ile Tyr Lys Val Ser Leu Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Pro Thr Phe Gly Gly Gly Thr Lys Leu Glu Ile Lys
            100                 105                 110

Arg

<210> SEQ ID NO 5
<211> LENGTH: 327
<212> TYPE: PRT
<213> ORGANISM: Equus caballus

<400> SEQUENCE: 5

Ala Ser Thr Thr Ala Pro Lys Val Phe Pro Leu Ala Ser His Ser Ala
1               5                   10                  15

Ala Thr Ser Gly Ser Thr Val Ala Leu Gly Cys Leu Val Ser Ser Tyr
            20                  25                  30

Phe Pro Glu Pro Val Thr Val Ser Trp Asn Ser Gly Ala Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ala Ser Ser Leu Lys Ser Gln Thr
65                  70                  75                  80

Tyr Ile Cys Asn Val Ala His Pro Ala Ser Ser Thr Lys Val Asp Lys
                85                  90                  95

Lys Ile Val Ile Lys Glu Cys Asn Gly Gly Cys Pro Ala Glu Cys Leu
            100                 105                 110

Gln Val Gly Pro Ser Val Phe Ile Phe Pro Pro Lys Pro Lys Asp Val
            115                 120                 125

Leu Met Ile Ser Arg Thr Pro Thr Val Thr Cys Val Val Asp Val
    130                 135                 140

Gly His Asp Phe Pro Asp Val Gln Phe Asn Trp Tyr Val Asp Gly Val
145                 150                 155                 160

Glu Thr His Thr Ala Thr Thr Glu Pro Lys Gln Glu Gln Phe Asn Ser
                165                 170                 175

Thr Tyr Arg Val Val Ser Val Leu Pro Ile Gln His Lys Asp Trp Leu
            180                 185                 190

Ser Gly Lys Glu Phe Lys Cys Lys Val Asn Asn Lys Ala Leu Pro Ala
        195                 200                 205

Pro Val Glu Arg Thr Ile Ser Lys Pro Thr Gly Gln Pro Arg Glu Pro
    210                 215                 220
```

-continued

```
Gln Val Tyr Val Leu Ala Pro His Arg Asp Glu Leu Ser Lys Asn Lys
225                 230                 235                 240

Val Ser Val Thr Cys Leu Val Lys Asp Phe Tyr Pro Thr Asp Ile Asp
            245                 250                 255

Ile Glu Trp Lys Ser Asn Gly Gln Pro Glu Pro Glu Thr Lys Tyr Ser
        260                 265                 270

Thr Thr Pro Ala Gln Leu Asp Ser Asp Gly Ser Tyr Phe Leu Tyr Ser
    275                 280                 285

Lys Leu Thr Val Glu Thr Asn Arg Trp Gln Gln Gly Thr Thr Phe Thr
290                 295                 300

Cys Ala Val Met His Glu Ala Leu His Asn His Tyr Thr Glu Lys Ser
305                 310                 315                 320

Val Ser Lys Ser Pro Gly Lys
                325

<210> SEQ ID NO 6
<211> LENGTH: 415
<212> TYPE: PRT
<213> ORGANISM: Equus caballus

<400> SEQUENCE: 6

Ser Leu Glu Asp Thr Ala Val Ile Pro Leu Phe Ser Glu Cys Lys Ala
1               5                   10                  15

Pro Lys Glu Asp Val Val Ser Leu Ala Cys Leu Val Lys Gly Tyr
            20                  25                  30

Phe Pro Glu Pro Val Gln Val Thr Trp Glu Pro Glu Met Gln Asn Gln
        35                  40                  45

Lys Pro Trp Thr Phe Pro Ala Met Lys Lys Gly Gln Glu Tyr Ile His
    50                  55                  60

Val Phe Ser Leu Thr Thr Trp Trp Lys Pro Gly Ser His Ser Cys Thr
65                  70                  75                  80

Val His His Lys Ala Ser Ser Phe Arg Lys Lys Met Thr Phe Gln Glu
                85                  90                  95

Pro Ala Ser Trp Ala Pro Gln Arg Thr Ser Ala Leu Pro Val Thr Ser
            100                 105                 110

Lys Glu Pro Thr Pro Ala Pro Thr Thr Leu Arg Lys Ser Glu Pro Ser
        115                 120                 125

Thr Arg His Thr Gln Pro Glu Thr Gln Lys Pro Arg Ile Pro Val Asp
    130                 135                 140

Thr Pro Leu Lys Glu Cys Gln Ser His Thr His Pro Pro Ser Ile Tyr
145                 150                 155                 160

Leu Leu His Pro Pro Leu Gln Gly Leu Trp Leu Lys Gly Glu Ala Thr
                165                 170                 175

Phe Thr Cys Leu Val Val Gly Asp Asp Leu Lys Asp Ala His Leu Ser
            180                 185                 190

Trp Glu Leu Ser Glu Arg Ser Asn Gly Met Phe Val Glu Ser Gly Pro
        195                 200                 205

Leu Glu Lys His Thr Asn Gly Ser Gln Ser Arg Ser Arg Leu Ala
    210                 215                 220

Leu Pro Arg Ser Ser Trp Ala Met Gly Thr Ser Val Thr Cys Lys Leu
225                 230                 235                 240

Ser Tyr Pro Asn Leu Leu Ser Ser Met Glu Val Val Gly Leu Lys Glu
                245                 250                 255

His Ala Ala Ser Ala Pro Arg Ser Leu Thr Val His Ala Leu Thr Thr
```

```
                    260                 265                 270
Pro Gly Leu Asn Ala Ser Pro Gly Ala Thr Ser Trp Leu Gln Cys Lys
                275                 280                 285

Val Ser Gly Phe Ser Pro Pro Glu Ile Val Leu Thr Trp Leu Glu Gly
            290                 295                 300

Gln Arg Glu Val Asp Pro Ser Trp Phe Ala Thr Ala Arg Pro Thr Ala
305                 310                 315                 320

Gln Pro Gly Asn Thr Thr Phe Gln Thr Trp Ser Ile Leu Leu Val Pro
                325                 330                 335

Thr Ile Pro Gly Pro Pro Thr Ala Thr Tyr Thr Cys Val Val Gly His
            340                 345                 350

Glu Ala Ser Arg Gln Leu Leu Asn Thr Ser Trp Ser Leu Asp Thr Gly
            355                 360                 365

Gly Leu Ala Met Thr Pro Glu Ser Lys Asp Glu Asn Ser Asp Asp Tyr
        370                 375                 380

Ala Asp Leu Asp Asp Ala Gly Ser Leu Trp Leu Thr Phe Met Ala Leu
385                 390                 395                 400

Phe Leu Ile Thr Leu Leu Tyr Ser Gly Phe Val Thr Phe Ile Lys
                405                 410                 415

<210> SEQ ID NO 7
<211> LENGTH: 334
<212> TYPE: PRT
<213> ORGANISM: Canis familiaris

<400> SEQUENCE: 7

Ser Lys Thr Ser Pro Ser Val Phe Pro Leu Ser Leu Cys His Gln Glu
1               5                   10                  15

Ser Glu Gly Tyr Val Val Ile Gly Cys Leu Val Gln Gly Phe Phe Pro
            20                  25                  30

Pro Glu Pro Val Asn Val Thr Trp Asn Ala Gly Lys Asp Ser Thr Ser
        35                  40                  45

Val Lys Asn Phe Pro Pro Met Lys Ala Ala Thr Gly Ser Leu Tyr Thr
50                  55                  60

Met Ser Ser Gln Leu Thr Leu Pro Ala Ala Gln Cys Pro Asp Asp Ser
65                  70                  75                  80

Ser Val Lys Cys Gln Val Gln His Ala Ser Ser Pro Ser Lys Ala Val
                85                  90                  95

Ser Val Pro Cys Lys Asp Asn Ser His Pro Cys His Pro Cys Pro Ser
            100                 105                 110

Cys Asn Glu Pro Arg Leu Ser Leu Gln Lys Pro Ala Leu Glu Asp Leu
        115                 120                 125

Leu Leu Gly Ser Asn Ala Ser Leu Thr Cys Thr Leu Ser Gly Leu Lys
130                 135                 140

Asp Pro Lys Gly Ala Thr Phe Thr Trp Asn Pro Ser Lys Gly Lys Glu
145                 150                 155                 160

Pro Ile Gln Lys Asn Pro Glu Arg Asp Ser Cys Gly Cys Tyr Ser Val
                165                 170                 175

Ser Ser Val Leu Pro Gly Cys Ala Asp Pro Trp Asn His Gly Asp Thr
            180                 185                 190

Phe Ser Cys Thr Ala Thr His Pro Glu Ser Lys Ser Pro Ile Thr Val
        195                 200                 205

Ser Ile Thr Lys Thr Thr Glu His Ile Pro Pro Gln Val His Leu Leu
210                 215                 220
```

```
Pro Pro Pro Ser Glu Glu Leu Ala Leu Asn Glu Leu Val Thr Leu Thr
225                 230                 235                 240

Cys Leu Val Arg Gly Phe Lys Pro Lys Asp Val Leu Val Arg Trp Leu
                245                 250                 255

Gln Gly Thr Gln Glu Leu Pro Gln Glu Lys Tyr Leu Thr Trp Glu Pro
            260                 265                 270

Leu Lys Glu Pro Asp Gln Thr Asn Met Phe Ala Val Thr Ser Met Leu
        275                 280                 285

Arg Val Thr Ala Glu Asp Trp Lys Gln Gly Lys Phe Ser Cys Met
        290                 295                 300

Val Gly His Glu Ala Leu Pro Met Ser Phe Thr Gln Lys Thr Ile Asp
305                 310                 315                 320

Arg Leu Ala Gly Lys Pro Thr His Val Asn Val Ser Val Val
                325                 330

<210> SEQ ID NO 8
<211> LENGTH: 426
<212> TYPE: PRT
<213> ORGANISM: Canis familiaris

<400> SEQUENCE: 8

Thr Ser Gln Asp Leu Ser Val Phe Pro Leu Ala Ser Cys Cys Lys Asp
1               5                   10                  15

Asn Ile Ala Ser Thr Ser Val Thr Leu Gly Cys Leu Val Thr Gly Tyr
            20                  25                  30

Leu Pro Met Ser Thr Thr Val Thr Trp Asp Thr Gly Ser Leu Asn Lys
        35                  40                  45

Asn Val Thr Thr Phe Pro Thr Thr Phe His Glu Thr Tyr Gly Leu His
    50                  55                  60

Ser Ile Val Ser Gln Val Thr Ala Ser Gly Lys Trp Ala Lys Gln Arg
65                  70                  75                  80

Phe Thr Cys Ser Val Ala His Ala Glu Ser Thr Ala Ile Asn Lys Thr
                85                  90                  95

Phe Ser Ala Cys Ala Leu Asn Phe Ile Pro Pro Thr Val Lys Leu Phe
            100                 105                 110

His Ser Ser Cys Asn Pro Val Gly Asp Thr His Thr Thr Ile Gln Leu
        115                 120                 125

Leu Cys Leu Ile Ser Gly Tyr Val Pro Gly Asp Met Glu Val Ile Trp
    130                 135                 140

Leu Val Asp Gly Gln Lys Ala Thr Asn Ile Phe Pro Tyr Thr Ala Pro
145                 150                 155                 160

Gly Thr Lys Glu Gly Asn Val Thr Ser Thr His Ser Glu Leu Asn Ile
                165                 170                 175

Thr Gln Gly Glu Trp Val Ser Gln Lys Thr Tyr Thr Cys Gln Val Thr
            180                 185                 190

Tyr Gln Gly Phe Thr Phe Lys Asp Glu Ala Arg Lys Cys Ser Glu Ser
        195                 200                 205

Asp Pro Arg Gly Val Thr Ser Tyr Leu Ser Pro Pro Ser Pro Leu Asp
    210                 215                 220

Leu Tyr Val His Lys Ala Pro Lys Ile Thr Cys Leu Val Val Asp Leu
225                 230                 235                 240

Ala Thr Met Glu Gly Met Asn Leu Thr Trp Tyr Arg Glu Ser Lys Glu
                245                 250                 255

Pro Val Asn Pro Gly Pro Leu Asn Lys Lys Asp His Phe Asn Gly Thr
            260                 265                 270
```

```
Ile Thr Val Thr Ser Thr Leu Pro Val Asn Thr Asn Asp Trp Ile Glu
            275                 280                 285

Gly Glu Thr Tyr Tyr Cys Arg Val Thr His Pro His Leu Pro Lys Asp
            290                 295                 300

Ile Val Arg Ser Ile Ala Lys Ala Pro Gly Lys Arg Ala Pro Pro Asp
305                 310                 315                 320

Val Tyr Leu Phe Leu Pro Pro Glu Glu Gln Gly Thr Lys Asp Arg
            325                 330                 335

Val Thr Leu Thr Cys Leu Ile Gln Asn Phe Phe Pro Ala Asp Ile Ser
            340                 345                 350

Val Gln Trp Leu Arg Asn Asp Ser Pro Ile Gln Thr Asp Gln Tyr Thr
            355                 360                 365

Thr Thr Gly Pro His Lys Val Ser Gly Ser Arg Pro Ala Phe Phe Ile
            370                 375                 380

Phe Ser Arg Leu Glu Val Ser Arg Val Asp Trp Glu Gln Lys Asn Lys
385                 390                 395                 400

Phe Thr Cys Gln Val Val His Glu Ala Leu Ser Gly Ser Arg Ile Leu
            405                 410                 415

Gln Lys Trp Val Ser Lys Thr Pro Gly Lys
            420                 425

<210> SEQ ID NO 9
<211> LENGTH: 335
<212> TYPE: PRT
<213> ORGANISM: Felis catus

<400> SEQUENCE: 9

Ala Ser Thr Thr Ala Ser Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
            35                  40                  45

Gly Val His Thr Phe Pro Ser Val Leu Gln Ala Ser Gly Leu Tyr Ser
        50                  55                  60

Leu Ser Ser Met Val Thr Val Pro Ser Ser Arg Trp Leu Ser Asp Thr
65                  70                  75                  80

Phe Thr Cys Asn Val Ala His Arg Pro Ser Thr Lys Val Asp Lys
            85                  90                  95

Thr Val Pro Lys Thr Ala Ser Thr Ile Glu Ser Lys Thr Gly Glu Gly
            100                 105                 110

Pro Lys Cys Pro Val Pro Glu Ile Pro Gly Ala Pro Ser Val Phe Ile
            115                 120                 125

Phe Pro Pro Lys Pro Lys Asp Thr Leu Ser Ile Ser Arg Thr Pro Glu
            130                 135                 140

Val Thr Cys Leu Val Val Asp Leu Gly Pro Asp Asp Ser Asn Val Gln
145                 150                 155                 160

Ile Thr Trp Phe Val Asp Asn Thr Glu Met His Thr Ala Lys Thr Arg
            165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Ala Met Glu Arg Thr Ile Ser Lys
```

-continued

```
                210                 215                 220
Ala Lys Gly Gln Pro His Glu Pro Gln Val Tyr Val Leu Pro Pro Thr
225                 230                 235                 240

Gln Glu Glu Leu Ser Glu Asn Lys Val Ser Val Thr Cys Leu Ile Lys
                245                 250                 255

Gly Phe His Pro Pro Asp Ile Ala Val Glu Trp Glu Ile Thr Gly Gln
            260                 265                 270

Pro Glu Pro Glu Asn Asn Tyr Gln Thr Thr Pro Pro Gln Leu Asp Ser
        275                 280                 285

Asp Gly Thr Tyr Phe Leu Tyr Ser Arg Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335
```

<210> SEQ ID NO 10
<211> LENGTH: 96
<212> TYPE: PRT
<213> ORGANISM: Camelus dromedarius

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Arg Glu Arg Glu Gly Val
        35                  40                  45

Ala Ala Ile Asn Ser Gly Gly Gly Ser Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95
```

<210> SEQ ID NO 11
<211> LENGTH: 96
<212> TYPE: PRT
<213> ORGANISM: Camelus dromedarius

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ser Thr Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Met Leu Tyr
65                  70                  75                  80

Leu Gln Met Asn Ser Leu Lys Pro Glu Asp Thr Ala Met Tyr Tyr Cys
                85                  90                  95
```

<210> SEQ ID NO 12
<211> LENGTH: 1434
<212> TYPE: DNA

<213> ORGANISM: Artificial sequence
<220> FEATURE:
<223> OTHER INFORMATION: Murine anti-AGE IgG2b heavy chain

<400> SEQUENCE: 12

| | |
|---|---|
| atggacccca agggcagcct gagctggaga atcctgctgt tcctgagcct ggccttcgag | 60 |
| ctgagctacg ccaggtgca gctgctgcag ccaggtgccg agctcgtgaa acctggcgcc | 120 |
| tctgtgaagc tggcctgcaa ggcttccggc tacctgttca ccacctactg gatgcactgg | 180 |
| ctgaagcaga ggccaggcca gggcctggaa tggatcggcg atatctcccc caccaacggc | 240 |
| agagcctact acaacgcccg gttcaagtcc gaggccaccc tgaccgtgga caagtcctcc | 300 |
| aacaccgcct acatgcagct gtcctccctg acctctgagg cctccgccgt gtactactgc | 360 |
| gccagagctt acggcaacta cgagttcgcc tactggggcc agggcaccct cgtgacagtg | 420 |
| tctgtggcta agaccacccc tcccctcgtg taccctctgg ctcctggctg tggcgacacc | 480 |
| accggatcct ctgtgaccct gggctgcctc gtgaagggct acttccctga gtccgtgacc | 540 |
| gtgacctgga actccggctc cctgtcctcc tccgtgcaca cctttccagc cctgctgcag | 600 |
| tccggcctgt acaccatgtc ctccagcgtg acagtgccct cctccacctg gccttcccag | 660 |
| accgtgacat gctctgtggc ccaccctgcc tcttccacca ccgtggacaa gaagctggaa | 720 |
| ccctccggcc ccatctccac catcaaccct tgccctccct gcaaagaatg ccacaagtgc | 780 |
| cctgcccca acctggaagg cggcccttcc gtgttcatct ccccacccaa catcaaggac | 840 |
| gtgctgatga tctccctgac ccccaaagtg acctgcgtgg tggtggacgt gtccgaggac | 900 |
| gaccctgacg tgcagatcag ttggttcgtg aacaacgtgg aagtgcacac cgcccagacc | 960 |
| cagacacaca gagaggacta caacagcacc atcagagtgg tgtctaccct gcccatccag | 1020 |
| caccaggact ggatgtccgg caaagaattc aagtgcaaag tgaacaacaa ggacctgccc | 1080 |
| agccccatcg agcggaccat ctccaagatc aagggcctcg tgcgggctcc ccaggtgtac | 1140 |
| attctgcctc caccagccga gcagctgtcc cggaaggatg tgtctctgac atgtctggtc | 1200 |
| gtgggcttca ccccggcga catctccgtg gaatggacct ccaacggcca caccgaggaa | 1260 |
| aactacaagg acaccgcccc tgtgctggac tccgacggcc cctacttcat ctactccaag | 1320 |
| ctgaacatga agacctccaa gtgggaaaag accgactcct ctcctgcaa cgtgcggcac | 1380 |
| gagggcctga gaactactac cctgaagaaa accatctccc cgtcccccgg ctag | 1434 |

<210> SEQ ID NO 13
<211> LENGTH: 1416
<212> TYPE: DNA
<213> ORGANISM: Artificial sequence
<220> FEATURE:
<223> OTHER INFORMATION: Chimeric anti-AGE human IgG1 antibody heavy chain

<400> SEQUENCE: 13

| | |
|---|---|
| atggacccca agggcagcct gagctggaga atcctgctgt tcctgagcct ggccttcgag | 60 |
| ctgagctacg ccaggtgca gctgctgcag ccaggtgccg agctcgtgaa acctggcgcc | 120 |
| tctgtgaagc tggcctgcaa ggcttccggc tacctgttca ccacctactg gatgcactgg | 180 |
| ctgaagcaga ggccaggcca gggcctggaa tggatcggcg atatctcccc caccaacggc | 240 |
| agagcctact acaacgcccg gttcaagtcc gaggccaccc tgaccgtgga caagtcctcc | 300 |
| aacaccgcct acatgcagct gtcctccctg acctctgagg cctccgccgt gtactactgc | 360 |
| gccagagctt acggcaacta cgagttcgcc tactggggcc agggcaccct cgtgacagtg | 420 |

```
tctgtggcta gcaccaaggg ccccagcgtg ttccctctgg ccccccagcag caagagcacc        480 agcggcggaa ccgccgccct gggctgcctg gtgaaggact acttccccga gcccgtgacc        540
gtgtcctgga acagcggcgc tctgaccagc ggagtgcaca ccttccctgc cgtgctgcag        600
agcagcggcc tgtactccct gagcagcgtg gtgaccgtgc ccagcagcag cctgggcacc        660
cagacctaca tctgcaacgt gaaccacaag ccctccaaca ccaaggtgga caagaaggtg        720
gagcctaaga gctgcgacaa gacccacacc tgcccctccct gccccgcccc cgagctgctg        780
ggcggaccca gcgtgttcct gttccctccc aagcccaagg acaccctgat gatcagccgc        840 accccgagg tgacctgcgt ggtggtggac gtgagccacg aggaccccga ggtgaagttc         900
aactggtacg tggacggcgt ggaggtgcac aacgccaaga ccaagcctcg ggaggagcag        960
tacaactcca cctaccgcgt ggtgagcgtg ctgaccgtgc tgcaccagga ctggctgaac       1020
ggcaaggagt acaagtgcaa ggtgagcaac aaggcccctgc ccgctcccat cgagaagacc      1080
atcagcaagg ccaagggcca gccccgggag cctcaggtgt acaccctgcc cccccagccgc      1140 gacgagctga ccaagaacca ggtgagcctg acctgcctgg tgaagggctt ctaccccctcc      1200 gacatcgccg tggagtggga gagcaacggc cagcctgaga caactacaa gaccaccct        1260 cccgtgctgg acagcgacgg cagcttcttc ctgtacagca agctgaccgt ggacaagtcc      1320
cggtggcagc agggcaacgt gttcagctgc agcgtgatgc acgaggccct gcacaaccac      1380
tacacccaga gagcctgag cctgagcccc ggatag                                  1416
```

<210> SEQ ID NO 14
<211> LENGTH: 720
<212> TYPE: DNA
<213> ORGANISM: Artificial sequence
<220> FEATURE:
<223> OTHER INFORMATION: Murine anti-AGE Kappa light chain

<400> SEQUENCE: 14

```
atggagaccg acaccctgct gctctgggtg ctgctgctct gggtgcccgg ctccaccgga         60
gacgtcgtga tgacccagac ccctctgtcc ctgcctgtgt ctctgggcga ccaggcctcc       120
atctcctgcc ggtctagaca gtccctcgta actccaacg gcaacacctt cctgcagtgg        180
tatctgcaga agcccggcca gtcccccaag ctgctgatct acaaggtgtc cctgcggttc       240
tccggcgtgc ccgacagatt ttccggctct ggctctggca ccgacttcac cctgaagatc      300 tcccggggtgg aagccgagga cctgggcctg tacttctgca gccagtccac ccacgtgccc      360
cctacatttg gcgaggcac caagctggaa atcaaacggg cagatgctgc accaactgta       420
tccatcttcc caccatccag tgagcagtta acatctggag gtgcctcagt cgtgtgcttc      480
ttgaacaact ctaccccaa agacatcaat gtcaagtgga agattgatgg cagtgaacga      540
caaaatggcg tcctgaacag ttggactgat caggacagca agacagcac ctacagcatg      600 agcagcaccc tcacgttgac caaggacgag tatgaacgac ataacagcta tacctgtgag     660
gccactcaca gagacatcaac ttcacccatt gtcaagagct caacaggaa tgagtgttga    720
```

<210> SEQ ID NO 15
<211> LENGTH: 720
<212> TYPE: DNA
<213> ORGANISM: Artificial sequence
<220> FEATURE:
<223> OTHER INFORMATION: Chimeric anti-AGE human kappa light chain

<400> SEQUENCE: 15

```
atggagaccg acaccctgct gctctgggtg ctgctgctct gggtgcccgg ctccaccgga         60
```

```
gacgtcgtga tgacccagac ccctctgtcc ctgcctgtgt ctctgggcga ccaggcctcc     120
atctcctgcc ggtctagaca gtccctcgtg aactccaacg caacaccttt cctgcagtgg     180
tatctgcaga agcccggcca gtcccccaag ctgctgatct acaaggtgtc cctgcggttc     240
tccggcgtgc ccgacagatt ttccggctct ggctctggca ccgacttcac cctgaagatc     300 tcccggggtgg aagccgagga cctgggcctg tacttctgca gccagtccac ccacgtgccc     360
cctacatttg gcggaggcac caagctggaa atcaagcgga ccgtggccgc ccccagcgtg     420
ttcatcttcc ctcccagcga cgagcagctg aagtctggca ccgccagcgt ggtgtgcctg     480
ctgaacaact tctaccccccg cgaggccaag gtgcagtgga aggtggacaa cgccctgcag     540
agcggcaaca gccaggagag cgtgaccgag caggactcca aggacagcac ctacagcctg     600
agcagcaccc tgaccctgag caaggccgac tacgagaagc acaaggtgta cgcctgcgag     660
gtgacccacc agggactgtc tagccccgtg accaagagct tcaaccgggg cgagtgctaa     720
```

<210> SEQ ID NO 16
<211> LENGTH: 477
<212> TYPE: PRT
<213> ORGANISM: Artificial sequence
<220> FEATURE:
<223> OTHER INFORMATION: Murine anti-AGE IgG2b heavy chain

<400> SEQUENCE: 16

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Leu Gln Pro Gly
            20                  25                  30

Ala Glu Leu Val Lys Pro Gly Ala Ser Val Lys Leu Ala Cys Lys Ala
        35                  40                  45

Ser Gly Tyr Leu Phe Thr Thr Tyr Trp Met His Trp Leu Lys Gln Arg
    50                  55                  60

Pro Gly Gln Gly Leu Glu Trp Ile Gly Glu Ile Ser Pro Thr Asn Gly
65                  70                  75                  80

Arg Ala Tyr Tyr Asn Ala Arg Phe Lys Ser Glu Ala Thr Leu Thr Val
                85                  90                  95

Asp Lys Ser Ser Asn Thr Ala Tyr Met Gln Leu Ser Ser Leu Thr Ser
            100                 105                 110

Glu Ala Ser Ala Val Tyr Tyr Cys Ala Arg Ala Tyr Gly Asn Tyr Glu
        115                 120                 125

Phe Ala Tyr Trp Gly Gln Gly Thr Leu Val Thr Val Ser Val Ala Lys
    130                 135                 140

Thr Thr Pro Pro Ser Val Tyr Pro Leu Ala Pro Gly Cys Gly Asp Thr
145                 150                 155                 160

Thr Gly Ser Ser Val Thr Leu Gly Cys Leu Val Lys Gly Tyr Phe Pro
                165                 170                 175

Glu Ser Val Thr Val Thr Trp Asn Ser Gly Ser Leu Ser Ser Ser Val
            180                 185                 190

His Thr Phe Pro Ala Leu Leu Gln Ser Gly Leu Tyr Thr Met Ser Ser
        195                 200                 205

Ser Val Thr Val Pro Ser Ser Thr Trp Pro Ser Gln Thr Val Thr Cys
    210                 215                 220

Ser Val Ala His Pro Ala Ser Ser Thr Val Asp Lys Lys Leu Glu
225                 230                 235                 240

Pro Ser Gly Pro Ile Ser Thr Ile Asn Pro Cys Pro Pro Cys Lys Glu
```

```
                    245                 250                 255
Cys His Lys Cys Pro Ala Pro Asn Leu Glu Gly Gly Pro Ser Val Phe
                260                 265                 270

Ile Phe Pro Asn Ile Lys Asp Val Leu Met Ile Ser Leu Thr Pro
        275                 280                 285

Lys Val Thr Cys Val Val Val Asp Val Ser Glu Asp Asp Pro Asp Val
        290                 295                 300

Gln Ile Ser Trp Phe Val Asn Asn Val Glu Val His Thr Ala Gln Thr
305                 310                 315                 320

Gln Thr His Arg Glu Asp Tyr Asn Ser Thr Ile Arg Val Val Ser Thr
                325                 330                 335

Leu Pro Ile Gln His Gln Asp Trp Met Ser Gly Lys Glu Phe Lys Cys
                340                 345                 350

Lys Val Asn Asn Lys Asp Leu Pro Ser Pro Ile Glu Arg Thr Ile Ser
                355                 360                 365

Lys Ile Lys Gly Leu Val Arg Ala Pro Gln Val Tyr Ile Leu Pro Pro
        370                 375                 380

Pro Ala Glu Gln Leu Ser Arg Lys Asp Val Ser Leu Thr Cys Leu Val
385                 390                 395                 400

Val Gly Phe Asn Pro Gly Asp Ile Ser Val Glu Trp Thr Ser Asn Gly
                405                 410                 415

His Thr Glu Glu Asn Tyr Lys Asp Thr Ala Pro Val Leu Asp Ser Asp
                420                 425                 430

Gly Ser Tyr Phe Ile Tyr Ser Lys Leu Asn Met Lys Thr Ser Lys Trp
                435                 440                 445

Glu Lys Thr Asp Ser Phe Ser Cys Asn Val Arg His Glu Gly Leu Lys
                450                 455                 460

Asn Tyr Tyr Leu Lys Lys Thr Ile Ser Arg Ser Pro Gly
465                 470                 475

<210> SEQ ID NO 17
<211> LENGTH: 471
<212> TYPE: PRT
<213> ORGANISM: Artificial sequence
<220> FEATURE:
<223> OTHER INFORMATION: Chimeric anti-AGE human IgG1 heavy chain

<400> SEQUENCE: 17

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Pro Gly
                20                  25                  30

Ala Glu Leu Val Lys Pro Gly Ala Ser Val Lys Leu Ala Cys Lys Ala
            35                  40                  45

Ser Gly Tyr Leu Phe Thr Thr Tyr Trp Met His Trp Leu Lys Gln Arg
    50                  55                  60

Pro Gly Gln Gly Leu Glu Trp Ile Gly Glu Ile Ser Pro Thr Asn Gly
65                  70                  75                  80

Arg Ala Tyr Tyr Asn Ala Arg Phe Lys Ser Glu Ala Thr Leu Thr Val
                85                  90                  95

Asp Lys Ser Ser Asn Thr Ala Tyr Met Gln Leu Ser Ser Leu Thr Ser
                100                 105                 110

Glu Ala Ser Ala Val Tyr Tyr Cys Ala Arg Ala Tyr Gly Asn Tyr Glu
            115                 120                 125

Phe Ala Tyr Trp Gly Gln Gly Thr Leu Val Thr Val Ser Val Ala Ser
```

```
                130                 135                 140
Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
        210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
        370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
        450                 455                 460

Ser Leu Ser Leu Ser Pro Gly
465                 470

<210> SEQ ID NO 18
<211> LENGTH: 239
<212> TYPE: PRT
<213> ORGANISM: Artificial sequence
<220> FEATURE:
<223> OTHER INFORMATION: Murine anti-AGE kappa light chain

<400> SEQUENCE: 18

Met Glu Thr Asp Thr Leu Leu Leu Trp Val Leu Leu Leu Trp Val Pro
1               5                   10                  15

Gly Ser Thr Gly Asp Val Val Met Thr Gln Thr Pro Leu Ser Leu Pro
```

```
                20                  25                  30
Val Ser Leu Gly Asp Gln Ala Ser Ile Ser Cys Arg Ser Arg Gln Ser
            35                  40                  45

Leu Val Asn Ser Asn Gly Asn Thr Phe Leu Gln Trp Tyr Leu Gln Lys
        50                  55                  60

Pro Gly Gln Ser Pro Lys Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Leu Tyr Phe
            100                 105                 110

Cys Ser Gln Ser Thr His Val Pro Pro Thr Phe Gly Gly Gly Thr Lys
            115                 120                 125

Leu Glu Ile Lys Arg Ala Asp Ala Ala Pro Thr Val Ser Ile Phe Pro
            130                 135                 140

Pro Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
        210                 215                 220

Thr Ser Thr Ser Pro Ile Val Lys Ser Phe Asn Arg Asn Glu Cys
225                 230                 235

<210> SEQ ID NO 19
<211> LENGTH: 239
<212> TYPE: PRT
<213> ORGANISM: Artificial sequence
<220> FEATURE:
<223> OTHER INFORMATION: Chimeric anti-AGE human kappa light chain

<400> SEQUENCE: 19

Met Glu Thr Asp Thr Leu Leu Leu Trp Val Leu Leu Leu Trp Val Pro
1               5                   10                  15

Gly Ser Thr Gly Asp Val Val Met Thr Gln Thr Pro Leu Ser Leu Pro
            20                  25                  30

Val Ser Leu Gly Asp Gln Ala Ser Ile Ser Cys Arg Ser Arg Gln Ser
            35                  40                  45

Leu Val Asn Ser Asn Gly Asn Thr Phe Leu Gln Trp Tyr Leu Gln Lys
        50                  55                  60

Pro Gly Gln Ser Pro Lys Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Leu Tyr Phe
            100                 105                 110

Cys Ser Gln Ser Thr His Val Pro Pro Thr Phe Gly Gly Gly Thr Lys
            115                 120                 125

Leu Glu Ile Lys Arg Thr Val Ala Ala Pro Ser Val Phe Ile Phe Pro
            130                 135                 140

Pro Ser Asp Glu Gln Leu Lys Ser Gly Thr Ala Ser Val Val Cys Leu
```

```
                145                 150                 155                 160
Leu Asn Asn Phe Tyr Pro Arg Glu Ala Lys Val Gln Trp Lys Val Asp
                    165                 170                 175

Asn Ala Leu Gln Ser Gly Asn Ser Gln Glu Ser Val Thr Glu Gln Asp
                    180                 185                 190

Ser Lys Asp Ser Thr Tyr Ser Leu Ser Ser Thr Leu Thr Leu Ser Lys
                    195                 200                 205

Ala Asp Tyr Glu Lys His Lys Val Tyr Ala Cys Glu Val Thr His Gln
                    210                 215                 220

Gly Leu Ser Ser Pro Val Thr Lys Ser Phe Asn Arg Gly Glu Cys
225                 230                 235

<210> SEQ ID NO 20
<211> LENGTH: 118
<212> TYPE: PRT
<213> ORGANISM: Artificial sequence
<220> FEATURE:
<223> OTHER INFORMATION: Murine anti-AGE IgG2b heavy chain (variable
      region)

<400> SEQUENCE: 20

Gln Val Gln Leu Leu Gln Pro Gly Ala Glu Leu Val Lys Pro Gly Ala
1               5                   10                  15

Ser Val Lys Leu Ala Cys Lys Ala Ser Gly Tyr Leu Phe Thr Thr Tyr
                20                  25                  30

Trp Met His Trp Leu Lys Gln Arg Pro Gly Gln Gly Leu Glu Trp Ile
            35                  40                  45

Gly Glu Ile Ser Pro Thr Asn Gly Arg Ala Tyr Tyr Asn Ala Arg Phe
        50                  55                  60

Lys Ser Glu Ala Thr Leu Thr Val Asp Lys Ser Ser Asn Thr Ala Tyr
65                  70                  75                  80

Met Gln Leu Ser Ser Leu Thr Ser Glu Ala Ser Ala Val Tyr Tyr Cys
                85                  90                  95

Ala Arg Ala Tyr Gly Asn Tyr Glu Phe Ala Tyr Trp Gly Gln Gly Thr
            100                 105                 110

Leu Val Thr Val Ser Val
            115

<210> SEQ ID NO 21
<211> LENGTH: 112
<212> TYPE: PRT
<213> ORGANISM: Artificial sequence
<220> FEATURE:
<223> OTHER INFORMATION: Murine anti-AGE kappa light chain (variable
      region)

<400> SEQUENCE: 21

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val Asn Ser
                20                  25                  30

Asn Gly Asn Thr Phe Leu Gln Trp Tyr Leu Gln Lys Pro Gly Gln Ser
            35                  40                  45

Pro Lys Leu Leu Ile Tyr Lys Val Ser Leu Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
```

```
                 85                  90                  95
Thr His Val Pro Pro Thr Phe Gly Gly Gly Thr Lys Leu Glu Ile Lys
                100                 105                 110
```

<210> SEQ ID NO 22
<211> LENGTH: 326
<212> TYPE: PRT
<213> ORGANISM: Artificial sequence
<220> FEATURE:
<223> OTHER INFORMATION: Human constant region

<400> SEQUENCE: 22

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

```
<210> SEQ ID NO 23
<211> LENGTH: 7
<212> TYPE: PRT
<213> ORGANISM: Artificial sequence
<220> FEATURE:
<223> OTHER INFORMATION: CDR1H (heavy chain)

<400> SEQUENCE: 23

Ser Tyr Thr Met Gly Val Ser
1               5

<210> SEQ ID NO 24
<211> LENGTH: 17
<212> TYPE: PRT
<213> ORGANISM: Artificial sequence
<220> FEATURE:
<223> OTHER INFORMATION: CDR2H (heavy chain)

<400> SEQUENCE: 24

Thr Ile Ser Ser Gly Gly Gly Ser Thr Tyr Tyr Pro Asp Ser Val Lys
1               5                   10                  15

Gly

<210> SEQ ID NO 25
<211> LENGTH: 10
<212> TYPE: PRT
<213> ORGANISM: Artificial sequence
<220> FEATURE:
<223> OTHER INFORMATION: CDR3H (heavy chain)
<220> FEATURE:
<221> NAME/KEY: misc_feature
<222> LOCATION: (10)..(10)
<223> OTHER INFORMATION: Xaa can be any naturally occurring amino acid

<400> SEQUENCE: 25

Gln Gly Gly Trp Leu Pro Pro Phe Ala Xaa
1               5                   10

<210> SEQ ID NO 26
<211> LENGTH: 17
<212> TYPE: PRT
<213> ORGANISM: Artificial sequence
<220> FEATURE:
<223> OTHER INFORMATION: CDR1L (light chain)

<400> SEQUENCE: 26

Arg Ala Ser Lys Ser Val Ser Thr Ser Ser Arg Gly Tyr Ser Tyr Met
1               5                   10                  15

His

<210> SEQ ID NO 27
<211> LENGTH: 7
<212> TYPE: PRT
<213> ORGANISM: Artificial sequence
<220> FEATURE:
<223> OTHER INFORMATION: CDR2L (light chain)

<400> SEQUENCE: 27

Leu Val Ser Asn Leu Glu Ser
1               5

<210> SEQ ID NO 28
<211> LENGTH: 9
<212> TYPE: PRT
<213> ORGANISM: Artificial sequence
<220> FEATURE:
<223> OTHER INFORMATION: CDR3L (light chain)
```

<400> SEQUENCE: 28

Gln His Ile Arg Glu Leu Thr Arg Ser
1               5

<210> SEQ ID NO 29
<211> LENGTH: 468
<212> TYPE: PRT
<213> ORGANISM: Artificial Sequence
<220> FEATURE:
<223> OTHER INFORMATION: Humanized heavy chain

<400> SEQUENCE: 29

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Leu Phe Thr Thr Tyr Trp Met His Trp Val Arg Gln Ala
    50                  55                  60

Pro Gly Gln Gly Leu Glu Trp Met Gly Glu Ile Ser Pro Thr Asn Gly
65                  70                  75                  80

Arg Ala Tyr Tyr Asn Gln Lys Phe Gln Gly Arg Val Thr Met Thr Val
                85                  90                  95

Asp Lys Ser Thr Asn Thr Val Tyr Met Glu Leu Ser Ser Leu Arg Ser
            100                 105                 110

Glu Asp Thr Ala Val Tyr Tyr Cys Ala Arg Ala Tyr Gly Asn Tyr Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

| | | | | | | | | | | | |
|---|---|---|---|---|---|---|---|---|---|---|---|
|Leu|Asn|Gly|Lys|Glu|Tyr|Lys|Cys|Lys|Val|Ser|Asn Lys Ala Leu Pro|
| | | |340| | | |345| | | |350|

Ala Pro Ile Glu Lys Thr Ile Ser Lys Ala Lys Gly Gln Pro Arg Glu
      355             360              365

Pro Gln Val Tyr Thr Leu Pro Pro Ser Arg Asp Glu Leu Lys Asn Gln
    370                     375            380

Val Ser Leu Thr Cys Leu Val Lys Gly Phe Tyr Pro Ser Asp Ile Ala
385                390                 395            400

Val Glu Trp Glu Ser Asn Gly Gln Pro Glu Asn Tyr Lys Thr Thr
          405             410               415

Pro Pro Val Leu Asp Ser Asp Gly Ser Phe Phe Leu Tyr Ser Lys Leu
        420                 425              430

Thr Val Asp Lys Ser Arg Trp Gln Gln Gly Asn Val Phe Ser Cys Ser
        435                 440              445

Val Met His Glu Ala Leu His Asn His Tyr Thr Gln Lys Ser Leu Ser
    450                   455            460

Leu Ser Pro Gly
465

<210> SEQ ID NO 30
<211> LENGTH: 1408
<212> TYPE: DNA
<213> ORGANISM: Artificial Sequence
<220> FEATURE:
<223> OTHER INFORMATION: Humanized heavy chain

<400> SEQUENCE: 30

| | | |
|---|---|---|
|atggacccca agggcagcct gagctggaga atcctgctgt cctgagcct ggccttcgag|60|
|ctgagctacg ccaggtgca gctggtgcag tctggcgccg aagtgaagaa acctggcgcc|120|
|tccgtgaggt gtcctgcaag gcttccggct acctgttcac cacctactgg atgcactggg|180|
|tgcgacaggc ccctggacag ggcctggaat ggatgggcga gatctcccct accaacggca|240|
|gagcctacta caacagaaat ccagggcag agtgaccatg accgtggaca gtccaccaa|300|
|caccgtgtac atggaactgt cctccctgcg gagcgaggac accgccgtgt actactgcgc|360|
|tagagcctac ggcaactacg attcgcctac tggggccagg gcaccctcgt gacagtgtcc|420|
|tctgctagca ccaagggccc cagcgtgttc cctctggccc ccagcagcaa gagcaccagc|480|
|ggcggaaccg ccgccctggg ctgcctggga aggactactt ccccgagccc gtgaccgtgt|540|
|cctggaacag cggcgctctg accagcggag tgcacacctt ccctgccgtg ctgcagagca|600|
|gcggcctgta ctccctgagc agcgtggtga ccgtgccagc agcagcctgg gcacccagac|660|
|ctacatctgc aacgtgaacc acaagccctc caacaccaag gtggacaaga aggtggagcc|720|
|taagagctgc gacaagaccc acacctgccc tccctgcccc gccccgagct gctgggcgga|780|
|cccagcgtgt tcctgttccc tcccaagccc aaggacaccc tgatgatcag ccgcacccc|840|
|gaggtgacct gcgtggtggt ggacgtgagc cacgaggacc ccgaggtgag ttcaactggt|900|
|acgtggacgg cgtggaggtg cacaacgcca agaccaagcc tcgggaggag cagtacaact|960|
|ccacctaccg cgtggtgagc gtgctgaccg tgctgcacca ggactggctg aacggcagga|1020|
|gtacaagtgc aaggtgagca acaaggccct gcccgctccc atcgagaaga ccatcagcaa|1080|
|ggccaagggc cagccccggg agcctcaggt gtacaccctg cccccagcc gcgacgagct|1140|
|gacaagaacc aggtgagcct gacctgcctg tgaagggct ctaccccctc cgacatcgcc|1200|
|gtggagtggg agagcaacgg ccagcctgag aacaactaca agaccacccc tcccgtgctg|1260|

```
gacagcgacg cagcttcttc ctgtacagca agctgaccgt ggacaagtcc cggtggcagc    1320
agggcaacgt gttcagctgc agcgtgatgc acgaggccct gcacaaccac tacacccaga    1380
agagcctgag cctgagcccg gatagtaa                                       1408
```

<210> SEQ ID NO 31
<211> LENGTH: 468
<212> TYPE: PRT
<213> ORGANISM: Artificial Sequence
<220> FEATURE:
<223> OTHER INFORMATION: Humanized heavy chain

<400> SEQUENCE: 31

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Leu Phe Thr Thr Tyr Trp Met His Trp Val Arg Gln Ala
    50                  55                  60

Pro Gly Gln Gly Leu Glu Trp Met Gly Glu Ile Ser Pro Thr Asn Gly
65                  70                  75                  80

Arg Ala Tyr Tyr Asn Ala Lys Phe Gln Gly Arg Val Thr Met Thr Val
                85                  90                  95

Asp Lys Ser Thr Asn Thr Ala Tyr Met Glu Leu Ser Ser Leu Arg Ser
            100                 105                 110

Glu Asp Thr Ala Val Tyr Tyr Cys Ala Arg Ala Tyr Gly Asn Tyr Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335
```

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 32
<211> LENGTH: 1408
<212> TYPE: DNA
<213> ORGANISM: Artificial Sequence
<220> FEATURE:
<223> OTHER INFORMATION: Humanized heavy chain

<400> SEQUENCE: 32

| | | | | | |
|---|---|---|---|---|---|
| atggacccca | agggcagcct | gagctggaga | atcctgctgt | tcctgagcct | ggccttcgag | 60 |
| ctgagctacg | ccaggtgca | gctggtgcag | tctggcgccg | aagtgaagaa | acctggcgcc | 120 |
| tccgtgaggt | gtcctgcaag | gcttccggct | acctgttcac | cacctactgg | atgcactggg | 180 |
| tgcgacaggc | ccctggacag | ggcctggaat | ggatgggcga | gatctcccct | accaacggca | 240 |
| gagcctacta | caaccaaaat | tccagggcag | agtgaccatg | accgtggaca | gtccaccaa | 300 |
| caccgcttac | atggaactgt | cctccctgcg | gagcgaggac | accgccgtgt | actactgcgc | 360 |
| tagagcctac | ggcaactacg | attcgcctac | tggggccagg | gcaccctcgt | gacagtgtcc | 420 |
| tctgctagca | ccaagggccc | cagcgtgttc | cctctggccc | ccagcagcaa | gagcaccagc | 480 |
| ggcggaaccg | ccgccctggg | ctgcctggga | aggactactt | ccccgagccc | gtgaccgtgt | 540 |
| cctggaacag | cggcgctctg | accagcggag | tgcacacctt | ccctgccgtg | ctgcagagca | 600 |
| gcggcctgta | ctccctgagc | agcgtggtga | ccgtgccagc | agcagcctgg | gcacccagac | 660 |
| ctacatctgc | aacgtgaacc | acaagccctc | caacaccaag | gtggacaaga | aggtggagcc | 720 |
| taagagctgc | gacaagaccc | acacctgccc | tccctgcccc | gccccgagct | gctgggcgga | 780 |
| cccagcgtgt | tcctgttccc | tcccaagccc | aaggacaccc | tgatgatcag | ccgcaccccc | 840 |
| gaggtgacct | gcgtggtggt | ggacgtgagc | cacgaggacc | ccgaggtgag | ttcaactggt | 900 |
| acgtggacgg | cgtggaggtg | cacaacgcca | agaccaagcc | tcgggaggag | cagtacaact | 960 |
| ccacctaccg | cgtggtgagc | gtgctgaccg | tgctgcacca | ggactggctg | aacggcagga | 1020 |
| gtacaagtgc | aaggtgagca | acaaggccct | gcccgctccc | atcgagaaga | ccatcagcaa | 1080 |
| ggccaagggc | cagccccggg | agcctcaggt | gtacaccctg | cccccagcc | gcgacgagct | 1140 |
| gacaagaacc | aggtgagcct | gacctgcctg | gtgaagggct | ctacccctc | cgacatcgcc | 1200 |
| gtggagtggg | agagcaacgg | ccagcctgag | aacaactaca | agaccacccc | tcccgtgctg | 1260 |

```
gacagcgacg cagcttcttc ctgtacagca agctgaccgt ggacaagtcc cggtggcagc    1320
agggcaacgt gttcagctgc agcgtgatgc acgaggccct gcacaaccac tacacccaga    1380
agagcctgag cctgagcccg gatagtaa                                       1408
```

<210> SEQ ID NO 33
<211> LENGTH: 468
<212> TYPE: PRT
<213> ORGANISM: Artificial Sequence
<220> FEATURE:
<223> OTHER INFORMATION: Humanized heavy chain

<400> SEQUENCE: 33

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Leu Phe Thr Thr Tyr Trp Met His Trp Val Arg Gln Ala
    50                  55                  60

Pro Gly Gln Gly Leu Glu Trp Met Gly Glu Ile Ser Pro Thr Asn Gly
65                  70                  75                  80

Arg Ala Tyr Tyr Asn Ala Lys Phe Gln Gly Arg Val Thr Met Thr Val
                85                  90                  95

Asp Lys Ser Ile Asn Thr Ala Tyr Met Glu Leu Ser Arg Leu Arg Ser
            100                 105                 110

Asp Asp Thr Ala Val Tyr Tyr Cys Ala Arg Ala Tyr Gly Asn Tyr Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335
```

```
Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly
465

<210> SEQ ID NO 34
<211> LENGTH: 1408
<212> TYPE: DNA
<213> ORGANISM: Artificial Sequence
<220> FEATURE:
<223> OTHER INFORMATION: Humanized heavy chain

<400> SEQUENCE: 34
atggacccca agggcagcct gagctggaga atcctgctgt tcctgagcct ggccttcgag      60
ctgagctacg ccaggtgca gctggtgcag tctggcgccg aagtgaagaa acctggcgcc     120
tccgtgaggt gtcctgcaag gcttccggct acctgttcac cacctactgg atgcactggg     180
tgcgacaggc ccctggacag ggcctggaat ggatgggcga gatctcccct accaacggca     240
gagcctacta caaccaaaat tccagggcag agtgaccatg accgtggaca gtccatcaa      300 caccgcttac atggaactgt ccagactgcg gagcgatgac accgccgtgt actactgcgc     360
tagagcctac ggcaactacg attcgcctac tggggccagg gcaccctcgt gacagtgtcc     420
tctgctagca ccaagggccc cagcgtgttc cctctggccc ccagcagcaa gagcaccagc     480
ggcggaaccg ccgccctggg ctgcctggga ggactactt ccccgagccc gtgaccgtgt      540
cctggaacag cggcgctctg accagcggag tgcacacctt ccctgccgtg ctgcagagca     600
gcggcctgta ctccctgagc agcgtggtga ccgtgccagc agcagcctgg gcacccagac     660
ctacatctgc aacgtgaacc acaagccctc caacaccaag gtggacaaga aggtggagcc     720
taagagctgc gacaagaccc acacctgccc tccctgcccc gccccgagct gctgggcgga     780
cccagcgtgt tcctgttccc tcccaagccc aaggacaccc tgatgatcag ccgcaccccc     840
gaggtgacct gcgtggtggt ggacgtgagc acgaggacc cgaggtgag ttcaactggt      900 acgtggacgg cgtggaggtg cacaacgcca agaccaagcc tcgggaggag cagtacaact     960
ccacctaccg cgtggtgagc gtgctgaccg tgctgcacca ggactggctg aacggcagga    1020
gtacaagtgc aaggtgagca acaaggccct gcccgctccc atcgagaaga ccatcagcaa    1080
ggccaagggc cagccccggg agcctcaggt gtacaccctg ccccccagcc gcgacgagct    1140
gacaagaacc aggtgagcct gacctgcctg gtgaagggct ctacccctc cgacatcgcc     1200 gtggagtggg agagcaacgg ccagcctgag aacaactaca gaccacccc tcccgtgctg    1260
```

```
gacagcgacg cagcttcttc ctgtacagca agctgaccgt ggacaagtcc cggtggcagc    1320
agggcaacgt gttcagctgc agcgtgatgc acgaggccct gcacaaccac tacacccaga    1380
agagcctgag cctgagcccg gatagtaa                                        1408
```

<210> SEQ ID NO 35
<211> LENGTH: 238
<212> TYPE: PRT
<213> ORGANISM: Artificial Sequence
<220> FEATURE:
<223> OTHER INFORMATION: Humanized light chain

<400> SEQUENCE: 35

```
Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val Asn Ser Asn Gly Asn Thr Phe Leu Gln Trp Tyr Gln Gln Arg
    50                  55                  60

Pro Gly Gln Ser Pro Arg Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Pro Thr Phe Gly Gly Gly Thr Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 36
<211> LENGTH: 715
<212> TYPE: DNA
<213> ORGANISM: Artificial Sequence
<220> FEATURE:
<223> OTHER INFORMATION: Humanized light chain

<400> SEQUENCE: 36

```
atggagaccg acaccctgct gctctgggtg ctgctgctct gggtgcccgg ctccaccgga      60
gacgtcgtga tgacccagtc ccctctgtcc ctgcctgtga ccctgggaca gcctgcctcc     120
atctcctcag atcctcccag tccctcgtga actccaacgg caacaccttc ctgcagtggt     180
atcagcagcg gcctggccag agccccagac tgctgatcta caaggtgtcc ctgcggttct     240
```

| | | |
|---|---|---|
| ccggcgtgcc cgacgatttt ccggctctgg ctctggcacc gacttcaccc tgaagatctc | 300 | |
| ccgggtggaa gccgaggacg tgggcgtgta ctactgctcc cagagcaccc acgtgccccc | 360 | |
| tacatttggc ggaggcacca agtggaaatc aagcggaccg tggccgcccc cagcgtgttc | 420 | |
| atcttccctc ccagcgacga gcagctgaag tctggcaccg ccagcgtggt gtgcctgctg | 480 | |
| aacaacttct accccgcga ggccaagggc agtggaaggt ggacaacgcc ctgcagagcg | 540 | |
| gcaacagcca ggagagcgtg accgagcagg actccaagga cagcacctac agcctgagca | 600 | |
| gcaccctgac cctgagcaag gccgactacg agaagacaag gtgtacgcct gcgaggtgac | 660 | |
| ccaccaggga ctgtctagcc ccgtgaccaa gagcttcaac cggggcgagt gctaa | 715 | |

```
<210> SEQ ID NO 37
<211> LENGTH: 238
<212> TYPE: PRT
<213> ORGANISM: Artificial Sequence
<220> FEATURE:
<223> OTHER INFORMATION: Humanized light chain

<400> SEQUENCE: 37
```

Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
            20                  25                  30

Val Thr Leu Gly Gln Pro Ala Ser Ile Ser Cys Arg Ser Arg Gln Ser
        35                  40                  45

Leu Val Asn Ser Asn Gly Asn Thr Phe Leu Gln Trp Tyr Gln Gln Arg
    50                  55                  60

Pro Gly Gln Ser Pro Arg Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Pro Thr Phe Gly Gly Gly Thr Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

```
<210> SEQ ID NO 38
<211> LENGTH: 715
<212> TYPE: DNA
<213> ORGANISM: Artificial Sequence
<220> FEATURE:
<223> OTHER INFORMATION: Humanized light chain
```

<400> SEQUENCE: 38

```
atggagaccg acaccctgct gctctgggtg ctgctgctct gggtgcccgg ctccaccgga      60
gacgtcgtga tgacccagtc ccctctgtcc ctgcctgtga ccctgggaca gcctgcctcc     120
atctcctcag atccaggcag tccctcgtga actccaacgg caacaccttc ctgcagtggt     180
atcagcagcg gcctggccag agccccagac tgctgatcta aaggtgtcc ctgcggttct      240
ccggcgtgcc cgacgatttt ccggctctgg ctctggcacc gacttcaccc tgaagatctc     300
ccgggtggaa gccgaggacg tgggcgtgta ctactgctcc cagagcaccc acgtgccccc     360
tacatttggc ggaggcacca agtggaaatc aagcggaccg tggccgcccc cagcgtgttc     420
atcttccctc ccagcgacga gcagctgaag tctggcaccg ccagcgtggt gtgcctgctg     480
aacaacttct accccgcgca ggccaagggc agtggaaggt ggacaacgcc ctgcagagcg     540
gcaacagcca ggagagcgtg accgagcagg actccaagga cagcacctac agcctgagca     600
gcaccctgac cctgagcaag gccgactacg agaagcacaa gtgtacgcct gcgaggtgac     660
ccaccaggga ctgtctagcc ccgtgaccaa gagcttcaac cggggcgagt gctaa          715
```

<210> SEQ ID NO 39
<211> LENGTH: 238
<212> TYPE: PRT
<213> ORGANISM: Artificial Sequence
<220> FEATURE:
<223> OTHER INFORMATION: Humanized light chain

<400> SEQUENCE: 39

```
Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Ser Pro
            20                  25                  30

Val Thr Leu Gly Gln Pro Ala Ser Ile Ser Cys Arg Ser Ser Gln Ser
        35                  40                  45

Leu Val Asn Ser Asn Gly Asn Thr Phe Leu Gln Trp Tyr His Gln Arg
    50                  55                  60

Pro Gly Gln Pro Pro Arg Leu Leu Ile Tyr Lys Val Ser Leu Arg Phe
65                  70                  75                  80

Ser Gly Val Pro Asp Arg Phe Ser Gly Ser Gly Ala Gly Lys Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Pro Thr Phe Gly Gln Gly Thr Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
```

<210> SEQ ID NO 40
<211> LENGTH: 715
<212> TYPE: DNA
<213> ORGANISM: Artificial Sequence
<220> FEATURE:
<223> OTHER INFORMATION: Humanized light chain

<400> SEQUENCE: 40

```
atggagaccg acaccctgct gctctgggtg ctgctgctct gggtgcccgg ctccaccgga    60
gacgtcgtga tgacccagtc ccctctgtcc agtcctgtga ccctgggaca gcctgcctcc   120
atctcctcag atcctcccag tccctcgtga actccaacgg caacaccttc ctgcagtggt   180
atcaccagcg gctggccag cctcccagac tgctgatcta caaggtgtcc ctgcggttct   240
ccggcgtgcc cgacgatttt ccggctctgg cgctggcaag acttcaccc tgaagatctc   300
ccgggtggaa gccgaggacg tgggcgtgta ctactgctcc cagagcaccc acgtgccccc   360
tacatttggc cagggcacca actggaaatc aagcggaccg tggccgcccc cagcgtgttc   420
atcttccctc ccagcgacga gcagctgaag tctggcaccg ccagcgtggt gtgcctgctg   480
aacaacttct accccgcga ggccaagggc agtggaaggt ggacaacgcc ctgcagagcg   540
gcaacagcca ggagagcgtg accgagcagg actccaagga cagcacctac agcctgagca   600
gcaccctgac cctgagcaag gccgactacg agaagcacaag gtgtacgcct gcgaggtgac   660
ccaccaggga ctgtctagcc ccgtgaccaa gagcttcaac cggggcgagt gctaa        715
```

<210> SEQ ID NO 41
<211> LENGTH: 5
<212> TYPE: PRT
<213> ORGANISM: Mus musculus

<400> SEQUENCE: 41

Thr Tyr Trp Met His
1               5

<210> SEQ ID NO 42
<211> LENGTH: 17
<212> TYPE: PRT
<213> ORGANISM: Mus musculus

<400> SEQUENCE: 42

Glu Ile Ser Pro Thr Asn Gly Arg Ala Tyr Tyr Asn Ala Arg Phe Lys
1               5                   10                  15
Ser

<210> SEQ ID NO 43
<211> LENGTH: 9
<212> TYPE: PRT
<213> ORGANISM: Mus musculus

<400> SEQUENCE: 43

Ala Tyr Gly Asn Tyr Glu Phe Ala Tyr
1               5

<210> SEQ ID NO 44
<211> LENGTH: 16
<212> TYPE: PRT
<213> ORGANISM: Mus musculus

<400> SEQUENCE: 44

Arg Ser Arg Gln Ser Leu Val Asn Ser Asn Gly Asn Thr Phe Leu Gln
1               5                   10                  15

<210> SEQ ID NO 45
<211> LENGTH: 7
<212> TYPE: PRT
<213> ORGANISM: Mus musculus

<400> SEQUENCE: 45

Lys Val Ser Leu Arg Phe Ser
1               5

<210> SEQ ID NO 46
<211> LENGTH: 9
<212> TYPE: PRT
<213> ORGANISM: Mus musculus

<400> SEQUENCE: 46

Ser Gln Ser Thr His Val Pro Pro Thr
1               5

<210> SEQ ID NO 47
<211> LENGTH: 467
<212> TYPE: PRT
<213> ORGANISM: Mus musculus

<400> SEQUENCE: 47

Met Gly Trp Thr Leu Val Phe Leu Phe Leu Leu Ser Val Thr Ala Gly
1               5                   10                  15

Val His Ser Gln Val Gln Leu Leu Gln Pro Gly Ala Glu Leu Val Lys
            20                  25                  30

Pro Gly Ala Ser Val Lys Leu Ala Cys Lys Ala Ser Gly Tyr Leu Phe
        35                  40                  45

Thr Thr Tyr Trp Met His Trp Leu Lys Gln Arg Pro Gly Gln Gly Leu
    50                  55                  60

Glu Trp Ile Gly Glu Ile Ser Pro Thr Asn Gly Arg Ala Tyr Tyr Asn
65                  70                  75                  80

Ala Arg Phe Lys Ser Glu Ala Thr Leu Thr Val Asp Lys Ser Ser Asn
                85                  90                  95

Thr Ala Tyr Met Gln Leu Ser Ser Leu Thr Ser Glu Ala Ser Ala Val
            100                 105                 110

Tyr Tyr Cys Ala Arg Ser Phe Gly Asn Tyr Glu Phe Ala Tyr Trp Gly
        115                 120                 125

Gln Gly Thr Leu Val Thr Val Ser Val Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly

```
                    245                 250                 255
    Gly Pro Ser Val Phe Leu Phe Pro Pro Lys Pro Lys Asp Thr Leu Met
                    260                 265                 270

Ile Ser Arg Thr Pro Glu Val Thr Cys Val Val Val Asp Val Ser His
                    275                 280                 285

Glu Asp Pro Glu Val Lys Phe Asn Trp Tyr Val Asp Gly Val Glu Val
    290                 295                 300

His Asn Ala Lys Thr Lys Pro Arg Glu Gln Tyr Asn Ser Thr Tyr
    305                 310                 315                 320

Arg Val Val Ser Val Leu Thr Val Leu His Gln Asp Trp Leu Asn Gly
                    325                 330                 335

Lys Glu Tyr Lys Cys Lys Val Ser Asn Lys Ala Leu Pro Ala Pro Ile
                    340                 345                 350

Glu Lys Thr Ile Ser Lys Ala Lys Gly Gln Pro Arg Glu Pro Gln Val
                    355                 360                 365

Tyr Thr Leu Pro Pro Ser Arg Asp Glu Leu Thr Lys Asn Gln Val Ser
                    370                 375                 380

Leu Thr Cys Leu Val Lys Gly Phe Tyr Pro Ser Asp Ile Ala Val Glu
    385                 390                 395                 400

Trp Glu Ser Asn Gly Gln Pro Glu Asn Asn Tyr Lys Thr Thr Pro Pro
                    405                 410                 415

Val Leu Asp Ser Asp Gly Ser Phe Phe Leu Tyr Ser Lys Leu Thr Val
                    420                 425                 430

Asp Lys Ser Arg Trp Gln Gln Gly Asn Val Phe Ser Cys Ser Val Met
                    435                 440                 445

His Glu Ala Leu His Asn His Tyr Thr Gln Lys Ser Leu Ser Leu Ser
        450                 455                 460

Pro Gly Lys
    465

<210> SEQ ID NO 48
<211> LENGTH: 467
<212> TYPE: PRT
<213> ORGANISM: Artificial sequence
<220> FEATURE:
<223> OTHER INFORMATION: Humanized heavy chain

<400> SEQUENCE: 48

Met Gly Trp Thr Leu Val Phe Leu Phe Leu Leu Ser Val Thr Ala Gly
    1               5                   10                  15

Val His Ser Glu Val Gln Leu Leu Glu Ser Gly Ala Glu Ala Lys Lys
                    20                  25                  30

Pro Gly Ala Ser Val Lys Leu Ser Cys Lys Ala Ser Gly Tyr Leu Phe
                    35                  40                  45

Thr Thr Tyr Trp Met His Trp Val His Gln Ala Pro Gly Gln Arg Leu
        50                  55                  60

Glu Trp Met Gly Glu Ile Ser Pro Thr Asn Gly Arg Ala Tyr Tyr Asn
    65                  70                  75                  80

Ala Arg Phe Lys Ser Arg Val Thr Ile Thr Val Asp Lys Ser Ala Ser
                    85                  90                  95

Thr Ala Tyr Met Glu Leu Ser Ser Leu Arg Ser Glu Asp Thr Ala Val
                    100                 105                 110

Tyr Tyr Cys Ala Arg Ser Phe Gly Asn Tyr Glu Phe Ala Tyr Trp Gly
                    115                 120                 125

Gln Gly Thr Leu Val Thr Val Ser Ser Ala Ser Thr Lys Gly Pro Ser
```

```
            130                 135                 140
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 49
<211> LENGTH: 467
<212> TYPE: PRT
<213> ORGANISM: Artificial sequence
<220> FEATURE:
<223> OTHER INFORMATION: Humanized heavy chain

<400> SEQUENCE: 49

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
```

```
                20                  25                  30
Pro Gly Ala Ser Val Lys Val Ser Cys Lys Ala Ser Gly Tyr Leu Phe
            35                  40                  45
Thr Thr Tyr Trp Met His Trp Val Arg Gln Ala Pro Gly Gln Arg Leu
        50                  55                  60
Glu Trp Ile Gly Glu Ile Ser Pro Thr Asn Gly Arg Ala Tyr Tyr Asn
65                  70                  75                  80
Ala Arg Phe Lys Ser Arg Val Thr Ile Thr Arg Asp Thr Ser Ala Ser
                85                  90                  95
Thr Ala Tyr Met Glu Leu Ser Ser Leu Arg Ser Glu Asp Thr Ala Val
            100                 105                 110
Tyr Tyr Cys Ala Arg Ser Phe Gly Asn Tyr Glu Phe Ala Tyr Trp Gly
        115                 120                 125
Gln Gly Thr Leu Val Thr Val Ser Ser Ala Ser Thr Lys Gly Pro Ser
    130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Gln Thr Tyr Ile Cys Asn Val Asn His
    210                 215                 220
Lys Pro Ser Asn Thr Lys Val Asp Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
```

```
His Glu Ala Leu His Asn His Tyr Thr Gln Lys Ser Leu Ser Leu Ser
    450                 455                 460

Pro Gly Lys
465

<210> SEQ ID NO 50
<211> LENGTH: 467
<212> TYPE: PRT
<213> ORGANISM: Artificial sequence
<220> FEATURE:
<223> OTHER INFORMATION: Humanized heavy chain

<400> SEQUENCE: 50

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Leu Phe
        35                  40                  45

Thr Thr Tyr Trp Met His Trp Val Arg Gln Ala Pro Gly Gln Gly Leu
    50                  55                  60

Glu Trp Met Gly Glu Ile Ser Pro Thr Asn Gly Arg Ala Tyr Tyr Asn
65                  70                  75                  80

Ala Arg Phe Lys Ser Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Phe Gly Asn Tyr Glu Phe Ala Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335
```

```
Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 51
<211> LENGTH: 467
<212> TYPE: PRT
<213> ORGANISM: Artificial sequence
<220> FEATURE:
<223> OTHER INFORMATION: Humanized heavy chain

<400> SEQUENCE: 51

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Glu Ala Ser Gly Tyr Leu Phe
            35                  40                  45

Thr Thr Tyr Trp Met His Trp Val Arg Gln Ala Pro Gly Gln Gly Leu
        50                  55                  60

Glu Trp Met Gly Glu Ile Ser Pro Thr Asn Gly Arg Ala Tyr Tyr Asn
65                  70                  75                  80

Ala Arg Phe Lys Ser Arg Val Thr Ile Thr Arg Asp Thr Ser Ile Asn
                85                  90                  95

Thr Ala Tyr Met Glu Leu Ser Arg Leu Arg Ser Asp Asp Thr Ala Val
            100                 105                 110

Tyr Tyr Cys Ala Arg Ser Phe Gly Asn Tyr Glu Phe Ala Tyr Trp Gly
        115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220
```

-continued

```
Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 52
<211> LENGTH: 118
<212> TYPE: PRT
<213> ORGANISM: Mus musculus

<400> SEQUENCE: 52

Gln Val Gln Leu Leu Gln Pro Gly Ala Glu Leu Val Lys Pro Gly Ala
1               5                   10                  15

Ser Val Lys Leu Ala Cys Lys Ala Ser Gly Tyr Leu Phe Thr Thr Tyr
            20                  25                  30

Trp Met His Trp Leu Lys Gln Arg Pro Gly Gln Gly Leu Glu Trp Ile
        35                  40                  45

Gly Glu Ile Ser Pro Thr Asn Gly Arg Ala Tyr Tyr Asn Ala Arg Phe
    50                  55                  60

Lys Ser Glu Ala Thr Leu Thr Val Asp Lys Ser Ser Asn Thr Ala Tyr
65                  70                  75                  80

Met Gln Leu Ser Ser Leu Thr Ser Glu Ala Ser Ala Val Tyr Tyr Cys
            85                  90                  95

Ala Arg Ser Phe Gly Asn Tyr Glu Phe Ala Tyr Trp Gly Gln Gly Thr
        100                 105                 110

Leu Val Thr Val Ser Val
```

```
<210> SEQ ID NO 53
<211> LENGTH: 118
<212> TYPE: PRT
<213> ORGANISM: Artificial sequence
<220> FEATURE:
<223> OTHER INFORMATION: Humanized heavy chain variable region

<400> SEQUENCE: 53

Glu Val Gln Leu Leu Glu Ser Gly Ala Glu Ala Lys Lys Pro Gly Ala
1               5                   10                  15

Ser Val Lys Leu Ser Cys Lys Ala Ser Gly Tyr Leu Phe Thr Thr Tyr
            20                  25                  30

Trp Met His Trp Val His Gln Ala Pro Gly Gln Arg Leu Glu Trp Met
        35                  40                  45

Gly Glu Ile Ser Pro Thr Asn Gly Arg Ala Tyr Tyr Asn Ala Arg Phe
    50                  55                  60

Lys Ser Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Gly Asn Tyr Glu Phe Ala Tyr Trp Gly Gln Gly Thr
            100                 105                 110

Leu Val Thr Val Ser Ser
        115

<210> SEQ ID NO 54
<211> LENGTH: 118
<212> TYPE: PRT
<213> ORGANISM: Artificial sequence
<220> FEATURE:
<223> OTHER INFORMATION: Humanized heavy chain variable region

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Thr Tyr
            20                  25                  30

Trp Met His Trp Val Arg Gln Ala Pro Gly Gln Arg Leu Glu Trp Ile
        35                  40                  45

Gly Glu Ile Ser Pro Thr Asn Gly Arg Ala Tyr Tyr Asn Ala Arg Phe
    50                  55                  60

Lys Ser Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Gly Asn Tyr Glu Phe Ala Tyr Trp Gly Gln Gly Thr
            100                 105                 110

Leu Val Thr Val Ser Ser
        115

<210> SEQ ID NO 55
<211> LENGTH: 118
<212> TYPE: PRT
<213> ORGANISM: Artificial sequence
<220> FEATURE:
<223> OTHER INFORMATION: Humanized heavy chain variable region

<400> SEQUENCE: 55
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Leu Phe Thr Thr Tyr
            20                  25                  30

Trp Met His Trp Val Arg Gln Ala Pro Gly Gln Gly Leu Glu Trp Met
        35                  40                  45

Gly Glu Ile Ser Pro Thr Asn Gly Arg Ala Tyr Tyr Asn Ala Arg Phe
    50                  55                  60

Lys Ser Arg Val Thr Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Gly Asn Tyr Glu Phe Ala Tyr Trp Gly Gln Gly Thr
            100                 105                 110

Leu Val Thr Val Ser Ser
            115
```

```
<210> SEQ ID NO 56
<211> LENGTH: 118
<212> TYPE: PRT
<213> ORGANISM: Artificial sequence
<220> FEATURE:
<223> OTHER INFORMATION: Humanized heavy chain variable region

<400> SEQUENCE: 56

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Leu Phe Thr Thr Tyr
            20                  25                  30

Trp Met His Trp Val Arg Gln Ala Pro Gly Gln Gly Leu Glu Trp Met
        35                  40                  45

Gly Glu Ile Ser Pro Thr Asn Gly Arg Ala Tyr Tyr Asn Ala Arg Phe
    50                  55                  60

Lys Ser Arg Val Thr Ile Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Phe Gly Asn Tyr Glu Phe Ala Tyr Trp Gly Gln Gly Thr
            100                 105                 110

Leu Val Thr Val Ser Ser
            115
```

```
<210> SEQ ID NO 57
<211> LENGTH: 239
<212> TYPE: PRT
<213> ORGANISM: Mus musculus

<400> SEQUENCE: 57

Met Val Ser Ser Ala Gln Phe Leu Gly Leu Leu Leu Leu Cys Phe Gln
1               5                   10                  15

Gly Thr Arg Cys Asp Val Val Met Thr Gln Thr Pro Leu Ser Leu Pro
            20                  25                  30

Val Ser Leu Gly Asp Gln Ala Ser Ile Ser Cys Arg Ser Arg Gln Ser
        35                  40                  45

Leu Val Asn Ser Asn Gly Asn Thr Phe Leu Gln Trp Tyr Leu Gln Lys
    50                  55                  60
```

```
Pro Gly Gln Ser Pro Lys Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Leu Tyr Phe
            100                 105                 110

Cys Ser Gln Ser Thr His Val Pro Pro Thr Phe Gly Gly Gly Thr Lys
            115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 58
<211> LENGTH: 239
<212> TYPE: PRT
<213> ORGANISM: Artificial sequence
<220> FEATURE:
<223> OTHER INFORMATION: Humanized light chain

<400> SEQUENCE: 58

Met Val Ser Ser Ala Gln Phe Leu Gly Leu Leu Leu Cys Phe Gln
1               5                   10                  15

Gly Thr Arg Cys Asp Ile Val Met Thr Gln Thr Pro Leu Ser Leu Pro
                20                  25                  30

Val Thr Leu Gly Gln Pro Ala Ser Ile Ser Cys Arg Ser Arg Gln Ser
            35                  40                  45

Leu Val Asn Ser Asn Gly Asn Thr Phe Leu Gln Trp Leu Gln Gln Arg
50                  55                  60

Pro Gly Gln Pro Pro Arg Leu Leu Ile Tyr Lys Val Ser Leu Arg Phe
65                  70                  75                  80

Ser Gly Val Pro Asp Arg Phe Ser Gly Ser Gly Ala Gly Thr Asp Phe
                85                  90                  95

Thr Leu Thr Ile Ser Arg Val Glu Ala Glu Asp Val Gly Ile Tyr Phe
            100                 105                 110

Cys Ser Gln Ser Thr His Val Pro Pro Thr Phe Gly Gln Gly Thr Lys
            115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190
```

```
Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 59
<211> LENGTH: 239
<212> TYPE: PRT
<213> ORGANISM: Artificial sequence
<220> FEATURE:
<223> OTHER INFORMATION: Humanized light chain

<400> SEQUENCE: 59

Met Val Ser Ser Ala Gln Phe Leu Gly Leu Leu Leu Leu Cys Phe Gln
1               5                   10                  15

Gly Thr Arg Cys Asp Ile Val Met Thr Gln Thr Pro Leu Ser Leu Ser
            20                  25                  30

Val Thr Pro Gly Gln Pro Ala Ser Ile Ser Cys Arg Ser Arg Gln Ser
            35                  40                  45

Leu Val Asn Ser Asn Gly Asn Thr Phe Leu Gln Trp Tyr Leu Gln Lys
    50                  55                  60

Pro Gly Gln Ser Pro Gln Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Pro Glu Asp Val Gly Val Tyr Tyr
            100                 105                 110

Cys Ser Gln Ser Thr His Val Pro Pro Thr Phe Gly Gly Gly Thr Lys
            115                 120                 125

Val Glu Val Lys Arg Thr Val Ala Ala Pro Ser Val Phe Ile Phe Pro
            130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 60
<211> LENGTH: 239
<212> TYPE: PRT
<213> ORGANISM: Artificial sequence
<220> FEATURE:
<223> OTHER INFORMATION: Humanized light chain

<400> SEQUENCE: 60

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Leu Ser Leu Pro
            20                  25                  30
```

```
Val Thr Leu Gly Gln Pro Ala Ser Ile Ser Cys Arg Ser Arg Gln Ser
        35                  40                  45

Leu Val Asn Ser Asn Gly Asn Thr Phe Leu Gln Trp Phe Gln Gln Arg
    50                  55                  60

Pro Gly Gln Ser Pro Arg Arg Leu Ile Tyr Lys Val Ser Leu Arg Phe
65                  70                  75                  80

Ser Gly Val Pro Asp Arg Phe Ser Gly Ser Gly Ser Asp Thr Asp Phe
                85                  90                  95

Thr Leu Arg Ile Ser Arg Val Glu Ala Glu Asp Val Gly Leu Tyr Tyr
            100                 105                 110

Cys Ser Gln Ser Thr His Val Pro Pro Thr Phe Gly Gln Gly Thr Lys
            115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 61
<211> LENGTH: 239
<212> TYPE: PRT
<213> ORGANISM: Artificial sequence
<220> FEATURE:
<223> OTHER INFORMATION: Humanized light chain

<400> SEQUENCE: 61

Met Val Ser Ser Ala Gln Phe Leu Gly Leu Leu Leu Leu Cys Phe Gln
1               5                   10                  15

Gly Thr Arg Cys Asp Ile Val Met Thr Gln Thr Pro Leu Ser Leu Ser
            20                  25                  30

Val Thr Pro Gly Gln Pro Ala Ser Ile Ser Cys Arg Ser Arg Gln Ser
        35                  40                  45

Leu Val Asn Ser Asn Gly Asn Thr Phe Leu Gln Trp Leu Leu Gln Lys
    50                  55                  60

Pro Gly Gln Pro Pro Gln Leu Leu Ile Tyr Lys Val Ser Leu Arg Phe
65                  70                  75                  80

Ser Gly Val Pro Asn Arg Phe Ser Gly Ser Gly Ser Gly Thr Asp Phe
                85                  90                  95

Thr Leu Lys Ile Ser Arg Val Glu Ala Glu Asp Val Gly Leu Tyr Tyr
            100                 105                 110

Cys Ser Gln Ser Thr His Val Pro Pro Thr Phe Gly Gly Gly Thr Lys
            115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160
```

```
Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 62
<211> LENGTH: 112
<212> TYPE: PRT
<213> ORGANISM: Mus musculus

<400> SEQUENCE: 62

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val Asn Ser
            20                  25                  30

Asn Gly Asn Thr Phe Leu Gln Trp Tyr Leu Gln Lys Pro Gly Gln Ser
        35                  40                  45

Pro Lys Leu Leu Ile Tyr Lys Val Ser Leu Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 63
<211> LENGTH: 112
<212> TYPE: PRT
<213> ORGANISM: Artificial sequence
<220> FEATURE:
<223> OTHER INFORMATION: Humanized light chain variable region

<400> SEQUENCE: 63

Asp Ile Val Met Thr Gln Thr Pro Leu Ser Leu Pro Val Thr Leu Gly
1               5                   10                  15

Gln Pro Ala Ser Ile Ser Cys Arg Ser Arg Gln Ser Leu Val Asn Ser
            20                  25                  30

Asn Gly Asn Thr Phe Leu Gln Trp Leu Gln Gln Arg Pro Gly Gln Pro
        35                  40                  45

Pro Arg Leu Leu Ile Tyr Lys Val Ser Leu Arg Phe Ser Gly Val Pro
    50                  55                  60

Asp Arg Phe Ser Gly Ser Gly Ala Gly Thr Asp Phe Thr Leu Thr Ile
65                  70                  75                  80

Ser Arg Val Glu Ala Glu Asp Val Gly Ile Tyr Phe Cys Ser Gln Ser
                85                  90                  95

Thr His Val Pro Pro Thr Phe Gly Gln Gly Thr Lys Val Glu Ile Lys
            100                 105                 110

<210> SEQ ID NO 64
<211> LENGTH: 112
```

```
<212> TYPE: PRT
<213> ORGANISM: Artificial sequence
<220> FEATURE:
<223> OTHER INFORMATION: Humanized light chain variable region

<400> SEQUENCE: 64

Asp Ile Val Met Thr Gln Thr Pro Leu Ser Leu Ser Val Thr Pro Gly
1               5                   10                  15

Gln Pro Ala Ser Ile Ser Cys Arg Ser Arg Gln Ser Leu Val Asn Ser
            20                  25                  30

Asn Gly Asn Thr Phe Leu Gln Trp Tyr Leu Gln Lys Pro Gly Gln Ser
        35                  40                  45

Pro Gln Leu Leu Ile Tyr Lys Val Ser Leu Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Pro Glu Asp Val Gly Val Tyr Tyr Cys Ser Gln Ser
                85                  90                  95

Thr His Val Pro Pro Thr Phe Gly Gly Gly Thr Lys Val Glu Val Lys
            100                 105                 110

<210> SEQ ID NO 65
<211> LENGTH: 112
<212> TYPE: PRT
<213> ORGANISM: Artificial sequence
<220> FEATURE:
<223> OTHER INFORMATION: Humanized light chain variable region

<400> SEQUENCE: 65

Asp Val Val Met Thr Gln Ser Pro Leu Ser Leu Pro Val Thr Leu Gly
1               5                   10                  15

Gln Pro Ala Ser Ile Ser Cys Arg Ser Arg Gln Ser Leu Val Asn Ser
            20                  25                  30

Asn Gly Asn Thr Phe Leu Gln Trp Phe Gln Gln Arg Pro Gly Gln Ser
        35                  40                  45

Pro Arg Arg Leu Ile Tyr Lys Val Ser Leu Arg Phe Ser Gly Val Pro
    50                  55                  60

Asp Arg Phe Ser Gly Ser Gly Ser Asp Thr Asp Phe Thr Leu Arg Ile
65                  70                  75                  80

Ser Arg Val Glu Ala Glu Asp Val Gly Leu Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 66
<211> LENGTH: 112
<212> TYPE: PRT
<213> ORGANISM: Artificial sequence
<220> FEATURE:
<223> OTHER INFORMATION: Humanized light chain variable region

<400> SEQUENCE: 66

Asp Ile Val Met Thr Gln Thr Pro Leu Ser Leu Ser Val Thr Pro Gly
1               5                   10                  15

Gln Pro Ala Ser Ile Ser Cys Arg Ser Arg Gln Ser Leu Val Asn Ser
            20                  25                  30

Asn Gly Asn Thr Phe Leu Gln Trp Leu Leu Gln Lys Pro Gly Gln Pro
        35                  40                  45

Pro Gln Leu Leu Ile Tyr Lys Val Ser Leu Arg Phe Ser Gly Val Pro
```

```
                50                  55                  60
Asn Arg Phe Ser Gly Ser Gly Ser Gly Thr Asp Phe Thr Leu Lys Ile
 65                  70                  75                  80

Ser Arg Val Glu Ala Glu Asp Val Gly Leu Tyr Tyr Cys Ser Gln Ser
                 85                  90                  95

Thr His Val Pro Pro Thr Phe Gly Gly Gly Thr Lys Val Glu Ile Lys
                100                 105                 110
```

METHODS AND COMPOSITIONS FOR TREATING DIABETES AND DIABETIC COMPLICATIONS

BACKGROUND

Diabetes mellitus, commonly referred to as diabetes or DM, is the general term for diseases and disorders that are characterized by recurrent or persistent elevated levels of blood glucose. Diabetes occurs when beta cells in the pancreas do not produce sufficient insulin and/or when the body cannot effectively use the insulin produced by beta cells. The most common forms of diabetes are Type 1 diabetes (also known as juvenile diabetes, juvenile-onset diabetes or insulin-dependent diabetes) and Type 2 diabetes (also known as adult-onset diabetes or non-insulin-dependent diabetes). Type 1 diabetes is an autoimmune disease in which the body attacks insulin-producing beta cells in the pancreas. Type 2 diabetes is a progressive metabolic disease in which the body becomes unable to properly regulate insulin and beta cells become unable to produce sufficient insulin.

Diabetes is a significant public health problem. The World Health Organization estimates that 422 million adults worldwide have diabetes ("Global Report on Diabetes", World Health Organization, 2016). The United States Centers for Disease Control and Prevention (CDC) estimates that 29.1 million people in the U.S. currently have diabetes, which is 9.3% of the total population ("National Diabetes Statistics Report: Estimates of Diabetes and Its Burden in the United States, 2014", U.S. Department of Health and Human Services, Centers for Disease Control and Prevention, 2014). Diabetes is currently the seventh leading cause of death in the U.S. and the estimated total costs of diabetes in the U.S. is $245 billion. The prevalence of diabetes is increasing and the CDC projects that one in three adults in the U.S. will have diabetes by 2050.

Diabetes is associated with a number of complications, including heart disease such as cardiomyopathy, stroke, diabetic retinopathy, cataracts, glaucoma, kidney disease such as nephropathy, hypoglycemia, hyperglycemic crisis, high blood pressure, high blood LDL cholesterol, nerve disease, diabetic neuropathy (peripheral and autonomic neuropathy), neuropathic pain, cognitive impairment, non-alcoholic fatty liver disease, periodontal (gum) disease, hearing loss, erectile dysfunction, depression, complications with pregnancy, diabetic ketoacidosis, hyperosmolar hyperglycemic state and diabetic coma. These complications can result in severe consequences such as blindness, kidney failure, amputations, infections and even death.

Diabetic complications may be studied in the mouse strain BTBR with the ob/ob leptin-deficiency mutation, a recently developed animal model of type 2 diabetes. The BTBR mouse has been recognized as a good animal model of diabetic neuropathy (O'Brien, P. D. et al., "BTBR ob/ob mice as a novel diabetic neuropathy model: Neurological characterization and gene expression analyses", Neurobiology of Disease, Vol. 73, pp. 348-355 (2015)). The BTBR mouse also serves as an animal model of nephropathy and cardiomyopathy (Alpers, C. E. et al., "Mouse models of diabetic nephropathy", Current Opinion in Nephrology and Hypertension, Vol. 20, No. 3, pp. 278-284 (2011); O'Brien, K. D. et al., "Divergent effects of vasodilators on cardiac hypertrophy and inflammation in a murine model of diabetic cardiomyopathy", Journal of the American College of Cardiology, Vol. 57, Issue 17, p. E193 (2011)). The BTBR mouse has the potential to advance the development of treatments for diabetes and diabetic complications.

Current treatments for diabetes and diabetic complications focus on maintaining blood glucose at normal levels. Type 1 diabetes is not preventable and blood glucose must be managed with insulin therapy, such as insulin injections or an implantable insulin pump. Type 2 diabetes may be prevented, treated or reversed with lifestyle changes, such as maintaining a healthy weight, eating a healthy diet, being physically active and avoiding tobacco use. If lifestyle changes are insufficient, Type 2 diabetics may manage their blood glucose by consuming oral glucose or regulating insulin levels through insulin injections or an implantable insulin pump. Bariatric surgery is a radical treatment option, but has been shown to prevent or even reverse Type 2 diabetes. Pharmacotherapies for treating and/or preventing diabetes and diabetic complications are limited.

Senescent cells are cells that are partially-functional or non-functional and are in a state of proliferative arrest. Senescence is a distinct state of a cell, and is associated with biomarkers, such as activation of the biomarker $p16^{Ink4a}$, and expression of $\beta$-galactosidase. Senescence begins with damage or stress (such as overstimulation by growth factors) of cells.

Advanced glycation end-products (AGEs; also referred to as AGE-modified proteins or peptides, or glycation end-products) arise from a non-enzymatic reaction of sugars with protein side-chains (Ando, K. et al., Membrane Proteins of Human Erythrocytes Are Modified by Advanced Glycation End Products during Aging in the Circulation, *Biochem Biophys Res Commun.*, Vol. 258, 123, 125 (1999)). This process begins with a reversible reaction between the reducing sugar and the amino group to form a Schiff base, which proceeds to form a covalently-bonded Amadori rearrangement product. Once formed, the Amadori product undergoes further rearrangement to produce AGEs. Hyperglycemia and oxidative stress promote this post-translational modification of membrane proteins (Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009)). AGEs may also be formed from other processes. For example, the advanced glycation end product, $N^\varepsilon$-(carboxymethyl)lysine, is a product of both lipid peroxidation and glycoxidation reactions. AGEs have been associated with several pathological conditions including inflammation, atherosclerosis, stroke, endothelial cell dysfunction, and neurodegenerative disorders (Bierhaus A, "AGEs and their interaction with AGE-receptors in vascular disease and diabetes mellitus. I. The AGE concept," Cardiovasc Res, Vol. 37(3), 586-600 (1998)).

AGE-modified proteins are also a marker of senescent cells. This association between AGEs and senescence is well known in the art. See, for example, Gruber, L. (WO 2009/143411, 26 Nov. 2009), Ando, K. et al. (Membrane Proteins of Human Erythrocytes Are Modified by Advanced Glycation End Products during Aging in the Circulation, *Biochem Biophys Res Commun.*, Vol. 258, 123, 125 (1999)), Ahmed, E. K. et al. ("Protein Modification and Replicative Senescence of WI-38 Human Embryonic Fibroblasts" *Aging Cells*, vol. 9, 252, 260 (2010)), Vlassara, H. et al. (Advanced Glycosylation Endproducts on Erythrocyte Cell Surface Induce Receptor-Mediated Phagocytosis by Macrophages, *J. Exp. Med.*, Vol. 166, 539, 545 (1987)) and Vlassara et al. ("High-affinity-receptor-mediated Uptake and Degradation of Glucose-modified Proteins: A Potential Mechanism for the Removal of Senescent Macromolecules" *Proc. Natl.*

*Acad. Sci. USAI*, Vol. 82, 5588, 5591 (1985)). Furthermore, Ahmed, E. K. et al. indicates that glycation end-products are "one of the major causes of spontaneous damage to cellular and extracellular proteins" (Ahmed, E. K. et al., see above, page 353). Accordingly, the accumulation of glycation end-products is associated with senescence and lack of function.

The damage or stress that causes cellular senescence also negatively impacts mitochondrial DNA in the cells to cause them to produce free radicals which react with sugars in the cell to form methyl glyoxal (MG). MG in turn reacts with proteins or lipids to generate advanced glycation end products. In the case of the protein component lysine, MG reacts to form carboxymethyllysine, which is an AGE.

Damage or stress to mitochondrial DNA also sets off a DNA damage response which induces the cell to produce cell cycle blocking proteins. These blocking proteins prevent the cell from dividing. Continued damage or stress causes mTOR production, which in turn activates protein synthesis and inactivates protein breakdown. Further stimulation of the cells leads to programmed cell death (apoptosis).

p16 is a protein involved in regulation of the cell cycle, by inhibiting the S phase (synthesis phase). It can be activated during ageing or in response to various stresses, such as DNA damage, oxidative stress or exposure to drugs. p16 is typically considered a tumor suppressor protein, causing a cell to become senescent in response to DNA damage and irreversibly preventing the cell from entering a hyperproliferative state. However, there has been some ambiguity in this regard, as some tumors show overexpression of p16, while others show downregulated expression. Evidence suggests that overexpression of p16 is some tumors results from a defective retinoblastoma protein ("Rb"). p16 acts on Rb to inhibit the S phase, and Rb downregulates p16, creating negative feedback. Defective Rb fails to both inhibit the S phase and downregulate p16, thus resulting in overexpression of p16 in hyperproliferating cells (Romagosa, C. et al., $p16^{Ink4a}$ overexpression in cancer: a tumor suppressor gene associated with senescence and high-grade tumors, *Oncogene*, Vol. 30, 2087-2097 (2011)).

Senescent cells are associated with secretion of many factors involved in intercellular signaling, including pro-inflammatory factors; secretion of these factors has been termed the senescence-associated secretory phenotype, or SASP (Freund, A. "Inflammatory networks during cellular senescence: causes and consequences" Trends Mol Med. 2010 May; 16(5):238-46). Autoimmune diseases, such as Crohn's disease and rheumatoid arthritis, are associated with chronic inflammation (Ferraccioli, G. et al. "Interleukin-1β, and Interleukin-6 in Arthritis Animal Models: Roles in the Early Phase of Transition from Acute to Chronic Inflammation and Relevance for Human Rheumatoid Arthritis" Mol Med. 2010 November-December; 16(11-12): 552-557). Chronic inflammation may be characterized by the presence of pro-inflammatory factors at levels higher than baseline near the site of pathology, but lower than those found in acute inflammation. Examples of these factors include TNF, IL-1α, IL-1β, IL-5, IL-6, IL-8, IL-12, IL-23, CD2, CD3, CD20, CD22, CD52, CD80, CD86, C5 complement protein, BAFF, APRIL, IgE, α4β1 integrin and α4β7 integrin. Senescent cells also upregulate genes with roles in inflammation including IL-1β, IL-8, ICAM1, TNFAP3, ESM1 and CCL2 (Burton, D. G. A. et al., "Microarray analysis of senescent vascular smooth muscle cells: a link to atherosclerosis and vascular calcification", Experimental Gerontology, Vol. 44, No. 10, pp. 659-665 (October 2009)). Because senescent cells produce pro-inflammatory factors, removal of these cells alone produces a profound reduction in inflammation as well as the amount and concentration of pro-inflammatory factors.

Senescent cells secrete reactive oxygen species ("ROS") as part of the SASP. ROS are believed to play an important role in maintaining senescence of cells. The secretion of ROS creates a bystander effect, where senescent cells induce senescence in neighboring cells: ROS create the very cellular damage known to activate p16 expression, leading to senescence (Nelson, G., A senescent cell bystander effect: senescence-induced senescence, *Aging Cell*, Vo. 11, 345-349 (2012)). The p16/Rb pathway leads to the induction of ROS, which in turn activates the protein kinase C delta creating a positive feedback loop that further enhance ROS, helping maintain the irreversible cell cycle arrest; it has even been suggested that exposing cancer cells to ROS might be effective to treat cancer by inducing cell phase arrest in hyperproliferating cells (Rayess, H. et al., Cellular senescence and tumor suppressor gene p16, *Int J Cancer*, Vol. 130, 1715-1725 (2012)).

Recent research demonstrates the therapeutic benefits of removing senescent cells. In vivo animal studies at the Mayo Clinic in Rochester, Minn., found that elimination of senescent cells in transgenic mice carrying a biomarker for elimination delayed age-related disorders associated with cellular senescence. Eliminating senescent cells in fat and muscle tissues substantially delayed the onset of sarcopenia and cataracts and reduced senescence indicators in skeletal muscle and the eye (Baker, D. J. et al., "Clearance of $p16^{Ink4a}$-positive senescent cells delays ageing-associated disorders", Nature, Vol. 479, pp. 232-236, (2011)). Mice that were treated to induce senescent cell elimination were found to have larger diameters of muscle fibers as compared to untreated mice. Treadmill exercise tests indicated that treatment also preserved muscle function. Continuous treatment of transgenic mice for removal of senescent cells had no negative side effects and selectively delayed age-related phenotypes that depend on cells. This data demonstrates that removal of senescent cells produces beneficial therapeutic effects and shows that these benefits may be achieved without adverse effects.

Additional In vivo animal studies in mice found that removing senescent cells using senolytic agents treats aging-related disorders and atherosclerosis. Short-term treatment with senolytic drugs in chronologically aged or progeroid mice alleviated several aging-related phenotypes (Zhu, Y. et al., "The Achilles' heel of senescent cells: from transcriptome to senolytic drugs", Aging Cell, vol. 14, pp. 644-658 (2015)). Long-term treatment with senolytic drugs improved vasomotor function in mice with established atherosclerosis and reduced intimal plaque calcification (Roos, C. M. et al., "Chronic senolytic treatment alleviates established vasomotor dysfunction in aged or atherosclerotic mice", Aging Cell (2016)). This data further demonstrates the benefits of removing senescent cells.

Vaccines have been widely used since their introduction by Edward Jenner in the 1770s to confer immunity against a wide range of diseases and afflictions. Vaccine preparations contain a selected immunogenic agent capable of stimulating immunity to an antigen. Typically, antigens are used as the immunogenic agent in vaccines, such as, for example, viruses, either killed or attenuated, and purified viral components. Antigens used in the production of cancer vaccines include, for example, tumor-associated carbohydrate antigens (TACAs), dendritic cells, whole cells and viral vectors. Different techniques are employed to produce the desired amount and type of antigen being sought. For example, pathogenic viruses are grown either in eggs or cells. Recombinant DNA technology is often utilized to generate attenuated viruses for vaccines.

Vaccines may therefore be used to stimulate the production of antibodies in the body and provide immunity against antigens. When an antigen is introduced to a subject that has been vaccinated and developed immunity to that antigen, the immune system may destroy or remove cells that express the antigen.

SUMMARY

In a first aspect, the invention is a method of treating or preventing the onset of diabetes or diabetic complications, comprising killing senescent cells by administering to a subject a composition comprising an anti-AGE antibody. The diabetic complication comprises at least one disease or disorder selected from the group consisting of stroke, diabetic retinopathy, cataracts, glaucoma, kidney disease, hypoglycemia, hyperglycemic crisis, high blood pressure, high blood LDL cholesterol, nerve disease, diabetic neuropathy, neuropathic pain, cognitive impairment, non-alcoholic fatty liver disease, periodontal disease, hearing loss, erectile dysfunction, depression, complications with pregnancy, diabetic ketoacidosis, hyperosmolar hyperglycemic state and diabetic coma.

Definitions

The term "diabetes" means a disease or disorder characterized by persistent elevated levels of blood glucose in which a subject has an A1C level greater than 5.7% when measured on two separate occasions. Diabetes includes Type 1 diabetes, Type 2 diabetes, gestational diabetes, prediabetes, latent autoimmune diabetes of adults, congenital diabetes, monogenic diabetes, maturity-onset diabetes of the young (MODY), cystic fibrosis-related diabetes and idiopathic diabetes.

The term "peptide" means a molecule composed of 2-50 amino acids.

The term "protein" means a molecule composed of more than 50 amino acids.

The terms "advanced glycation end-product", "AGE", "AGE-modified protein", "AGE-modified peptide" and "glycation end-product" refer to modified proteins or peptides that are formed as the result of the reaction of sugars with protein side chains that further rearrange and form irreversible cross-links. This process begins with a reversible reaction between a reducing sugar and an amino group to form a Schiff base, which proceeds to form a covalently-bonded Amadori rearrangement product. Once formed, the Amadori product undergoes further rearrangement to produce AGEs. AGE-modified proteins and antibodies to AGE-modified proteins are described in U.S. Pat. No. 5,702,704 to Bucala ("Bucala") and U.S. Pat. No. 6,380,165 to Al-Abed et al. ("Al-Abed"). Glycated proteins or peptides that have not undergone the necessary rearrangement to form AGEs, such as N-deoxyfructosyllysine found on glycated albumin, are not AGEs. AGEs may be identified by the presence of AGE modifications (also referred to as AGE epitopes or AGE moieties) such as 2-(2-furoyl)-4(5)-(2-furanyl)-1H-imidazole ("FFI"); 5-hydroxymethyl-1-alkylpyrrole-2-carbaldehyde ("Pyrraline"); 1-alkyl-2-formyl-3,4-diglycosyl pyrrole ("AFGP"), a non-fluorescent model AGE; carboxymethyllysine; carboxyethyllysine; and pentosidine. ALI, another AGE, is described in Al-Abed.

The term "AGE antigen" means a substance that elicits an immune response against an AGE-modified protein or peptide of a cell. The immune response against an AGE-modified protein or peptide of a cell does not include the production of antibodies to the non-AGE-modified protein or peptide.

"An antibody that binds to an AGE-modified protein on a cell", "anti-AGE antibody" or "AGE antibody" means an antibody, antibody fragment or other protein or peptide that binds to an AGE-modified protein or peptide which preferably includes a constant region of an antibody, where the protein or peptide which has been AGE-modified is a protein or peptide normally found bound on the surface of a cell, preferably a mammalian cell, more preferably a human, cat, dog, horse, camelid (for example, camel or alpaca), cattle, sheep, or goat cell. "An antibody that binds to an AGE-modified protein on a cell", "anti-AGE antibody" or "AGE antibody" does not include an antibody or other protein which binds with the same specificity and selectivity to both the AGE-modified protein or peptide, and the same non-AGE-modified protein or peptide (that is, the presence of the AGE modification does not increase binding). AGE-modified albumin is not an AGE-modified protein on a cell, because albumin is not a protein normally found bound on the surface of cells. "An antibody that binds to an AGE-modified protein on a cell", "anti-AGE antibody" or "AGE antibody" only includes those antibodies which lead to removal, destruction, or death of the cell. Also included are antibodies which are conjugated, for example to a toxin, drug, or other chemical or particle. Preferably, the antibodies are monoclonal antibodies, but polyclonal antibodies are also possible.

The term "senescent cell" means a cell which is in a state of proliferative arrest and expresses one or more biomarkers of senescence, such as activation of p16$^{Ink4a}$ or expression of senescence-associated β-galactosidase. Also included are cells which express one or more biomarkers of senescence, do not proliferate in vivo, but may proliferate in vitro under certain conditions, such as some satellite cells found in the muscles of ALS patients.

The term "variant" means a nucleotide, protein or amino acid sequence different from the specifically identified sequences, wherein one or more nucleotides, proteins or amino acid residues is deleted, substituted or added. Variants may be naturally-occurring allelic variants, or non-naturally-occurring variants. Variants of the identified sequences may retain some or all of the functional characteristics of the identified sequences.

The term "percent (%) sequence identity" is defined as the percentage of amino acid residues in a candidate sequence that are identical to the amino acid residues in a reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways using publicly available computer software such as BLAST, BLAST-2, ALIGN or Megalign (DNASTAR) software. Preferably, % sequence identity values are generated using the sequence comparison computer program ALIGN-2. The ALIGN-2 sequence comparison computer program is publicly available from Genentech, Inc. (South San Francisco, Calif.), or may be compiled from the source code, which has been filed with user documentation in the U.S. Copyright Office and is registered under U.S. Copyright Registration No. TXU510087. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. Where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained using the ALIGN-2 computer program.

BRIEF DESCRIPTION OF THE DRAWING

FIG. 1 is a graph of the response versus time in an antibody binding experiment.

DETAILED DESCRIPTION

Elevated blood glucose has long been considered to be the primary cause of diabetes. Recent research into the pathogenesis of diabetes and diabetic complications has revealed that the mechanism is more complex. A number of studies have indicated that cellular senescence is the main proponent in the development and progression of diabetes and diabetic complications.

Senescent cells have been identified as a contributing factor to the onset and progression of both Type 1 and Type 2 diabetes through the secretion of reactive oxygen species. Reactive oxygen species contribute to Type 1 diabetes by activating inflammatory and apoptotic processes involved in beta cell dysfunction (Radoi, V. et al., "Advanced glycation end-products in diabetes mellitus: mechanism of action and focused treatment", Proceedings of the Romanian Academy, Series B, No. 1, p. 9-19 (2012)). In Type 2 diabetes, reactive oxygen species disrupt transmission pathways between the insulin receptor and the glucose transport system, which causes insulin resistance and inactivation of anti-atherosclerotic enzymes. The interaction of toxic AGEs, a marker of senescent cells, with their receptors (RAGE) in endothelial and inflammatory cells also leads to intracellular generation of reactive oxygen species.

Senescent cells have been linked specifically with Type 2 diabetes. Elevated glucose is known to promote premature senescence in vitro in endothelial cells, renal mesangial cells, adipose-derived stem cells and fibroblasts (Palmer, A. K. et al., "Cellular senescence in Type 2 diabetes: a therapeutic opportunity", Diabetes, Vol 64, pp. 2289-2298 (2015)). Other metabolic and signaling changes seen in diabetes such as altered lipid metabolism and growth hormone axis perturbations also promote senescent cell formation. Inflammatory factors are part of the senescence-associated secretory phenotype (SASP) and are thought to be a major contributor to the development of insulin resistance. The association between inflammation and proinflammatory factors and cellular senescence is described in more detail in WO 2016/044252 and in Application No. 62/443,557. Cellular senescence may directly contribute to Type 2 diabetes through beta cell senescence. Senescent cells may be both a cause and a consequence of Type 2 diabetes as part of a pathogenic feedback loop (Palmer et al.). In addition, a high proportion of senescent islets of Langerhans, which decreases the beta cell number and islet mass to pathological levels, was found in a mouse model of Friedreich's ataxia, a disorder characterized by diabetes (Mollá, B. et al., "Two different pathogenic mechanisms, dying-back axonal neuropathy and pancreatic senescence, are present in the YG8R mouse model of Friedreich's ataxia", Disease Models & Mechanisms, Vol. 9, pp. 647-657 (2016)).

The relationship between AGEs and diabetes and diabetic complications also implicates cellular senescence. Carboxymethyllysine (CML), the most well-known AGE, induced cell death in human pancreatic beta cells in vitro and was accompanied by an increase in intracellular oxidative stress (Boesten, D. M. P. H. J. et al., "Effect of NE-carboxymethyllysine on oxidative stress and the glutathione system in beta cells", Toxicology Reports, Vol. 1, pp. 973-980 (2014)). AGEs have been associated with diabetic complications including diabetic retinopathy, diabetic nephropathy, diabetic neuropathy, diabetic cardiomyopathy, thrombogenesis, atherosclerosis, stroke, osteoporosis and erectile dysfunction. While the specific mechanism varies depending on the diabetic complication, many diabetic complications result from an increase in proinflammatory factors such as NE-κB, TNF-α and IL-6 or an increase in fibrosis by promoting profibrotic proteins such as TGF-β, both of which are promoted by AGEs and the AGE-RAGE interaction (Radoi et al.). AGEs have also been indirectly implicated in diabetic complications though methylglyoxal, a known cause of AGEs. For example, methylglyoxal increases the chronic extremity soreness in diabetic neuropathy ("Methylglyoxal", available online at en.wikipedia.org/wiki/Methylglyoxal (Jun. 5, 2017)). The presence of AGEs in skin, serum, saliva and urine has been correlated with diabetes and diabetic complications (Garay-Sevilla, M. E. et al., "Advanced glycosylation end products in skin, serum, saliva and urine and its association with complications of patients with Type 2 diabetes mellitus", Journal of Endocrinological Investigation, Vol. 28, No. 5, pp. 223-230 (2005); Yoon, M-S. et al., "Characterisation of advanced glycation endproducts in saliva from patients with diabetes mellitus", Biochemical and Biophysical Research Communications, Vol. 323, Issue 2, pp. 377-381 (2004)).

AGEs have also been associated with the development of diabetic complications through matrix metalloproteinases (MMPs). MMPs have been implicated in a number of diabetic microvascular complications including diabetic nephropathy, diabetic cardiomyopathy, diabetic peripheral arterial disease, cerebral circulation and stroke volume in diabetes and poor diabetic wound healing (Tsioufis, C. et al., "The role of matrix metalloproteinases in diabetes mellitus", Current Topics in Medicinal Chemistry, Vol. 12, No. 10, Pages 1159-1165 (2012)). Expression of the MMP macrophage metalloelastase (MMP12) is correlated positively and significantly with insulin resistance, TNF-α expression and the number of CD14+CD206+ macrophages in adipose tissue (Lee, J-T. et al., "Macrophage metalloelastase (MMP12) regulates adipose tissue expansion, insulin sensitivity, and expression of inducible nitric oxide synthase", Endocrinology, Vol. 155, No. 9, p. 3409-3420 (2014)). AGEs can be one of the major factors influencing the progression of diabetic nephropathy by modulating the expression of MMPs (Xu, X. et al., "A glimpse of matrix metalloproteinases in diabetic nephropathy", Current Medicinal Chemistry, Vol. 21, No. 28, p. 3244-3260 (2014)).

The recognition of a link between AGEs and diabetes has resulted in research into therapies that target AGEs for treating diabetic complications. Therapies that have been investigated for treating diabetic complications include aminoguanidine, pyridoxamine, benfotiamine, LR-90, soluble AGE receptor molecules, angiotensin-converting-enzyme (ACE) inhibitors, angiotensin II receptor antagonists, superoxide dismutase (SOD)/catalase mimetics, bisphosphonates, minodronate, statins, AGE-breakers, pyridinium (TRC4186), alagebrium (ALT-711) and Janus kinase (JAK) inhibitors (Radoi et al.)). However, none of these therapies targets senescent cells, the root cause of diabetes and diabetic complications.

The therapeutic benefits of removing senescent cells has been demonstrated in atherosclerosis and in age-related diseases, such as sarcopenia (Xu, M. et al., "Targeting senescent cells enhances adipogenesis and metabolic function in old age", eLife (2015)). The identification of a link between cellular senescence, either directly or through AGEs, and diabetes and diabetic complications allows for similar treatment possibilities. The present invention uses enhanced clearance of cells expressing AGE-modified proteins or peptides (AGE-modified cells) to treat, ameliorate or prevent the onset of diabetes and diabetic complications by removing or killing senescent cells. This may be accomplished by administering anti-AGE antibodies to a subject.

Vaccination against AGE-modified proteins or peptides of a cell may also be used to control the presence of AGE-modified cells in a subject. The continuous and virtually ubiquitous surveillance exercised by the immune system in the body in response to a vaccination allows maintaining low levels of AGE-modified cells in the body. Vaccination against AGE-modified proteins or peptides of a cell removes or kills senescent cells. The process of senescent cell removal or destruction allows vaccination against AGE-modified proteins or peptides of a cell to be used to treat or prevent the onset of diabetes and diabetic complications.

An antibody that binds to an AGE-modified protein on a cell ("anti-AGE antibody" or "AGE antibody") is known in the art. Examples include those described in U.S. Pat. No. 5,702,704 (Bucala) and U.S. Pat. No. 6,380,165 (Al-Abed et al.). The antibody may bind to one or more AGE-modified proteins or peptides having an AGE modification such as FFI, pyrraline, AFGP, ALI, carboxymethyllysine, carboxyethyllysine and pentosidine, and mixtures of such antibodies. Preferably, the antibody binds carboxymethyllysine-modified or carboxyethyllysine-modified proteins. Preferably, the antibody is non-immunogenic to the animal in which it will be used, such as non-immunogenic to humans; companion animals including cats, dogs and horses; and commercially important animals, such camels (or alpaca), cattle (bovine), sheep, and goats. More preferably, the antibody has the same species constant region as antibodies of the animal to reduce the immune response against the antibody, such as being humanized (for humans), felinized (for cats), caninized (for dogs), equuinized (for horses), camelized (for camels or alpaca), bovinized (for cattle), ovinized (for sheep), or caperized (for goats). Most preferably, the antibody is identical to that of the animal in which it will be used (except for the variable region), such as a human antibody, a cat antibody, a dog antibody, a horse antibody, a camel antibody, a bovine antibody, a sheep antibody or a goat antibody. Details of the constant regions and other parts of antibodies for these animals are described below. The antibody may be monoclonal or polyclonal. Preferably, the antibody is a monoclonal antibody.

Preferred anti-AGE antibodies include those which bind to proteins or peptides that exhibit a carboxymethyllysine or carboxyethyllysine AGE modification. Carboxymethyllysine (also known as N(epsilon)-(carboxymethyl)lysine, N(6)-carboxymethyllysine, or 2-Amino-6-(carboxymethylamino)hexanoic acid) and carboxyethyllysine (also known as N-epsilon-(carboxyethyl)lysine) are found on proteins or peptides and lipids as a result of oxidative stress and chemical glycation. CML- and CEL-modified proteins or peptides are recognized by the receptor RAGE which is expressed on a variety of cells. CML and CEL have been well-studied and CML- and CEL-related products are commercially available. For example, Cell Biolabs, Inc. sells CML-BSA antigens, CML polyclonal antibodies, CML immunoblot kits, and CML competitive ELISA kits (www.cellbiolabs.com/cml-assays) as well as CEL-BSA antigens and CEL competitive ELISA kits (www.cellbiolabs.com/cel-n-epsilon-carboxyethyl-lysine-assays-and-reagents). A particularly preferred antibody includes the variable region of the commercially available mouse anti-glycation end-product antibody raised against carboxymethyl lysine conjugated with keyhole limpet hemocyanin, the carboxymethyl lysine MAb (Clone 318003) available from R&D Systems, Inc. (Minneapolis, Minn.; catalog no. MAB3247), modified to have a human constant region (or the constant region of the animal into which it will be administered). Commercially-available antibodies, such as the carboxymethyl lysine antibody corresponding to catalog no. MAB3247 from R&D Systems, Inc., may be intended for diagnostic purposes and may contain material that is not suited for use in animals or humans. Preferably, commercially-available antibodies are purified and/or isolated prior to use in animals or humans to remove toxins or other potentially-harmful material.

The anti-AGE antibody has low rate of dissociation from the antibody-antigen complex, or $k_d$ (also referred to as $k_{back}$ or off-rate), preferably at most $9 \times 10^{-3}$, $8 \times 10^{-3}$, $7 \times 10^{-3}$ or $6 \times 10^{-3}$ (sec$^{-1}$). The anti-AGE antibody has a high affinity for the AGE-modified protein of a cell, which may be expressed as a low dissociation constant $K_D$ of at most $9 \times 10^{-6}$, $8 \times 10^{-6}$, $7 \times 10^{-6}$, $6 \times 10^{-6}$, $5 \times 10^{-6}$, $4 \times 10^{-6}$ or $3 \times 10^{-6}$ (M). Preferably, the binding properties of the anti-AGE antibody are similar to, the same as, or superior to the carboxymethyl lysine MAb (Clone 318003) available from R&D Systems, Inc. (Minneapolis, Minn.; catalog no. MAB3247), illustrated in FIG. 1.

The anti-AGE antibody may destroy AGE-modified cells through antibody-dependent cell-mediated cytotoxicity (ADCC). ADCC is a mechanism of cell-mediated immune defense in which an effector cell of the immune system actively lyses a target cell whose membrane-surface antigens have been bound by specific antibodies. ADCC may be mediated by natural killer (NK) cells, macrophages, neutrophils or eosinophils. The effector cells bind to the Fc portion of the bound antibody. The anti-AGE antibody may also destroy AGE-modified cells through complement-dependent cytotoxicity (CDC). In CDC, the complement cascade of the immune system is triggered by an antibody binding to a target antigen.

The anti-AGE antibody may be conjugated to an agent that causes the destruction of AGE-modified cells. Such agents may be a toxin, a cytotoxic agent, magnetic nanoparticles, and magnetic spin-vortex discs.

A toxin, such as pore-forming toxins (PFT) (Aroian R. et al., "Pore-Forming Toxins and Cellular Non-Immune Defenses (CNIDs)," *Current Opinion in Microbiology*, 10:57-61 (2007)), conjugated to an anti-AGE antibody may be injected into a patient to selectively target and remove AGE-modified cells. The anti-AGE antibody recognizes and binds to AGE-modified cells. Then, the toxin causes pore formation at the cell surface and subsequent cell removal through osmotic lysis.

Magnetic nanoparticles conjugated to the anti-AGE antibody may be injected into a patient to target and remove AGE-modified cells. The magnetic nanoparticles can be heated by applying a magnetic field in order to selectively remove the AGE-modified cells.

As an alternative, magnetic spin-vortex discs, which are magnetized only when a magnetic field is applied to avoid self-aggregation that can block blood vessels, begin to spin when a magnetic field is applied, causing membrane disruption of target cells. Magnetic spin-vortex discs, conjugated to anti-AGE antibodies specifically target AGE-modified cell types, without removing other cells.

Antibodies are Y-shaped proteins composed of two heavy chains and two light chains. The two arms of the Y shape form the fragment antigen-binding (Fab) region while the base or tail of the Y shape forms the fragment crystallizable (Fc) region of the antibody. Antigen binding occurs at the terminal portion of the fragment antigen-binding region (the tips of the arms of the Y shape) at a location referred to as the paratope, which is a set of complementarity determining regions (also known as CDRs or the hypervariable region). The complementarity determining regions vary among different antibodies and gives a given antibody its specificity for binding to a given antigen. The fragment crystallizable region of the antibody determines the result of antigen binding and may interact with the immune system, such as by triggering the complement cascade or initiating antibody-dependent cell-mediated cytotoxicity (ADCC). When antibodies are prepared recombinantly, it is also possible to have a single antibody with variable regions (or complementary determining regions) that bind to two different antigens, with each tip of the Y shape being specific to one of the antigens; these are referred to as bi-specific antibodies.

A humanized anti-AGE antibody according to the present invention may have the human constant region sequence of amino acids shown in SEQ ID NO: 22. The heavy chain complementarity determining regions of the humanized anti-AGE antibody may have one or more of the protein sequences shown in SEQ ID NO: 23 (CDR1H), SEQ ID NO: 24 (CDR2H) and SEQ ID NO: 25 (CDR3H). The light chain complementarity determining regions of the humanized anti-AGE antibody may have one or more of the protein sequences shown in SEQ ID NO: 26 (CDR1L), SEQ ID NO: 27 (CDR2L) and SEQ ID NO: 28 (CDR3L).

The heavy chain of a humanized anti-AGE antibody may have or may include the protein sequence of SEQ ID NO: 1. The variable domain of the heavy chain may have or may include the protein sequence of SEQ ID NO: 2. The complementarity determining regions of the variable domain of the heavy chain (SEQ ID NO: 2) are shown in SEQ ID NO: 41, SEQ ID NO: 42 and SEQ ID NO: 43. The kappa light chain of a humanized anti-AGE antibody may have or may include the protein sequence of SEQ ID NO: 3. The variable domain of the kappa light chain may have or may include the protein sequence of SEQ ID NO: 4. Optionally, the arginine (Arg or R) residue at position 128 of SEQ ID NO: 4 may be omitted. The complementarity determining regions of the variable domain of the light chain (SEQ ID NO: 4) are shown in SEQ ID NO: 44, SEQ ID NO: 45 and SEQ ID NO: 46. The variable regions may be codon-optimized, synthesized and cloned into expression vectors containing human immunoglobulin G1 constant regions. In addition, the variable regions may be used in the preparation of non-human anti-AGE antibodies.

The antibody heavy chain may be encoded by the DNA sequence of SEQ ID NO: 12, a murine anti-AGE immunoglobulin G2b heavy chain. The protein sequence of the murine anti-AGE immunoglobulin G2b heavy chain encoded by SEQ ID NO: 12 is shown in SEQ ID NO: 16. The variable region of the murine antibody is shown in SEQ ID NO: 20, which corresponds to positions 25-142 of SEQ ID NO: 16. The antibody heavy chain may alternatively be encoded by the DNA sequence of SEQ ID NO: 13, a chimeric anti-AGE human immunoglobulin G1 heavy chain. The protein sequence of the chimeric anti-AGE human immunoglobulin G1 heavy chain encoded by SEQ ID NO: 13 is shown in SEQ ID NO: 17. The chimeric anti-AGE human immunoglobulin includes the murine variable region of SEQ ID NO: 20 in positions 25-142. The antibody light chain may be encoded by the DNA sequence of SEQ ID NO: 14, a murine anti-AGE kappa light chain. The protein sequence of the murine anti-AGE kappa light chain encoded by SEQ ID NO: 14 is shown in SEQ ID NO: 18. The variable region of the murine antibody is shown in SEQ ID NO: 21, which corresponds to positions 21-132 of SEQ ID NO: 18. The antibody light chain may alternatively be encoded by the DNA sequence of SEQ ID NO: 15, a chimeric anti-AGE human kappa light chain. The protein sequence of the chimeric anti-AGE human kappa light chain encoded by SEQ ID NO: 15 is shown in SEQ ID NO: 19. The chimeric anti-AGE human immunoglobulin includes the murine variable region of SEQ ID NO: 21 in positions 21-132.

A humanized anti-AGE antibody according to the present invention may have or may include one or more humanized heavy chains or humanized light chains. A humanized heavy chain may be encoded by the DNA sequence of SEQ ID NO: 30, 32 or 34. The protein sequences of the humanized heavy chains encoded by SEQ ID NOs: 30, 32 and 34 are shown in SEQ ID NOs: 29, 31 and 33, respectively. A humanized light chain may be encoded by the DNA sequence of SEQ ID NO: 36, 38 or 40. The protein sequences of the humanized light chains encoded by SEQ ID NOs: 36, 38 and 40 are shown in SEQ ID NOs: 35, 37 and 39, respectively. Preferably, the humanized anti-AGE antibody maximizes the amount of human sequence while retaining the original antibody specificity. A complete humanized antibody may be constructed that contains a heavy chain having a protein sequence chosen from SEQ ID NOs: 29, 31 and 33 and a light chain having a protein sequence chosen from SEQ ID NOs: 35, 37 and 39.

Particularly preferred anti-AGE antibodies may be obtained by humanizing murine monoclonal anti-AGE antibodies. Murine monoclonal anti-AGE antibodies have the heavy chain protein sequence shown in SEQ ID NO: 47 (the protein sequence of the variable domain is shown in SEQ ID NO: 52) and the light chain protein sequence shown in SEQ ID NO: 57 (the protein sequence of the variable domain is shown in SEQ ID NO: 62). A preferred humanized heavy chain may have the protein sequence shown in SEQ ID NO: 48, SEQ ID NO: 49, SEQ ID NO: 50 or SEQ ID NO: 51 (the protein sequences of the variable domains of the humanized heavy chains are shown in SEQ ID NO: 53, SEQ ID NO: 54, SEQ ID NO: 55 and SEQ ID NO: 56, respectively). A preferred humanized light chain may have the protein sequence shown in SEQ ID NO: 58, SEQ ID NO: 59, SEQ ID NO: 60 or SEQ ID NO: 61 (the protein sequences of the variable domains of the humanized light chains are shown in SEQ ID NO: 63, SEQ ID NO: 64, SEQ ID NO: 65 and SEQ ID NO: 66, respectively). Preferably, a humanized anti-AGE monoclonal antibody is composed a heavy chain having a protein sequence selected from the group consisting of SEQ ID NO: 48, SEQ ID NO: 49, SEQ ID NO: 50 and SEQ ID NO: 51 and a light chain having a protein sequence selected from the group consisting of SEQ ID NO: 58, SEQ ID NO: 59, SEQ ID NO: 60 and SEQ ID NO: 61. Humanized monoclonal anti-AGE antibodies composed of these protein sequences may have better binding and/or improved activation of the immune system, resulting in greater efficacy.

The protein sequence of an antibody from a non-human species may be modified to include the variable domain of the heavy chain having the sequence shown in SEQ ID NO: 2 or the kappa light chain having the sequence shown in SEQ ID NO: 4. The non-human species may be a companion animal, such as the domestic cat or domestic dog, or livestock, such as cattle, the horse or the camel. Preferably, the non-human species is not the mouse. The heavy chain of the horse (*Equus caballus*) antibody immunoglobulin gamma 4 may have or may include the protein sequence of SEQ ID NO: 5 (EMBL/GenBank accession number AY445518). The heavy chain of the horse (*Equus caballus*) antibody immunoglobulin delta may have or may include the protein sequence of SEQ ID NO: 6 (EMBL/GenBank accession number AY631942). The heavy chain of the dog (*Canis familiaris*) antibody immunoglobulin A may have or may include the protein sequence of SEQ ID NO: 7 (GenBank accession number L36871). The heavy chain of the dog (*Canis familiaris*) antibody immunoglobulin E may have or may include the protein sequence of SEQ ID NO: 8 (GenBank accession number L36872). The heavy chain of the cat (*Fells catus*) antibody immunoglobulin G2 may have or may include the protein sequence of SEQ ID NO: 9 (DDBJ/EMBL/GenBank accession number KF811175).

Animals of the camelid family, such as camels (*Camelus dromedarius* and *Camelus bactrianus*), llamas (*Lama glama, Lama pacos* and *Lama vicugna*), alpacas (*Vicugna pacos*) and guanacos (*Lama guanicoe*), have a unique antibody that is not found in other mammals. In addition to conventional immunoglobulin G antibodies composed of heavy and light chain tetramers, camelids also have heavy chain immunoglobulin G antibodies that do not contain light chains and exist as heavy chain dimers. These antibodies are known as heavy chain antibodies, HCAbs, single-domain antibodies or sdAbs, and the variable domain of a camelid heavy chain antibody is known as the VHH. The camelid heavy chain antibodies lack the heavy chain CH1 domain and have a hinge region that is not found in other species. The variable region of the Arabian camel (*Camelus dromedarius*) single-domain antibody may have or may include the protein sequence of SEQ ID NO: 10 (GenBank accession number AJ245148). The variable region of the heavy chain of the Arabian camel (*Camelus dromedarius*) tetrameric immunoglobulin may have or may include the protein sequence of SEQ ID NO: 11 (GenBank accession number AJ245184).

In addition to camelids, heavy chain antibodies are also found in cartilaginous fishes, such as sharks, skates and rays. This type of antibody is known as an immunoglobulin new antigen receptor or IgNAR, and the variable domain of an IgNAR is known as the VNAR. The IgNAR exists as two identical heavy chain dimers composed of one variable domain and five constant domains each. Like camelids, there is no light chain.

The protein sequences of additional non-human species may be readily found in online databases, such as the International ImMunoGeneTics Information System (www.imgt.org), the European Bioinformatics Institute (www.ebi.ac.uk), the DNA Databank of Japan (ddbj.nig.ac.jp/arsa) or the National Center for Biotechnology Information (www.ncbi.nlm.nih.gov).

An anti-AGE antibody or a variant thereof may include a heavy chain having at least 90%, 91%, 92%, 93%, 94%, 95%, 96%, 97%, 98%, 99%, or 100% sequence identity to the amino acid sequence of SEQ ID NO: 1, SEQ ID NO: 16, SEQ ID NO: 17, SEQ ID NO: 29, SEQ ID NO: 31, SEQ ID NO: 33, SEQ ID NO: 47, SEQ ID NO: 48, SEQ ID NO: 49, SEQ ID NO: 50 or SEQ ID NO: 51, including post-translational modifications thereof. A heavy chain having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE.

An anti-AGE antibody or a variant thereof may include a heavy chain variable region having at least 90%, 91%, 92%, 93%, 94%, 95%, 96%, 97%, 98%, 99%, or 100% sequence identity to the amino acid sequence of SEQ ID NO: 2, SEQ ID NO: 20, SEQ ID NO: 23, SEQ ID NO: 24, SEQ ID NO: 25, SEQ ID NO: 41, SEQ ID NO: 42, SEQ ID NO: 43, SEQ ID NO: 52, SEQ ID NO: 53, SEQ ID NO: 54, SEQ ID NO: 55, or SEQ ID NO: 56, including post-translational modifications thereof. A variable region having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in regions outside the variable region.

An anti-AGE antibody or a variant thereof may include a light chain having at least 90%, 91%, 92%, 93%, 94%, 95%, 96%, 97%, 98%, 99%, or 100% sequence identity to the amino acid sequence of SEQ ID NO: 3, SEQ ID NO: 18, SEQ ID NO: 19, SEQ ID NO: 35, SEQ ID NO: 37, SEQ ID NO: 39, SEQ ID NO: 57, SEQ ID NO: 58, SEQ ID NO: 59, SEQ ID NO: 60 or SEQ ID NO: 61, including post-translational modifications thereof. A light chain having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in regions outside the variable region.

An anti-AGE antibody or a variant thereof may include a light chain variable region having at least 90%, 91%, 92%, 93%, 94%, 95%, 96%, 97%, 98%, 99%, or 100% sequence identity to the amino acid sequence of SEQ ID NO: 4, SEQ ID NO: 21, SEQ ID NO: 26, SEQ ID NO: 27, SEQ ID NO: 28, SEQ ID NO: 44, SEQ ID NO: 45, SEQ ID NO: 46, SEQ ID NO: 62, SEQ ID NO: 63, SEQ ID NO: 64, SEQ ID NO: 65 or SEQ ID NO: 66, including post-translational modifications thereof. A variable region having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in regions outside the variable region.

Alternatively, the antibody may have the complementarity determining regions of commercially available mouse anti-glycation end-product antibody raised against carboxymethyl lysine conjugated with keyhole limpet hemocyanin (CML-KLH), the carboxymethyl lysine MAb (Clone 318003) available from R&D Systems, Inc. (Minneapolis, Minn.; catalog no. MAB3247).

The antibody may have or may include constant regions which permit destruction of targeted cells by a subject's immune system.

Mixtures of antibodies that bind to more than one type AGE of AGE-modified proteins may also be used.

Bi-specific antibodies, which are anti-AGE antibodies directed to two different epitopes, may also be used. Such antibodies will have a variable region (or complementary determining region) from those of one anti-AGE antibody, and a variable region (or complementary determining region) from a different antibody.

Antibody fragments may be used in place of whole antibodies. For example, immunoglobulin G may be broken down into smaller fragments by digestion with enzymes. Papain digestion cleaves the N-terminal side of inter-heavy chain disulfide bridges to produce Fab fragments. Fab fragments include the light chain and one of the two N-terminal domains of the heavy chain (also known as the Fd fragment). Pepsin digestion cleaves the C-terminal side of the inter-heavy chain disulfide bridges to produce F(ab')$_2$ fragments. F(ab')$_2$ fragments include both light chains and the two N-terminal domains linked by disulfide bridges. Pepsin digestion may also form the Fv (fragment variable) and Fc (fragment crystallizable) fragments. The Fv fragment contains the two N-terminal variable domains. The Fc fragment contains the domains which interact with immunoglobulin receptors on cells and with the initial elements of the complement cascade. Pepsin may also cleave immunoglobulin G before the third constant domain of the heavy chain ($C_H3$) to produce a large fragment F(abc) and a small fragment pFc'. Antibody fragments may alternatively be produced recombinantly. Preferably, such antibody fragments are conjugated to an agent that causes the destruction of AGE-modified cells.

If additional antibodies are desired, they can be produced using well-known methods. For example, polyclonal antibodies (pAbs) can be raised in a mammalian host by one or more injections of an immunogen, and if desired, an adjuvant. Typically, the immunogen (and adjuvant) is injected in a mammal by a subcutaneous or intraperitoneal injection. The immunogen may be an AGE-modified protein of a cell, such as AGE-antithrombin III, AGE-calmodulin, AGE-insulin, AGE-ceruloplasmin, AGE-collagen, AGE-cathepsin B, AGE-albumin such as AGE-bovine serum albumin (AGE-BSA), AGE-human serum albumin and ovalbumin, AGE-crystallin, AGE-plasminogen activator, AGE-endothelial plasma membrane protein, AGE-aldehyde reductase, AGE-transferrin, AGE-fibrin, AGE-copper/zinc SOD, AGE-apo B, AGE-fibronectin, AGE-pancreatic ribose, AGE-apo A-I and II, AGE-hemoglobin, AGE-Na$^+$/K$^+$-ATPase, AGE-plasminogen, AGE-myelin, AGE-lysozyme, AGE-immunoglobulin, AGE-red cell Glu transport protein, AGE-6-N-acetyl hexominase, AGE-apo E, AGE-red cell membrane protein, AGE-aldose reductase, AGE-ferritin, AGE-red cell spectrin, AGE-alcohol dehydrogenase, AGE-haptoglobin, AGE-tubulin, AGE-thyroid hormone, AGE-fibrinogen, AGE-$\beta_2$-microglobulin, AGE-sorbitol dehydrogenase, AGE-$\alpha_1$-antitrypsin, AGE-carbonate dehydratase, AGE-RNAse, AGE-low density lipoprotein, AGE-hexokinase, AGE-apo C-I, AGE-RNAse, AGE-hemoglobin such as AGE-human hemoglobin, AGE-low density lipoprotein (AGE-LDL) and AGE-collagen IV. AGE-modified cells, such as AGE-modified erythrocytes, whole, lysed, or partially digested, may also be used as AGE antigens. Examples of adjuvants include Freund's complete, monophosphoryl Lipid A synthetic-trehalose dicorynomycolate, aluminum hydroxide (alum), heat shock proteins HSP 70 or HSP96, squalene emulsion containing monophosphoryl lipid A, a2-macroglobulin and surface active substances, including oil emulsions, pleuronic polyols, polyanions and dinitrophenol. To improve the immune response, an immunogen may be conjugated to a polypeptide that is immunogenic in the host, such as keyhole limpet hemocyanin (KLH), serum albumin, bovine thyroglobulin, cholera toxin, labile enterotoxin, silica particles or soybean trypsin inhibitor. A preferred immunogen conjugate is AGE-KLH. Alternatively, pAbs may be made in chickens, producing IgY molecules.

Monoclonal antibodies (mAbs) may also be made by immunizing a host or lymphocytes from a host, harvesting the mAb-secreting (or potentially secreting) lymphocytes, fusing those lymphocytes to immortalized cells (for example, myeloma cells), and selecting those cells that secrete the desired mAb. Other techniques may be used, such as the EBV-hybridoma technique. Techniques for the generation of chimeric antibodies by splicing genes encoding the variable domains of antibodies to genes of the constant domains of human (or other animal) immunoglobulin result in "chimeric antibodies" that are substantially human (humanized) or substantially "ized" to another animal (such as cat, dog, horse, camel or alpaca, cattle, sheep, or goat) at the amino acid level. If desired, the mAbs may be purified from the culture medium or ascites fluid by conventional procedures, such as protein A-sepharose, hydroxyapatite chromatography, gel electrophoresis, dialysis, ammonium sulfate precipitation or affinity chromatography. Additionally, human monoclonal antibodies can be generated by immunization of transgenic mice containing a third copy IgG human trans-loci and silenced endogenous mouse Ig loci or using human-transgenic mice. Production of humanized monoclonal antibodies and fragments thereof can also be generated through phage display technologies.

A "pharmaceutically acceptable carrier" includes any and all solvents, dispersion media, coatings, antibacterial and antifungal agents, isotonic and absorption delaying agents, and the like, compatible with pharmaceutical administration. Preferred examples of such carriers or diluents include water, saline, Ringer's solutions and dextrose solution. Supplementary active compounds can also be incorporated into the compositions. Solutions and suspensions used for parenteral administration can include a sterile diluent, such as water for injection, saline solution, polyethylene glycols, glycerin, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The antibodies may be administered by injection, such as by intravenous injection or locally, such as by intra-articular injection into a joint. Pharmaceutical compositions suitable for injection include sterile aqueous solutions or dispersions for the extemporaneous preparation of sterile injectable solutions or dispersion. Various excipients may be included in pharmaceutical compositions of antibodies suitable for injection. Suitable carriers include physiological saline, bacteriostatic water, CREMOPHOR EL® (BASF; Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. Various antibacterial and anti-fungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin. Sterile injectable solutions can be prepared by incorporating antibodies, and optionally other therapeutic components, in the required amount in an appropriate solvent with one or a combination of ingredients as required, followed by sterilization. Methods of preparation of sterile solids for the preparation of sterile injectable solutions include vacuum drying and freeze-drying to yield a solid.

For administration by inhalation, the antibodies may be delivered as an aerosol spray from a nebulizer or a pressurized container that contains a suitable propellant, for example, a gas such as carbon dioxide. Antibodies may also be delivered via inhalation as a dry powder, for example using the iSPERSE™ inhaled drug delivery platform (PULMATRIX, Lexington, Mass.). The use of anti-AGE antibodies which are chicken antibodies (IgY) may be non-immunogenic in a variety of animals, including humans, when administered by inhalation.

An appropriate dosage level of each type of antibody will generally be about 0.01 to 500 mg per kg patient body weight. Preferably, the dosage level will be about 0.1 to about 250 mg/kg; more preferably about 0.5 to about 100 mg/kg. A suitable dosage level may be about 0.01 to 250 mg/kg, about 0.05 to 100 mg/kg, or about 0.1 to 50 mg/kg. Within this range the dosage may be 0.05 to 0.5, 0.5 to 5 or 5 to 50 mg/kg. Although each type of antibody may be administered on a regimen of 1 to 4 times per day, such as once or twice per day, antibodies typically have a long half-life in vivo. Accordingly, each type of antibody may be administered once a day, once a week, once every two or three weeks, once a month, or once every 60 to 90 days.

A subject that receives administration of an anti-AGE antibody may be tested to determine if the administration has been effective to treat diabetes or diabetic complications. Diabetes may be monitored with a blood test that measures blood glucose such as the fasting plasma glucose (FPG) test, the A1C test (also known as the hemoglobin A1C, HbA1C, glycated hemoglobin, and glycosylated hemoglobin test), the random plasma glucose (RPG) test, the glucose challenge test or the oral glucose tolerance test (OGTT). A subject may be considered to have received an effective antibody treatment if he or she demonstrates a reduction in blood glucose between subsequent measurements or over time. Diabetic complications may be monitored with a diagnostic test that is suitable for evaluating a given diabetic complication. For example, a reduction in blood pressure, a reduction in the development of cataracts, a reduction in neuropathic pain, reduced albumin in urine (diabetic nephropathy) or improved ventricular diastolic function (cardiomyopathy). Alternatively, the concentration and/or number of senescent cells may be measured over time. Administration of antibody and subsequent testing may be repeated until the desired therapeutic result is achieved.

Unit dosage forms can be created to facilitate administration and dosage uniformity. Unit dosage form refers to physically discrete units suited as single dosages for the subject to be treated, containing a therapeutically effective quantity of one or more types of antibodies in association with the required pharmaceutical carrier. Preferably, the unit dosage form is in a sealed container and is sterile.

Vaccines against AGE-modified proteins or peptides contain an AGE antigen, an adjuvant, optional preservatives and optional excipients. Examples of AGE antigens include AGE-modified proteins or peptides such as AGE-antithrombin III, AGE-calmodulin, AGE-insulin, AGE-ceruloplasmin, AGE-collagen, AGE-cathepsin B, AGE-albumin such as AGE-bovine serum albumin (AGE-BSA), AGE-human serum albumin and ovalbumin, AGE-crystallin, AGE-plasminogen activator, AGE-endothelial plasma membrane protein, AGE-aldehyde reductase, AGE-transferrin, AGE-fibrin, AGE-copper/zinc SOD, AGE-apo B, AGE-fibronectin, AGE-pancreatic ribose, AGE-apo A-I and II, AGE-hemoglobin, AGE-Na$^+$/K$^+$-ATPase, AGE-plasminogen, AGE-myelin, AGE-lysozyme, AGE-immunoglobulin, AGE-red cell Glu transport protein, AGE-$\beta$-N-acetyl hexominase, AGE-apo E, AGE-red cell membrane protein, AGE-aldose reductase, AGE-ferritin, AGE-red cell spectrin, AGE-alcohol dehydrogenase, AGE-haptoglobin, AGE-tubulin, AGE-thyroid hormone, AGE-fibrinogen, AGE-$\beta_2$-microglobulin, AGE-sorbitol dehydrogenase, AGE-$\alpha_1$-antitrypsin, AGE-carbonate dehydratase, AGE-RNAse, AGE-low density lipoprotein, AGE-hexokinase, AGE-apo C-I, AGE-RNAse, AGE-hemoglobin such as AGE-human hemoglobin, AGE-low density lipoprotein (AGE-LDL) and AGE-collagen IV. AGE-modified cells, such as AGE-modified erythrocytes, whole, lysed, or partially digested, may also be used as AGE antigens. Suitable AGE antigens also include proteins or peptides that exhibit AGE modifications (also referred to as AGE epitopes or AGE moieties) such as carboxymethyllysine (CML), carboxyethyllysine (CEL), pentosidine, pyrraline, FFI, AFGP and ALI. The AGE antigen may be an AGE-protein conjugate, such as AGE conjugated to keyhole limpet hemocyanin (AGE-KLH). Further details of some of these AGE-modified proteins or peptides and their preparation are described in Bucala.

Particularly preferred AGE antigens include proteins or peptides that exhibit a carboxymethyllysine or carboxyethyllysine AGE modification. Carboxymethyllysine (also known as N(epsilon)-(carboxymethyl)lysine, N(6)-carboxymethyllysine, or 2-Amino-6-(carboxymethylamino) hexanoic acid) and carboxyethyllysine (also known as N-epsilon-(carboxyethyl)lysine) are found on proteins or peptides and lipids as a result of oxidative stress and chemical glycation, and have been correlated with juvenile genetic disorders. CML- and CEL-modified proteins or peptides are recognized by the receptor RAGE which is expressed on a variety of cells. CML and CEL have been well-studied and CML- and CEL-related products are commercially available. For example, Cell Biolabs, Inc. sells CML-BSA antigens, CML polyclonal antibodies, CML immunoblot kits, and CML competitive ELISA kits (www-.cellbiolabs.com/cml-assays) as well as CEL-BSA antigens and CEL competitive ELISA kits (www.cellbiolabs.com/cel-n-epsilon-carboxyethyl-lysine-assays-and-reagents).

AGE antigens may be conjugated to carrier proteins to enhance antibody production in a subject. Antigens that are not sufficiently immunogenic alone may require a suitable carrier protein to stimulate a response from the immune system. Examples of suitable carrier proteins include keyhole limpet hemocyanin (KLH), serum albumin, bovine thyroglobulin, cholera toxin, labile enterotoxin, silica particles and soybean trypsin inhibitor. Preferably, the carrier protein is KLH (AGE-KLH). KLH has been extensively studied and has been identified as an effective carrier protein in experimental cancer vaccines. Preferred AGE antigen-carrier protein conjugates include CML-KLH and CEL-KLH.

The administration of an AGE antigen allows the immune system to develop immunity to the antigen. Immunity is a long-term immune response, either cellular or humoral. A cellular immune response is activated when an antigen is presented, preferably with a co-stimulator to a T-cell which causes it to differentiate and produce cytokines. The cells involved in the generation of the cellular immune response are two classes of T-helper (Th) cells, Th1 and Th2. Th1 cells stimulate B cells to produce predominantly antibodies of the IgG2A isotype, which activates the complement cascade and binds the Fc receptors of macrophages, while Th2 cells stimulate B cells to produce IgG1 isotype antibodies in mice, IgG4 isotype antibodies in humans, and IgE isotype antibodies. The human body also contains "professional" antigen-presenting cells such as dendritic cells, macrophages, and B cells.

A humoral immune response is triggered when a B cell selectively binds to an antigen and begins to proliferate, leading to the production of a clonal population of cells that produce antibodies that specifically recognize that antigen and which may differentiate into antibody-secreting cells, referred to as plasma-cells or memory-B cells. Antibodies are molecules produced by B-cells that bind a specific antigen. The antigen-antibody complex triggers several responses, either cell-mediated, for example by natural killers (NK) or macrophages, or serum-mediated, for example by activating the complement system, a complex of several serum proteins that act sequentially in a cascade that result in the lysis of the target cell.

Immunological adjuvants (also referred to simply as "adjuvants") are the component(s) of a vaccine which augment the immune response to the immunogenic agent. Adjuvants function by attracting macrophages to the immunogenic agent and then presenting the agent to the regional lymph nodes to initiate an effective antigenic response. Adjuvants may also act as carriers themselves for the immunogenic agent. Adjuvants may induce an inflammatory response, which may play an important role in initiating the immune response.

Adjuvants include mineral compounds such as aluminum salts, oil emulsions, bacterial products, liposomes, immunostimulating complexes and squalene. Aluminum compounds are the most widely used adjuvants in human and veterinary vaccines. These aluminum compounds include aluminum salts such as aluminum phosphate ($AlPO_4$) and aluminum hydroxide ($Al(OH)_3$) compounds, typically in the form of gels, and are generically referred to in the field of vaccine immunological adjuvants as "alum." Aluminum hydroxide is a poorly crystalline aluminum oxyhydroxide having the structure of the mineral boehmite. Aluminum phosphate is an amorphous aluminum hydroxyphosphate. Negatively charged species (for example, negatively charged antigens) can absorb onto aluminum hydroxide gels at neutral pH, whereas positively charged species (for example, positively charged antigens) can absorb onto aluminum phosphate gels at neutral pH. It is believed that these aluminum compounds provide a depot of antigen at the site of administration, thereby providing a gradual and continuous release of antigen to stimulate antibody production. Aluminum compounds tend to more effectively stimulate a cellular response mediated by Th2, rather than Th1 cells.

Emulsion adjuvants include water-in-oil emulsions (for example, Freund's adjuvants, such as killed mycobacteria in oil emulsion) and oil-in-water emulsions (for example, MF-59). Emulsion adjuvants include an immunogenic component, for example squalene (MF-59) or mannide oleate (Incomplete Freund's Adjuvants), which can induce an elevated humoral response, increased T cell proliferation, cytotoxic lymphocytes and cell-mediated immunity.

Liposomal or vesicular adjuvants (including paucilamellar lipid vesicles) have lipophilic bilayer domains and an aqueous milieu which can be used to encapsulate and transport a variety of materials, for example an antigen. Paucilamellar vesicles (for example, those described in U.S. Pat. No. 6,387,373) can be prepared by mixing, under high pressure or shear conditions, a lipid phase comprising a non-phospholipid material (for example, an amphiphile surfactant; see U.S. Pat. Nos. 4,217,344; 4,917,951; and 4,911,928), optionally a sterol, and any water-immiscible oily material to be encapsulated in the vesicles (for example, an oil such as squalene oil and an oil-soluble or oil-suspended antigen); and an aqueous phase such as water, saline, buffer or any other aqueous solution used to hydrate the lipids. Liposomal or vesicular adjuvants are believed to promote contact of the antigen with immune cells, for example by fusion of the vesicle to the immune cell membrane, and preferentially stimulate the Th1 sub-population of T-helper cells.

Other types of adjuvants include *Mycobacterium bovis* bacillus Calmette-Guérin (BCG), quill-saponin and unmethylated CpG dinucleotides (CpG motifs). Additional adjuvants are described in U.S. Patent Application Publication Pub. No. US 2010/0226932 (Sep. 9, 2010) and Jiang, Z-H. et al. "Synthetic vaccines: the role of adjuvants in immune targeting", *Current Medicinal Chemistry*, Vol. 10(15), pp. 1423-39 (2003). Preferable adjuvants include Freund's complete adjuvant and Freund's incomplete adjuvant.

The vaccine may optionally include one or more preservatives, such as antioxidants, antibacterial and antimicrobial agents, as well as combinations thereof. Examples include benzethonium chloride, ethylenediamine-tetraacetic acid sodium (EDTA), thimerosal, phenol, 2-phenoxyethanol, formaldehyde and formalin; antibacterial agents such as amphotericin B, chlortetracycline, gentamicin, neomycin, polymyxin B and streptomycin; antimicrobial surfactants such as polyoxyethylene-9, 10-nonyl phenol (Triton N-101, octoxynol-9), sodium deoxycholate and polyoxyethylated octyl phenol (Triton X-100). The production and packaging of the vaccine may eliminate the need for a preservative. For example, a vaccine that has been sterilized and stored in a sealed container may not require a preservative.

Other components of vaccines include pharmaceutically acceptable excipients, such as stabilizers, thickening agents, toxin detoxifiers, diluents, pH adjusters, tonicity adjustors, surfactants, antifoaming agents, protein stabilizers, dyes and solvents. Examples of such excipients include hydrochloric acid, phosphate buffers, sodium acetate, sodium bicarbonate, sodium borate, sodium citrate, sodium hydroxide, potassium chloride, potassium chloride, sodium chloride, polydimethylsilozone, brilliant green, phenol red (phenolsulfonphthalein), glycine, glycerin, sorbitol, histidine, monosodium glutamate, potassium glutamate, sucrose, urea, lactose, gelatin, sorbitol, polysorbate 20, polysorbate 80 and glutaraldehyde. A variety of these components of vaccines, as well as adjuvants, are described in www.cdc.gov/vaccines/pubs/pinkbook/downloads/appendices/B/excipient-table-2.pdf and Vogel, F. R. et al., "A compendium of vaccine adjuvants and excipients", *Pharmaceutical Biotechnology*, Vol. 6, pp. 141-228 (1995).

The vaccine may contain from 1 µg to 100 mg of at least one AGE antigen, including 10, 20, 30, 40, 50, 60, 70, 80, 90, 100, 200, 400, 800 or 1000 μg, or 2, 3, 4, 5, 6, 7, 8, 9, 10, 20, 30, 40, 50, 60, 70, 80 or 90 mg. The amount used for a single injection corresponds to a unit dosage.

The vaccine may be provided in unit dosage form or in multidosage form, such as 2-100 or 2-10 doses. The unit dosages may be provided in a vial with a septum, or in a syringe with or without a needle. The vaccine may be administered intravenously, subdermally or intraperitoneally. Preferably, the vaccine is sterile.

The vaccine may be administered one or more times, such as 1 to 10 times, including 2, 3, 4, 5, 6, 7, 8 or 9 times, and may be administered over a period of time ranging from 1 week to 1 year, 2-10 weeks or 2-10 months. Furthermore, booster vaccinations may be desirable, over the course of 1 year to 20 years, including 2, 5, 10 and 15 years.

A subject that receives a vaccine for AGE-modified proteins or peptides of a cell may be tested to determine if he or she has developed an immunity to the AGE-modified proteins or peptides. Suitable tests may include blood tests for detecting the presence of an antibody, such as immunoassays or antibody titers. An immunity to AGE-modified proteins or peptides may also be determined by monitoring the concentration and/or number of senescent cells over time. In addition to testing for the development of an immunity to AGE-modified proteins or peptides, a subject may also be tested to determine if the vaccination has been effective to treat diabetes or diabetic complications. A subject may be considered to have received an effective vaccination if he or she demonstrates a reduction in blood glucose or an improvement in diabetic complications between subsequent measurements or over time, or by measuring the concentration and/or number of senescent cells. Vaccination and subsequent testing may be repeated until the desired therapeutic result is achieved.

The vaccination process may be designed to provide immunity against multiple AGE moieties. A single AGE antigen may induce the production of AGE antibodies which are capable of binding to multiple AGE moieties. Alternatively, the vaccine may contain multiple AGE antigens. In addition, a subject may receive multiple vaccines, where each vaccine contains a different AGE antigen.

Any mammal that could develop diabetes or diabetic complications may be treated by the methods herein described. Humans are a preferred mammal for treatment. Other mammals that may be treated include mice, rats, goats, sheep, cows, horses and companion animals, such as dogs or cats. Alternatively, any of the mammals or subjects identified above may be excluded from the patient population in need of treatment for diabetes or diabetic complications.

A subject may be identified as in need of treatment based on a diagnosis of diabetes. Diabetes may be diagnosed with a blood test that measures blood glucose such as the fasting plasma glucose (FPG) test, the A1C test (also known as the hemoglobin A1C, HbA1C, glycated hemoglobin, and glycosylated hemoglobin test), the random plasma glucose (RPG) test, the glucose challenge test or the oral glucose tolerance test (OGTT). For example, a subject may be diagnosed with diabetes if he or she has an A1C level greater than 5.7% when measured on two separate occasions.

A subject may be identified as in need of treatment based on a diagnosis of one or more diabetic complications. Examples of diabetic complications include heart disease such as cardiomyopathy, stroke, diabetic retinopathy, cataracts, glaucoma, kidney disease such as nephropathy, hypoglycemia, hyperglycemic crisis, high blood pressure, high blood LDL cholesterol, nerve disease, diabetic neuropathy (peripheral and autonomic neuropathy), neuropathic pain, cognitive impairment, non-alcoholic fatty liver disease, periodontal (gum) disease, hearing loss, erectile dysfunction, depression, complications with pregnancy, diabetic ketoacidosis, hyperosmolar hyperglycemic state and diabetic coma. Diabetic complications may be diagnosed with any suitable diagnostic test for a given diabetic complication. For example, measuring blood pressure, examining the eye for cataracts, a liver ultrasound indicating steatosis (non-alcoholic fatty liver disease), urinalysis measuring albumin in urine (diabetic nephropathy) or echocardiography to measure ventricular diastolic function (cardiomyopathy).

Subjects may also be identified as in need of treatment based on detection of advanced glycation end products in a sample obtained from the subject. Suitable samples include blood, skin, serum, saliva and urine. The diagnostic use of anti-AGE antibodies is discussed in more detail in Application No. 62/501,424.

The one-letter amino acid sequence that corresponds to SEQ ID NO: 1 is shown below:

```
            10         20         30         40         50
     MNLLLILTFV AAAVAQVQLL QPGAELVKPG ASVKLACKAS GYLFTTYWMH 60         70         80         90
     WLKQRPGQGL EWIGEISPTN GRAYYNARFK SEATLTVDKS 100        110        120        130
     SNTAYMQLSS LTSEASAVYY CARAYGNYEF AYWGQGTLVT 140        150        160        170
     VSVASTKGPS VFPLAPSSKS TSGGTAALGC LVKDYFPEPV 180        190        200        210        220
     TVSWNSGALT SGVHTFPAVL QSSGLYSLSS VVTVPSSSLG TQTYICNVNH 230        240        250        260
     KPSNTKVDKK VEPKSCDKTH TCPPCPAPEL LGGPSVFLFP 270        280        290        300
     PKPKDTLMIS RTPEVTCVVV DVSHEDPEVK FNWYVDGVEV 310        320        330        340
     HNAKTKPREE QYNSTYRVVS VLTVLHQDWL NGKEYKCKVS 350        360        370        380        390
     NKALPAPIEK TISKAKGQPR EPQVYTLPPS REEMTKNQVS LTCLVKGFYP
```

```
              400        410        420        430
       SDIAVEWESN GQPENNYKTT PPVLDSDGSF FLYSKUTVDK 440        450        460
       SRWQQGNVFS CSVMHEALHN HYTQKSLSLS PGK
```

Positions 16-133 of the above amino acid sequence correspond to SEQ ID NO: 2. Positions 46-50 of the above amino acid sequence correspond to SEQ ID NO: 41. Positions 65-81 of the above amino acid sequence correspond to SEQ ID NO: 42. Positions 114-122 of the above amino acid sequence correspond to SEQ ID NO: 43.

The one-letter amino acid sequence that corresponds to SEQ ID NO: 3 is shown below:

```
               10         20         30         40         50
       MNLLLILTFV AAAVADVVMT QTPLSLPVSL GDQASISCRS RQSLVNSNGN 60         70         80         90        100
       TFLQWYLQKP GQSPKLLIYK VSLRFSGVPD RFSGSGSGTD FTLKISRVEA 110        120        130        140        150
       EDLGLYFCSQ STHVPPTFGG GTKLEIKRTV AAPSVFIFPP SDEQLKSGTA 160        170        180        190
       SVVCLLNNFY PREAKVQWKV DNALQSGNSQ ESVTEQDSKD 200        210        220        230
       STYSLSSTLT LSKADYEKHK VYACEVTHQG LSSPVTKSFN RGEC
```

Positions 16-128 of the above amino acid sequence correspond to SEQ ID NO: 4. Optionally, the arginine (Arg or R) residue at position 128 of SEQ ID NO: 4 may be omitted. Positions 39-54 of the above amino acid sequence correspond to SEQ ID NO: 44. Positions 70-76 of the above amino acid sequence correspond to SEQ ID NO: 45. Positions 109-117 of the above amino acid sequence correspond to SEQ ID NO: 46.

The DNA sequence that corresponds to SEQ ID NO: 12 is shown below:

```
ATGGACCCCAAGGGCAGCCTGAGCTGGAGAATCCTGCTGTTCCTGAGCC

TGGCCTTCGAGCTGAGCTACGGCCAGGTGCAGCTGCTGCAGCCAGGTGC

CGAGCTCGTGAAACCTGGCGCCTCTGTGAAGCTGGCCTGCAAGGCTTCC

GGCTACCTGTTCACCACCTACTGGATGCACTGGCTGAAGCAGAGGCCAG

GCCAGGGCCTGGAATGGATCGGCGAGATCTCCCCCACCAACGGCAGAGC

CTACTACAACGCCCGGTTCAAGTCCGAGGCCACCCTGACCGTGGACAAG

TCCTCCAACACCGCCTACATGCAGCTGTCCTCCCTGACCTCTGAGGCCT

CCGCCGTGTACTACTGCGCCAGAGCTTACGGCAACTACGAGTTCGCCTA

CTGGGGCCAGGGCACCCTCGTGACAGTGTCTGTGGCTAAGACCACCCCT

CCCTCCGTGTACCCTCTGGCTCCTGGCTGTGGCGACACCACCGGATCCT

CTGTGACCCTGGGCTGCCTCGTGAAGGGCTACTTCCCTGAGTCCGTGAC

CGTGACCTGGAACTCCGGCTCCCTGTCCTCCTCCGTGCACACCTTTCCA

GCCCTGCTGCAGTCCGGCCTGTACACCATGTCCTCCAGCGTGACAGTGC

CCTCCTCCACCTGGCCTTCCCAGACCGTGACATGCTCTGTGGCCCACCC

TGCCTCTTCCACCACCGTGGACAAGAAGCTGGAACCCTCCGGCCCCATC

TCCACCATCAACCCTTGCCCTCCCTGCAAAGAATGCCACAAGTGCCCTG

CCCCCAACCTGGAAGGCGGCCCTTCCGTGTTCATCTTCCCACCCAACAT

CAAGGACGTGCTGATGATCTCCCTGACCCCCAAAGTGACCTGCGTGGTG

GTGGACGTGTCCGAGGACGACCCTGACGTGCAGATCAGTTGGTTCGTGA
```

```
ACAACGTGGAAGTGCACACCGCCCAGACCCAGACACACAGAGAGGACTA

CAACAGCACCATCAGAGTGGTGTCTACCCTGCCCCATCCAGCACCAGGAC

TGGATGTCCGGCAAAGAATTCAAGTGCAAAGTGAACAACAAGGACCTGC

CCAGCCCCATCGAGCGGACCATCTCCAAGATCAAGGGCCTCGTGCGGGC

TCCCCAGGTGTACATTCTGCCTCCACCAGCCGAGCAGCTGTCCCGGAAG

GATGTGTCTCTGACATGTCTGGTCGTGGGCTTCAACCCCGGCGACATCT

CCGTGGAATGGACCTCCAACGGCCACACCGAGGAAAACTACAAGGACAC

CGCCCCTGTGCTGGACTCCGACGGCTCCTACTTCATCTACTCCAAGCTG

AACATGAAGACCTCCAAGTGGGAAAAGACCGACTCCTTCTCCTGCAACG

TGCGGCACGAGGGCCTGAAGAACTACTACCTGAAGAAAACCATCTCCCG

GTCCCCCGGCTAG
```

The DNA sequence that corresponds to SEQ ID NO: 13 is shown below:

```
ATGGACCCCAAGGGCAGCCTGAGCTGGAGAATCCTGCTGTTCCTGAGCC

TGGCCTTCGAGCTGAGCTACGGCCAGGTGCAGCTGCTGCAGCCAGGTGC

CGAGCTCGTGAAACCTGGCGCCTCTGTGAAGCTGGCCTGCAAGGCTTCC

GGCTACCTGTTCACCACCTACTGGATGCACTGGCTGAAGCAGAGGCCAG

GCCAGGGCCTGGAATGGATCGGCGAGATCTCCCCCACCAACGGCAGAGC

CTACTACAACGCCCGGTTCAAGTCCGAGGCCACCCTGACCGTGGACAAG

TCCTCCAACACCGCCTACATGCAGCTGTCCTCCCTGACCTCTGAGGCCT

CCGCCGTGTACTACTGCGCCAGAGCTTACGGCAACTACGAGTTCGCCTA
```

-continued
CTGGGGCCAGGGCACCCTCGTGACAGTGTCTGTGGCTAGCACCAAGGGC

CCCAGCGTGTTCCCTCTGGCCCCCAGCAGCAAGAGCACCAGCGGCGGAA

CCGCCGCCCTGGGCTGCCTGGTGAAGGACTACTTCCCCGAGCCCGTGAC

CGTGTCCTGGAACAGCGGCGCTCTGACCAGCGGAGTGCACACCTTCCCT

GCCGTGCTGCAGAGCAGCGGCCTGTACTCCCTGAGCAGCGTGGTGACCG

TGCCCAGCAGCAGCCTGGGCACCCAGACCTACATCTGCAACGTGAACCA

CAAGCCCTCCAACACCAAGGTGGACAAGAAGGTGGAGCCTAAGAGCTGC

GACAAGACCCACACCTGCCCTCCCTGCCCCGCCCCCGAGCTGCTGGGCG

GACCCAGCGTGTTCCTGTTCCCTCCCAAGCCCAAGGACACCCTGATGAT

CAGCCGCACCCCCGAGGTGACCTGCGTGGTGGTGGACGTGAGCCACGAG

GACCCCGAGGTGAAGTTCAACTGGTACGTGGACGGCGTGGAGGTGCACA

ACGCCAAGACCAAGCCTCGGGAGGAGCAGTACAACTCCACCTACCGCGT

GGTGAGCGTGCTGACCGTGCTGCACCAGGACTGGCTGAACGGCAAGGAG

TACAAGTGCAAGGTGAGCAACAAGGCCCTGCCCGCTCCCATCGAGAAGA

CCATCAGCAAGGCCAAGGGCCAGCCCCGGGAGCCTCAGGTGTACACCCT

GCCCCCCAGCCGCGACGAGCTGACCAAGAACCAGGTGAGCCTGACCTGC

CTGGTGAAGGGCTTCTACCCCTCCGACATCGCCGTGGAGTGGGAGAGCA

ACGGCCAGCCTGAGAACAACTACAAGACCACCCCTCCCGTGCTGGACAG

CGACGGCAGCTTCTTCCTGTACAGCAAGCTGACCGTGGACAAGTCCCGG

TGGCAGCAGGGCAACGTGTTCAGCTGCAGCGTGATGCACGAGGCCCTGC

ACAACCACTACACCCAGAAGAGCCTGAGCCTGAGCCCCGGATAG

The DNA sequence that corresponds to SEQ ID NO: 14 is shown below:

ATGGAGACCGACACCCTGCTGCTCTGGGTGCTGCTGCTCTGGGTGCCCG

GCTCCACCGGAGACGTCGTGATGACCCAGACCCCTCTGTCCCTGCCTGT

GTCTCTGGGCGACCAGGCCTCCATCTCCTGCCGGTCTAGACAGTCCCTC

GTGAACTCCAACGGCAACACCTTCCTGCAGTGGTATCTGCAGAAGCCCG

GCCAGTCCCCCAAGCTGCTGATCTACAAGGTGTCCCTGCGGTTCTCCGG

CGTGCCCGACAGATTTTCCGGCTCTGGCTCTGGCACCGACTTCACCCTG

AAGATCTCCCGGGTGGAAGCCGAGGACCTGGGCCTGTACTTCTGCAGCC

AGTCCACCCACGTGCCCCCTACATTTGGCGGAGGCACCAAGCTGGAAAT

CAAACGGGCAGATGCTGCACCAACTGTATCCATCTTCCCACCATCCAGT

GAGCAGTTAACATCTGGAGGTGCCTCAGTCGTGTGCTTCTTGAACAACT

TCTACCCCAAAGACATCAATGTCAAGTGGAAGATTGATGGCAGTGAACG

ACAAAATGGCGTCCTGAACAGTTGGACTGATCAGGACAGCAAAGACAGC

ACCTACAGCATGAGCAGCACCCTCACGTTGACCAAGGACGAGTATGAAC

GACATAACAGCTATACCTGTGAGGCCACTCACAAGACATCAACTTCACC

CATTGTCAAGAGCTTCAACAGGAATGAGTGTTGA

The DNA sequence that corresponds to SEQ ID NO: 15 is shown below:

ATGGAGACCGACACCCTGCTGCTCTGGGTGCTGCTGCTCTGGGTGCCCG

GCTCCACCGGAGACGTCGTGATGACCCAGACCCCTCTGTCCCTGCCTGT

GTCTCTGGGCGACCAGGCCTCCATCTCCTGCCGGTCTAGACAGTCCCTC

GTGAACTCCAACGGCAACACCTTCCTGCAGTGGTATCTGCAGAAGCCCG

GCCAGTCCCCCAAGCTGCTGATCTACAAGGTGTCCCTGCGGTTCTCCGG

CGTGCCCGACAGATTTTCCGGCTCTGGCTCTGGCACCGACTTCACCCTG

AAGATCTCCCGGGTGGAAGCCGAGGACCTGGGCCTGTACTTCTGCAGCC

AGTCCACCCACGTGCCCCCTACATTGGCGGAGGCACCAAGCTGGAAAT

CAAGCGGACCGTGGCCGCCCCCAGCGTGTTCATCTTCCCTCCCAGCGAC

GAGCAGCTGAAGTCTGGCACCGCCAGCGTGGTGTGCCTGCTGAACAACT

TCTACCCCGCGAGGCCAAGGTGCAGTGGAAGGTGGACAACGCCCTGCA

GAGCGGCAACAGCCAGGAGAGCGTGACCGAGCAGGACTCCAAGGACAGC

ACCTACAGCCTGAGCAGCACCCTGACCCTGAGCAAGGCCGACTACGAGA

AGCACAAGGTGTACGCCTGCGAGGTGACCCACCAGGGACTGTCTAGCCC

CGTGACCAAGAGCTTCAACCGGGGCGAGTGCTAA

The one-letter amino acid sequence that corresponds to SEQ ID NO: 16 is shown below:

MDPKGSLSWRILLFLSLAFELSYGQVQLLQPGAELVKPGASVKLACKAS

GYLFTTYWMHWLKQRPGQGLEWIGEISPTNGRAYYNARFKSEATLTVDK

SSNTAYMQLSSLTSEASAVYYCARAYGNYEFAYWGQGTLVTVSVAKTTP

PSVYPLAPGCGDTTGSSVTLGCLVKGYFPESVTVTWNSGSLSSSVHTFP

ALLQSGLYTMSSSVTVPSSTWPSQTVTCSVAHPASSTTVDKKLEPSGP

ISTINPCPPCKECHKCPAPNLEGGPSVFIFPPNIKDVLMISLTPKVTCV

VVDVSEDDPDVQISWFVNNVEVHTAQTQTHREDYNSTIRVVSTLPIQHQ

DWMSGKEFKCKVNNKDLPSPIERTISKIKGLVRAPQVYILPPPAEQLSR

KDVSLTCLVVGFNPGDISVEWTSNGHTEENYKDTAPVLDSDGSYFIYS

KLNMKTSKWEKTDSFSCNVRHEGLKNYYLKKTISRSPG*

The alanine residue at position 123 of the above amino acid sequence may optionally be replaced with a serine residue. The tyrosine residue at position 124 of the above amino acid sequence may optionally be replaced with a phenylalanine residue. Positions 25-142 of the above amino acid sequence correspond to SEQ ID NO: 20. SEQ ID NO: 20 may optionally include the substitutions at positions 123 and 124. SEQ ID NO: 20 may optionally contain one additional lysine residue after the terminal valine residue.

The one-letter amino acid sequence that corresponds to SEQ ID NO: 17 is shown below:

MDPKGSLSWRILLFLSLAFELSYGQVQLLQPGAELVKPGASVKLACKAS

GYLFTTYWMHWLKQRPGQGLEWIGEISPTNGRAYYNARFKSEATLTVDK

SSNTAYMQLSSLTSEASAVYYCARAYGNYEFAYWGQGTLVIVSVASTKG

-continued

PSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSC

DKTHTCPPCPAPELLGGPSVFLFPPKPKDTLMISRTPEVTCVVVDVSHE

DPEVKFNWYVDGVEVHNAKTKPREEQYNSTYRVVSVLWLHQDWLNGKEY

KCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRW

QQGNVFSCSVMHEALHNHYTQKSLSLSPG*

The one-letter amino acid sequence that corresponds to SEQ ID NO: 18 is shown below:

METDTLLLWVLLLWVPGSTGDVVMTQTPLSLPVSLGDQASISCRSRQ

SLVNSNGNTFLQWYLQKPGQSPKLLIYKVSLRFSGVPDRFSGSGSGTDF

TLKISRVEAEDLGLYFCSQSTHVPPTFGGGTKLEIKRADAAPTVSIFPP

SSEQLTSGGASVVCFLNNFYPKDINVKWKIDGSERQNGVLNSWTDQDS

KDSTYSMSSTLTLTKDEYERHNSYTCEATHKTSTSPIVKSFNRNEC*

Positions 21-132 of the above amino acid sequence correspond to SEQ ID NO: 21.

The one-letter amino acid sequence that corresponds to SEQ ID NO: 19 is shown below:

METDTLLLWVLLLWVPGSTGDVVMTQTPLSLPVSLGDQASISCRSRQ

SLVNSNGNTFLQWYLQKPGQSPKWYKVSLRFSGVPDRFSGSGSGTDFT

LKISRVEAEDLGLYFCSQSTHVPPTFGGGTKLEIKRTVAAPSVFIFPPS

DEQLKSGTASVVCLLNNFYPREAKVQWKVDNALQSGNSQESVTEQDSKD

STYSLSSTLTLSKADYEKHKVYACEVTHQGLSSPVTKSFNRGEC*

The one-letter amino acid sequence that corresponds to SEQ ID NO: 22 is shown below:

```
            10         20         30         40         50
    ASTKGPSVFP LAPCSRSTSE STAALGCLVK DYFPEPVTVS WNSGALTSGV
            60         70         80         90        100
    HTFPAVLQSS GLYSLSSVVT VPSSNFGTQT YTCNVDHKPS NTKVDKTVER
           110        120        130        140        150
    KCCVECPPCP APPVAGPSVF LFPPKPKDTL MISRTPEVTC VVVDVSHEDP
           160        170        180        190
    EVQFNWYVDG VEVHNAKTKP REEQFNSTFR VVSVLTVVHQ
           200        210        220        230        240
    DWLNGKEYKC KVSNKGLPAP IEKTISKTKG QPREPQVYTL PPSREEMTKN
           250        260        270        280        290
    QVSLTCLVKG FYPSDISVEW ESNGQPENNY KTTPPMLDSD GSFFLYSKLT
           300        310        320
    VDKSRWQQGN VFSCSVMHEA LHNHYTQKSL SLSPGK
```

The one-letter amino acid sequence that corresponds to SEQ ID NO: 23 is SYTMGVS.

The one-letter amino acid sequence that corresponds to SEQ ID NO: 24 is TISSGGGSTYYPDSVKG.

The one-letter amino acid sequence that corresponds to SEQ ID NO: 25 is QGGWLPPFAX, where X may be any naturally occurring amino acid.

The one-letter amino acid sequence that corresponds to SEQ ID NO: 26 is RASKSVSTSSRGYSYMH.

The one-letter amino acid sequence that corresponds to SEQ ID NO: 27 is LVSNLES.

The one-letter amino acid sequence that corresponds to SEQ ID NO: 28 is QHIRELTRS.

The one-letter amino acid sequence that corresponds to SEQ ID NO: 29 is

MDPKGSLSWRILLFLSLAFELSYGQVQLVQSGAEVKKPGASVKVSCKAS

GYLFTTYWMHVVVRQAPGQGLEWMGEISPTNGRAYYNQKFQGRVTMTVD

KSTNTVYMELSSLRSEDTAVYYCARAYGNYFAYWGQGTLVTVSSASTKG

PSVFPLAPSSKSTSGGTAALGCLVKDYFPEPVWSWNSGALTSGVHTFPA

VLQSSGLYSLSSVVIVPSSSLGTQTYICNVNHKPSNTKVDKKVEPKSCD

KTHTCPPCPPELLGGPSVFLFPPKPKDTLMISRTPEVTCVVVDVSHEDP

EVKFNWYVDGVEVHNAKTKPREEQYNSTYRVVSVUTVLHQDWLNGKEYK

CKVSNKALPAPIEKTISKAKGQPREPQVYTLPPSRDELKNQVSLTCLVK

GFYPSDIAVEWESNGQPENNYKTTPPVLDSDGSFFLYSKLTVDKSRWQQ

GNVFSCSVMHEALHNHYTQKSLSLSPG.

The DNA sequence that corresponds to SEQ ID NO: 30 is

ATGGACCCCAAGGGCAGCCTGAGCTGGAGAATCCTGCTGTTCCTGAGCC

TGGCCTTCGAGCTGAGCTACGGCCAGGTGCAGCTGGTGCAGTCTGGCGC

CGAAGTGAAGAAACCTGGCGCCTCCGTGAGGTGTCCTGCAAGGCTTCCG

GCTACCTGTTCACCACCTACTGGATGCACTGGGTGCGACAGGCCCCTGG

ACAGGGCCTGGAATGGATGGGCGAGATCTCCCCTACCAACGGCAGAGCC

TACTACAACAGAAATTCCAGGGCAGAGTGACCATGACCGTGGACAAGTC

-continued

CACCAACACCGTGTACATGGAACTGTCCTCCCTGCGGAGCGAGGACACC

GCCGTGTACTACTGCGCTAGAGCCTACGGCAACTACGATTCGCCTACTG

GGGCCAGGGCACCCTCGTGACAGTGTCCTCTGCTAGCACCAAGGGCCCC

```
AGCGTGTTCCCTCTGGCCCCCAGCAGCAAGAGCACCAGCGGCGGAACCG
CCGCCCTGGGCTGCCTGGGAAGGACTACTTCCCCGAGCCCGTGACCGTG
TCCTGGAACAGCGGCGCTCTGACCAGCGGAGTGCACACCTTCCCTGCCG
TGCTGCAGAGCAGCGGCCTGTACTCCCTGAGCAGCGTGGTGACCGTGCC
AGCAGCAGCCTGGGCACCCAGACCTACATCTGCAACGTGAACCACAAGC
CCTCCAACACCAAGGTGGACAAGAAGGTGGAGCCTAAGAGCTGCGACAA
GACCCACACCTGCCCTCCCTGCCCCGCCCCGAGCTGCTGGGCGGACCCA
GCGTGTTCCTGTTCCCTCCCAAGCCCAAGGACACCCTGATGATCAGCCG
CACCCCCGAGGTGACCTGCGTGGTGGTGGACGTGAGCCACGAGGACCCC
GAGGTGAGTTCAACTGGTACGTGGACGGCGTGGAGGTGCACAACGCCAA
GACCAAGCCTCGGGAGGAGCAGTACAACTCCACCTACCGCGTGGTGAGC
GTGCTGACCGTGCTGCACCAGGACTGGCTGAACGGCAGGAGTACAAGTG
CAAGGTGAGCAACAAGGCCCTGCCCGCTCCCATCGAGAAGACCATCAGC
AAGGCCAAGGGCCAGCCCCGGGAGCCTCAGGTGTACACCCTGCCCCCCA
GCCGCGACGAGCTGACAAGAACCAGGTGAGCCTGACCTGCCTGGTGAAG
GGCTTCTACCCCTCCGACATCGCCGTGGAGTGGGAGAGCAACGGCCAGC
CTGAGAACAACTACAAGACCACCCCTCCCGTGCTGGACAGCGACGCAGC
TTCTTCCTGTACAGCAAGCTGACCGTGGACAAGTCCCGGTGGCAGCAGG
GCAACGTGTTCAGCTGCAGCGTGATGCACGAGGCCCTGCACAACCACTA
CACCCAGAAGAGCCTGAGCCTGAGCCCGGATAGTAA.
```

The one-letter amino acid sequence that corresponds to SEQ ID NO: 31 is

```
MDPKGSLSWRILLFLSLAFELSYGQVQLVQSGAEVKKPGASVKVSCKASG
YLFTTYWMHVVVRQAPGQGLEWMGEISPTNGRAYYNAKFQGRVTMTVDKS
TNTAYMELSSLRSEDTAVYYCARAYGNYFAYWGQGTLVTVSSASTKGPSV
FPLAPSSKSTSGGTAALGCLVKDYFPEPVTVSWNSGALTSGVHTFPAVLQ
SSGLYSLSSVVIVPSSSLGTQTYICNVNHKPSNTKVDKKVEPKSCDKTHT
CPPCPPELLGGPSVFLFPPKPKDTLMISRTPEVTCWVDVSHEDPEVKFNW
YVDGVEVHNAKTKPREEQYNSTYRVVSVLTVLHQDWLNGKEYKCKVSNKA
LPAPIEKTISMKGQPREPQVYTLPPSRDELKNQVSLTCLVKGFYPSDIAV
EWESNGQPENNYKTTPPVLDSDGSFFLYSKLTVDKSRWQQGNVFSCSVMH
EALHNHYTQKSLSLSPG.
```

The DNA sequence that corresponds to SEQ ID NO: 32 is

```
ATGGACCCCAAGGGCAGCCTGAGCTGGAGAATCCTGCTGTTCCTGAGCCT
GGCCTTCGAGCTGAGCTACGGCCAGGTGCAGCTGGTGCAGTCTGGCGCCG
AAGTGAAGAAACCTGGCGCCTCCGTGAGGTGTCCTGCAAGGCTTCCGGCT
ACCTGTTCACCACCTACTGGATGCACTGGGTGCGACAGGCCCCTGGACAG
GGCCTGGAATGGATGGGCGAGATCTCCCCTACCAACGGCAGAGCCTACTA
CAACCAAAATTCCAGGGCAGAGTGACCATGACCGTGGACAAGTCCACCAA
CACCGCTTACATGGAACTGTCCTCCCTGCGGAGCGAGGACACCGCCGTGT
ACTACTGCGCTAGAGCCTACGGCAACTACGATTCGCCTACTGGGGCCAGG
GCACCCTCGTGACAGTGTCCTCTGCTAGCACCAAGGGCCCCAGCGTGTTC
CCTCTGGCCCCCAGCAGCAAGAGCACCAGCGGCGGAACCGCCGCCCTGGG
CTGCCTGGGAAGGACTACTTCCCCGAGCCCGTGACCGTGTCCTGGAACAG
CGGCGCTCTGACCAGCGGAGTGCACACCTTCCCTGCCGTGCTGCAGAGCA
GCGGCCTGTACTCCCTGAGCAGCGTGGTGACCGTGCCAGCAGCAGCCTGG
GCACCCAGACCTACATCTGCAACGTGAACCACAAGCCCTCCAACACCAAG
GTGGACAAGAAGGTGGAGCCTAAGAGCTGCGACAAGACCCACACCTGCCC
TCCCTGCCCCGCCCCGAGCTGCTGGGCGGACCCAGCGTGTTCCTGTTCCC
TCCCAAGCCCAAGGACACCCTGATGATCAGCCGCACCCCCGAGGTGACCT
GCGTGGTGGTGGACGTGAGCCACGAGGACCCCGAGGTGAGTTCAACTGGT
ACGTGGACGGCGTGGAGGTGCACAACGCCAAGACCAAGCCTCGGGAGGAG
CAGTACAACTCCACCTACCGCGTGGTGAGCGTGCTGACCGTGCTGCACCA
GGACTGGCTGAACGGCAGGAGTACAAGTGCAAGGTGAGCAACAAGGCCCT
GCCCGCTCCCATCGAGAAGACCATCAGCAAGGCCAAGGGCCAGCCCCGGG
AGCCTCAGGTGTACACCCTGCCCCCCAGCCGCGACGAGCTGACAAGAACC
AGGTGAGCCTGACCTGCCTGGTGAAGGGCTTCTACCCCTCCGACATCGCC
GTGGAGTGGGAGAGCAACGGCCAGCCTGAGAACAACTACAAGACCACCCC
TCCCGTGCTGGACAGCGACGCAGCTICTTCCIGTACAGCAAGCTGACCGT
GGACAAGTCCCGGTGGCAGCAGGGCAACGTGTTCAGCTGCAGCGTGATGC
ACGAGGCCCTGCACAACCACTACACCCAGAAGAGCCTGAGCCTGAGCCCG
GATAGTAA.
```

The one-letter amino acid sequence that corresponds to SEQ ID NO: 33 is

```
MDPKGSLSWRILLFLSLAFELSYGQVQLVQSGAEVKKPGASVKVSCKASG
YLFTTYWMHVVVRQAPGQGLEWMGEISPTNGRAYYNAKFQGRVTMTVDKS
INTAYMELSRLRSDDTAVYYCARAYGNYFAYWGQGTLVTVSSASTKGPSV
FPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHT
CPPCPPELLGGPSVFLFPPKPKDTLMISRTPEVTCVVVDVSHEDPEVKFN
INYVDGVEVHNAKTKPREEQYNSTYRWSVLTVLHQDWLNGKEYKCKVSNK
ALPAPIEKTISKAKGQPREPQVYTLPPSRDELKNQVSLTCLVKGFYPSDI
AVEWESNGQPENNYKTTPPVLDSDGSFFLYSKLTVDKSRWQQGNVFSCSV
MHEALHNHYTQKSLSLSPG.
```

The DNA sequence that corresponds to SEQ ID NO: 34 is

```
ATGGACCCCAAGGGCAGCCTGAGCTGGAGAATCCTGCTGTTCCTGAGCCT
GGCCTTCGAGCTGAGCTACGGCCAGGTGCAGCTGGTGCAGTCTGGCGCCG
```

```
AAGTGAAGAAACCTGGCGCCTCCGTGAGGTGTCCTGCAAGGCTTCCGGCT

ACCTGTTCACCACCTACTGGATGCACTGGGTGCGACAGGCCCCTGGACAG

GGCCTGGAATGGATGGGCGAGATCTCCCCTACCAACGGCAGAGCCTACTA

CAACCAAAATTCCAGGGCAGAGTGACCATGACCGTGGACAAGTCCATCAA

CACCGCTTACATGGAACTGTCCAGACTGCGGAGCGATGACACCGCCGTGT

ACTACTGCGCTAGAGCCTACGGCAACTACGATTCGCCTACTGGGGCCAGG

GCACCCTCGTGACAGTGTCCTCTGCTAGCACCAAGGGCCCCAGCGTGTTC

CCTCTGGCCCCCAGCAGCAAGAGCACCAGCGGCGAACCGCCGCCCTGGG

CTGCCTGGGAAGGACTACTTCCCCGAGCCCGTGACCGTGTCCTGGAACAG

CGGCGCTCTGACCAGCGGAGTGCACACCTTCCCTGCCGTGCTGCAGAGCA

GCGGCCTGTACTCCCTGAGCAGCGTGGTGACCGTGCCAGCAGCAGCCTGG

GCACCCAGACCTACATCTGCAACGTGAACCACAAGCCCTCCAACACCAAG

GTGGACAAGAAGGTGGAGCCTAAGAGCTGCGACAAGACCCACACCTGCCC

TCCCTGCCCCGCCCCGAGCTGCTGGGCGGACCCAGCGTGTTCCTGTTCCC

TCCCAAGCCCAAGGACACCCTGATGATCAGCCGCACCCCCGAGGTGACCT

GCGTGGTGGTGGACGTGAGCCACGAGGACCCCGAGGTGAGTTCAACTGGT

ACGTGGACGGCGTGGAGGTGCACAACGCCAAGACCAAGCCTCGGGAGGAG

CAGTACAACTCCACCTACCGCGTGGTGAGCGTGCTGACCGTGCTGCACCA

GGACTGGCTGAACGGCAGGAGTACAAGTGCAAGGTGAGCAACAAGGCCCT

GCCCGCTCCCATCGAGAAGACCATCAGCAAGGCCAAGGGCCAGCCCCGGG

AGCCTCAGGTGTACACCCTGCCCCCAGCCGCGACGAGCTGACAAGAACC

AGGTGAGCCTGACCTGCCTGGTGAAGGGCTTCTACCCCTCCGACATCGCC

GTGGAGTGGGAGAGCAACGGCCAGCCTGAGAACAACTACAAGACCACCCC

TCCCGTGCTGGACAGCGACGCAGCTTCTTCCTGTACAGCAAGCTGACCGT

GGACAAGTCCCGGTGGCAGCAGGGCAACGTGTTCAGCTGCAGCGTGATGC

ACGAGGCCCTGCACAACCACTACACCCAGAAGAGCCTGAGCCTGAGCCCG

GATAGTAA.
```

The one-letter amino acid sequence that corresponds to SEQ ID NO: 35 is

```
METDTLLLVVVLLLVVVPGSTGDWMTQSPLSLPVTLGQPASISCRSSQSL

VNSNGNTFLQVVYQQRPGQSPRWYKVSLRFSGVPDRFSGSGSGTDFTLKI

SRVEAEDVGVYYCSQSTHVPPTFGGGTVEIKRTVAAPSVFIFPPSDEQLK

SGTASWCLLNNFYPREAKVQWKVDNALQSGNSQESVTEQDSKDSTYSLSS

TLTLSKADYEKHKVYACEVTHQGLSSPVTKSFNRGEC.
```

The DNA sequence that corresponds to SEQ ID NO: 36 is

```
ATGGAGACCGACACCCTGCTGCTCTGGGTGCTGCTGCTCTGGGTGCCCGG

CTCCACCGGAGACGTCGTGATGACCCAGTCCCCTCTGTCCCTGCCTGTGA

CCCTGGGACAGCCTGCCTCCATCTCCTCAGATCCTCCCAGTCCCTCGTGA

ACTCCAACGGCAACACCTTCCTGCAGTGGTATCAGCAGCGGCCTGGCCAG

AGCCCCAGACTGCTGATCTACAAGGTGTCCCTGCGGTTCTCCGGCGTGCC

CGACGATTTTCCGGCTCTGGCTCTGGCACCGACTTCACCCTGAAGATCTC

CCGGGTGGAAGCCGAGGACGTGGGCGTGTACTACTGCTCCCAGAGCACCC

ACGTGCCCCCTACATTTGGCGGAGGCACCAAGTGGAAATCAAGCGGACCG

TGGCCGCCCCCAGCGTGTTTCATCTTCCCTCCCAGCGACGAGCAGCTGAA

GTCTGGCACCGCCAGCGTGGTGTGCCTGCTGAACAACTTCTACCCCCGCG

AGGCCAAGGGCAGTGGAAGGTGGACAACGCCCTGCAGAGCGGCAACAGCC

AGGAGAGCGTGACCGAGCAGGACTCCAAGGACAGCACCTACAGCCTGAGC

AGCACCCTGACCCTGAGCAAGGCCGACTACGAGAAGACAAGGTGTACGCC

TGCGAGGTGACCCACCAGGGACTGTCTAGCCCCGTGACCAAGAGCTTCAA

CCGGGGCGAGTGCTAA.
```

The one-letter amino acid sequence that corresponds to SEQ ID NO: 37 is

```
METDTLLLVVVLLLVVVPGSTGDVVMTQSPLSLPVTLGQPASISCRSRQS

LVNSNGNTFLQVVYQQRPGQSPRLLIYKVSLRFSGVPDRFSGSGSGTDFT

LKISRVEAEDVGVYYCSQSTHVPPTFGGGTVEIKRTVAAPSVFIFPPSDE

QLKSGTASVVCLLNNFYPREAKVQWKVDNALQSGNSQESVTEQDSKDSTY

SLSSTLTLSKADYEKHKVYACEVTHQGLSSPVTKSFNRGEC.
```

The DNA sequence that corresponds to SEQ ID NO: 38 is

```
ATGGAGACCGACACCCTGCTGCTCTGGGTGCTGCTGCTCTGGGTGCCCGG

CTCCACCGGAGACGTCGTGATGACCCAGTCCCCTCTGTCCCTGCCTGTGA

CCCTGGGACAGCCTGCCTCCATCTCCTCAGATCCAGGCAGTCCCTCGTGA

ACTCCAACGGCAACACCTTCCTGCAGTGGTATCAGCAGCGGCCTGGCCAG

AGCCCCAGACTGCTGATCTACAAGGTGTCCCTGCGGTTCTCCGGCGTGCC

CGACGATTTTCCGGCTCTGGCTCTGGCACCGACTTCACCCTGAAGATCTC

CCGGGTGGAAGCCGAGGACGTGGGCGTGTACTACTGCTCCCAGAGCACCC

ACGTGCCCCCTACATTTGGCGGAGGCACCAAGTGGAAATCAAGCGGACCG

TGGCCGCCCCCAGCGTGTTCATCTTCCCTCCCAGCGACGAGCAGCTGAAG

TCTGGCACCGCCAGCGTGGTGTGCCTGCTGAACAACTTCTACCCCCGCGA

GGCCAAGGGCAGTGGAAGGTGGACAACGCCCTGCAGAGCGGCAACAGCCA

GGAGAGCGTGACCGAGCAGGACTCCAAGGACAGCACCTACAGCCTGAGCA

GCACCCTGACCCTGAGCAAGGCCGACTACGAGAAGACAAGGTGTACGCCT

GCGAGGTGACCCACCAGGGACTGTCTAGCCCCGTGACCAAGAGCTTCAAC

CGGGGCGAGTGCTAA.
```

The one-letter amino acid sequence that corresponds to SEQ ID NO: 39 is

```
METDTLLLVVVLLLVVVPGSTGDVVMTQSPLSSPVTLGQPASISCRSSQS

LVNSNGNTFLQWYHQRPGQPPRLLIYKVSLRFSGVPDRFSGSGAGKDFTL
```

-continued
KISRVEAEDVGVYYCSQSTHVPPTFGQGTLEIKRTVAAPSVFIFPPSDEQ

LKSGTASVVGLLNNFYPREAKVQWKVDNALQSGNSQESVTEQDSKDSTYS

LSSTLTLSKADYEKHKVYACEVTHQGLSSPVTKSFNRGEC.

The DNA sequence that corresponds to SEQ ID NO: 40 is

ATGGAGACCGACACCCTGCTGCTCTGGGTGCTGCTGCTCTGGGTGCCCGG

CTCCACCGGAGACGTCGTGATGACCCAGTCCCCTCTGTCCAGTCCTGTGA

CCCTGGGACAGCCTGCCTCCATCTCCTCAGATCCTCCCAGTCCCTCGTGA

ACTCCAACGGCAACACCTTCCTGCAGTGGTATCACCAGCGGCCTGGCCAG

CCTCCCAGACTGCTGATCTACAAGGTGTCCCTGCGGTTCTCCGGCGTGCC

CGACGATTTTCCGGCTCTGGCGCTGGCAAGGACTTCACCCTGAAGATCTC

CCGGGTGGAAGCCGAGGACGTGGGCGTGTACTACTGCTCCCAGAGCACCC

ACGTGCCCCTACATTTGGCCAGGGCACCAACTGGAAATCAAGCGGACCG

TGGCCGCCCCCAGCGTGTTCATCTTCCCTCCCAGCGACGAGCAGCTGAAG

TCTGGCACCGCCAGCGTGGTGTGCCTGCTGAACAACTTCTACCCCCGCGA

GGCCAAGGGCAGTGGAAGGTGGACAACGCCCTGCAGAGCGGCAACAGCCA

GGAGAGCGTGACCGAGCAGGACTCCAAGGACAGCACCTACAGCCTGAGCA

GCACCCTGACCCTGAGCAAGGCCGACTACGAGAAGACAAGGTGTACGCCT

GCGAGGTGACCCACCAGGGACTGTCTAGCCCCGTGACCAAGAGCTTCAAC

CGGGGCGAGTGCTAA.

The one-letter amino acid sequence that corresponds to SEQ ID NO: 47 is

MGINTLVFLFLLSVTAGVHSQVQLLQPGAELVKPGASVKLACKASGYLFT

TYWMHWLKQRPGQGLEWIGEISPTNGRAYYNARFKSEATLTVDKSSNTAY

MQLSSLTSEASAVYYCARSFGNYEFAYWGQGTLVTVSVASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNINY

VDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVM

HEALHNHYTQKSLSLSPGK.

The one-letter amino acid sequence that corresponds to SEQ ID NO: 48 is

MGVVTLVFLFLLSVTAGVHSEVQLLESGAEAKKPGASVKLSCKASGYLFT

TYWMHVVVHQAPGQRLEWMGEISPTNGRAYYNARFKSRVTITVDKSASTA

YMELSSLRSEDTAVYYCARSFGNYEFAYWGQGTLVTVSSASTKGPSVFPL

APSSKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNVV

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK.

The one-letter amino acid sequence that corresponds to SEQ ID NO: 49 is

MGWTLVFLFLLSVTAGVHSQVQLVQSGAEVKKPGASVKVSCKASGYLFTT

YWMHVVVRQAPGQRLEWIGEISPTNGRAYYNARFKSRVTITRDTSASTAY

MELSSLRSEDTAVYYCARSFGNYEFAYWGQGTLVTVSSASTKGPSVFPLA

PSSKSTSGGTAALGCLVKDYFPEPVTVSWNSGALTSGVHTFPAVLQSSGL

YSLSSVVIVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTIPPVLDSDGSFFLYSKUTVDKSRWQQGNVFSCSVMHE

ALHNHYTQKSLSLSPGK.

The one-letter amino acid sequence that corresponds to SEQ ID NO: 50 is

MGVVTLVFLFLLSVTAGVHSQVQLVQSGAEVKKPGSSVKVSCKASGYLFT

TYWMHVVVRQAPGQGLEWMGEISPTNGRAYYNARFKSRVTITADKSTSTA

YMELSSLRSEDTAVYYCARSFGNYEFAYWGQGTLVTVSSASTKGPSVFPL

APSSKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHTCPP

CPAPELLGGPSVFLFPPKPKDTLMISRTPEVTCWVVDVSHEDPEVKFNWYV

DGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK.

The one-letter amino acid sequence that corresponds to SEQ ID NO: 51 is

MGWTLVFLFLLSVTAGVHSQVQLVQSGAEVKKPGASVKVSCEASGYLFTT

YWMHVVVRQAPGQGLEWMGEISPTNGRAYYNARFKSRVTITRDTSINTAY

MELSRLRSDDTAVYYCARSFGNYEFAYWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRWSVLTVLHQDWLNGKEYKCKVSNKALPA

-continued

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK.

The one-letter amino acid sequence that corresponds to SEQ ID NO: 52 is

QVQLLQPGAELVKPGASVKLACKASGYLFTTYWMHWLKQRPGQ

GLEWIGEISPTNGRAYYNARFKSEATLTVDKSSNTAYMQLSSL

TSEASAVYYCARSFGNYEFAYWGQGTLVTVSV.

The one-letter amino acid sequence that corresponds to SEQ ID NO: 53 is

EVQLLESGAEAKKPGASVKLSCKASGYLFTTYWMHVVVHQAPGQ

RLEWMGEISPTNGRAYYNARFKSRVTITVDKSASTAYMELSSLR

SEDTAVYYCARSFGNYEFAYWGQGTLVTVSS.

The one-letter amino acid sequence that corresponds to SEQ ID NO: 54 is

QVQLVQSGAEVKKPGASVKVSCKASGYLFTTYWMHVVVRQAPGQRLE

WIGEISPTNGRAYYNARFKSRVTITRDTSASTAYMELSSLRSEDTAV

YYCARSFGNYEFAYWGQGTLVTVSS.

The one-letter amino acid sequence that corresponds to SEQ ID NO: 55 is

QVQLVQSGAEVKKPGSSVKVSCKASGYLFTTYWMHINVRQAPGQG

LEWMGEISPTNGRAYYNARFKSRVTITADKSTSTAYMELSSLRSE

DTAVYYCARSFGNYEFAYWGQGTLVTVSS.

The one-letter amino acid sequence that corresponds to SEQ ID NO: 56 is

QVQLVQSGAEVKKPGASVKVSCEASGYLFTTYWMHWVRQAPGQ

GLEWMGEISPTNGRAYYNARFKSRVTITRDTSINTAYMELSRL

RSDDTAVYYCARSFGNYEFAYWGQGTLVTVSS.

The one-letter amino acid sequence that corresponds to SEQ ID NO: 57 is

MVSSAQFLGLLLLCFQGTRCDVVMTQTPLSLPVSLGDQASISCR

SRQSLVNSNGNTFLQWYLQKPGQSPK

LLIWYKVSLRFSGVPDRFSGSGSGTDFTLKISRVEAEDLGLYFCSQS

THVPPTFGGGTKLEIKRTVAAPSVFIFPPSDEQLKSGTASVVCLLNN

FYPREAKVQWKVDNALQSGNSQESVTEQDSKDSTYSLSSTLTLSKAD

YEKHKVYACEVTHQGLSSPVTKSFNRGEC.

The one-letter amino acid sequence that corresponds to SEQ ID NO: 58 is

MVSSAQFLGLLLLCFQGTRCDIVMTQTPLSLPV

TLGQPASISCRSRQSLVNSNGNTFLQWYLQKPG

QSPQLLIYKVSLRFSGVPDRFSGSGGTDFTLTL

KISRVEPEDVGYYCSQSTHVPPTFGQGTKVEIK

RTVAAPSVFIFPPSDEQLKSGTASVVCLLNNFYPRE

AKVQWKVDNALQSGNSQESVTEQDSKDSTYSLSSTL

TLSKADYEKHKVYACEVTHQGLSSPVTKSFNRGEC.

The one-letter amino acid sequence that corresponds to SEQ ID NO: 59 is

MVSSAQFLGLLLLCFQGTRCDIVMTQTPLSLSVTPGQPASISCRSRQSL

VNSNGNTFLQWYLQKPGQSPQLLIYKVSLRFSGVPDRFSGSGSGTDFTL

KISRVEPEDVGVYYCSQSTHVPPTFGGGTKVEVKRTVAAPSVFIFPPSD

EQLKSGTASVVCLLNNFYPREAKVQWKVDNALQSGNSQESVTEQDSKDS

TYSLSSTLTLSKADYEKHKVYACEVTHQGLSSPVTKSFNRGEC.

The one-letter amino acid sequence that corresponds to SEQ ID NO: 60 is

MVSSAQFLGLLLLCFQGTRCDVVMTQSPLSLPVTLGQPASISCRSRQS

LVNSNGNTFLQWFQQRPGQSPRRLIYKVSLRFSGVPDRFSGSGSDTDF

TLRISRVEAEDVGLYYCSQSTHVPPTFGQGTKLEIKRTVAAPSVFIFP

PSDEQLKSGTASVVCLLNNFYPREAKVQWKVDNALQSGNSQESVTEQD

SKDSTYSLSSTLTLSKADYEKHKVYACEVTHQGLSSPVTKSFNRGEC.

The one-letter amino acid sequence that corresponds to SEQ ID NO: 61 is

MVSSAQFLGLLLLCFQGTRCDIVMTQTPLSLSVTPGQPASISCRSR

QSLVNSNGNTFLQWLLQKPGQPPQLLIYKVSLRFSGVPNRFSGSGS

GTDFTLKISRVEAEDVGLYYCSQSTHVPPTFGGGTKVEIKRTVAAP

SVFIFPPSDEQLKSGTASVVCLLNNFYPREAKVQWKVDNALQSGNS

QESVTEQDSKDSTYSLSSTLTLSKADYEKHKVYACEVTHQGLSSPV

TKSFNRGEC.

The one-letter amino acid sequence that corresponds to SEQ ID NO: 62 is

DVVMTQTPLSLPVSLGDQASISCRSRQSLVNSNGNTFLQVVY

LQKPGQSPKWYKVSLRFSGVPDRFSGSGSGTDFTLKISRVEA

EDLGLYFCSQSTHVPPTFGGGTKLEIK.

The one-letter amino acid sequence that corresponds to SEQ ID NO: 63 is

DIVMTQTPLSLPVTLGQPASISCRSRQSLVNSNGNTFLQ

WLQQRPGQPPRLLIYKVSLRFSGVPDRFSGSGAGTDFTL

TISRVEAEDVGIYFCSQSTHVPPTFGQGTKVEIK.

The one-letter amino acid sequence that corresponds to SEQ ID NO: 64 is

DIVMTQTPLSLSVTPGQPASISCRSRQSLVNSN

GNTFLQWYLQKPGQSPQLLIYKVSLRFSGVPDR

FSGSGSGTDFTLKISRVEPEDVGVYYCSQSTHV

PPTFGGGTKVEVK.

The one-letter amino acid sequence that corresponds to SEQ ID NO: 65 is

DVVMTQSPLSLPVTLGQPASISCRSRQSLVNSNGN

TFLQWFQQRPGQSPRRLIYKVSLRFSGVPDRFSGS

GSDTDFTLRISRVEAEDVGLYYCSQSTHVPPTFGQGTKLEIK.

The one-letter amino acid sequence that corresponds to SEQ ID NO: 66 is

DIVMTQTPLSLSVTPGQPASISCRSRQSLVNSNGNT

FLQWLLQKPGQPPQLLIYKVSLRFSGVPNRFSGSGS

GTDFTLKISRVEAEDVGLYYCSQSTHVPPTFGGGTKVEIK.

EXAMPLES

Example 1: In Vivo Study of the Administration of Anti-Glycation End-Product Antibody To examine the effects of an anti-glycation end-product antibody, the antibody was administered to the aged CD1 (ICR) mouse (Charles River Laboratories), twice daily by intravenous injection, once a week, for three weeks (Days 1, 8 and 15), followed by a 10 week treatment-free period. The test antibody was a commercially available mouse anti-glycation end-product antibody raised against carboxymethyl lysine conjugated with keyhole limpet hemocyanin, the carboxymethyl lysine MAb (Clone 318003) available from R&D Systems, Inc. (Minneapolis, Minn.; catalog no. MAB3247). A control reference of physiological saline was used in the control animals.

Mice referred to as "young" were 8 weeks old, while mice referred to as "old" were 88 weeks (±2 days) old. No adverse events were noted from the administration of the antibody. The different groups of animals used in the study are shown in Table 1.

TABLE 1

The different groups of animals used in the study

| | | | | Number of Animals | |
|---|---|---|---|---|---|
| Group No. | Test Material | Mice | Dose Level (µg/gm/BID/week) | Main Study Females | Treatment-Free Females |
| 1 | Saline | young | 0 | 20 | — |
| 2 | Saline | old | 0 | 20 | 20 |
| 3 | Antibody | old | 2.5 | 20 | 20 |
| 4 | None | old | 0 | 20 | pre |
| 5 | Antibody | old | 5.0 | 20 | 20 |

— = Not Applicable, Pre = Subset of animals euthanized prior to treatment start for collection of adipose tissue.

$p16^{INK4a}$ mRNA, a marker for senescent cells, was quantified in adipose tissue of the groups by Real Time-qPCR. The results are shown in Table 2. In the table $\Delta\Delta Ct = \Delta Ct$ mean control Group (2)−$\Delta Ct$ mean experimental Group (1 or 3 or 5); Fold Expression=$2^{-\Delta\Delta Ct}$.

TABLE 2

$P16^{INK4a}$ mRNA quantified in adipose tissue

| Calculation (unadjusted to Group 4: 5.59) | Group 2 vs Group 1 | | Group 2 vs Group 3 | | Group 2 vs Group 5 | |
|---|---|---|---|---|---|---|
| | Group 2 | Group 1 | Group 2 | Group 3 | Group 2 | Group 5 |
| Mean ΔCt | 5.79 | 7.14 | 5.79 | 6.09 | 5.79 | 7.39 |
| ΔΔCt | −1.35 | | −0.30 | | −1.60 | |
| Fold Expression | 2.55 | | 1.23 | | 3.03 | |

The table above indicates that untreated old mice (Control Group 2) express 2.55-fold more $p16^{Ink4a}$ mRNA than the untreated young mice (Control Group 1), as expected. This was observed when comparing Group 2 untreated old mice euthanized at end of recovery Day 85 to Group 1 untreated young mice euthanized at end of treatment Day 22. When results from Group 2 untreated old mice were compared to results from Group 3 treated old mice euthanized Day 85, it was observed that $p16^{Ink4a}$ mRNA was 1.23-fold higher in Group 2 than in Group 3. Therefore, the level of $p16^{Ink4a}$ mRNA expression was lower when the old mice were treated with 2.5 µg/gram/BID/week of antibody.

When results from Group 2 (Control) untreated old mice were compared to results from Group 5 (5 µg/gram) treated old mice euthanized Day 22, it was observed that $p16^{Ink4a}$ mRNA was 3.03-fold higher in Group 2 (controls) than in Group 5 (5 µg/gram). This comparison indicated that the Group 5 animals had lower levels of $p16^{Ink4a}$ mRNA expression when they were treated with 5.0 µg/gram/BID/week, providing $p16^{Ink4a}$ mRNA expression levels comparable to that of the young untreated mice (i.e. Group 1). Unlike Group 3 (2.5 µg/gram) mice that were euthanized at end of recovery Day 85, Group 5 mice were euthanized at end of treatment Day 22.

These results indicate the antibody administration resulted in the killing of senescent cells.

The mass of the gastrocnemius muscle was also measured, to determine the effect of antibody administration on sarcopenia. The results are provided in Table 3. The results indicate that administration of the antibody increased muscle mass as compared to controls, but only at the higher dosage of 5.0 µg/gm/BID/week.

TABLE 3

Effect of antibody administration on mass of the gastrocnemius muscle

| Group | Summary Information | Absolute weight of Gastrocnemius Muscle (g) | Weight relative to body mass of Gastrocnemius Muscle (%) |
|---|---|---|---|
| 1 | Mean | 0.3291 | 1.1037 |
|   | SD   | 0.0412 | 0.1473 |
|   | N    | 20     | 20 |
| 2 | Mean | 0.3304 | 0.7671 |
|   | SD   | 0.0371 | 0.1246 |
|   | N    | 20     | 20 |
| 3 | Mean | 0.3410 | 0.7706 |
|   | SD   | 0.0439 | 0.0971 |
|   | N    | 19     | 19 |
| 5 | Mean | 0.4074 | 0.9480 |
|   | SD   | 0.0508 | 0.2049 |
|   | N    | 9      | 9 |

These results demonstrate that administration of antibodies that bind to AGEs of a cell resulted in a reduction of cells expressing $p16^{Ink4a}$, a biomarker of senescence. The data show that reducing senescent cells leads directly to an increase in muscle mass in aged mice. These results indicate that the loss of muscle mass, a classic sign of sarcopenia, can be treated by administration of antibodies that bind to AGEs of a cell. The results suggest that administration of the antibodies would be effective in treating or preventing the onset of diabetes and diabetic complications by removing senescent cells.

Example 2: Affinity and Kinetics of Test Antibody

The affinity and kinetics of the test antibody used in Example 1 were analyzed using Nα,Nα-bis(carboxymethyl)-L-lysine trifluoroacetate salt (Sigma-Aldrich, St. Louis, Mo.) as a model substrate for an AGE-modified protein of a cell. Label-free interaction analysis was carried out on a BIACORE™ T200 (GE Healthcare, Pittsburgh, Pa.), using a Series S sensor chip CM5 (GE Healthcare, Pittsburgh, Pa.), with Fc1 set as blank, and Fc2 immobilized with the test antibody (molecular weigh of 150,000 Da). The running buffer was a HBS-EP buffer (10 mM HEPES, 150 mM NaCl, 3 mM EDTA and 0.05% P-20, pH of 7.4), at a temperature of 25° C. Software was BIACORE™ T200 evaluation software, version 2.0. A double reference (Fc2-1 and only buffer injection), was used in the analysis, and the data was fitted to a Langmuir 1:1 binding model.

TABLE 4

Experimental set-up of affinity and kinetics analysis
Association and dissociation

| Flow path | Fc1 and Fc2 |
|---|---|
| Flow rate (µl/min.) | 30 |
| Association time (s) | 300 |
| Dissociation time (s) | 300 |
| Sample concentration (µM) | 20 – 5 – 1.25 (×2) – 0.3125 – 0.078 – 0 |

A graph of the response versus time is illustrated in FIG. 1. The following values were determined from the analysis: $k_a$ (1/Ms)=1.857×10³; $k_d$ (1/s)=6.781×10⁻³; $K_D$ (M)=3.651×10⁻⁶; $R_{max}$ (RU)=19.52; and Chi²=0.114. Because the Chi² value of the fitting is less than 10% of $R_{max}$, the fit is reliable.

Example 3: Construction and Production of Murine Anti-AGE IgG2b Antibody and Chimeric Anti-AGE IgG1 Antibody Murine and chimeric human anti-AGE antibodies were prepared. The DNA sequence of murine anti-AGE antibody IgG2b heavy chain is shown in SEQ ID NO: 12. The DNA sequence of chimeric human anti-AGE antibody IgG1 heavy chain is shown in SEQ ID NO: 13. The DNA sequence of murine anti-AGE antibody kappa light chain is shown in SEQ ID NO: 14. The DNA sequence of chimeric human anti-AGE antibody kappa light chain is shown in SEQ ID NO: 15. The gene sequences were synthesized and cloned into high expression mammalian vectors. The sequences were codon optimized. Completed constructs were sequence confirmed before proceeding to transfection.

HEK293 cells were seeded in a shake flask one day before transfection, and were grown using serum-free chemically defined media. The DNA expression constructs were transiently transfected into 0.03 liters of suspension HEK293 cells. After 20 hours, cells were sampled to obtain the viabilities and viable cell counts, and titers were measured (Octet QKe, ForteBio). Additional readings were taken throughout the transient transfection production runs. The cultures were harvested on day 5, and an additional sample for each was measured for cell density, viability and titer.

The conditioned media for murine and chimeric anti-AGE antibodies were harvested and clarified from the transient transfection production runs by centrifugation and filtration. The supernatants were run over a Protein A column and eluted with a low pH buffer. Filtration using a 0.2 µm membrane filter was performed before aliquoting. After purification and filtration, the protein concentrations were calculated from the OD280 and the extinction coefficient. A summary of yields and aliquots is shown in Table 5:

TABLE 5

Yields and aliquots

| Protein | Concentration (mg/mL) | Volume (mL) | No. of vials | Total Yield (mg) |
|---|---|---|---|---|
| Murine anti-AGE | 0.08 | 1.00 | 3 | 0.24 |
| Chimeric anti-AGE | 0.23 | 1.00 | 3 | 0.69 |

Antibody purity was evaluated by capillary electrophoresis sodium-dodecyl sulfate (CE-SDS) analysis using LabChip® GXII, (PerkinElmer).

Example 4: Binding of Murine (Parental) and Chimeric Anti-AGE Antibodies

The binding of the murine (parental) and chimeric anti-AGE antibodies described in Example 3 was investigated by a direct binding ELISA. An anti-carboxymethyl lysine (CML) antibody (R&D Systems, MAB3247) was used as a control. CML was conjugated to KLH (CML-KLH) and both CML and CML-KLH were coated overnight onto an ELISA plate. HRP-goat anti-mouse Fc was used to detect the control and murine (parental) anti-AGE antibodies. HRP-goat anti-human Fc was used to detect the chimeric anti-AGE antibody.

The antigens were diluted to 1 μg/mL in 1× phosphate buffer at pH 6.5. A 96-well microtiter ELISA plate was coated with 100 μL/well of the diluted antigen and let sit at 4° C. overnight. The plate was blocked with 1×PBS, 2.5% BSA and allowed to sit for 1-2 hours the next morning at room temperature. The antibody samples were prepared in serial dilutions with 1×PBS, 1% BSA with the starting concentration of 50 μg/mL. Secondary antibodies were diluted 1:5,000. 100 μL of the antibody dilutions was applied to each well. The plate was incubated at room temperature for 0.5-1 hour on a microplate shaker. The plate was washed 3 times with 1×PBS. 100 μL/well diluted HRP-conjugated goat anti-human Fc secondary antibody was applied to the wells. The plate was incubated for 1 hour on a microplate shaker. The plate was then washed 3 times with 1×PBS. 100 μL HRP substrate TMB was added to each well to develop the plate. After 3-5 minutes elapsed, the reaction was terminated by adding 100 μL of 1N HCl. A second direct binding ELISA was performed with only CML coating. The absorbance at OD450 was read using a microplate reader.

The OD450 absorbance raw data for the CML and CML-KLH ELISA is shown in the plate map below. 48 of the 96 wells in the well plate were used. Blank wells in the plate map indicate unused wells.

| Conc. (μg/mL) | 1 | 2 | 3 | 4 | 5 | 6 | 7 |
|---|---|---|---|---|---|---|---|
| 50 | 0.462 | 0.092 | 0.42 | | 1.199 | 0.142 | 1.852 |
| 16.67 | 0.312 | 0.067 | 0.185 | | 0.31 | 0.13 | 0.383 |
| 5.56 | 0.165 | 0.063 | 0.123 | | 0.19 | 0.115 | 0.425 |
| 1.85 | 0.092 | 0.063 | 0.088 | | 0.146 | 0.099 | 0.414 |
| 0.62 | 0.083 | 0.072 | 0.066 | | 0.108 | 0.085 | 0.248 |
| 0.21 | 0.075 | 0.066 | 0.09 | | 0.096 | 0.096 | 0.12 |
| 0.07 | 0.086 | 0.086 | 0.082 | | 0.098 | 0.096 | 0.098 |
| 0 | 0.09 | 0.085 | 0.12 | | 0.111 | 0.083 | 0.582 |
| | R&D Positive Control | Parental Anti-AGE | Chimeric Anti-AGE | | R&D Positive Control | Parental Anti-AGE | Chimeric Anti-AGE |
| | CML-KLH Coat | | | | CML Coat | | |

The OD450 absorbance raw data for the CML-only ELISA is shown in the plate map below. 24 of the 96 wells in the well plate were used. Blank wells in the plate map indicate unused wells.

| Conc. (μg/mL) | 1 | 2 | 3 | 4 | 5 | 6 | 7 |
|---|---|---|---|---|---|---|---|
| 50 | 1.913 | 0.165 | 0.992 | | | | |
| 16.66667 | 1.113 | 0.226 | 0.541 | | | | |
| 5.555556 | 0.549 | 0.166 | 0.356 | | | | |
| 1.851852 | 0.199 | 0.078 | 0.248 | | | | |
| 0.617284 | 0.128 | 0.103 | 0.159 | | | | |
| 0.205761 | 0.116 | 0.056 | 0.097 | | | | |
| 0.068587 | 0.073 | 0.055 | 0.071 | | | | |
| 0 | 0.053 | 0.057 | 0.06 | | | | |
| | R&D Positive Control | Parental Anti-AGE | Chimeric Anti-AGE | | | | |

The control and chimeric anti-AGE antibodies showed binding to both CML and CML-KLH. The murine (parental) anti-AGE antibody showed very weak to no binding to either CML or CML-KLH. Data from repeated ELISA confirms binding of the control and chimeric anti-AGE to CML. All buffer control showed negative signal.

Example 5: Humanized Antibodies

Humanized antibodies were designed by creating multiple hybrid sequences that fuse select parts of the parental (mouse) antibody sequence with the human framework sequences. Acceptor frameworks were identified based on the overall sequence identity across the framework, matching interface position, similarly classed CDR canonical positions, and presence of N-glycosylation sites that would have to be removed. Three humanized light chains and three humanized heavy chains were designed based on two different heavy and light chain human acceptor frameworks. The amino acid sequences of the heavy chains are shown in SEQ ID NO: 29, 31 and 33, which are encoded by the DNA sequences shown in SEQ ID NO: 30, 32 and 34, respectively. The amino acid sequences of the light chains are shown in SEQ ID NO: 35, 37 and 39, which are encoded by the DNA sequences shown in SEQ ID NO: 36, 38 and 40, respectively. The humanized sequences were methodically analyzed by eye and computer modeling to isolate the sequences that would most likely retain antigen binding. The goal was to maximize the amount of human sequence in the final humanized antibodies while retaining the original antibody specificity. The light and heavy humanized chains could be combined to create nine variant fully humanized antibodies.

The three heavy chains and three light chains were analyzed to determine their humanness. Antibody humanness scores were calculated according to the method described in Gao, S. H., et al., "Monoclonal antibody humanness score and its applications", BMC Biotechnology, 13:55 (Jul. 5, 2013). The humanness score represents how human-like an antibody variable region sequence looks. For heavy chains a score of 79 or above is indicative of looking human-like; for light chains a score of 86 or above is indicative of looking human-like. The humanness of the three heavy chains, three light chains, a parental (mouse) heavy chain and a parental (mouse) light chain are shown below in Table 6:

TABLE 6

Antibody humanness

| Antibody | Humanness (Framework + CDR) |
| --- | --- |
| Parental (mouse) heavy chain | 63.60 |
| Heavy chain 1 (SEQ ID NO: 29) | 82.20 |
| Heavy chain 2 (SEQ ID NO: 31) | 80.76 |
| Heavy chain 3 (SEQ ID NO: 33) | 81.10 |
| Parental (mouse) light chain | 77.87 |
| Light chain 1 (SEQ ID NO: 35) | 86.74 |
| Light chain 2 (SEQ ID NO: 37) | 86.04 |
| Light chain 3 (SEQ IN NO: 39) | 83.57 |

Full-length antibody genes were constructed by first synthesizing the variable region sequences. The sequences were optimized for expression in mammalian cells. These variable region sequences were then cloned into expression vectors that already contain human Fc domains; for the heavy chain, the IgG1 was used.

Small scale production of humanized antibodies was carried out by transfecting plasmids for the heavy and light chains into suspension HEK293 cells using chemically defined media in the absence of serum. Whole antibodies in the conditioned media were purified using MabSelect SuRe Protein A medium (GE Healthcare).

Nine humanized antibodies were produced from each combination of the three heavy chains having the amino acid sequences shown in SEQ ID NO: 29, 31 and 33 and three light chains having the amino acid sequences shown in SEQ ID NO: 35, 37 and 39. A comparative chimeric parental antibody was also prepared. The antibodies and their respective titers are shown below in Table 7:

TABLE 7

Antibody titers

| Antibody | Titer (mg/L) |
| --- | --- |
| Chimeric parental | 23.00 |
| SEQ ID NO: 29 + SEQ ID NO: 35 | 24.67 |
| SEQ ID NO: 29 + SEQ ID NO: 37 | 41.67 |
| SEQ ID NO: 29 + SEQ ID NO: 39 | 29.67 |
| SEQ ID NO: 31 + SEQ ID NO: 35 | 26.00 |
| SEQ ID NO: 31 + SEQ ID NO: 37 | 27.33 |
| SEQ ID NO: 31 + SEQ ID NO: 39 | 35.33 |
| SEQ ID NO: 33 + SEQ ID NO: 35 | 44.00 |
| SEQ ID NO: 33 + SEQ ID NO: 37 | 30.33 |
| SEQ ID NO: 33 + SEQ ID NO: 39 | 37.33 |

The binding of the humanized antibodies may be evaluated, for example, by dose-dependent binding ELISA or cell-based binding assay.

Example 6 (Prophetic): An AGE-RNAse Containing Vaccine in a Human Subject

AGE-RNAse is prepared by incubating RNAse in a phosphate buffer solution containing 0.1-3 M glucose, glucose-6-phosphate, fructose or ribose for 10-100 days. The AGE-RNAse solution is dialyzed and the protein content is measured. Aluminum hydroxide or aluminum phosphate, as an adjuvant, is added to 100 μg of the AGE-RNAse. Formaldehyde or formalin is added as a preservative to the preparation. Ascorbic acid is added as an antioxidant. The vaccine also includes phosphate buffer to adjust the pH and glycine as a protein stabilizer. The composition is injected intravenously into a subject with diabetes.

Example 7 (Prophetic): Injection Regimen for an AGE-RNAse Containing Vaccine in a Human Subject The same vaccine as described in Example 6 is injected intra-articularly into a subject with diabetic neuropathy. The titer of antibodies to AGE-RNAse is determined by ELISA after two weeks. Additional injections are performed after three weeks and six weeks, respectively. Further titer determination is performed two weeks after each injection.

Example 8 (Prophetic): An AGE-Hemoglobin Containing Vaccine in a Human Subject AGE-hemoglobin is prepared by incubating human hemoglobin in a phosphate buffer solution containing 0.1-3 M glucose, glucose-6-phosphate, fructose or ribose for 10-100 days. The AGE-hemoglobin solution is dialyzed and the protein content is measured. All vaccine components are the same as in Example 6, except AGE-hemoglobin is substituted for AGE-RNAse. Administration is carried out as in Example 6, or as in Example 7.

Example 9 (Prophetic): An AGE-Human Serum Albumin Containing Vaccine in a Human Subject AGE-human serum albumin is prepared by incubating human serum albumin in a phosphate buffer solution containing 0.1-3 M glucose, glucose-6-phosphate, fructose or ribose for 10-100 days. The AGE-human serum albumin solution is dialyzed and the protein content is measured. All vaccine components are the same as in Example 6, except AGE-human serum albumin is substituted for AGE-RNAse. Administration is carried out as in Example 6, or as in Example 7.

Example 10: Carboxymethyllysine-Modified Protein Vaccine for a Human Subject (Prophetic)

A vaccine is prepared by combining a carboxymethyllysine-modified protein as an AGE antigen, aluminum hydroxide as an adjuvant, formaldehyde as a preservative, ascorbic acid as an antioxidant, a phosphate buffer to adjust the pH of the vaccine and glycine as a protein stabilizer. The vaccine is injected subcutaneously into a subject with diabetic cardiomyopathy.

Example 11: Carboxyethyllysine-Modified Peptide Vaccine for a Human Subject (Prophetic)

A vaccine is prepared by combining a carboxyethyllysine-modified peptide conjugated to KLH as an AGE antigen, aluminum hydroxide as an adjuvant, formaldehyde as a preservative, ascorbic acid as an antioxidant, a phosphate buffer to adjust the pH of the vaccine and glycine as a protein stabilizer. The vaccine is injected subcutaneously into a subject with diabetic nephropathy.

Example 12: In Vivo Study of the Administration of a Carboxymethyl Lysine Monoclonal Antibody The effect of a carboxymethyl lysine antibody on tumor growth, metastatic potential and cachexia was investigated. In vivo studies were carried out in mice using a murine breast cancer tumor model. Female BALB/c mice (BALB/cAnNCrl, Charles River) were eleven weeks old on Day 1 of the study.

4T1 murine breast tumor cells (ATCC CRL-2539) were cultured in RPMI 1640 medium containing 10% fetal bovine serum, 2 mM glutamine, 25 µg/mL gentamicin, 100 units/mL penicillin G Na and 100 µg/mL streptomycin sulfate. Tumor cells were maintained in tissue culture flasks in a humidified incubator at 37° C. in an atmosphere of 5% $CO_2$ and 95% air.

The cultured breast cancer cells were then implanted in the mice. 4T1 cells were harvested during log phase growth and re-suspended in phosphate buffered saline (PBS) at a concentration of $1 \times 10^6$ cells/mL on the day of implant. Tumors were initiated by subcutaneously implanting $1 \times 10^5$ 4T1 cells (0.1 mL suspension) into the right flank of each test animal. Tumors were monitored as their volumes approached a target range of 80-120 $mm^3$. Tumor volume was determined using the formula: tumor volume=(tumor width)$^2$(tumor length)/2. Tumor weight was approximated using the assumption that 1 $mm^3$ of tumor volume has a weight of 1 mg. Thirteen days after implantation, designated as Day 1 of the study, mice were sorted into four groups (n=15/group) with individual tumor volumes ranging from 108 to 126 $mm^3$ and a group mean tumor volume of 112 $mm^3$. The four treatment groups are shown in Table 8 below:

TABLE 8

Treatment groups

| Group | Description | Agent | Dosing (µg/g) |
|---|---|---|---|
| 1 | Control | phosphate buffered saline (PBS) | N/A |
| 2 | Low-dose | carboxymethyl lysine monoclonal antibody | 5 |
| 3 | High-dose | carboxymethyl lysine monoclonal antibody | 10 |
| 4 | Observation only | None | N/A |

An anti-carboxymethyl lysine monoclonal antibody was used as a therapeutic agent. 250 mg of carboxymethyl lysine monoclonal antibody was obtained from R&D Systems (Minneapolis, Minn.). Dosing solutions of the carboxymethyl lysine monoclonal antibody were prepared at 1 and 0.5 mg/mL in a vehicle (PBS) to provide the active dosages of 10 and 5 µg/g, respectively, in a dosing volume of 10 mL/kg. Dosing solutions were stored at 4° C. protected from light.

All treatments were administered intravenously (i.v.) twice daily for 21 days, except on Day 1 of the study where the mice were administered one dose. On Day 19 of the study, i.v. dosing was changed to intraperitoneal (i.p.) dosing for those animals that could not be dosed i.v. due to tail vein degradation. The dosing volume was 0.200 mL per 20 grams of body weight (10 mL/kg), and was scaled to the body weight of each individual animal.

The study continued for 23 days. Tumors were measured using calipers twice per week. Animals were weighed daily on Days 1-5, then twice per week until the completion of the study. Mice were also observed for any side effects. Acceptable toxicity was defined as a group mean body weight loss of less than 20% during the study and not more than 10% treatment-related deaths. Treatment efficacy was determined using data from the final day of the study (Day 23).

The ability of the anti-carboxymethyl lysine antibody to inhibit tumor growth was determined by comparing the median tumor volume (MTV) for Groups 1-3. Tumor volume was measured as described above. Percent tumor growth inhibition (% TGI) was defined as the difference between the MTV of the control group (Group 1) and the MN of the drug-treated group, expressed as a percentage of the MTV of the control group. % TGI may be calculated according to the formula: % TGI=$(1-MTV_{treated}/MTV_{control}) \times 100$.

The ability of the anti-carboxymethyl lysine antibody to inhibit cancer metastasis was determined by comparing lung cancer foci for Groups 1-3. Percent inhibition (% Inhibition) was defined as the difference between the mean count of metastatic foci of the control group and the mean count of metastatic foci of a drug-treated group, expressed as a percentage of the mean count of metastatic foci of the control group. % Inhibition may be calculated according to the following formula: % Inhibition=$(1 - \text{Mean Count of Foci}_{treated}/\text{Mean Count of Foci}_{control}) \times 100$.

The ability of the anti-carboxymethyl lysine antibody to inhibit cachexia was determined by comparing the weights of the lungs and gastrocnemius muscles for Groups 1-3. Tissue weights were also normalized to 100 g body weight.

Treatment efficacy was also evaluated by the incidence and magnitude of regression responses observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 $mm^3$ for one or more of these three measurements. In a CR response, the tumor volume was less than 13.5 $mm^3$ for three consecutive measurements during the course of the study.

Statistical analysis was carried out using Prism (GraphPad) for Windows 6.07. Statistical analyses of the differences between Day 23 mean tumor volumes (MTVs) of two groups were accomplished using the Mann-Whitney U test. Comparisons of metastatic foci were assessed by ANOVA-Dunnett. Normalized tissue weights were compared by ANOVA. Two-tailed statistical analyses were conducted at significance level P=0.05. Results were classified as statistically significant or not statistically significant.

The results of the study are shown below in Table 9:

TABLE 9

| | Results | | | | | | | |
|---|---|---|---|---|---|---|---|---|
| Group | MTV ($mm^3$) | % TGI | Lung foci | % Inhibition | PR | CR | Gastroc. weight/ normalized (mg) | Lung weight/ normalized (mg) |
| 1 | 1800 | N/A | 70.4 | N/A | 0 | 0 | 353.4/19.68 | 2799.4/292.98 |
| 2 | 1568 | 13% | 60.3 | 14% | 0 | 0 | 330.4/21.62 | 2388.9/179.75 |
| 3 | 1688 | 6% | 49.0 | 30% | 0 | 0 | 398.6/24.91 | 2191.6/214.90 |

All treatment regimens were acceptably tolerated with no treatment-related deaths. The only animal deaths were non-treatment-related deaths due to metastasis. The % TGI trended towards significance (P >0.05, Mann-Whitney) for the 5 µg/g (Group 2) or 10 µg/g treatment group (Group 3). The % Inhibition trended towards significance (P >0.05, ANOVA-Dunnett) for the 5 µg/g treatment group. The % Inhibition was statistically significant (P≤0.01, ANOVA-Dunnett) for the 10 µg/g treatment group. The ability of the carboxymethyl lysine antibody to treat cachexia trended towards significance (P >0.05, ANOVA) based on a comparison of the organ weights of the lung and gastrocnemius between treatment groups and the control group. The results indicate that administration of an anti-carboxymethyl lysine monoclonal antibody is able to reduce cancer metastases. This data provides additional evidence that in vivo administration of anti-AGE antibodies can provide therapeutic benefits safely and effectively.

Example 13: In Vivo Diabetic Complication Study (Prophetic)

In vivo studies are carried out in mice to study the effect of treatment with anti-AGE antibodies on diabetic complications including diabetic neuropathy and diabetic cardiomyopathy. Male and female BTBR ob/ob mice are used for the study. The male mice are primarily intended for studying diabetic neuropathy while the female mice are primarily intended for studying diabetic cardiomyopathy. All mice are 6-8 weeks old on Day 1 of the study. The mice are separated into four treatment groups of 10-15 mice each: (1) male—control; (2) female—control; (3) male—anti-AGE antibody; and (4) female—anti-AGE antibody.

Dosing begins on Day 1 of the study. Groups 1 and 2 receive phosphate-buffered saline (PBS) delivered intravenously. Groups 3 and 4 receive 10 µg/g of an anti-AGE antibody twice daily for 21 days delivered intravenously. The dosing volume is 0.200 mL per 20 grams of body weight (10 mL/kg), and is scaled to the body weight of each individual animal.

All Groups are monitored daily for morbidity/mortality. Diabetic neuropathy is measured by tail flick thermal testing. Blood is drawn and percent of glycosylated hemoglobin (A1C) is measured 1 day before Day 1 of the study, at 12 weeks, at 16 weeks and at 24 weeks. Treatment will end at 9-11 weeks (21 days after treatment commences).

Half of the animals are sacrificed at 16 weeks. The remaining animals are sacrificed at 24 weeks. The sacrificed animals are analyzed for p16INK4a qRT PCR measured in inguinal adipose tissue. The p16INK4a qRT PCR is preserved for qRT PCR analysis. Diabetic cardiomyopathy is studied by analyzing the left ventricle including measuring myocardial cross-sectional area, myocyte size, fibrosis and macrophage content. Diabetic nephropathy is studied by histologically examining the kidneys for loss of podocytes and by measuring the glomerular basement membrane thickness, the amount of mesangial matrix and the presence/absence of mesangial sclerosis. Diabetic neuropathy is studied by determining the epidermal nerve fiber density.

The anti-AGE antibody will specifically bind to cells expressing cell-surface AGEs, such as senescent beta cells, and allow the immune system to destroy those cells. Killing and removing senescent cells will prevent the onset of diabetes and the development of diabetic complications.

REFERENCES

1. American Diabetes Association, "Diagnosis and Classification of Diabetes", Diabetes Care, Vol. 31, Supp. 1, pp. S62-S67 (2008).
2. "Global Report on Diabetes", World Health Organization, 2016.
3. "National Diabetes Statistics Report: Estimates of Diabetes and Its Burden in the United States, 2014", U.S. Department of Health and Human Services, Centers for Disease Control and Prevention, 2014.
4. O'Brien, P. D. et al., "Mouse models of diabetic neuropathy", Institute for Laboratory Animal Research Journal, Vol. 54, No. 3, (2014).
5. O'Brien, P. D. et al., "BTBR ob/ob mice as a novel diabetic neuropathy model: Neurological characterization and gene expression analyses", Neurobiology of Disease, Vol. 73, pp. 348-355 (2015).
6. Alpers, C. E. et al., "Mouse models of diabetic nephropathy", Current Opinion in Nephrology and Hypertension, Vol. 20, No. 3, pp. 278-284 (2011).
7. Hudkins, K. L et al., "BTBR ob/ob mutant mice model progressive diabetic nephropathy", Journal of the American Society of Nephrology, Vol. 21, pp. 1533-1542 (2010).
8. O'Brien, K. D. et al., "Divergent effects of vasodilators on cardiac hypertrophy and inflammation in a murine model of diabetic cardiomyopathy", Journal of the American College of Cardiology, Vol. 57, Issue 17, p. E193 (2011).
9. Lee, J-T. et al., "Macrophage metalloelastase (MMP12) regulates adipose tissue expansion, insulin sensitivity, and expression of inducible nitric oxide synthase", Endocrinology, Vol. 155, No. 9, p. 3409-3420 (2014).
10. Xu, X. et al., "A glimpse of matrix metalloproteinases in diabetic nephropathy", Current Medicinal Chemistry, Vol. 21, No. 28, p. 3244-3260 (2014).
11. Tsioufis, C. et al., "The role of matrix metalloproteinases in diabetes mellitus", Current Topics in Medicinal Chemistry, Vol. 12, No. 10, Pages 1159-1165 (2012).
12. Watkins, L. R. et al., "Mechanisms of tumor necrosis factor-α (TNF-α) hyperalgesia", Brain Research, Vol. 692, No. 1-2, p. 244-250 (1995).
13. Pechhold, K. et al., "Blood Glucose Levels Regulate Pancreatic β-Cell Proliferation during Experimentally-Induced and Spontaneous Autoimmune Diabetes in Mice", PLoS One, Vol. 4, No. 3, e4827 (2009).
14. Oh, K-J. et al., "Metabolic Adaptation in Obesity and Type II Diabetes: Myokines, Adipokines and Hepatokines", International Journal of Molecular Sciences, Vol. 18, No. 1, Article 8 (2017).
15. Micov, A. et al., "Levetiracetam synergises with common analgesics in producing antinociception in a mouse model of painful diabetic neuropathy", Pharmacological Research, Vol. 97, pp. 131-142 (2015).
16. Feldman, E., "Tail flick assay", Animal Models of Diabetic Complications Consortium (2004).
17. Bratwur, W., "ABT 263 was formulated in 10 ethano", available online at www.selleckchem.com/blog/ABT-263-was-formulated-in-10-ethano.html (2013).
18. Kohnert, K. D. et al., "Destruction of pancreatic beta cells in rats by complete Freund's adjuvant combined with non-diabetogenic doses of streptozotocin", Diabetes Research, Vol. 5, No. 1, pp. 1-11 (1987).
19. Xu, M. et al., "Targeting senescent cells enhances adipogenesis and metabolic function in old age", eLife (2015).
20. Larsen, S. A. et al., "Glucose metabolite glyoxal induces senescence in telomerase-immortalized human mesenchymal stem cells", Chemistry Central Journal, Vol. 6, No. 18 (2012).

21. "Beta cell dysfunction", Diabetes and the Environment, available online at www.diabetesandenvironment.org/home/mech/betacells (accessed Mar. 28, 2017).
22. Edelman, D., "Understanding beta cell exhaustion in Type 2 diabetics", Diabetes Daily, available online at www.diabetesdaily.com/blog/2008/06/podcast-understanding-beta-cell-exhaustion-in-type-2-diabetics (2008).
23. Cao, Y. et al., "Mechanisms of endothelial to mesenchymal transition in the retina in diabetes", Investigative Ophthalmology & Visual Science, Vol. 55, p. 7321-7331 (2014).
24. Radoi, V. et al., "Advanced glycation end-products in diabetes mellitus: mechanism of action and focused treatment", Proceedings of the Romanian Academy, Series B, No. 1, p. 9-19 (2012).
25. Palmer, A. K. et al., "Cellular senescence in Type 2 diabetes: a therapeutic opportunity", Diabetes, Vol 64, pp. 2289-2298 (2015).
26. Cummings, B. P. et al., "Maternal Heal interposition surgery confers metabolic improvements to offspring independent of effects on maternal body weight in UCD-T2DM rats", Obesity Surgery, Vol. 23, No. 12, pp. 2042-2049 (2013).
27. Cummings, B. P. et al., "Development and characterization of a novel rat model of type 2 diabetes mellitus: the UC Davis type 2 diabetes mellitus UCD-T2DM rat", American Journal of Physiology Regulatory, Integrative and Comparative Physiology, Vol. 295, pp. R1782-R1793 (2008).
28. Cummings, B. P. et al., "Bile-acid-mediated decrease in endoplasmic reticulum stress: a potential contributor to the metabolic benefits of ileal interposition surgery in UCD-T2DM rats", Disease Models & Mechanisms, Vol. 6. No. 2, pp. 443-456.
29. Cummings, B. P., et al., "Vertical sleeve gastrectomy improves glucose and lipid metabolism and delays diabetes onset in UCD-T2DM rats", Endocrinology, Vol. 153. No. 8, pp. 3620-3632 (2012).
30. Cummings, B. P. et al., "Ileal interposition surgery improves glucose and lipid metabolism and delays diabetes onset in the UCD-T2DM rat", Gastroenterology, Vol. 138, pp. 2437-2446 (2010).
31. American Diabetes Association, "Standards of medical care in diabetes—2016 abridged for primary care providers", Diabetes, Vol. 34, No. 1, pp. 3-21 (2016).
32. Yoon, M-S. et al., "Characterisation of advanced glycation endproducts in saliva from patients with diabetes mellitus", Biochemical and Biophysical Research Communications, Vol. 323, Issue 2, pp. 377-381 (2004).
33. "Methylglyoxal", available online at en.wikipedia.org/wiki/Methylglyoxal (Jun. 5, 2017).
34. Boesten, D. M. P. H. J. et al., "Effect of NE-carboxymethyllysine on oxidative stress and the glutathione system in beta cells", Toxicology Reports, Vol. 1, pp. 973-980 (2014).
35. Moll& B. et al., "Two different pathogenic mechanisms, dying-back axonal neuropathy and pancreatic senescence, are present in the YG8R mouse model of Friedreich's ataxia", Disease Models & Mechanisms, Vol. 9, pp. 647-657 (2016).
36. Kender, Z. et al., "Effect of metformin on methylglyoxal metabolism in patients with type 2 diabetes", Experimental and Clinical Endocrinology & Diabetes, Vol. 122, No. 5, pp. 316-319 (2014).
37. Brown, J. N. et al., "Class effect of erythropoietin therapy on hemoglobin $A_{1C}$ in a patient with diabetes mellitus and chronic kidney disease not undergoing hemodialysis", Pharmacotherapy: The Journal of Human Pharmacology and Drug Therapy, Vol. 29, No. 4, pp. 468-472 (2009).
38. Garay-Sevilla, M. E. et al., "Advanced glycosylation end products in skin, serum, saliva and urine and its association with complications of patients with Type 2 diabetes mellitus", Journal of Endocrinological Investigation, Vol. 28, No. 5, pp. 223-230 (2005).

What is claimed is:

1. A method of treating diabetes or diabetic complications, comprising killing senescent cells by administering to a subject a composition comprising an anti-AGE antibody, wherein the diabetic complication comprises at least one disease or disorder selected from the group consisting of stroke, diabetic retinopathy, cataracts, glaucoma, kidney disease, hypoglycemia, hyperglycemic crisis, high blood pressure, high blood LDL cholesterol, nerve disease, diabetic neuropathy, neuropathic pain, cognitive impairment, non-alcoholic fatty liver disease, periodontal disease, hearing loss, erectile dysfunction, depression, complications with pregnancy, diabetic ketoacidosis, hyperosmolar hyperglycemic state and diabetic coma.

2. The method of claim 1, wherein the subject is selected from the group consisting of humans, goats, sheep, cows, horses, dogs and cats.

3. The method of claim 1, wherein the anti-AGE antibody is non-immunogenic to a species selected from the group consisting of humans, cats, dogs, horses, camels, alpaca, cattle, sheep, and goats.

4. The method of claim 1, wherein the anti-AGE antibody binds an AGE antigen comprising at least one protein or peptide that exhibits AGE modifications selected from the group consisting of FFI, pyrraline, AFGP, ALI, carboxymethyllysine, carboxyethyllysine and pentosidine.

5. The method of claim 1, wherein the antibody is a humanized antibody.

6. The method of claim 1, wherein the antibody is monoclonal.

7. The method of claim 1, wherein the anti-AGE antibody includes a first complementarity determining region comprising the amino acid sequence of SEQ ID NO: 23,
a second complementarity determining region comprising the amino acid sequence of SEQ ID NO: 24,
a third complementarity determining region comprising the amino acid sequence of SEQ ID NO: 25,
a fourth complementarity determining region comprising the amino acid sequence of SEQ ID NO: 26,
a fifth complementarity determining region comprising the amino acid sequence of SEQ ID NO: 27, and
a sixth complementarity determining region comprising the amino acid sequence of SEQ ID NO: 28.

8. The method of claim 1, wherein the subject is human, the antibody is a humanized monoclonal antibody, and the anti-AGE antibody binds a carboxymethyllysine-modified protein.

9. The method of claim 1, wherein the anti-AGE antibody binds a carboxymethyllysine-modified protein.

10. The method of claim 1, wherein the killing is through antibody-dependent cell-mediated cytotoxicity (ADCC).

11. The method of claim 1, wherein the killing is through complement-dependent cytotoxicity (CDC).

12. A method of treating a subject with diabetes or diabetic complications, comprising:
killing senescent cells by a first administering of an anti-AGE antibody; followed by
testing the subject for effectiveness of the first administration at treating diabetes or diabetic complications; followed by
a second administering of the anti-AGE antibody,
wherein the diabetic complication comprises at least one disease or disorder selected from the group consisting of stroke, diabetic retinopathy, cataracts, glaucoma, kidney disease, hypoglycemia, hyperglycemic crisis, high blood pressure, high blood LDL cholesterol, nerve disease, diabetic neuropathy, neuropathic pain, cognitive impairment, non-alcoholic fatty liver disease, periodontal disease, hearing loss, erectile dysfunction, depression, complications with pregnancy, diabetic ketoacidosis, hyperosmolar hyperglycemic state and diabetic coma.

13. The method of claim 12, wherein the anti-AGE antibody includes a first complementarity determining region comprising the amino acid sequence of SEQ ID NO: 23,
a second complementarity determining region comprising the amino acid sequence of SEQ ID NO: 24,
a third complementarity determining region comprising the amino acid sequence of SEQ ID NO: 25,
a fourth complementarity determining region comprising the amino acid sequence of SEQ ID NO: 26,
a fifth complementarity determining region comprising the amino acid sequence of SEQ ID NO: 27, and
a sixth complementarity determining region comprising the amino acid sequence of SEQ ID NO: 28.

14. The method of claim 12, wherein the subject is selected from the group consisting of humans, goats, sheep, cows, horses, dogs and cats.

15. The method of claim 12, wherein the anti-AGE antibody binds an AGE antigen comprises at least one protein or peptide that exhibits AGE modifications selected from the group consisting of FFI, pyrraline, AFGP, ALI, carboxymethyllysine, carboxyethyllysine and pentosidine.

16. The method of claim 12, wherein the subject is human, the antibody is a humanized monoclonal antibody, and the anti-AGE antibody binds a carboxymethyllysine-modified protein.

17. The method of claim 12, wherein the anti-AGE antibody is non-immunogenic to a species selected from the group consisting of humans, cats, dogs, horses, camels, alpaca, cattle, sheep, and goats.

18. The method of claim 12, wherein the anti-AGE antibody binds a carboxymethyllysine-modified protein.

19. The method of claim 12, wherein the killing is through antibody-dependent cell-mediated cytotoxicity (ADCC).

20. The method of claim 12, wherein the killing is through complement-dependent cytotoxicity (CDC).

* * * * *